United States Patent
Gaige et al.

(10) Patent No.: US 11,969,504 B2
(45) Date of Patent: *Apr. 30, 2024

(54) NON-NATURALLY OCCURRING VESICLES COMPRISING A CHIMERIC VESICLE LOCALIZATION MOIETY, METHODS OF MAKING AND USES THEREOF

(71) Applicant: Mantra Bio, inc., San Francisco, CA (US)

(72) Inventors: Terry Gaige, San Francisco, CA (US); Colin David Gottlieb, San Francisco, CA (US)

(73) Assignee: MANTRA BIO, INC., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/888,862

(22) Filed: Aug. 16, 2022

(65) Prior Publication Data

US 2023/0218527 A1   Jul. 13, 2023

Related U.S. Application Data

(63) Continuation of application No. 17/795,857, filed as application No. PCT/US2021/015334 on Jan. 27, 2021.

(60) Provisional application No. 62/966,487, filed on Jan. 27, 2020.

(51) Int. Cl.

| | |
|---|---|
| *A61K 9/127* | (2006.01) |
| *A61K 9/00* | (2006.01) |
| *A61K 47/69* | (2017.01) |
| *C07K 14/705* | (2006.01) |
| *C12N 15/62* | (2006.01) |
| *C12N 15/63* | (2006.01) |

(52) U.S. Cl.
CPC .......... *A61K 9/127* (2013.01); *A61K 9/0019* (2013.01); *A61K 47/6901* (2017.08); *C07K 14/705* (2013.01); *C12N 15/62* (2013.01); *C12N 15/63* (2013.01)

(58) Field of Classification Search
CPC .. A61K 9/127; A61K 9/0019; A61K 47/6901; C07K 14/705; C12N 15/62; C12N 15/63
See application file for complete search history.

(56) References Cited

U.S. PATENT DOCUMENTS

| | | | |
|---|---|---|---|
| 10,624,849 B2* | 4/2020 | Leonard | A61K 47/46 |
| 2004/0219204 A1 | 11/2004 | Huang et al. | |
| 2005/0119210 A1 | 6/2005 | Be et al. | |
| 2013/0156801 A1 | 6/2013 | Bond et al. | |
| 2015/0202203 A1 | 7/2015 | Monahan et al. | |
| 2016/0137716 A1 | 5/2016 | El Andaloussi et al. | |
| 2017/0182182 A1 | 6/2017 | Seow et al. | |
| 2018/0028687 A1 | 2/2018 | Selaru et al. | |
| 2018/0179553 A1 | 6/2018 | Watson et al. | |
| 2018/0276339 A1 | 9/2018 | Planey et al. | |
| 2019/0074085 A1 | 3/2019 | Caffarel et al. | |
| 2019/0160097 A1* | 5/2019 | Pusic | A61P 25/06 |
| 2019/0276820 A1 | 9/2019 | Gaige et al. | |
| 2019/0352708 A1 | 11/2019 | Gaige et al. | |
| 2020/0281982 A1 | 9/2020 | Marcucci et al. | |
| 2021/0379192 A1 | 12/2021 | Szabo et al. | |
| 2022/0323412 A1 | 10/2022 | Kang et al. | |

FOREIGN PATENT DOCUMENTS

| | | | | |
|---|---|---|---|---|
| WO | WO 2020/154746 A1 | 7/2003 | | |
| WO | WO 2017/196175 A1 | 11/2017 | | |
| WO | WO 2019/040920 A1 | 2/2019 | | |
| WO | WO-2019040920 A1 * | 2/2019 | | A61K 35/22 |
| WO | WO 2020/061550 A1 | 3/2020 | | |
| WO | WO 2021/211633 A2 | 10/2021 | | |

OTHER PUBLICATIONS

Do et al. (Scientific Reports, (2019) 9:17274, pp. 1-11). (Year: 2019).*
Do et al., Targeted delivery of lysosomal enzymes to the endocytic compartment in human cells using engineered extracellular vesicles, Scientific Reports (2019) 9:17274 -*Exhibit 1*.
Mazurov et al. Tetraspanin protein CD9 interacts with CD10 and enhances its release via exosomes. The FEBS Journal. Mar. 2013, Epub Feb. 6, 2013 (Feb. 6, 2013), vol. 280, No. 5 p. 1200-1213; especially abstract; p. 1203, col. 2, para 1, p. 1204, col. 2, para 2;. p. 1206, col. 2, para 3; p. 1207, col. 1, para 1; p. 1209, col. 2, para 3; p. col 1, para 1; p. 1210, col. 2, para 2-p. 1211, col. 1, para 1; Fig. 2A (Exhibit 16).

* cited by examiner

*Primary Examiner* — Janet L Epps-Smith
(74) *Attorney, Agent, or Firm* — ADRIANO & ASSOCIATES

(57) ABSTRACT

Disclosed herein are non-naturally occurring vesicle comprising a chimeric vesicle localization moiety comprising a surface-and-transmembrane domain of a first vesicle localization moiety and a cytosolic domain of a second vesicle localization moiety, the method of making said vesicle and uses thereof.

9 Claims, 16 Drawing Sheets

Figure 14:
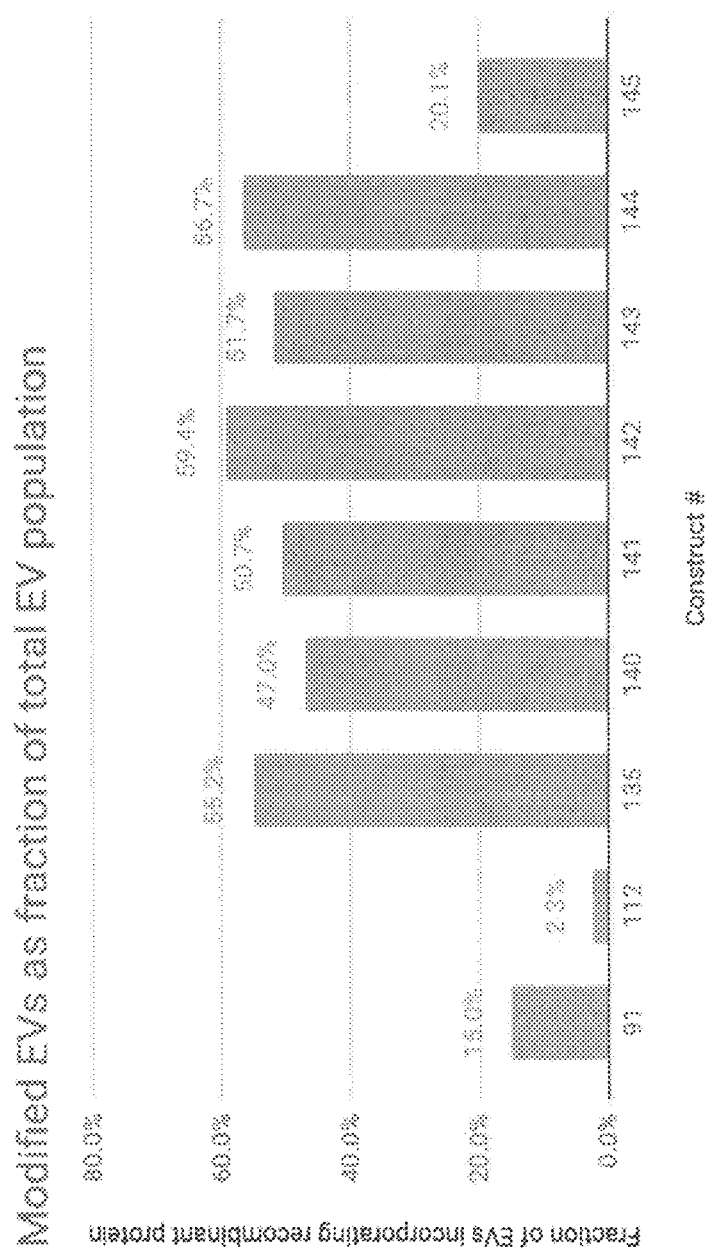

Specification includes a Sequence Listing.

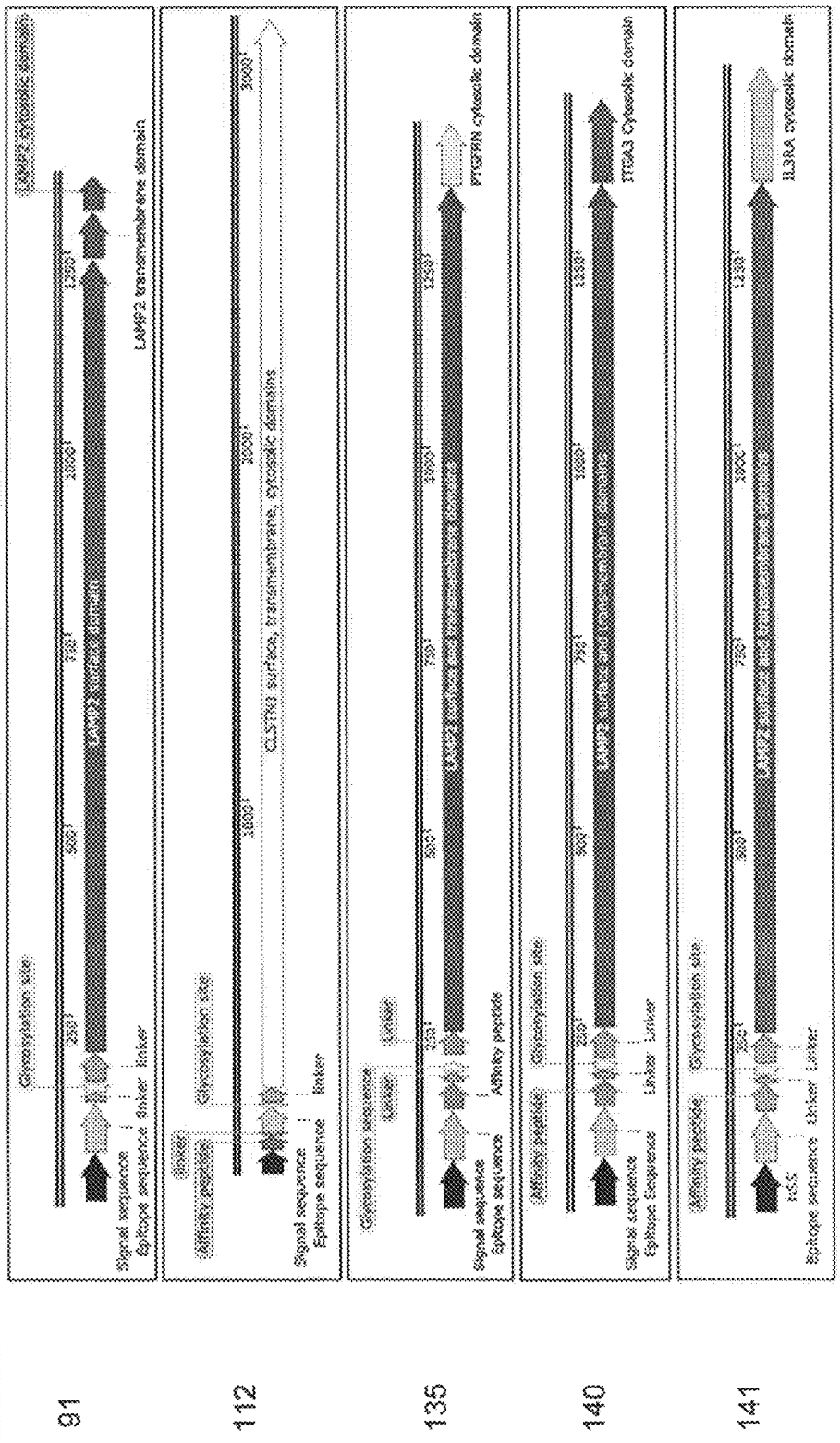

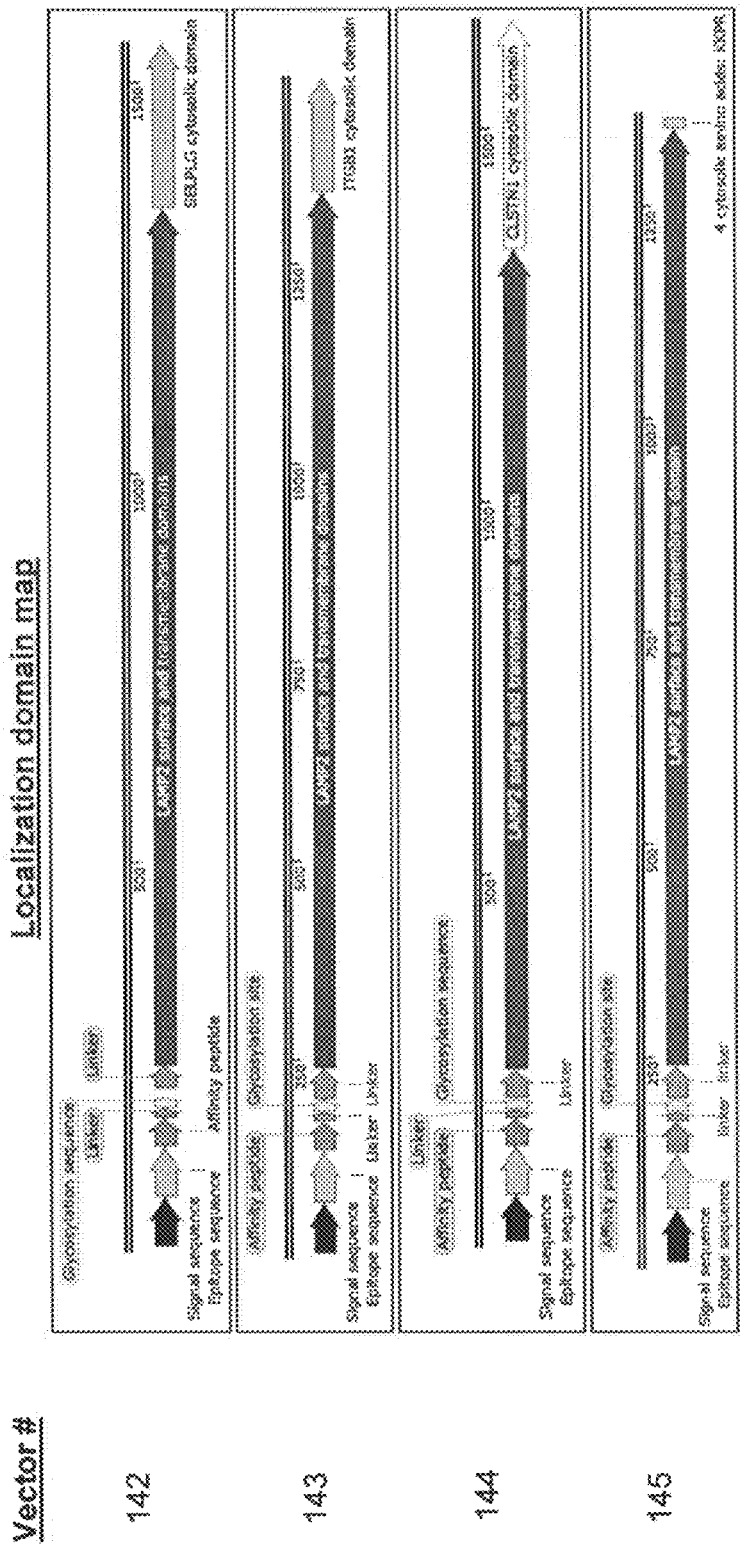

Construct sequences

91:
MWWRLWWLLLLLLLWPMVWADYKDHDGDYKDHDIDYKDDDDKGGGSgnstmGSGGGGSGGGGSGGGGSLELNLTDS
ENATCLYAKWQMNFTVRYETTNKTYKTVTISDHGTVTYNGSICGDDQNGPKIAVQFGPGFSWIANFTKAASTYSIDSV
SFSYNTGDNTTFPDAEDKGILTVDELLAIRIPLNDLFRCNSLSTLEKNDVVQHYWDVLVQAFVQNGTVSTNEFLCDKD
KTSTVAPTIHTTVPSPTTPTPKEKPEAGTYSVNNGNDTCLLATMGLQLNITQDKVASVININPNTTHSTGSCRSHTAL
LRLNSSTIKYLDFVFAVKNENRFYLKEVNISMYLVNGSVFSIANNNLSYWDAPLGSSYMCNKEQTVSVSGAFQINTFD
LRVQPFNVTQGKYSTAQECSLDDDTILIPIVGAGLSGLIVVIAYVIGRRKSYAGYQTL

Figure 3

Construct sequences

Figure 4

112:
MWWRLWWLLLLLLLWPMVWA`HPTMTSPN`GGGSDYKDHDGDYKDHDIDYKDDDDKgnstnGSGGGGS
GGGSARVNKHKPWLEPTYHGIVTENDNTVLLDPPLIALDKDAPLRFAESFEVTVTKEGEICGFKIHGQNVPFDAVVV
DKSTGEGVIRSKEKLDCELQKDYSFTIQAYDCGKGPDGTNVKKSHKATVHIQVNDVNEYAPVFKEKSYKATVIEGKQ
YDSILRVEAVDADCSPQFSQICSYEIITPDVPFTVDKDGYIKNTEKLNYGKEHQYKLTVTAYDCGKKRATEDVLVKISIK
PTCTPGWQGWNNRIEYEPGTGALAVFPNIHLETQDEPVASVQATVELETSHIGKGCDRDTYSEKSLHRLCGAAGTA
ELLPSPSGSLNWTMGLPTDNGHDSDQVFEFNGTQAVRIPDGVVSVSPKEPFTISVWMRHGPFGRKKETILCSSDKT
DMNRHHYSLYVHGCRLIFLFRQDPSEEKKYRPAEFHMKLNQVCDEEWHHYVLNVEFPSVTLYVDGTSHEPFSVTED
YPLHPSKIETQLVVGACWQEFSGVENDNETEPVTVASAGGDLHMTQFFRGNLAGLTLRSGKLADKKVIDCLYTCKEG
LDLQVLEDSGRGVQIQAHPSQLVLTLEGEDLGELDKAMQHISYLNSRQFPTPGIRRLKITSTIKCFNEATCISVPPVDG
YVMVLQPEEPKISLSGVHHFARAASEFESSEGVFLFPELRIISTITREVEPEGDGAEDPTVQESLVSEEIVHDLDTCEVT
VEGEELNHEQESLEVDMARLQQKGIEVSSSELGMTFTGVDTMASYEEVLHLLRYRNWHARSLLDRKFKLICSELNGR
YISNEFKVEVNVIHTANPMEHAAAAAQPQFVHPEHRSFVDLSGHNLANPHPFAVVPSTATVVVCVSFLVFMIILGV
FRIRAAHRRTMRDQDTGKENEMDWDDSALTITVNPMETYEDQHSSEEEEEEESEDGEEEDITSAESESSEE
*EEGEQGDPONATRQQLEMDDSTLSY*

Construct sequences

Figure 5

- 135:

MWWRLWWLLLLLLLWPMVWADYKDHDGDYKDHDIDYKDDDDK*GGGSELNLTDSENATCLYAKWQMNFTVRYETTNKTYKTVTISDHGTVTYNGSICGDDQNGPKIAVQFGPGFSWIANFTKAASTYSIDSVSFSYNTGDNTTFPDAEDKGILTVDELLAIRIPLNDLFRCNSLSTLEKNDVVQHYWDVLVQAFVQNGTVSTNEFLCQDKDKTSTVAPTIHTTVPSPTTTPTPKEKPEAGTYSVNNGNDTCLLATMGLQLNITQDKVASVNINPNTTHSTGSCRSHTALLRLNSSTIKYLDFVFAVKNENRFYLKEVNISMYLVNGSVFSIANNNLSYWDAPLGSSYMCNKEQTVSVSGAFQINTFDLRVQPFNVTQGKYSTAQECSLDDDTILPIIVGAGLSGLIIVIASSHWCCKKEVQETRRERRLMSMEMD*

- 140:

MWWRLWWLLLLLLLWPMVWADYKDHDGDYKDHDIDYKDDDDK*GGGSELNLTDSENATCLYAKWQMNFTVRYETTNKTYKTVTISDHGTVTYNGSICGDDQNGPKIAVQFGPGFSWIANFTKAASTYSIDSVSFSYNTGDNTTFPDAEDKGILTVDELLAIRIPLNDLFRCNSLSTLEKNDVVQHYWDVLVQAFVQNGTVSTNEFLCQDKDKTSTVAPTIHTTVPSPTTTPTPKEKPEAGTYSVNNGNDTCLLATMGLQLNITQDKVASVNINPNTTHSTGSCRSHTALLRLNSSTIKYLDFVFAVKNENRFYLKEVNISMYLVNGSVFSIANNNLSYWDAPLGSSYMCNKEQTVSVSGAFQINTFDLRVQPFNVTQGKYSTAQECSLDDDTILPIIVGAGLSGLIIVIAKCGFFKRARTRALYEAKRQKAEMKSQPSETERLTDDY*

Construct sequences

Figure 6

- 141:

MWWRLWWLLLLLLLLWPMVWADYKDHDGDYKDHDIDYKDDDDK*HHHHHH*GGGSgnstnGSGGGGGSG
  GGGS*ELNLTDSENATCLYAKWQMNFTVRYETTNKTYKTVTISDHGTVTYNGSICGDDQNGPKIAVQFGPGFSWIAN
  FTKAASTYSIDSVSFSYNTGDNTTFPDAEDKGILTVDELLAIRIPLNDLFRCNSLSTLEKNDVVQHYWDVLVQAFVQNG
  TVSTNEFLCDKDKTSTVAPTIHTTVPSPTTTPTPKEKPEAGTYSVNNGNDTCLLATMGLQLNITQDKVASVININPNTT
  HSTGSCRSHTALLRLNSSTIKYLDFVFAVKNENRFYLKEVNISMYLVNGSVFSIANNNLSYWDAPLGSSYMCNKEQTV
  SVSGAFQINTFDLRVQPFNVTQGKYSTAQECSLDDDTILPIIVGAGLSGLIIVVIA*VWQRLFPRIPHMKDPIGDSFQND
  KLVVWEAGKAGLEECLVITEVQVQKT*

- 142:

MWWRLWWLLLLLLLLWPMVWADYKDHDGDYKDHDIDYKDDDDK*HHHHHH*GGGSgnstnGSGGGGGSG
  GGGS*ELNLTDSENATCLYAKWQMNFTVRYETTNKTYKTVTISDHGTVTYNGSICGDDQNGPKIAVQFGPGFSWIAN
  FTKAASTYSIDSVSFSYNTGDNTTFPDAEDKGILTVDELLAIRIPLNDLFRCNSLSTLEKNDVVQHYWDVLVQAFVQNG
  TVSTNEFLCDKDKTSTVAPTIHTTVPSPTTTPTPKEKPEAGTYSVNNGNDTCLLATMGLQLNITQDKVASVININPNTT
  HSTGSCRSHTALLRLNSSTIKYLDFVFAVKNENRFYLKEVNISMYLVNGSVFSIANNNLSYWDAPLGSSYMCNKEQTV
  SVSGAFQINTFDLRVQPFNVTQGKYSTAQECSLDDDTILPIIVGAGLSGLIIVVIA*RLSRKGHMYPVRNYSPTEMVCIS
  SLLPDGGEGPSATANGGLSKAKSPGLTPEPREDREGDDLTLHSFLP*

Construct sequences

143:

MWWRLWWLLLLLLLLLWPMVWADYKDHDGDYKDHDIDYKDDDDKHSPNHSLGGGSGnstnGSGGGGGSG
GGGSLELNLTDSENATCLYAKWQMNFTVRYETTNKTYKTVTISDHGTVTYNGSICGDDQNGPKIAVQFGPGFSWIAN
FTKAASTYSIDSVSFSYNTGDNTTFPDAEDKGILTVDELLAIRIPLNDLFRCNSLSTLEKNDVVQHYWDVLVQAFVQNG
TVSTNEFLCDKDKTSTVAPTIHTTVPSPTTTPTPKEKPEAGTYSVNNGNDTCLLATMGLQLNITQDKVASVININPNTT
HSTGSCRSHTALLRLNSSTIKYLDFVFAVKNENRFYLKEVNISMYLVNGSVFSIANNNLSYWDAPLGSSYMCNKEQTV
SVSGAFQINTFDLRVQPFNVTQGKYSTAQECSLDDDTILIPIIVGAGLSGLIIVMIALMIIHDRREFAKFEKMNAKW
DTGENPIYKSAVTTVVNPKYEGK

144:

MWWRLWWLLLLLLLLLWPMVWADYKDHDGDYKDHDIDYKDDDDKHSPNHSLGGGSGnstnGSGGGGGSG
GGGSLELNLTDSENATCLYAKWQMNFTVRYETTNKTYKTVTISDHGTVTYNGSICGDDQNGPKIAVQFGPGFSWIAN
FTKAASTYSIDSVSFSYNTGDNTTFPDAEDKGILTVDELLAIRIPLNDLFRCNSLSTLEKNDVVQHYWDVLVQAFVQNG
TVSTNEFLCDKDKTSTVAPTIHTTVPSPTTTPTPKEKPEAGTYSVNNGNDTCLLATMGLQLNITQDKVASVININPNTT
HSTGSCRSHTALLRLNSSTIKYLDFVFAVKNENRFYLKEVNISMYLVNGSVFSIANNNLSYWDAPLGSSYMCNKEQTV
SVSGAFQINTFDLRVQPFNVTQGKYSTAQECSLDDDTILPIIVGAGLSGLIIVMIARIRAAHRRTMRDQDTGKENEMD
WDDSALTITVVNPMETYEDQHSSEEEEEEEEEESEDDITSAESESSEEEGEQGDPQNATRQQLEWDDS
TLSY

Figure 7

Construct sequences

145:

MWWRLVWWLLLLLLLLWPMVWADYKDHDGDYKDHDIDYKDDDDK̲T̲S̲P̲K̲K̲K̲R̲K̲V̲E̲GGGSgnsmGSGGGGSG ELNLTDSENATCLYAKWQMNFTVRYETTNKTYKTVTISDHGTVTYNGSICGDDQNGPKIAVQFGPGFSWIAN FTKAASTYSIDSVSFSYNTGDNTTFPDAEDKGILTVDELLAIRIPLNDLFRCNSLSTLEKNDVVQHYWDVLVQAFVQNG TVSTNEFLCDKDKTSTVAPTIHTTVPSPTTTPTPKEKPEAGTYSVNNGNDTCLLATMGLQLNITQDKVASVININPNTT HSTGSCRSHTALLRLNSSTIKYLDFVFAVKNENRFYLKEVNISMYLVNGSVFSIANNNLSYWDAPLGSSYMCNKEQTV SVSGAFQINTFDLRVQPFNVTQGKYSTAQECSLDDDTILPIIVGAGLSGLIVIVIAKPR

Figure 8

Figure 9

Construct sequences (surface, transmembrane, cytosolic domain only)

- 91:
LELNLTDSENATCLYAKWQMNFTVRYETTNKTYKTVTISDHGTVTYNGSICGDDQNGPKIAVQFGPGFSWIANFTKAASTYSIDSVSFS
YNTGDNTTFPDAEDKGILTVDELLAIRIPLNDLFRCNSLSTLEKNDVVQHYWDVLVQAFVQNGTVSTNEFLCDKDKTSTVAPTIHTTVPS
PTTTPTPKEKPEAGTYSVNNGNDTCLLATMGLQLNITQDKVASVININPNTTHSTGSCRSHTALLRLNSSTIKYLDFVFAVKNENRFYLK
EVNISMYLVNGSVFSIANNNLSYWDAPLGSSYMCNKEQTVSVSGAFQINTFDLRVQPFNVTQGKYSTAQECSLDDITILIPIIVGAGLSG
LIIVIAYVIGRRKSYAGYQTL

- 112:
ARVNKHKPWLEPTYHGIVTENDNTVLLDPPLIALDKDAPLRFAESFEVTVTKEGEICGFKIHGQNVPFDAVVVDKSTGEGVIRSKEKLDC
ELQKDYSFTIQAYDCGKGPDGTNVKKSHKATVHIQVNDVNEYAPVFKEKSYKATVIEGKQYDSILRVEAVDADCSPQFSQICSYEIITPD
VPFTVDKDGYIKNTEKLNYGKEHQYKLTVTAYDCGKKRATEDVLVKISIKPTCTPGWQGWNNRIEYEPGTGALAVFPNIHLETCDEPVA
SVQATVELETSHIGKGCDRDTYSEKSLHRLCGAAAGTAELLPSPSGSLNMTMGLPTDNGHDSDQVFEFNGTQAVRIPDGVVSVSPKE
PFTISVMMRHGPFGRKKETILCSSDKTDMNRHHYSLYVHGCRLIFLFRQDPSEEKYRPAEFHWKLNQVCDEEWHHYLNVEFPSVT
LYVDGTSHEPFSVTEDYPLHPSKIETQLVVGACWQEFSGVENDNETEPVTVASAGGDLHMTQFFRGNLAGLTLRSGKLADKKVIDCLY
TCKEGLDLQVLEDSGRGVQIQAHPSQLVLTLEGEDLGELDKAMQHISYLNSRQFPTPGIRRLKITSTIKCFNEATCISVPPVDGYVMVLQ
PEEPKISLSGVHHFARAASEFESSEGVFLFPELRIISTITREVEPEPGDGAEDPTVQESLVSEEIVHDLDTCEVTVEGEELNHEQESLEVD
MARLQQKGIEVSSSELGMTFTGVDTMASYEEVLHLLRYRNWHARSLLDRKFKLJCSELNGRYISNEFKVEVNVIHTANPMEHAAAAA
QPQFVHPEHRSFVDLSGHNLANPHPFAVVPSTATVMVVCVSFLVFMIILGVFRIRAAHRRTMPDCDTGKENEMDWDDSALTITVNPM
ETYEDDHSSEEEEEEEEEEEESEDGEEEEEEEEESEDDITSAESESSEEEEGEOGDPQNATRQDOLEWDDSTLSY

Figure 10

Construct sequences (surface, transmembrane, cytosolic domain only)

- 135:
LELNLTDSENATCLYAKWQMNFTVRYETTNKTYKTVTISDHGTVTYNGSICGDDQNGPKIAVQFGPGFSWIANFTKAASTYSIDSVSFS
YNTGDNTTFPDAEDKGILTVDELLAIRIPLNDLFRCNSLSTLEKNDVQHYWDVLVQAFVQNGTVSTNEFLCDKDKTSTVAPTIHTTVPS
PTTTPTPKEKPEAGTYSVNNGNDTCLLATMGLQLNITQDKVASVININPNTTHSTGSCRSHTALLRLNSSTIKYLDFVFAVKNENRFYLK
EVNISMYLVNGSVFSIANNNLSYWDAPLGSSYMCNKEQTVSVSGAFQINTFDLRVQPFNVTQGKYSTAQECSLDDDTILIPIIVGAGLSG
LIWIASSHWCCKKEVQETRRERFRLMSMEMD

- 140:
LELNLTDSENATCLYAKWQMNFTVRYETTNKTYKTVTISDHGTVTYNGSICGDDQNGPKIAVQFGPGFSWIANFTKAASTYSIDSVSFS
YNTGDNTTFPDAEDKGILTVDELLAIRIPLNDLFRCNSLSTLEKNDVQHYWDVLVQAFVQNGTVSTNEFLCDKDKTSTVAPTIHTTVPS
PTTTPTPKEKPEAGTYSVNNGNDTCLLATMGLQLNITQDKVASVININPNTTHSTGSCRSHTALLRLNSSTIKYLDFVFAVKNENRFYLK
EVNISMYLVNGSVFSIANNNLSYWDAPLGSSYMCNKEQTVSVSGAFQINTFDLRVQPFNVTQGKYSTAQECSLDDDTILIPIIVGAGLSG
LIWIAKCGFFKRAFTRALYEAKROKAEMKSQPSETERLTDDY

- 141:
LELNLTDSENATCLYAKWQMNFTVRYETTNKTYKTVTISDHGTVTYNGSICGDDQNGPKIAVQFGPGFSWIANFTKAASTYSIDSVSFS
YNTGDNTTFPDAEDKGILTVDELLAIRIPLNDLFRCNSLSTLEKNDVQHYWDVLVQAFVQNGTVSTNEFLCDKDKTSTVAPTIHTTVPS
PTTTPTPKEKPEAGTYSVNNGNDTCLLATMGLQLNITQDKVASVININPNTTHSTGSCRSHTALLRLNSSTIKYLDFVFAVKNENRFYLK
EVNISMYLVNGSVFSIANNNLSYWDAPLGSSYMCNKEQTVSVSGAFQINTFDLRVQPFNVTQGKYSTAQECSLDDDTILIPIIVGAGLSG
LIWIAVMQRLFPRIPIHMKQPIGDSFQNDKLVMEAGKAGLEEQLVTEVQIVQKT

Figure 11

Construct sequences (surface, transmembrane, cytosolic domain only)

- 142:

LELNLTDSENATCLYAKWQMNFTVRYETTNKTYKTVTISDHGTVTYNGSICGDDQNGPKIAVQFGPGFSWIANFTKA
  ASTYSIDSVSFSYNTGDNTTFPDAEDKGILTVDELLAIRIPLNDLFRCNSLSTLEKNDVVQHYMDVLVQAFVQNGTVST
  NEFLCQDKDKTSTVAPTIHTTVPSPTTTPPKEKPEAGTYSVNNGNDTCLLATMGLQLNITQDKVASVININPNTTHSTG
  SCRSHTALLRLNSSTIKYLDFVFAVKNENRFYLKEVNISMYLVNGSVFSIANNNLSYWDAPLGSSYMCNKEQTVSVSG
  AFQINTFDLRVQPFNVTQGKYSTAQECSLDDDTILPIIVGAGLSGLIVVVIARLSRKGHMYPVRNYSPTEMVCISSLLP
  DGGEGPSATANGGLSKAKSPGLTPEPREDREGDDLTLHSFLP

- 143:

LELNLTDSENATCLYAKWQMNFTVRYETTNKTYKTVTISDHGTVTYNGSICGDDQNGPKIAVQFGPGFSWIANFTKA
  ASTYSIDSVSFSYNTGDNTTFPDAEDKGILTVDELLAIRIPLNDLFRCNSLSTLEKNDVVQHYMDVLVQAFVQNGTVST
  NEFLCQDKDKTSTVAPTIHTTVPSPTTTPPKEKPEAGTYSVNNGNDTCLLATMGLQLNITQDKVASVININPNTTHSTG
  SCRSHTALLRLNSSTIKYLDFVFAVKNENRFYLKEVNISMYLVNGSVFSIANNNLSYWDAPLGSSYMCNKEQTVSVSG
  AFQINTFDLRVQPFNVTQGKYSTAQECSLDDDTILPIIVGAGLSGLIVVIALLMIIHDRREFAKFEKMNAKWDTGE
  NPIYKSAVTTVVNPKYEGK

Figure 12

Construct sequences (surface, transmembrane, cytosolic domain only)

- 144:
LELNLTDSENATCLYAKWQMNFTVRYETTNKTYKTVTISDHGTVTYNGSICGDDQNGPKIAVQFGPGFSWIANFTKA
ASTYSIDSVSFSYNTGDNTTFPDAEDKGILTVDELLAIRIPLNDLFRCNSLSTLEKNDVVQHYWDLVQAFVQNGTVST
NEFLCDKDKTSTVAPTIHTTVPSPTTTPTPKEKPEAGTYSVNNGNDTCLLATMGLQLNITQDKVASVININPNTTHSTG
SCRSHTALRLNSSTIKYLDFVFAVKNENRFYLKEVNISMYLVNGSVFSIANNNLSYWDAPLGSSYMCNKEQTVSVSG
AFQINTFDLRVQPFNVTQGKYSTAQECSLDDDTILPIIVGAGLSGLIWVIARIRAAHRRTMRDQDTGKENEMDWDDS
ALTIVNPMETYEDQHSSEEEEEEESEDGEEEDITSAESESSEEEGEQGDPONATRQQQLEWDDSTLSY

- 145:
LELNLTDSENATCLYAKWQMNFTVRYETTNKTYKTVTISDHGTVTYNGSICGDDQNGPKIAVQFGPGFSWIANFTKA
ASTYSIDSVSFSYNTGDNTTFPDAEDKGILTVDELLAIRIPLNDLFRCNSLSTLEKNDVVQHYWDLVQAFVQNGTVST
NEFLCDKDKTSTVAPTIHTTVPSPTTTPTPKEKPEAGTYSVNNGNDTCLLATMGLQLNITQDKVASVININPNTTHSTG
SCRSHTALRLNSSTIKYLDFVFAVKNENRFYLKEVNISMYLVNGSVFSIANNNLSYWDAPLGSSYMCNKEQTVSVSG
AFQINTFDLRVQPFNVTQGKYSTAQECSLDDDTILPIIVGAGLSGLIWVIAKKPR

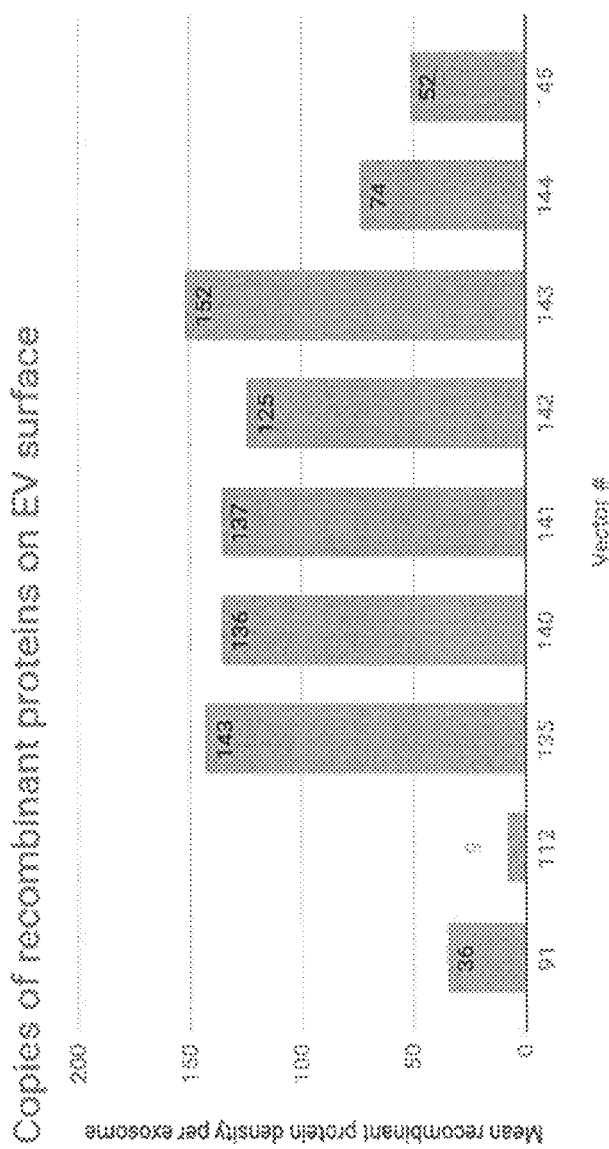

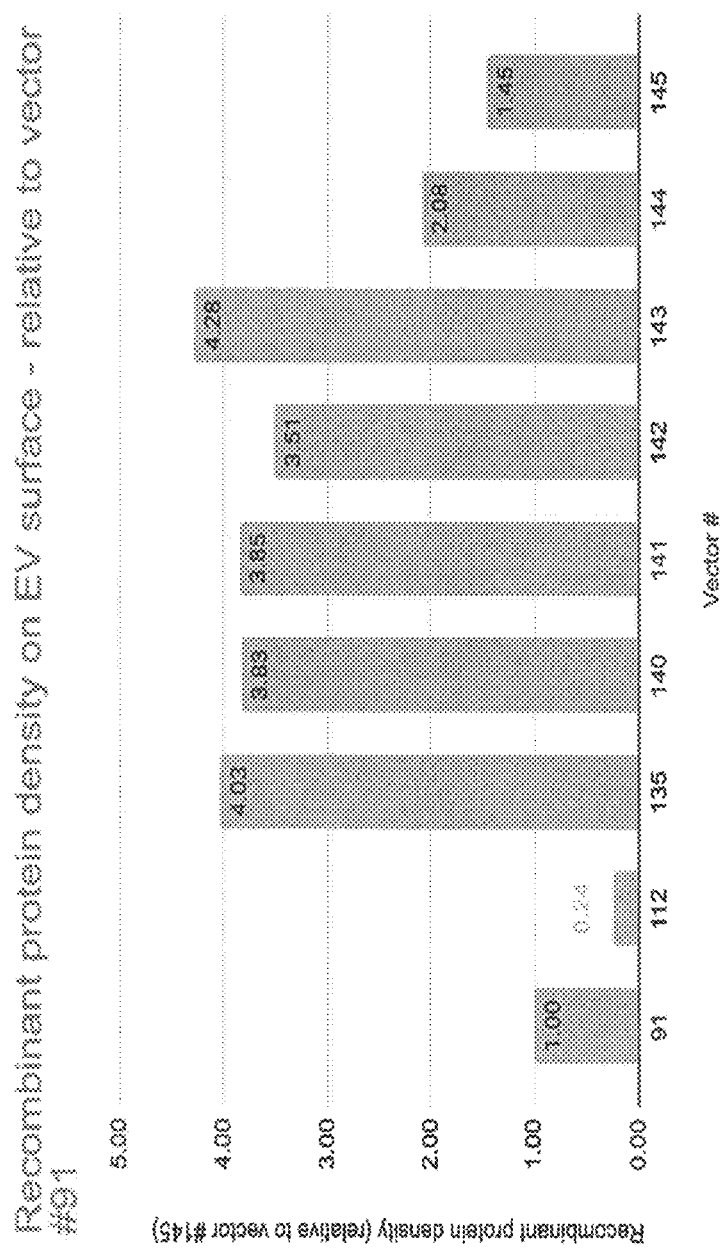

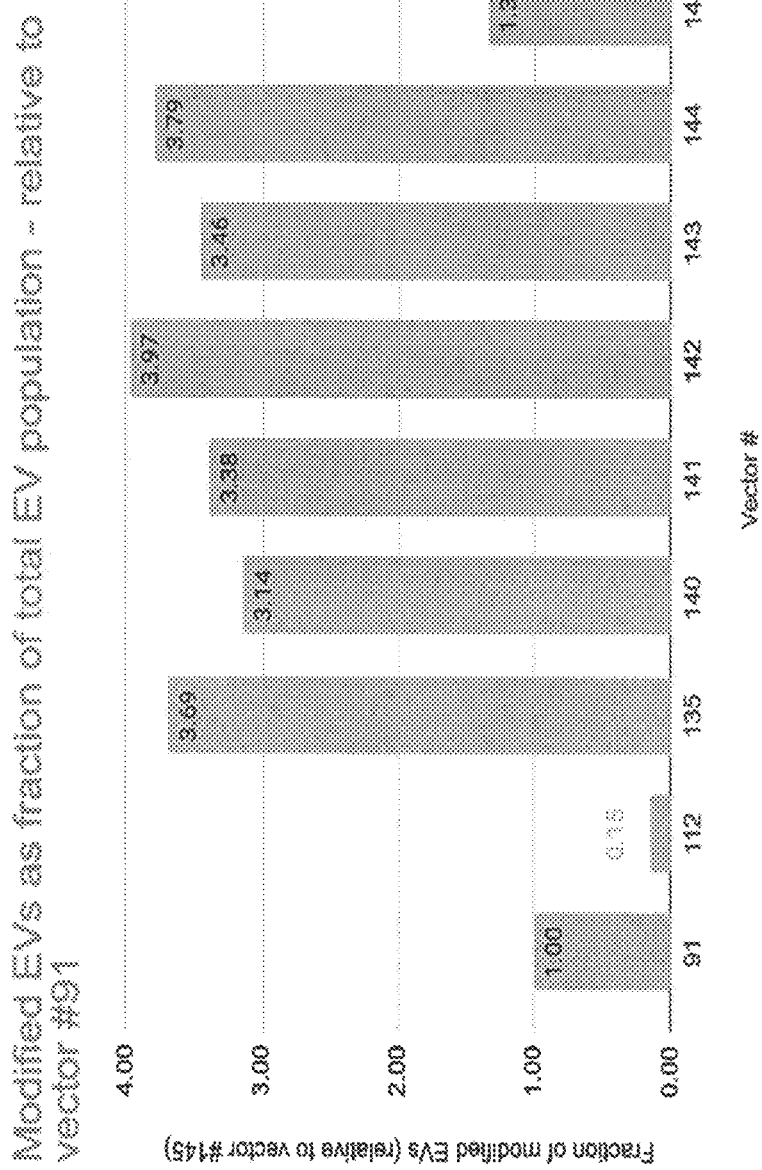

SEQUENCE LISTING

```
Sequence total quantity: 84
SEQ ID NO: 1            moltype = DNA  length = 2247
FEATURE                 Location/Qualifiers
source                  1..2247
                        mol_type = other DNA
                        organism = Homo sapiens
CDS                     1..2247
SEQUENCE: 1
atggtgttgc tgagagtgtt aattctgctc ctctcctggg cggcggggat gggaggtcag    60
tatgggaatc ctttaaataa atatatcaga cattatgaag gattatctta caatgtggat   120
tcattacacc aaaaacacca gcgtgccaaa agagcagtct cacatgaaga ccaattttta   180
cgtctagatt tccatgccca tggaagacat ttcaacctac gaatgaagag ggacacttcc   240
ctttttcagtg atgaatttaa agtagaaaca tcaaataaag tacttgatta tgatacctct   300
catatttaca ctggacatat ttatggtgaa gaaggaagtt ttagccatgg gtctgttatt   360
gatggaagat ttgaaggatt catccagact cgtggtggca cattttatgt tgagccagca   420
gagagatata ttaaagaccg aactctgcca tttcactctg tcatttatca tgaagatgat   480
attaactatc cccataaata cggtcctcag ggggctgtg cagatcattc agtatttgaa   540
agaatgagga aataccagat gactggtgta gaggaagtaa cacagatacc tcaagaagaa   600
catgctgcta atggtccaga acttctgagg aaaaaacgta caacttcagc tgaaaaaaat   660
acttgtcagc tttatattca gactgatcat ttgttcttta aatattacgg aacacgagaa   720
gctgtgattg cccagatatc cagtcatgtt aaagcgattg atacaattta ccagaccaca   780
gacttctccg gaatccgtaa catcagtttc atggtgaaac gcataagaat caatacaact   840
gctgatgaga aggacctac aaatcctttc cgtttcccaa atattggtgt ggagaagttt   900
ctggaattga attctgagca gaatcatgat gactactgtt tggcctatgt cttcacagac   960
cgagattttg atgatggcgt acttggtctg gcttgggttg gagcaccttc aggaagctct  1020
ggaggaatat gtgaaaaaag taaactctat tcagatggta agaagaagtc cttaaacact  1080
ggaattatta ctgttcagaa ctatgggtct catgtacctc ccaaagtctc tcacattact  1140
tttgctcacg aagttggaca taactttgga tcccacatg attctggaac agagtgcaca  1200
ccaggagaat ctaagaattt gggtcaaaaa gaaaatggca attacatcat gtatgcaaga  1260
gcaacatctg gggacaaact taacaacaat aaattctcac tctgtagtat tagaaatata  1320
agccaagttc ttgagaagaa gagaaacaac tgttttgttg aatctggcca acctatttgt  1380
ggaaatggaa tggtagaaca aggtgaagaa tgtgattgtg gctatagtga ccagtgtaaa  1440
gatgaatgct gcttcgatgc aaatcaacca gagggaagaa aatgcaaact gaaacctggg  1500
aaacagtgca gtccaagtca aggtccttgt tgtacagcac agtgtgcatt caagtcaaag  1560
tctgagaagt gtcgggatga ttcagactgt gcaagggaag gaatatgtaa tggcttcaca  1620
gctctctgcc cagcatctga ccctaaacca aacttcacag actgtaatga gcatacacaa  1680
gtgtgcatta atgggcaatg tgcaggttct atctgtgaga aatatggctt agaggagtgt  1740
acgtgtgcca gttctgatgg caaagatgat aaagaattat gccatgtatg ctgtatgaag  1800
aaaatggacc catcaacttg tgccagtaca gggtctgtgc agtggagtag gcacttcagt  1860
ggtcgaacca tcaccctgca acctggaagc ccttgcaacg attttagagg ttactgtgat  1920
gttttcatgc ggtgcagatt agtagatgct gatggtcctc tagctaggct taaaaaagca  1980
attttttagtc cagagctcta tgaaaacatt gctgaatgga ttgtggctca ttggtgggca  2040
gtattactta tgggaattgc tctgatcatg ctaatgggct gatttattaa gatatgcagt  2100
gttcatactc caagtagtaa tccaaagttg cctcctccta aaccacttcc aggcacttta  2160
aagaggagga gacctccaca gcccattcag caaccccagc gtcagcggcc ccgagagagt  2220
tatcaaatgg gacacatgag acgctaa                                      2247

SEQ ID NO: 2            moltype = AA  length = 748
FEATURE                 Location/Qualifiers
source                  1..748
                        mol_type = protein
                        organism = Homo sapiens
SEQUENCE: 2
MVLLRVLILL LSWAAGMGGQ YGNPLNKYIR HYEGLSYNVD SLHQKHQRAK RAVSHEDQFL    60
RLDFHAHGRH FNLRMKRDTS LFSDEFKVET SNKVLDYDTS HIYTGHIYGE EGSFSHGSVI   120
DGRFEGFIQT RGGTFYVEPA ERYIKDRTLP FHSVIYHEDD INYPHKYGPQ GGCADHSVFE   180
RMRKYQMTGV EEVTQIPQEE HAANGPELLR KKRTTSAEKN TCQLYIQTDH LFFKYYGTRE   240
AVIAQISSHV KAIDTIYQTT DFSGIRNISF MVKRIRINTT ADEKDPTNPF RFPNIGVEKF   300
LELNSEQNHD DYCLAYVFTD RDFDDGVLGL AWVGAPSGSS GGICEKSKLY SDGKKKSLNT   360
GIITVQNYGS HVPPKVSHIT FAHEVGHNFG SPHDSGTECT PGESKNLGQK ENGNYIMYAR   420
ATSGDKLNNN KFSLCSIRNI SQVLEKKRNN CFVESGQPIC GNGMVEQGEE CDCGYSDQCK   480
DECCFDANQP EGRKCKLKPG KQCSPSQGPC CTAQCAFKSK SEKCRDDSDC AREGICNGFT   540
ALCPASDPKP NFTDCNRHTQ VCINGQCAGS ICEKYGLEEC TCASSDGKDD KELCHVCCMK   600
KMDPSTCAST GSVQWSRHFS GRTITLQPGS PCNDFRGYCD VFMRCRLVDA DGPLARLKKA   660
IFSPELYENI AEWIVAHWWA VLLMGIALIM LMAGFIKICS VHTPSSNPKL PPPKPLPGTL   720
```

KRRRPPQPIQ QPQRQRPRES YQMGHMRR                                              748

SEQ ID NO: 3            moltype = DNA  length = 1752
FEATURE                 Location/Qualifiers
source                  1..1752
                        mol_type = other DNA
                        organism = Homo sapiens
CDS                     1..1752
SEQUENCE: 3
atggaatcca aggggccag ttcctgccgt ctgctcttct gcctcttgat ctccgccacc     60
gtcttcaggc caggccttgg atggtatact gtaaattcag catatggaga taccattatc    120
ataccttgcc gacttgacgt acctcagaat ctcatgtttg gcaatggaaa atatgaaaag    180
cccgatggcc ccccagtatt tattgccttc agatcctcta caaagaaaag tgtgcagtac    240
gacgatgtac cagaatacaa agacagattg aacctctcag aaaactacac tttgtctatc    300
agtaatgcaa ggatcagtga tgaaaagaga tttgtgtgca tgctagtaac tgaggacaac    360
gtgtttgagg cacctacaat agtcaaggtg ttcaagcaac catctaaacc tgaaattgta    420
agcaaagcac tgtttctcga aacagagcag ctaaaaaagt tgggtgactg catttcagaa    480
gacagttatc cagatggcaa tatcacatgg tacaggaatg gaaaagtgct acatcccctt    540
gaaggagcgg tggtcataat ttttaaaaag gaaatggacc cagtgactca gctctatacc    600
atgacttcca ccctggagta caagacaacc aaggctgaca tacaaatgcc attcacctgc    660
tcggtgacat attatggacc atctggccag aaaacaattc attctgaaca ggcagttttt    720
gatatttact atcctacaga gcaggtgaca atacaagtgc tgccaccaaa aaatgccatc    780
aaagaagggg ataacatcac tcttaaatgc ttagggaatg gcaaccctcc cccagaggaa    840
ttttttgttt acttaccagg acagcccgaa ggaataagaa gctcaaatac ttacacactg    900
acggatgtga ggcgcaatgc aacaggagac tacaagtgtt ccctgataga caaaaaagc     960
atgattgcct caacagctat cacagttcac tatttgattt tgtccttaaa cccaagtgga   1020
gaagtgacta gacagattgg tgatgcccta cccgtgtcat gcacaatatc tgctagcagg   1080
aatgcaactg tggtatggat gaaagataac atcaggcttc gatctagccc gtcatttttct  1140
agtcttcatt atcaggatgc tggaaactat gtctgcgaaa ctgctctgca ggaggttgaa   1200
ggactaaaga aaagagtc attgactctc atttgtagaag cgaaacctca aataaaaatg   1260
acaaagaaaa ctgatcccag tggactatct aaaacaataa tctgccatgt ggaaggtttt   1320
ccaaagccag ccattcaatg gacaattact ggcagtggaa gcgtcataaa ccaaacagag   1380
gaatctcctt atattaatgg caggtattat agtaaaatta tcatttcccc tgaagagaat   1440
gttacattaa cttgcacagc agaaaaccaa cttgagagaa cagtcaaactc cttgaatgtc   1500
tctgctataa gtattccaga acacgatgag gcagacgaa taagtgatga aaacagagaa    1560
aaggtgaatg accaggcaaa actaattgtg ggaatcgttg ttggtctcct ccttgctgcc   1620
cttgttgctg gtgtcgtcta ctggctgtac atgaagaagt caaagactgc atcaaaacat   1680
gtaaacaagg acctcggtaa tatggaagaa aacaaaagt tagaagaaaa caatcacaaa    1740
actgaagcct aa                                                       1752

SEQ ID NO: 4            moltype = AA  length = 583
FEATURE                 Location/Qualifiers
source                  1..583
                        mol_type = protein
                        organism = Homo sapiens
SEQUENCE: 4
MESKGASSCR LLFCLLISAT VFRPGLGWYT VNSAYGDTII IPCRLDVPQN LMFGKWKYEK     60
PDGSPVFIAF RSSTKKSVQY DDVPEYKDRL NLSENYTLSI SNARISDEKR FVCMLVTEDN    120
VFEAPTIVKV FKQPSKPEIV SKALFLETEQ LKKLGDCISE DSYPDGNITW YRNGKVLHPL    180
EGAVVIIFKK EMDPVTQLYT MTSTLEYKTT KADIQMPFTC SVTYYGPSGQ KTIHSEQAVF    240
DIYYPTEQVT IQVLPPKNAI KEGDNITLKC LGNGNPPPEE FLFYLPGQPE GIRSSNTYTL    300
TDVRRNATGD YKCSLIDKKS MIASTAITVH YLDLSLNPSG EVTRQIGDAL PVSCTISASR    360
NATVVWMKDN IRLRSSPSFS SLHYQDAGNY VCETALQEVE GLKKRESLTL IVEGKPQIKM    420
TKKTDPSGLS KTIICHVEGF PKPAIQWTIT GSGSVINQTE ESPYINGRYY SKIIISPEEN    480
VTLTCTAENQ LERTVNSLNV SAISIPEHDE ADEISDENRE KVNDQAKLIV GIVVGLLLAA    540
LVAGVVYWLY MKKSKTASKH VNKDLGNMEE NKKLEENNHK TEA                      583

SEQ ID NO: 5            moltype = DNA  length = 1713
FEATURE                 Location/Qualifiers
source                  1..1713
                        mol_type = other DNA
                        organism = Homo sapiens
CDS                     1..1713
SEQUENCE: 5
atggaatcca aggggccag ttcctgccgt ctgctcttct gcctcttgat ctccgccacc     60
gtcttcaggc caggccttgg atggtatact gtaaattcag catatggaga taccattatc    120
ataccttgcc gacttgacgt acctcagaat ctcatgtttg gcaatggaaa atatgaaaag    180
cccgatggct ccccagtatt tattgccttc agatcctcta caaagaaaag tgtgcagtac    240
gacgatgtac cagaatacaa agacagattg aacctctcag aaaactacac tttgtctatc    300
agtaatgcaa ggatcagtga tgaaaagaga tttgtgtgca tgctagtaac tgaggacaac    360
gtgtttgagg cacctacaat agtcaaggtg ttcaagcaac catctaaacc tgaaattgta    420
agcaaagcac tgtttctcga aacagagcag ctaaaaaagt tgggtgactg catttcagaa    480
gacagttatc cagatggcaa tatcacatgg tacaggaatg gaaaagtgct acatcccctt    540
gaaggagcgg tggtcataat ttttaaaaag gaaatggacc cagtgactca gctctatacc    600
atgacttcca ccctggagta caagacaacc aaggctgaca tacaaatgcc attcacctgc    660
tcggtgacat attatggacc atctggccag aaaacaattc attctgaaca ggcagttttt    720
gatatttact atcctacaga gcaggtgaca atacaagtgc tgccaccaaa aaatgccatc    780
aaagaagggg ataacatcac tcttaaatgc ttagggaatg gcaaccctcc cccagaggaa    840
ttttttgttt acttaccagg acagcccgaa ggaataagaa gctcaaatac ttacacactg    900

```
acggatgtga ggcgcaatgc aacaggagac tacaagtgtt ccctgataga caaaaaaagc    960
atgattgctt caacagctat cacagttcac tatttggatt tgtccttaaa cccaagtgga   1020
gaagtgacta gacagattgg tgatgcccta cccgtgtcat gcacaatatc tgctagcagg   1080
aatgcaactg tggtatggat gaaagataac atcaggcttc gatctagccc gtcatttttct  1140
agtcttcatt atcaggatgc tggaaactat gtctgcgaaa ctgctctgca ggaggttgaa   1200
ggactaaaga aaagagagtc attgactctc attgtagaag gcaaacctca aataaaaatg   1260
acaaagaaaa ctgatcccag tggactatct aaaacaataa tctgccatgt ggaaggtttt   1320
ccaaagccag ccattcaatg gacaattact ggcagtggaa gcgtcataaa ccaaacagag   1380
gaatctcctt atattaatgg caggtattat agtaaaatta tcatttcccc tgaagagaat   1440
gttacattaa cttgcacagc agaaaaccaa ctggagagaa cagtaaactc cttgaatgtc   1500
tctgctaatg aaaacagaga aaaggtgaat gaccaggcaa aactaattgt gggaatcgtt   1560
gttggtctcc tccttgctgc ccttgttgct ggtgtcgtct actggctgta catgaagaag   1620
tcaaagactg catcaaaaca tgtaaacaag gacctcggta atatggaaga aaacaaaaag   1680
ttagaagaaa acaatcacaa aactgaagcc taa                                1713

SEQ ID NO: 6              moltype = AA   length = 570
FEATURE                   Location/Qualifiers
source                    1..570
                          mol_type = protein
                          organism = Homo sapiens
SEQUENCE: 6
MESKGASSCR LLFCLLISAT VFRPGLGWYT VNSAYGDTII IPCRLDVPQN LMFGKWKYEK      60
PDGSPVFIAF RSSTKKSVQY DDVPEYKDRL NLSENYTLSI SNARISDEKR FVCMLVTEDN    120
VPEAPTIVKV FKQPSKPEIV SKALFLETEQ LKKLGDCISE DSYPDGNITW YRNGKVLHPL    180
EGAVVIIFKK EMDPVTQLYT MTSTLEYKTT KADIQMPFTC SVTYYGPSGQ KTIHSEQAVF    240
DIYYPTEQVT IQVLPPKNAI KEGDNITLKC LGNGNPPPEE FLFYLPGQPE GIRSSNTYTL    300
TDVRRNATGD YKCSLIDKKS MIASTAITVH YLDLSLNPSG EVTRQIGDAL PVSCTISASR    360
NATVVWMKDN IRLRSSPSFS SLHYQDAGNY VCETALQEVE GLKKRESLTL IVEGKPQIKM    420
TKKTDPSGLS KTIICHVEGF PKPAIQWTIT GSGSVINQTE ESPYINGRYY SKIIISPEEN    480
VTLTCTAENQ LERTVNSLNV SANENREKVN DQAKLIVGIV VGLLLAALVA GVVYWLYMKK    540
SKTASKHVNK DLGNMEENKK LEENNHKTEA                                     570

SEQ ID NO: 7              moltype = DNA   length = 2916
FEATURE                   Location/Qualifiers
source                    1..2916
                          mol_type = other DNA
                          organism = Homo sapiens
CDS                       1..2916
SEQUENCE: 7
atgctgcgcc gccccgctcc cgcgctggcc ccggccgccc ggctgctgct ggccgggctg     60
ctgtgcggcg gcggggtctg ggccgcgcga gttaacaagc acaagccctg gctggagccc    120
acctaccacg gcatagtcac agagaacgac aacaccgtgc cctcgacccc ccactgatc     180
gcgctggata aagatgcgcc tctcgcgatt gcaggtgagc tttgttggatt taaaattcac    240
gggcagaatg tcccctttga tgcagtggta gtggataaat ccactggtga gggagtcatt    300
cgctccaaag agaaactgga ctgtgagctg cagaaagact attcattcac catccaggcc    360
tatgattgtg ggaaggggacc tgatggcacc aacgtgaaaa agtctcataa agcaactgtt    420
catattcagg tgaacgacgt gaatgagtac gcgcccgtgt tcaaggagaa gtcctacaaa    480
gccacggtca tcgagggaa gcagtacgac agcattttga gggtggaggc cgtggatgcc     540
gactgctccc tcagttcag ccagatttgc agctacgaaa tcatcactcc agacgtgccc     600
tttactgttg acaaagatgg ttatataaaa aacacagaga aattaaacta cgggaaagaa    660
catcaatata agctgaccgt cactgcctat gactgtggga agaaaaagac cacagaagat    720
gttttggtga agatcagcat taagcccacc tgcaccctg gtggcaagg atggaacaac      780
aggattgagt atgagccggg cacggcgcg ttgccgtct ttccaaatat ccacctggag     840
acatgtgacg agccagtcgc ctcagtacga gccacagtgg agctagaaac cagccacata    900
gggaaaggct gcgaccgaga caactactca gagaagtccc tccaccggct ctgtggtgcg   960
gccgcgggca ctgccgagct gctgccatcc ccgagtggat ccctcaactg gaccatggc    1020
ctgcccaccg acaatggcca cgacagcgac caggtgtttg agttcaacgg cacccaggca   1080
gtgaggatcc cggatggcgt cgtgtcggtc agccccaaag agccgttcac catctcggtc   1140
tggatgagac atgggccatt cggcaggaag aaggagacaa ttctttgcag ttctgataaa    1200
acagatatga atcggcacca ctactccctc tatgtccacg gtgccggct gatcttcctc    1260
ttccgtcagg atccttctga ggagaagaaa tacagacctg cagagttcca ctggaagttg   1320
aatcaggtct gtgatgagga atggcaccac tacgtcctca atgtagaatt cccgagtgtg   1380
actctctatg tggatggcac gtcccacgag cccttctctg tgactgagga ttacccgctc    1440
catccatcca agatagaaac tcagtcgtg gtggggggcta tccaacaaga gttttcagga    1500
gttgaaaatg acaatgaaac tgagcctgtg actggcct ctgcaggtgg cgacctgcac      1560
atgacccagt ttttccgagg caatctggct ggcttaactc tccgttccgg gaactcgcg    1620
gataagaagg tgatcgactg tctgtatacc tgcaaggagg ggctggacct gcaggtcctc    1680
gaagacagtg gcagaggcgt gcagatccaa gcacaccccca gccagtttgg attgacctg    1740
gagggagaag acctcgggga attggataag gccatgcagc acatctgta cctgaactcc    1800
cggcagttcc ccacgcccgg aattcgcaga ctcaaaatca ccagcacaat caagtgtttt    1860
aacgaggcca cctgcatttc ggtccccccg gtagatggct acgtgatggt tttacagccc   1920
gaggagccca agatcagcct gagtggcgtc accattttg cccagcagc ttctgaattt      1980
gaaagctcag aaggggtgtt cctttttcct gagcttcgca tcatcagcac catcacgaga   2040
gaagtgcaag ctgaagggga cggggcctgag gaccccacag ttcaagaatc actggtgtcc   2100
gaggagatcc tgcacgacct ggatacctgt gaggtcacgg tggagggaga ggagctgaac    2160
cacgagcagg agagcctgga ggtggacatg cccgcctgc agcagaaggg cattgaagtg    2220
agcagctctg aactgggcat gaccttcaca ggcgtggaca ccatgccag ctacgaggag    2280
gtttgcacc tgctgcgcta tcggaactgg catgccaggt ccttgcttga ccggaagttt    2340
aagctcatct gctcagagct gaatggccgc tacatcagca cgaatttaa ggtggaggtg    2400
```

```
aatgtaatcc acacggccaa ccccatggaa cacgccaacc acatggctgc ccagccacag 2460
ttcgtgcacc cggaacaccg ctcctttgtt gacctgtcag gccacaacct ggccaacccc 2520
cacccgttcg cagtcgtccc cagcactgcg acagttgtga tcgtggtgtg cgtcagcttc 2580
ctggtgttca tgattatcct gggggtattt cggatccggg ccgcacatcg gcggaccatg 2640
cgggatcagg acaccgggaa ggagaacgag atggactgga acgactctgc cctgaccatc 2700
accgtcaacc ccatggagac ctatgaggac cagcacagca gtgaggagga ggaggaagag 2760
gaagaggaag aggaaagcga ggacggcgaa gaagaggatg acatcaccag cgccgagtcg 2820
gagagcagcg aggaggagga gggggagcag ggcgaccccc agaacgcaac ccggcagcag 2880
cagctggagt gggatgactc caccctcagc tactga                           2916

SEQ ID NO: 8              moltype = AA  length = 971
FEATURE                   Location/Qualifiers
source                    1..971
                          mol_type = protein
                          organism = Homo sapiens
SEQUENCE: 8
MLRRPAPALA PAARLLLAGL LCGGGVWAAR VNKHKPWLEP TYHGIVTEND NTVLLDPPLI   60
ALDKDAPLRF AGEICGFKIH GQNVPFDAVV VDKSTGEGVI RSKEKLDCEL QKDYSFTIQA  120
YDCGKGPDGT NVKKSHKATV HIQVNDVNEY APVFKEKSYK ATVIEGKQYD SILRVEAVDA  180
DCSPQFSQIC SYEIITPDVP FTVDKDGYIK NTEKLNYGKE HQYKLTVTAY DCGKKRATED  240
VLVKISIKPT CTPGWQGWNN RIEYEPGTGA LAVFPNIHLE TCDEPVASVQ ATVELETSHI  300
GKGCDRDTYS EKSLHRLCGA AAGTAELLPS PSGSLNWTMG LPTDNGHDSD QVFEFNGTQA  360
VRIPDGVVSV SPKEPFTISV WMRHGPFGRK KETILCSSDK TDMNRHHYSL YVHGCRLIFL  420
FRQDPSEEKK YRPAEFHWKL NQVCDEEWHH YVLNVEFPSV TLYVDGTSHE PFSVTEDYPL  480
HPSKIETQLV VGACWQEFSG VENDNETEPV TVASAGGDLH MTQFFRGNLA GLTLRSGKLA  540
DKKVIDCLYT CKEGLDLQVL EDSGRGVQIQ AHPSQLVLTL EGEDLGELDK AMQHISYLNS  600
RQFPTPGIRR LKITSTIKCF NEATCISVPP VDGYVMVLQP EEPKISLSGV HHFARAASEF  660
ESSEGVFLFP ELRIISTITR EVEPEGDGAE DPTVQESLVS EEIVHDLDTC EVTVEGEELN  720
HEQESLEVDM ARLQQKGIEV SSSELGMTFT GVDTMASYEE VLHLLRYRNW HARSLLDRKF  780
KLICSELNGR YISNEFKVEV NVIHTANPME HANHMAAQPQ FVHPEHRSFV DLSGHNLANP  840
HPFAVVPSTA TVVIVVCVSF LVFMIILGVF RIRAAHRRTM RDQDTGKENE MDWDDSALTI  900
TVNPMETYED QHSSEEEEEE EEEEESEDGE EEDDITSAES ESSEEEEGEQ GDPQNATRQQ  960
QLEWDDSTLS Y                                                      971

SEQ ID NO: 9              moltype = DNA  length = 2946
FEATURE                   Location/Qualifiers
source                    1..2946
                          mol_type = other DNA
                          organism = Homo sapiens
CDS                       1..2946
SEQUENCE: 9
atgctgcgcc gccccgctcc cgcgctggcc ccggccgccc ggctgctgct ggccgggctg   60
ctgtgcgggg gcggggtctg ggccgcgcga gttaacaagc acaagccctg gctggagccc  120
acctaccacg gcatagtcac agagaacgac aacaccgtgc tcctcgaccc cccactgatc  180
gcgctggata aagatgcgcc tctgcgattt gcagagagtt ttgaggtgac agtcaccaaa  240
gaaggtgaga tttgtggatt taaaattcac gggcagaatg tcccctttga tgcagtggta  300
gtggataaat ccactggtga gggagtcatt cgctccaaag aaactgaact ctgtgagctg  360
cagaaagact attcattcac catccaggcc tatgattgtg ggaagggacc tgatggcacc  420
aacgtgaaaa agtctcataa agcaactgtt catattcagg tgaacgacgt gaatgagtac  480
gcgccccgtgt tcaaggagaa gtcctacaaa gccacggtca tcgagggaaa gcagtacgac  540
agcatttttga gggtggaggc cgtggatgcc gactgctccc ctcagttcag ccagatttgc  600
agctacgaaa tcatcactcc agacgtgccc tttactgttg acaaagatgg ttatataaaa  660
aacacagaga aattaaacta cgggaaagaa catcaatata gctgaccgt cactgcctat  720
gactgtggga agaaaagagc cacagaagat gttttggtga agatcagcat taagcccacc  780
tgcaccctg ggtggcaagg atggaacaac aggattgagt atgagccggg caccggcgg  840
ttggccgtct ttccaaatat ccacctggag acatgtgacg agccagtcgc ctcagtacag  900
gccacagtgg agctagaaac cagccacata gggaaggct gcgaccgaga cacctactca  960
gagaagtccc tccaccggct ctgtggtgcg ccgcgggca ctgccgagct gctgccatcc 1020
ccgagtggat ccctcaactg gaccatgggc ctgcccaccg acaatggcca cgacagcgac 1080
caggtgtttg agttcaacgg cacccaggca gtgaggatcc cggatggcgt cgtgtcggtc 1140
agccccaaag agccgttcac catctcggtg tggatgagac atgggccatt cggcaggaag 1200
aaggagacaa ttctttgcag ttctgataaa acagatatga tcggcacca ctactccctc 1260
tatgtccacg gtgccggct gatcttcctc ttccgtcagg atccttctga ggagaagaaa 1320
tacagacctg cagagttcca ctggaagttg aatcaggtct ggacgaggga atggcaccac 1380
tacgtcctca atgtagaatt cccgagtgtg actctctatg tggatggcac gtcccacgag 1440
cccttctctg tgactgagga ttaccccgctc catccatcca agataagaaac tcagctcgtg 1500
gtgggggctt gctggcaaga gttttcagga gttgaaaatg acaatgaaac tgagcctgtg 1560
actgtggcct ctgcaggtgg cgacctgcac atgacccagt ttttccgagg caatctggct 1620
ggcttaactc tccgttccgg gaaactcgcg gataagagg tgatcgactg tctgtatacc 1680
tgcaaggagg gctgacct gcaggtcctc gaagacagtg gcagaggcgt gcagatccaa 1740
gcacacccca gccagttggt attgaccttg gaggagaag acctcgggga attggataag 1800
gccatgcagc acatctcgta cctgaactcc ggcagttcc ccacgccgg aattcgcaga 1860
ctcaaaatca ccagcacaat caagtgttt aacgaggcca cctgcatttc ggtccccgcg 1920
gtagatggct acgtagtggt tttacagccc gaggagccca agatcagcct gagtggcgtc 1980
caccattttg cccgagcagc ttctgaattt gaaagctcag aagggggtgtt ccttttccct 2040
gagcttcgca tcatcagcac catcacgaga gaagtggagc ctgaaggga cggggctgag 2100
gaccccacag ttcaagaatc actggtgtcc gaggagatcg tgcacgacct ggatacctgt 2160
gaggtcacgg tggagggaga ggagctgaac cacgagcagg agagcctgga ggtggacatg 2220
gcccgcctgc agcagaaggg cattgaagtg agcagcctg aactgggcat gaccttcaca 2280
```

-continued

```
ggcgtggaca ccatggccag ctacgaggag gttttgcacc tgctgcgcta tcggaactgg    2340
catgccaggt ccttgcttga ccggaagttt aagctcatct gctcagagct gaatggccgc    2400
tacatcagca acgaatttaa ggtggaggtg aatgtaatcc acacggccaa ccccatggaa    2460
cacgccaacc acatggctgc ccagccacag ttcgtgcacc cggaacaccg ctcctttgtt    2520
gacctgtcag gccacaacct ggccaacccc cacccgttcg cagtcgtccc cagcactgcg    2580
acagttgtga tcgtggtgtg cgtcagcttc ctggtgttca tgattatcct gggggtatttt   2640
cggatccggg ccgcacatcg gcggaccatg cgggatcagg acaccgggaa ggagaacgag    2700
atggactggg acgactctgc cctgaccatc accgtcaacc catggagac ctatgaggac     2760
cagcacagca gtgaggagga ggaggaagag gaagaggaag aggaaagcga ggacggcgaa    2820
gaagaggatg acatcaccag cgccgagtcg gagagcagcg aggaggagga ggggagcag    2880
ggcgacccc agaacgcaac ccggcagcag cagctggagt gggatgactc caccctcagc    2940
tactga                                                              2946

SEQ ID NO: 10           moltype = AA  length = 981
FEATURE                 Location/Qualifiers
source                  1..981
                        mol_type = protein
                        organism = Homo sapiens
SEQUENCE: 10
MLRRPAPALA PAARLLLAGL LCGGGVWAAR VNKHKPWLEP TYHGIVTEND NTVLLDPPLI     60
ALDKDAPLRF AESFEVTVTK EGEICGFKIH GQNVPFDAVV VDKSTGEGVI RSKEKLDCEL    120
QKDYSFTIQA YDCGKGPDGT NVKKSHKATV HIQVNDVNEY APVFKEKSYK ATVIEGKQYD    180
SILRVEAVDA DCSPQFSQIC SYEIITPDVP FTVDKDGYIK NTEKLNYGKE HQYKLTVTAY    240
DCGKKRATED VLVKISIKPT CTPGWQGWNN RIEYEPGTGA LAVFPNIHLE TCDEPVASVQ    300
ATVELETSHI GKGCDRDTYS EKSLHRLCGA AAGTAELLPS PSGSLNWTMG LPTDNGHDSD    360
QVFEFNGTQA VRIPDGVVSV SPKEPFTISV WMRHGPFGRK KETILCSSDK TDMNRHHYSL    420
YVHGCRLIFL FRQDPSEEKK YRPAEFHWKL NQVCDEEWHH YVLNVEFPSV TLYVDGTSHE    480
PPFSVTEDYPL HPSKIETQLV VGACWQEFSG VENDNETEPV TVASAGGDLH MTQFFRGNLA   540
GLTLRSGKLA DKKVIDCLYT CKEGLDLQVL EDSGRGVQIQ AHPSQLVLTL EGEDLGELDK    600
AMQHISYLNS RQFPTPGIRR LKITSTIKCF NEATCISVPP VDGYVMVLQP EEPKISLSGV    660
HHFARAASEF ESSEGVFLFP ELRIISTITR EVEPEGDGAE DPTVQESLVS EEIVHDLDTC    720
EVTVEGEELN HEQESLEVDM ARLQQKGIEV SSSELGMTFT GVDTMASYEE VLHLLRYRNW    780
HARSLLDRKF KLICSELNGR YISNEFKVEV NVIHTANPME HANHMAAQPQ FVHPEHRSFV    840
DLSGHNLANP HPFAVVPSTA TVVIVVCVSF LVFMIILGVF RIRAAHRRTM RDQDTGKENE    900
MDWDDSALTI TVNPMETYED QHSSEEEEEE EEEEESEDGE EEDDITSAES ESSEEEEGEQ    960
GDPQNATRQQ QLEWDDSTLS Y                                             981

SEQ ID NO: 11           moltype = DNA  length = 1842
FEATURE                 Location/Qualifiers
source                  1..1842
                        mol_type = other DNA
                        organism = Homo sapiens
CDS                     1..1842
SEQUENCE: 11
atgggcgccc tcaggcccac gctgctgccg ccttcgctgc cgctgctgct gctgctaatg     60
ctaggaatgg gatgctgggc ccgggaggtg ctggtcccg aggggccctt gtaccgcgtg    120
gctggcacag ctgtctccat ctcctgcaat gtgaccggct atgagggccc tgcccagcag    180
aacttcgagt ggttcctgta taggcccgag gccccagata ctgcactggg cattgtcagt    240
accaaggata cccagttctc ctatgctgtc ttcaagtccc gagtggtggc gggtgaggtg    300
caggtgcagc gcctacaagg tgatgccgtg gtgctcaaga ttgcccgcct gcaggcccag    360
gatgccaagg tttatgagtg ccacaccccc tccactgata cccgctaccg ggcagctac     420
agcggcaagg tggagctgag agttcttcca gatgtcctcc aggtgtctgc tgcccccca     480
gggccccgag gcgccaggc cccaacctca ccccacgca tgacggtgca tgaggggcag     540
gagctggcac tgggctgcct ggcgaggaca agcacacaga gcacacaca cctggcagtg    600
tcctttgggc gatctgtgcc cgaggcacca gttgggcggt caactctgca ggaagtggtg    660
ggaatccggt cagacttggc cgtgtgaggct ggagctccct atgctgagcg attggctgca  720
ggggagcttc gtctgggcaa ggaagggacc gatcggtacc gcatggtagt aggggggtgcc 780
caggcagggg acgcaggcac ctaccactgc actgccgctg agtggattca ggatcctgat    840
ggcagctggg cccagattgc agagaaaagg gccgtcctgg cccacgtgga tgtgcagacg    900
ctgtccagcc agctggcagt gacagtgggg cctggtgaac gtcggatcgg cccagggag    960
cccttggaac tgctgtgcaa tgtgtcaggg gcacttcccc cagcaggccg tcatgctgca   1020
tactctgtag gttgggagat ggcacctgcg ggggcacctg gcccggccg cctggtagcc   1080
cagctggaca cagaggggtgt gggcagcctg ggccctggct atgagggccg acacattgcc   1140
atggagaagg tggcatccag aacataccgg ctacgggtca ggtgccag gcctggtgta    1200
gcgggcacct accgctgcct cgccaaagcc tatgttcgag ggtctgggac ccggcttcgt   1260
gaagcagcca gtcccgttc ccggcctctc cctgtacatg tgcgggagga aggtgtggtg    1320
ctggaggctg tggcatggct agcaggaggc acagtgtacc gcggggagac tgcctccctg   1380
ctgtgcaaca tctctgtgcg gggtggcccc ccaggactgc ggctggccgc cagctggtgg   1440
gtgagcgac cagaggacgg agagctcagc tctgtccctg cccagctggt ggggcgta     1500
ggccaggatg gtgtggcaga gctgggagtc cggcctggag gaggcccgt cagcgtagag    1560
ctggtggggc cccgaagcca tcggctgaga ctacacagct tggggcccga ggatgaaggc   1620
gtgtaccact gtccccccag cgcctgggtg cagcatgccg actacagctg gtaccaggcg   1680
ggcagtgccc gctcagggcc tgttacagtc tacccctaca tgcatgccct ggacacccta   1740
tttgtgcctc tgctggtgg tacaggggtg gcccagtca ctggtgccac tgtccttggt    1800
accatcactt gctgcttcat gaagaggctt cgaaaacggt ga                     1842

SEQ ID NO: 12           moltype = AA  length = 613
FEATURE                 Location/Qualifiers
source                  1..613
```

```
                    mol_type = protein
                    organism = Homo sapiens
SEQUENCE: 12
MGALRPTLLP PSLPLLLLLM LGMGCWAREV LVPEGPLYRV AGTAVSISCN VTGYEGPAQQ     60
NFEWFLYRPE APDTALGIVS TKDTQFSYAV FKSRVVAGEV QVQRLQGDAV VLKIARLQAQ    120
DAGIYECHTP STDTRYLGSY SGKVELRVLP DVLQVSAAPP GPRGRQAPTS PPRMTVHEGQ    180
ELALGCLART STQKHTHLAV SFGRSVPEAP VGRSTLQEVV GIRSDLAVEA GAPYAERLAA    240
GELRLGKEGT DRYRMVVGGA QAGDAGTYHC TAAEWIQDPD GSWAQIAEKR AVLAHVDVQT    300
LSSQLAVTVG PGERRIGPGE PLELLCNVSG ALPPAGRHAA YSVGWEMAPA GAPGPGRLVA    360
QLDTEGVGSL GPGYEGRHIA MEKVASRTYR LRLEAARPGD AGTYRCLAKA YVRGSGTRLR    420
EAASARSRPL PVHVREEGVV LEAVAWLAGG TVYRGETASL LCNISVRGGP PGLRLAASWW    480
VERPEDGELS SVPAQLVGGV GQDGVAELGV RPGGGPVSVE LVGPRSHRLR LHSLGPEDEG    540
VYHCAPSAWV QHADYSWYQA GSARSGPVTV YPYMHALDTL FVPLLVGTGV ALVTGATVLG    600
TITCCFMKRL RKR                                                      613

SEQ ID NO: 13         moltype = DNA   length = 1137
FEATURE               Location/Qualifiers
source                1..1137
                      mol_type = other DNA
                      organism = Homo sapiens
CDS                   1..1137
SEQUENCE: 13
atggtcctcc tttggctcac gctgctcctg atcgccctgc cctgtctcct gcaaacgaag      60
gaagatccaa acccaccaat cacgaaccta aggatgaaag caaaggctca gcagttgacc     120
tgggaccttaa acagaaatgt gaccgatatc gagtgtgtta agacgccga ctattctatg     180
ccggcagtga acaatagcta ttgccagttt ggagcaattt cctatgtga agtgaccaac     240
tacaccgtcc gagtggccaa cccaccattc tccacgtggat tcctcttccc tgagaacagt     300
gggaagcctt gggcaggtgc ggagaatctg acctgctgga ttcatgacgt ggatttcttg     360
agctgcagct gggcggtagg cccggggggcc ccgcgacg tccagtacga cctgtacttg      420
aacgttgcca acaggcgtca acagtacgag tgtcttcact acaaaacgga tgctcaggga     480
acacgtatcg ggtgtcgttt cgatgacatc tctcgactct ccagcggttc tcaaagttcc     540
cacatcctgg tgcggggcag gagcgcagcc ttcggtatcc cctgcacaga taagtttgtc     600
gtcttttcac agattgagat attaactcca cccaacatga ctgcaaagtg taataagaca     660
cattccttta tgcactggaa aatgagaagt catttcaatc gcaaatttcg ctatgagctt     720
cagatacaaa agagaatgca gcctgtaatc acagaacagg tcagagacag aacctccttc     780
cagctactca atcctggaac gtacacagta caaataagag cccgggaaag agtgtatgaa     840
ttcttgagcg cctggagcac cccccagcgc ttcgagtgcg accaggagga gggcgcaaac     900
acacgtgcct ggcggacgtc gctgctgatc gcgctgggga cgctgctggc cctggtctgt     960
gtcttcgtga tctcagaagg tatctggtg atgcagagac tctttccccg catccctcac    1020
atgaaagacc ccatcggtga cagcttccaa aacgacaagc tggtggtctg ggaggcgggc    1080
aaagccggcc tggaggagtg tctggtgact gaagtacagg tcgtgcagaa aacttga       1137

SEQ ID NO: 14         moltype = AA   length = 378
FEATURE               Location/Qualifiers
source                1..378
                      mol_type = protein
                      organism = Homo sapiens
SEQUENCE: 14
MVLLWLTLLL IALPCLLQTK EDPNPPITNL RMKAKAQQLT WDLNRNVTDI ECVKDADYSM     60
PAVNNSYCQF GAISLCEVTN YTVRVANPPF STWILFPENS GKPWAGAENL TCWIHDVDFL    120
SCSWAVGPGA PADVQYDLYL NVANRRQQYE CLHYKTDAQG TRIGCRFDDI SRLSSGSQSS    180
HILVRGRSAA FGIPCTDKFV VFSQIEILTP PNMTAKCNKT HSFMHWKMRS HFNRKFRYEL    240
QIQKRMQPVI TEQVRDRTSF QLLNPGTYTV QIARERVYE FLSAWSTPQR FECDQEEGAN     300
TRAWRTSLLI ALGTLLALVC VFVICRRYLV MQRLFPRIPH MKDPIGDSFQ NDKLVVWEAG    360
KAGLEECLVT EVQVVQKT                                                  378

SEQ ID NO: 15         moltype = DNA   length = 903
FEATURE               Location/Qualifiers
source                1..903
                      mol_type = other DNA
                      organism = Homo sapiens
CDS                   1..903
SEQUENCE: 15
atggtcctcc tttggctcac gctgctcctg atcgccctgc cctgtctcct gcaaacgaag      60
gaaggtggga agccttgggc aggtgcgag aatctgacct gctggattca tgacgtggat     120
ttcttgagct gcagctgggc ggtaggcccg gggcccccg cggacgtcca gtacgacctg     180
tacttgaact tgccaacag gcgtcaacag tacgagtgtc ttcactacaa aacgatgct      240
cagggaacac gtatcgggtg tcgtttcgat gacatctctc gactctccag cggttctcaa     300
agttcccaca tcctggtgcg gggcaggagc gcagccttcg gtatccctg cacagataag     360
tttgtcgtct tttcacagat tgagatatta actccaccca acatgactgc aaagtgtaat     420
aagacacatt cctttatgca ctggaaaatg agaagtcatt tcaatcgcaa atttcgctat     480
gagcttcaga tacaaaagag aatgcagcct gtaatcacag aacaggtcag agacagaacc     540
tccttccagc tactcaatcc tggaacgtac acagtacaaa taagagcccg ggaaagagtg     600
tatgaattct tgagcgcctg gagcaccccc cagcgcttcg agtgcgacca ggaggagggc     660
gcaaacacac gtgcctggcg gacgtcgctg ctgatcgcgc tggggacgct gctggccctg     720
gtctgtgtct tcgtgatctg cagaaggtat ctggtgatgc agagactctt ccccgcatc     780
cctcacatga agacccccat cggtgacagc ttccaaaacg acaagctggt ggtctgggag     840
gcgggcaaac ccggcctgga ggagtgtctg gtgactgaag tacaggtcgt gcagaaaact     900
tga                                                                   903
```

```
SEQ ID NO: 16            moltype = AA  length = 300
FEATURE                  Location/Qualifiers
source                   1..300
                         mol_type = protein
                         organism = Homo sapiens
SEQUENCE: 16
MVLLWLTLLL IALPCLLQTK EGGKPWAGAE NLTCWIHDVD FLSCSWAVGP GAPADVQYDL   60
YLNVANRRQQ YECLHYKTDA QGTRIGCRFD DISRLSSGSQ SSHILVRGRS AAFGIPCTDK  120
FVVFSQIEIL TPPNMTAKCN KTHSFMHWKM RSHFNRKFRY ELQIQKRMQP VITEQVRDRT  180
SFQLLNPGTY TVQIRARERV YEFLSAWSTP QRFECDQEEG ANTRAWRTSL LIALGTLLAL  240
VCVFVICRRY LVMQRLFPRI PHMKDPIGDS FQNDKLVVWE AGKAGLEECL VTEVQVVQKT  300

SEQ ID NO: 17            moltype = DNA  length = 3201
FEATURE                  Location/Qualifiers
source                   1..3201
                         mol_type = other DNA
                         organism = Homo sapiens
CDS                      1..3201
SEQUENCE: 17
atgggcccg gccccagccg cgcgccccgc gccccacgcc tgatgctctg tgcgctcgcc     60
ttgatggtgg cggccggcgg ctgcgtcgtc tccgccttca acctggatac ccgattcctg   120
gtagtgaagg aggccgggaa cccgggcagc ctcttcggct actcggtcgc cctccatcgg   180
cagacagagc ggcagcagcg ctacctgctc ctggctggtg ccccccggga gctcgctgtg   240
cccgatggct acaccaaccg gactggtgct gtgtacctgt gccactcac tgcccacaag   300
gatgactgtg agcggatgaa catcacagtg aaaaatgacc ctggccatca cattattgag   360
gacatgtggc ttggagtgac tgtgccagc cagggccctg caggcagagt tctggtctgt   420
gcccaccgct acacccaggt gctgtggtca gggtcagaag accagcggcg catggtgggc   480
aagtgctacg tgcgaggcaa tgacctagag ctggactcca gtgatgactg gcagacctac   540
cacaacgaga tgtgcaatag caacacagac tacctgagca cgggcatgtg ccagctggcg   600
accagcggtg gcttcacccca gaacactgtg tacttcggcg cccccggtgc ctacaactgg   660
aaaggaaaca gctacatgat tcagcgcaag gagtgggact tatctgagta tagttacaag   720
gacccagagg accaaggaaa cctctatatt gggtacacga tgcaggtagg cagcttcatc   780
ctgcacccca aaaacatcac cattgtgaca ggtgccccac ggcaccgaca tatgggcgcg   840
gtgttcttgc tgagccagga ggcaggcgga gacctgccga ggaggcaggt gctggaggc   900
tcgcaggtgg cgccctattt tggcagcgcc attgccctgg cagacctgaa caatgatggg   960
tggcaggacc tcctggtggg cgcccccttac tacttcgaga ggaaagagga gtaggggt  1020
gccatctatg tcttcatgaa ccaggcggga acctccttcc ctgctcaccc ctcactcctt  1080
cttcatggcc ccagtggctc tgcctttggt ttatctgtgc ccagcattgg tgacatcaac  1140
caggatggat ttcaggatat tgctgtggga gctccgtttg aaggcttggg caaagtgtac  1200
atctatcaca gtagctctaa ggggctcctt agacagcccc agcaggtaat ccatggagag  1260
aagctgggac tgcctgggtt ggccaccttc ggctattccc tcagtgggca gatggatgtg  1320
gatgagaact tctacccaga cctttcagtg ggaagcctgt cagaccacat tgtgctgctg  1380
cgggcccggc ccgtcatcaa catcgtccac aagaccttgg tgcccaggcc agctgtgctg  1440
gacccctgcac tttgcacggc cacctcttgt gtgcaagtgg agctgtgctt tgcttacaac  1500
cagagtgccg gaaccccaa ctacaggcga acatcaccc tggcctacac tctggaggct  1560
gacagggaca gccggccgcc ccggctccgc tttgccggca gtgagtccgc tgtcttccac  1620
ggcttcttct ccatgcccga gatgcgctgc cagaagctgg agctgctcct gatgggacaac  1680
ctccgtgaca aactccgccc catcatcatc tccatgaact actctttacc tttgcggatg  1740
cccgatcgcc ccggctgggg gctgcggtcc ctggacgcct acccgatcct caaccaggca  1800
caggctctgg agaaccacac tgaggtccaa ttccagaagg agtgcgggcc tgacaacaag  1860
tgtgagagca acttgcagat gcgggcagcc ttcgtgtcag agcagcagca gaagctgagc  1920
aggctccagt acagcagaga cgtccggaaa ttgctcctga gcatcaacgt gacgaacacc  1980
cggacctcgg agcgctccgg ggaggacgcc cacgaggcgc tgctcaccct ggtggtgcct  2040
cccgccctgc tgctgtcctc agtgcgcccc cccggggcct gccaagctaa tgagaccatc  2100
ttttgcgagc tggggaaccc cttcaaacgg aaccagagga tggagctgct catcgccttt  2160
gaggtcatcg gggtgaccct gcacacaagg gaccttcagg tgcagctgca gctctccacg  2220
tcgagtcacc aggacaacct gtgggccatg atcctcactc tgctggtgga ctatacactc  2280
cagaccctcgc ttagcatggt aaatcaccgg ctacaaagct tctttggggg gacagtgatg  2340
ggtgagtctg gcatgaaaac tgtggaggat gtaggaagcc ccctcaagta tgaattccag  2400
gtgggcccaa tgggggaggg gctggtgggc ctggggaccc tggtcctagg tctgagtgg  2460
ccctacgaag tcagcaatgg caagtggctg ctgtatccca cggagatcac cgtccatggc  2520
aatgggtcct ggccctgccg accacctgga gaccttatca accctctcaa cctcactctt  2580
tctgaccctg gggacaggcc atcatcccca cagcgcaggc ggcgacagct ggatccaggg  2640
ggaggccagg gcccccacc tgtcactctg gctgctgcca aaaagcaa gtctgagact  2700
gtgctgacct gtgccacagg gcgtgcccac tgtgtgtggc tagagtgccc catccctgat  2760
gccccccgttc tcaccaacgt gactgtgaag gcacgagtgt ggaacagcac cttcatcgag  2820
gattacagag actttgaccg agtccgggta aatggctggg ctaccctatt cctccgaacc  2880
agcatcccca ccatcaacat ggagaacaag accacgtggt tctctgtgga cattgactgc  2940
gagctggtgg aggagctgcc ggccgaaatc gagctgtggc tggtgctggt ggccgtgggt  3000
gcagggctgc tgctgctgg gctgatcatc ctcctgctgt ggaagtgtga cttctttaag  3060
cggaccgct attatcagat catgcccaag taccacgcag tgggatccg ggaggaggag  3120
cgctaccac ctccagggag caccctgccc accaagaagc actgggtgac cagctggcag  3180
actcgggacc aatactactg a                                           3201

SEQ ID NO: 18            moltype = AA  length = 1066
FEATURE                  Location/Qualifiers
source                   1..1066
                         mol_type = protein
```

```
                    organism = Homo sapiens
SEQUENCE: 18
MGPGPSRAPR APRLMLCALA LMVAAGGCVV SAFNLDTRFL VVKEAGNPGS LFGYSVALHR   60
QTERQQRYLL LAGAPRELAV PDGYTNRTGA VYLCPLTAHK DDCERMNITV KNDPGHHIIE  120
DMWLGVTVAS QGPAGRVLVC AHRYTQVLWS GSEDQRRMVG KCYVRGNDLE LDSSDDWQTY  180
HNEMCNSNTD YLETGMCQLG TSGGFTQNTV YFGAPGAYNW KGNSYMIQRK EWDLSEYSYK  240
DPEDQGNLYI GYTMQVGSFI LHPKNITIVT GAPRHRHMGA VFLLSQEAGG DLRRRQVLEG  300
SQVGAYFGSA IALADLNNDG WQDLLVGAPY YFERKEEVGG AIYVFMNQAG TSFPAHPSLL  360
LHGPSGSAFG LSVASIGDIN QDGFQDIAVG APFEGLGKVY IYHSSSKGLL RQPQQVIHGE  420
KLGLPGLATF GYSLSGQMDV DENFYPDLLV GSLSDHIVLL RARPVINIVH KTLVPRPAVL  480
DPALCTATSC VQVELCFAYN QSAGNPNYRR NITLAYTLEA DRDRRPPRLR FAGSESAVFH  540
GFFSMPEMRC QKLELLLMDN LRDKLRPIII SMNYSLPLRM PDRPRLGLRS LDAYPILNQA  600
QALENHTEVQ FQKECGPDNK CESNLQMRAA FVSEQQQKLS RLQYSRDVRK LLLSINVTNT  660
RTSERSGEDA HEALLTLVVP PALLLSSVRP PGACQANETI FCELGNPFKR NQRMELLIAF  720
EVIGVTLHTR DLQVQLQLST SSHQDNLWPM ILTLLVDYTL QTSLSMVNHR LQSFFGGTVM  780
GESGMKTVED VGSPLKYEFQ VGPMGEGLVG LGTLVLGLEW PYEVSNGKWL LYPTEITVHG  840
NGSWPCRPPG DLINPLNLTL SDPGDRPSSP QRRRRQLDPG GGQGPPPVTL AAAKKAKSET  900
VLTCATGRAH CVWLECPIPD APVVTNVTVK ARVWNSTFIE DYRDFDRVRV NGWATLFLRT  960
SIPTINMENK TTWFSVDIDS ELVEELPAEI ELWLVLVAVG AGLLLLGLII LLLWKCDFFK 1020
RTRYYQIMPK YHAVRIREEE RYPPPGSTLP TKKHWVTSWQ TRDQYY               1066

SEQ ID NO: 19           moltype = DNA   length = 3156
FEATURE                 Location/Qualifiers
source                  1..3156
                        mol_type = other DNA
                        organism = Homo sapiens
CDS                     1..3156
SEQUENCE: 19
atgggcccg  gccccagccg  cgcgccccgc  gccccacgcc  tgatgctctg  tgcgctcgcc    60
ttgatggtgg cggccggcgg ctgcgtcgtc tccgccttca acctggatac ccgattcctg   120
gtagtgaagg aggccgggaa ccccgggcag ctcttcggct actcggtcgc cctccatcgg   180
cagacagagc ggcagcagcg ctacctgctc tggctggtg ccccccggga gctcgctgtg    240
cccgatggct acaccaaccg gactggtgct gtgtacctgt gccactcac tgcccacaag    300
gatgactgtg agcggatgaa catcacagtg aaaatgacc ctggccatca cattattgag    360
gacatgtggc ttggagtgac tgtggccagc caggggcctg caggcagagt tctggtctgt   420
gcccaccgct cacccaggt gctgtggtca gggtcagaag accagcggcg catggtgggc   480
aagtgctacg tgcgaggcaa tgaccctagg ctggactcca gtgatgactg gcagacctac   540
cacaacgaga tgtgcaatag caacacagac tacctggaga cgggcatgtg ccagctgggc   600
accagcggtg gcttcaccca gaacactgtg tacttcggcg ccccggtgc ctacaactgg    660
aaaggaaaca gctacatgat tcagcgcaag gagtgggact atctgagta tagttacaag   720
gacccagagg accaaggaaa cctctatatt gggtacacga tgcaggtagg cagcttcatc   780
ctgcacccca aaaacatcac cattgtgaca ggtgccccac ggcaccgaca tatgggcgcg   840
gtgttcttgc tgagccagga ggcaggcgga gacctgcgga ggcggcaggt gctggaggc    900
tcgcaggtgg gcgccatttt ggcagcgcc attgccctgg cagacctgaa caatgatggg    960
tggcaggacc tcctggtggg cgcccctac tacttcgaga ggaaagagga agtaggggt    1020
gccatctatg tcttcatgaa ccaggcggga acctccttcc ctgctcaccc ctcactcctt   1080
cttcatggcc ccagtggctc tgcctttggt ttatctgcag ccagcattgg tgacatcaac   1140
caggatggat tcaggatat tgctgtggga gctccgtttg aaggcttggg caaagtgtac   1200
atctatcaca gtagctctaa ggggctcctt agacagcccc agcaggtaat ccatggagag   1260
aagctgggac tgcctgggtt ggccaccttc ggctattccc tcagtgggca gatggatgtg   1320
gatgagaact tctacccaga ccttctagtg ggaagcctgt cagaccacat tgtgctgctg   1380
cgggcccggc ccgtcatcaa catcgtccac aagaccttgg tgcccaggcc agctgtgctg   1440
gaccctgcac tttgcacggc cacctcttgt gtgcaagtgg agctgtgctt tgcttacaac   1500
cagagtgccg gaaccccaa ctacaggcga acatcaccc tggcctacac tctggaggct    1560
gacaggagcc gccggccgcc ccggctccgc tttgccggca gtgagtccgc tgtcttccac   1620
ggcttcttct ccatgcccga gatgcgctgc cagaagctgg agctgctcct gatggacaac   1680
ctccgtgaca aactccgccc catcatcatc tccatgaact actctttacc tttgcggatg   1740
cccgatcgcc cccggctggg gctgcggtcc ctggacgcct acccgatcct caaccaggca   1800
caggctctgg agaaccacac tgaggtccag ttccagaagg agtgcgggcc tgacaacaag   1860
tgtgagagca acttgcagat gcgggcagca ttcgtgtcag agcagcagca aagctgagc    1920
aggctccagt acagcagaga cgtccggaaa ttgctcctga gcatcaacgt gacgaacacc   1980
cggacctcgg agcgctccgg ggaggacgcc cacgaggcgc tgctcaccct ggtggtgcct   2040
cccgccctgc tgctgtcctc agtgcgcccc ccggggcct gccaagctaa tgagaccatc    2100
ttttgcgagc tgggggaaccc cttcaaacgg aaccagagga tggagctgct catcgccttt   2160
gaggtcatcg gggtgaccct gcacacaagg gaccttcagg tgcagctgca gctctccac    2220
tcgagtcacc aggacaacct gtggcccatg atcctcactc tgctggtgga ctatacactc   2280
cagacctcgc ttagcatggt aaatcaccgg ctacaaagct ctttgggggg acagtgatg    2340
ggtgagtctg gcatgaaaac tgtggaggat gtaggaagcc cctcaagta tgaattccag    2400
gtgggcccaa tgggggaggg gctggtgggc tggggagccc tggtcctagg tctggagtgg   2460
ccctacgaag tcagcaatgg caagtggctg ctgtatccca cggagatcac cgtccatggc   2520
aatgggtcct ggccctgccg accacctgga gaccttatca ccctctcaa cctcactctt    2580
tctgaccctg ggacaggcc atcatcccca gcgcaggc ggcgacagct ggatccaggg     2640
ggaggccagg gcccccacc tgtcactctg gctgctgcca aaaaagccaa gtctgagact   2700
gtgctgacct gtgccacagg gcgtgcccac tgtgtgtgg agtgccccat catcctgat    2760
gccccggttg tcaccaacgt gactgtgaag gcacgagtgt ggaacagcac cttcatcgag   2820
gattacagag actttgaccg agtccggta aatggctggg ctaccctat tctccgaacc     2880
agcatcccca ccatcaacat ggagaacaag accacgtggt tctctgtgga cattgactcg   2940
gagctggtgg aggagctgcc ggccgaaatc gagctgtggc tggtgctggt ggccgtgggt   3000
gcagggctgc tgctgctgg gctgatcatc ctcctgctgt ggaagtgcgg cttcttcaag   3060
```

```
                                       -continued
cgagcccgca ctcgcgccct gtatgaagct aagaggcaga aggcggagat gaagagccag   3120
ccgtcagaga cagagaggct gaccgacgac tactga                             3156

SEQ ID NO: 20           moltype = AA  length = 1051
FEATURE                 Location/Qualifiers
source                  1..1051
                        mol_type = protein
                        organism = Homo sapiens
SEQUENCE: 20
MGPGPSRAPR APRLMLCALA LMVAAGGCVV SAFNLDTRFL VVKEAGNPGS LFGYSVALHR    60
QTERQQRYLL LAGAPRELAV PDGYTNRTGA VYLCPLTAHK DDCERMNITV KNDPGHHIIE   120
DMWLGVTVAS QGPAGRVLVC AHRYTQVLWS GSEDQRRMVG KCYVRGNDLE LDSSDDWQTY   180
HNEMCNSNTD YLETGMCQLG TSGGFTQNTV YFGAPGAYNW KGNSYMIQRK EWDLSEYSYK   240
DPEDQGNLYI GYTMQVGSFI LHPKNITIVT GAPRHRHMGA VFLLSQEAGG DLRRRQVLEG   300
SQVGAYFGSA IALADLNNDG WQDLLVGAPY YFERKEEVGG AIYVFMNQAG TSFPAHPSLL   360
LHGPSGSAFG LSVASIGDIN QDGFQDIAVG APFEGLGKVY IYHSSSKGLL RQPQQVIHGE   420
KLGLPGLATF GYSLSGQMDV DENFYPDLLV GSLSDHIVLL RARPVINIVH KTLVPRPAVL   480
DPALCTATSC VQVELCFAYN QSAGNPNYRR NITLAYTLEA DRDRRPPRLR FAGSESAVFH   540
GFFSMPEMRC QKLELLLMDN LRDKLRPIII SMNYSLPLRM PDRPRLGLRS LDAYPILNQA   600
QALENHTEVQ FQKECGPDNK CESNLQMRAA FVSEQQQKLS RLQYSRDVRK LLLSINVTNT   660
RTSERSGEDA HEALLTLVVP PALLLSSVRP PGACQANETI FCELGNPFKR NQRMELLIAF   720
EVIGVTLHTR DLQVQLQLST SSHQDNLWPM ILTLLVDYTL QTSLSMVNHR LQSFFGGTVM   780
GESGMKTVED VGSPLKYEFQ VGPMGEGLVG LGTLVLGLEW PYEVSNGKWL LYPTEITVHG   840
NGSWPCRPPG DLINPLNLTL SDPGDRPSSP QRRRRQLDPG GGQGPPPVTL AAAKKAKSET   900
VLTCATGRAH CVWLECPIPD APVVTNVTVK ARVWNSTFIE DYRDFDRVRV NGWATLFLRT   960
SIPTINMENK TTWFSVDIDS ELVEELPAEI ELWLVLVAVG AGLLLLGLII LLLWKCGFFK  1020
RARTRALYEA KRQKAEMKSQ PSETERLTDD Y                                 1051

SEQ ID NO: 21           moltype = DNA  length = 2397
FEATURE                 Location/Qualifiers
source                  1..2397
                        mol_type = other DNA
                        organism = Homo sapiens
CDS                     1..2397
SEQUENCE: 21
atgaatttac aaccaattt  ctggattgga ctgatcagtt cagtttgctg tgtgtttgct    60
caaacagatg aaaatagatg tttaaaagca atgccaaat  catgtggaga atgtatacaa   120
gcagggccaa attgtgggtg gtgcacaaat tcaacatttt tacaggaagg aatgcctact   180
tctgcacgat gtgatgattt agaagcctta aaaagaaagg gttgccctcc agatgacata   240
gaaaatccca gaggctccaa agatataaag aaaaataaaa atgtaaccaa ccgtagcaaa   300
ggaacagcag agaagctcaa gccagaggat attactcaga tccaaccaca gcagttggtt   360
ttgcgattaa gatcagggga gccacagaca tttacattaa aattcaagag agctgaagac   420
tatcccaatg acctctacta ccttatgtac ctgtcttact caactgaaaga cgatttggag   480
aatgtaaaaa gtcttggaac agatctgatg aatgaaatga ggaggattac ttcggacttc   540
agaattggat ttggctcatt tgtggaaaag actgtgatgc cttacattag cacaacacca   600
gctaagctca ggaacccttg cacaagtgaa cagaactgca ccagcccatt tagctacaaa   660
aatgtgctca tgtcttacta taaaggagaa gtatttaatg aacttgttgg aaaacagcgc   720
atatctggaa atttggattc tccagaaggt ggtttcgatg ccatcatgca agttgcagtt   780
tgtggatcac tgattggctg gaggaatgtt acacggctgc tggtgttttc cacagatgcc   840
gggtttcact ttgctggaga tgggaaactt ggtggcattg ttttaccaaa tgatggacaa   900
tgtcacctgg aaaataatat gtacacaatg agccattatt atgattatcc ttctattgtt   960
caccttgtcc agaaactgag tgaaaataat attcagacaa ttttttgcagt tactgaagaa  1020
tttcagcctg tttacaagga gctgaaaaac ttgatcccta gtcagcagt aggaacatta  1080
tctgcaaatt ctagcaatgt aattcagttg atcattgatg catacaattc cctttcctca  1140
gaagtcattt tggaaaacgg caaattgtca gaaggcgtaa caataagtta caaatcttac  1200
tgcaagaacg gggtgaatga aacagggaa aatggaagaa aatgttccaa tatttccatt  1260
ggagatgagg ttcaatttga aattagcata acttcaaata agtgtccaaa aaaggattct  1320
gacagcttta aaattaggcc tctgggcttt acggaggaag tagaggttat tcttcagtac  1380
atctgtgaat gtgaatgcca aagcgaaggc atccctgaaa gtcccaagtg tcatgaagga  1440
aatgggacat ttgagtgtgg cgcgtgcagg tgcaattgga gcgtgttgt tagacattgt  1500
gaatgcagca cagatgaagt taacagtgaa gacatggatg cttactcag gaaagaaaac  1560
agttcagaaa tctgcagtaa caatggagag tcgtctgcg gacagtgtgt tgtaggaag  1620
agggataata caaatgaaat ttattctggc aaattctgcg agtgtgataa tttcaactgt  1680
gatagatcca atggctttaa ttgtggagga aatggttctt gcaagtgtcg tgtctggag  1740
tgcaacccca actacactgg cagtgcatgt gactgttctt tggatactag tacttgtgaa  1800
gccagcaacg gacagatctg caatggccgg gcatctgcg agtgtggtgt ctgtaagtgt  1860
acagatccga agtttcaagg gcaaacgtgt gagatgtgtc agacctgcct tggtgtctgt  1920
gctgagcata agaatgtgt tcagtgcaga gccttcaata aggagaaaa gaaagacaa  1980
tgcacacagg aatgttccta ttttaacatt accaaggtag aaagtcggga caaattcccc  2040
cagccggtcc aacctgatcc tgtgtcccat tgtaaggaga aggatgttga cgactgttgg  2100
ttctatttta cgtattcagt gaatgggaac aacgaggtca tggttcatgt tgtggagaat  2160
ccagagtgtc ccactggtcc agacatcatt ccaattgtag ctggtgtggt tgctggaatt  2220
gttcttattg gccttgcatt actgctgata tggaagcttt aatgataat tcatgacaga  2280
aggagttttg ctaaatttga aaaggagaaa atgaatgcca aatggacac gggtgaaaat  2340
cctatttata agagtgccgt aacaactgtg gtcaatccga gtatgaggg aaaatga      2397

SEQ ID NO: 22           moltype = AA  length = 798
FEATURE                 Location/Qualifiers
source                  1..798
```

```
                        mol_type = protein
                        organism = Homo sapiens
SEQUENCE: 22
MNLQPIFWIG LISSVCCVFA QTDENRCLKA NAKSCGECIQ AGPNCGWCTN STFLQEGMPT   60
SARCDDLEAL KKKGCPPDDI ENPRGSKDIK KNKNVTNRSK GTAEKLKPED ITQIQPQQLV  120
LRLRSGEPQT FTLKFKRAED YPIDLYYLMD LSYSMKDDLE NVKSLGTDLM NEMRRITSDF  180
RIGFGSFVEK TVMPYISTTP AKLRNPCTSE QNCTSPFSYK NVLSLTNKGE VFNELVGKQR  240
ISGNLDSPEG GFDAIMQVAV CGSLIGWRNV TRLLVFSTDA GFHFAGDGKL GGIVLPNDGQ  300
CHLENNMYTM SHYYDYPSIA HLVQKLSENN IQTIFAVTEE FQPVYKELKN LIPKSAVGTL  360
SANSSNVIQL IIDAYNSLSS EVILENGKLS EGVTISYKSY CKNGVNGTGE NGRKCSNISI  420
GDEVQFEISI TSNKCPKKDS DSFKIRPLGF TEEEVEVILQY ICECECQSEG IPESPKCHEG  480
NGTFECGACR CNEGRVGRHC ECSTDEVNSE DMDAYCRKEN SSEICSNNGE CVCGQCVCRK  540
RDNTNEIYSG KFCECDNFNC DRSNGLICGG NGVCKCRVCE CNPNYTGSAC DCSLDTSTCE  600
ASNGQICNGR GICECGVCKC TDPKFQGQTC EMCQTCLGVC AEHKECVQCR AFNKGEKKDT  660
CTQECSYFNI TKVESRDKLP QPVQPDPVSH CKEKDVDDCW FYFTYSVNGN NEVMVHVVEN  720
PECPTGPDII PIVAGVVAGI VLIGLALLLI WKLLMIIHDR REFAKFEKEK MNAKWDTGEN  780
PIYKSAVTTV VNPKYEGK                                                798

SEQ ID NO: 23           moltype = DNA  length = 2406
FEATURE                 Location/Qualifiers
source                  1..2406
                        mol_type = other DNA
                        organism = Homo sapiens
CDS                     1..2406
SEQUENCE: 23
atgaatttac aaccaattttt ctggattgga ctgatcagtt cagtttgctg tgtgtttgct   60
caaacagatg aaaatagatg tttaaaagca aatgccaaat catgtggaga atgtatacaa  120
gcagggccaa attgtgggtg gtgcacaaat tcaacatttt tacaggaagg aatgcctact  180
tctgcacgat gtgatgattt agaagcctta aaaaagaagg gttgccctcc agatgacata  240
gaaaatccca gaggctccaa agatataaag aaaaataaca atgtaaccaa ccgtagcaaa  300
ggaacagcag agaagctcaa gccagaggat attactcaga tccaaccaca gcagttggtt  360
ttgcgattaa gatcagggga gccacagaca tttacattaa aattcaagag agctgaagac  420
tatcccattg acctctacta cctttatggac ctgtcttact caatgaaaga cgatttggag  480
aatgtaaaaa gtcttggaac agatctgatg aatgaaatga ggaggattac ttcggacttc  540
agaattggat ttggctcatt tgtggaaaag actgtgatgc cttacattag cacaacacca  600
gctaagctca ggaaccctg cacaagtgaa cagaactgca ccagcccatt tagctacaaa  660
aatgtgctca gtcttactaa taaaggagaa gtatttaatg aacttgttgg aaaacagcgc  720
atatctggaa atttggattc tccagaaggt ggtttcgatg ccatcatgca agttgcagtt  780
tgtggatcac tgattggctg gaggaatgtt acacggctgc tggtgttttc cacagatgcc  840
gggtttcact ttgctggaga tgggaaactt ggtggcattg ttttaccaaa tgatggacaa  900
tgtcacctgg aaaataatat gtacacaatg agccattatt atgattatcc ttctattgct  960
caccttgtcc agaaactgag tgaaaataat attcagacaa ttttttgcagt tactgaagaa 1020
tttcagcctg tttacaagga gctgaaaaac ttgatcccta agtcagcagt aggaacatta 1080
tctgcaaatt ctagcaatgt aattcagttg atcattgatg catacaattc cctttcctca 1140
gaagtcattt tggaaaacgg caaattgtca gaaggcgtaa caataagtta caaatcttac 1200
tgcaagaacg gggtgaatgg aacaggggaa aatggaagaa aatgttccaa tatttccatt 1260
ggagatgagg ttcaatttga aattagcata acttcaaata gtgtccaaa aaaggattct 1320
gacagcttta aaattaggcc tctgggcttt acggaggaag tagaggttat tcttcagtac 1380
atctgtgaat gtgaatgcca aagcgaaggc atccctgaaa gtcccaagtg tcatgaagga 1440
aatgggacat ttgagtgtgg cgcgtgcagg tgcaatgaag ggcgtgttgg tagacattgt 1500
gaatgcagca cagatgaagt taacagtgaa gacatgaagt cttactgcag gaaagaaaac 1560
agttcagaaa tctgcagtaa caatggagag tgcgtctgcg gacagtgtgt ttgtaggaag 1620
agggataata caaatgaaat ttattctggc aaattctgcg agtgtgataa tttcaactgt 1680
gatagatcca atggcttaat ttgtggagga aatggtgttt gcaagtgtcg tgtgtgtgag 1740
tgcaacccca actacactgg cagtgcatgt gactgttctt tggatactag tacttgtgaa 1800
gccagcaacg gacagatctg caatggccgg ggcatctgcg agtgtggtgt ctgtaagtgt 1860
acagatccga gtttcaagg gcaaacgtgt gagatgtgtc agacctgcct tggtgtctgt 1920
gctgagcata agaatgtgt tcagtgcaga gccttcaata aggagaaaa gaaagacaca 1980
tgcacacagg aatgttccta tttttaacatt accaaggtag aaagtcggga caaattaccc 2040
cagccggtcc aacctgatcc tgtgtcccat tgtaaggaga aggatgttga cgactgttgg 2100
ttctatttta cgtattcagt gaatgggaac aacgaggtca tggttcatgt tgtggagaat 2160
ccagagtgtc ccactggtcc agacatcatt ccaattgtag ctggtgtggt tgctggaatt 2220
gttcttattg gccttgcatt actgctgata tggaagcttt taatgataat tcatgacaga 2280
agggagtttg ctaaatttga aaaggagaaa atgaatgcca aatgggacac gcaagaaaat 2340
ccgatttaca gagtccatat taataatttc aagaatccaa actacggacg taaagctggt 2400
ctctaa                                                             2406

SEQ ID NO: 24           moltype = AA  length = 801
FEATURE                 Location/Qualifiers
source                  1..801
                        mol_type = protein
                        organism = Homo sapiens
SEQUENCE: 24
MNLQPIFWIG LISSVCCVFA QTDENRCLKA NAKSCGECIQ AGPNCGWCTN STFLQEGMPT   60
SARCDDLEAL KKKGCPPDDI ENPRGSKDIK KNKNVTNRSK GTAEKLKPED ITQIQPQQLV  120
LRLRSGEPQT FTLKFKRAED YPIDLYYLMD LSYSMKDDLE NVKSLGTDLM NEMRRITSDF  180
RIGFGSFVEK TVMPYISTTP AKLRNPCTSE QNCTSPFSYK NVLSLTNKGE VFNELVGKQR  240
ISGNLDSPEG GFDAIMQVAV CGSLIGWRNV TRLLVFSTDA GFHFAGDGKL GGIVLPNDGQ  300
CHLENNMYTM SHYYDYPSIA HLVQKLSENN IQTIFAVTEE FQPVYKELKN LIPKSAVGTL  360
```

```
SANSSNVIQL  IIDAYNSLSS  EVILENGKLS  EGVTISYKSY  CKNGVNGTGE  NGRKCSNISI   420
GDEVQFEISI  TSNKCPKKDS  DSFKIRPLGF  TEEVEVILQY  ICECECQSEG  IPESPKCHEG   480
NGTFECGACR  CNEGRVGRHC  ECSTDEVNSE  DMDAYCRKEN  SSEICSNNGE  CVCGQCVCRK   540
RDNTNEIYSG  KFCECDNFNC  DRSNGLICGG  NGVCKCRVCE  CNPNYTGSAC  DCSLDTSTCE   600
ASNGQICNGR  GICECGVCKC  TDPKFQGQTC  EMCQTCLQAC  AEHKECVQCR  AFNKGEKKDT   660
CTQECSYFNI  TKVESRDKLP  QPVQPDPVSH  CKEKDVDDCW  FYFTYSVNGN  NEVMVHVVEN   720
PECPTGPDII  PIVAGVVAGI  VLIGLALLLI  WKLLMIIHDR  REFAKFEKEK  MNAKWDTQEN   780
PIYKSPINNF  KNPNYGRKAG  L                                               801

SEQ ID NO: 25          moltype = DNA  length = 1233
FEATURE                Location/Qualifiers
source                 1..1233
                       mol_type = other DNA
                       organism = Homo sapiens
CDS                    1..1233
SEQUENCE: 25
atggtgtgct tccgcctctt cccggttccg ggctcagggc tcgttctggt ctgcctagtc    60
ctgggagctg tgcggtctta tgcattgaaa cttaatttga cagattcaga aaatgccact   120
tgcctttatg caaaatggca gatgaatttc acagtacgct atgaaactac aaataaaact   180
tataaaactg taaccatttc agaccatggc actgtgacat ataatggaag catttgtggg   240
gatgatcaga atggtcccaa aatagcagtg cagttcggac ctggcttttc ctggattgcg   300
aattttacca aggcagcatc tacttattca attgacagtg tctcattttc ctacaacact   360
ggtgataaca caacatttcc tgatgctgaa gataaaggaa ttcttactgt tgatgaactt   420
ttggccatca gaattccatt gaatgacctt tttagatgca atagtttatc aactttggaa   480
aagaatgatg ttgtccaaca ctactgggat gttcttgtac aagcttttgt ccaaaatggc   540
acagtgagca caaatgagtt cctgtgtgat aagacaaaa cttcaacagt ggcacccacc    600
atacacacca ctgtgccatc tcctactaca cacctactc caaggaaaa accagaagct    660
ggaacctatt cagttaataa tggcaatgat acttgtctgc tggctaccat ggggctgcag   720
ctgaacatca ctcaggataa ggttgcttca gttattaaca tcaaccccaa tacaactcac   780
tccacaggca gctgccgttc tcacactgct tacttagac tcaatagcag caccattaag    840
tatctagact ttgtctttgc tgtgaaaaat gaaaaccgat tttatctgaa ggaagtgaac   900
atcagcatgt atttggttaa tggctccgtt ttcagcattg caaataacaa tctcagctac   960
tgggatgccc ccctgggaag ttcttatatg tgcaacaaag agcagactgt ttcagtgtct  1020
ggagcatttc agataaatac ctttgatcta agggttcagc ctttcaatgt gacacaagga  1080
aagtattcta cagcccaaga ctgcagtgca gatgacgaca ccttccttgt gcccatagcg  1140
gtgggagctg ccttggcagg agtactatt ctagtgttgc tggcttattt tattggtctc   1200
aagcaccatc atgctggata tgagcaattt tag                                1233

SEQ ID NO: 26          moltype = AA  length = 410
FEATURE                Location/Qualifiers
source                 1..410
                       mol_type = protein
                       organism = Homo sapiens
SEQUENCE: 26
MVCFRLFPVP  GSGLVLVCLV  LGAVRSYALE  LNLTDSENAT  CLYAKWQMNF  TVRYETTNKT    60
YKTVTISDHG  TVTYNGSICG  DDQNGPKIAV  QFGPGFSWIA  NFTKAASTYS  IDSVSFSYNT   120
GDNTTFPDAE  DKGILTVDEL  LAIRIPLNDL  FRCNSLSTLE  KNDVVQHYWD  VLVQAFVQNG   180
TVSTNEFLCD  KDKTSTVAPT  IHTTVPSPTT  TPTPKEKPEA  GTYSVNNGND  TCLLATMGLQ   240
LNITQDKVAS  VININPNTTH  STGSCRSHTA  LLRLNSSTIK  YLDFVFAVKN  ENRFYLKEVN   300
ISMYLVNGSV  FSIANNNLSY  WDAPLGSSYM  CNKEQTVSVS  GAFQINTFDL  RVQPFNVTQG   360
KYSTAQDCSA  DDDNFLVPIA  VGAALAGVLI  LVLLAYFIGL  KHHHAGYEQF               410

SEQ ID NO: 27          moltype = DNA  length = 1233
FEATURE                Location/Qualifiers
source                 1..1233
                       mol_type = other DNA
                       organism = Homo sapiens
CDS                    1..1233
SEQUENCE: 27
atggtgtgct tccgcctctt cccggttccg ggctcagggc tcgttctggt ctgcctagtc    60
ctgggagctg tgcggtctta tgcattgaaa cttaatttga cagattcaga aaatgccact   120
tgcctttatg caaaatggca gatgaatttc acagtacgct atgaaactac aaataaaact   180
tataaaactg taaccatttc agaccatggc actgtgacat ataatggaag catttgtggg   240
gatgatcaga atggtcccaa aatagcagtg cagttcggac ctggcttttc ctggattgcg   300
aattttacca aggcagcatc tacttattca attgacagcg tctcattttc ctacaacact   360
ggtgataaca caacatttcc tgatgctgaa gataaaggaa ttcttactgt tgatgaactt   420
ttggccatca gaattccatt gaatgacctt tttagatgca atagtttatc aactttggaa   480
aagaatgatg ttgtccaaca ctactgggat gttcttgtac aagcttttgt ccaaaatggc   540
acagtgagca caaatgagtt cctgtgtgat aagacaaaa cttcaacagt ggcacccacc    600
atacacacca ctgtgccatc tcctactaca cacctactc caaggaaaa accagaagct    660
ggaacctatt cagttaataa tggcaatgat acttgtctgc tggctaccat ggggctgcag   720
ctgaacatca ctcaggataa ggttgcttca gttattaaca tcaaccccaa tacaactcac   780
tccacaggca gctgccgttc tcacactgct tacttagac tcaatagcag caccattaag    840
tatctagact ttgtctttgc tgtgaaaaat gaaaaccgat tttatctgaa ggaagtgaac   900
atcagcatgt atttggttaa tggctccgtt ttcagcattg caaataacaa tctcagctac   960
tgggatgccc ccctgggaag ttcttatatg tgcaacaaag agcagactgt ttcagtgtct  1020
ggagcatttc agataaatac ctttgatcta agggttcagc ctttcaatgt gacacaagga  1080
aagtattcta cagcccaaga gtgttcgctg atgatgaca ccattctaat cccaattata   1140
gttggtgctg tctttcagg cttgattatc gttatagtga ttgcttacgt aattggcaga  1200
```

-continued

```
agaaaaagtt atgctggata tcagactctg taa                                  1233

SEQ ID NO: 28           moltype = AA  length = 410
FEATURE                 Location/Qualifiers
source                  1..410
                        mol_type = protein
                        organism = Homo sapiens
SEQUENCE: 28
MVCFRLFPVP GSGLVLVCLV LGAVRSYALE LNLTDSENAT CLYAKWQMNF TVRYETTNKT      60
YKTVTISDHG TVTYNGSICG DDQNGPKIAV QFGPGFSWIA NFTKAASTYS IDSVSFSYNT     120
GDNTTFPDAE DKGILTVDEL LAIRIPLNDL FRCNSLSTLE KNDVVQHYWD VLVQAFVQNG     180
TVSTNEFLCD KDKTSTVAPT IHTTVPSPTT TPTPKEKPEA GTYSVNNGND TCLLATMGLQ     240
LNITQDKVAS VININPNTTH STGSCRSHTA LLRLNSSTIK YLDFVFAVKN ENRFYLKEVN     300
ISMYLVNGSV FSIANNNLSY WDAPLGSSYM CNKEQTVSVS GAFQINTFDL RVQPFNVTQG     360
KYSTAQECSL DDDTILIPII VGAGLSGLII VIVIAYVIGR RKSYAGYQTL                410

SEQ ID NO: 29           moltype = DNA  length = 1236
FEATURE                 Location/Qualifiers
source                  1..1236
                        mol_type = other DNA
                        organism = Homo sapiens
CDS                     1..1236
SEQUENCE: 29
atggtgtgct tccgcctctt cccggttccg ggctcagggc tcgttctggt ctgcctagtc      60
ctgggagctg tgcggtctta tgcattggaa cttaatttga cagattcaga aaatgccact     120
tgcctttatg caaaatggca gatgaatttc acagtacgtc atgaaactac aaataaaact     180
tataaaactg taaccatttc agaccatggc actgtgacat ataatggaag catttgtggg     240
gatgatcaga atggtcccaa aatagcagtg cagttcggac ctggcttttc ctggattgcg     300
aattttacca aggcagcatc tacttattca attgacagcg tctcattttc ctacaacact     360
ggtgataaca acatttcc tgatgctgaa gataaaggaa ttcttactgt tgatgaactt     420
ttggccatca gaattccatt gaatgaccttt tttagatgca atagtttatc aactttggaa     480
aagaatgatg ttgtccaaca ctactgggat gttcttgtac aagcttttgt ccaaaatggc     540
acagtgagca caaatgagtt cctgtgtgat aagacaaaa cttcaacagt ggcacccacc     600
atacacacca ctgtgccatc tcctactaca caacctactc caaaggaaaa accagaagct     660
ggaacctatt cagttaataa tggcaatgat acttgtctgc tggctaccat ggggctgcag     720
ctgaacatca ctcaggataa ggttgcttca gttattaaca tcaaccccaa tacaactcac     780
tccacaggca gctgccgttc tcacactgct ctacttagac tcaatagcag caccattaag     840
tatctagact ttgtctttgc tgtgaaaaat gaaaaccgat tttatctgaa ggaagtgaac     900
atcagcatgt atttggttaa tggctccgtt tcagcattg caaataacaa tctcagctac     960
tgggatgccc ccctgggaag ttcttatatg tgcaacaaag agcagactgt ttcagtgtct    1020
ggagcatttc agataaatac ctttgatcta agggttcagc ctttcaatgt gacacaagga    1080
aagtattcta cagctgaaga atgttctgct gactctgacc tcaactttct tattcctgtt    1140
gcagtgggtg tggccttggg cttccttata attgttgtct ttatctctta tatgattgga    1200
agaaggaaaa gtcgtactgg ttatcagtct gtgtaa                              1236

SEQ ID NO: 30           moltype = AA  length = 411
FEATURE                 Location/Qualifiers
source                  1..411
                        mol_type = protein
                        organism = Homo sapiens
SEQUENCE: 30
MVCFRLFPVP GSGLVLVCLV LGAVRSYALE LNLTDSENAT CLYAKWQMNF TVRYETTNKT      60
YKTVTISDHG TVTYNGSICG DDQNGPKIAV QFGPGFSWIA NFTKAASTYS IDSVSFSYNT     120
GDNTTFPDAE DKGILTVDEL LAIRIPLNDL FRCNSLSTLE KNDVVQHYWD VLVQAFVQNG     180
TVSTNEFLCD KDKTSTVAPT IHTTVPSPTT TPTPKEKPEA GTYSVNNGND TCLLATMGLQ     240
LNITQDKVAS VININPNTTH STGSCRSHTA LLRLNSSTIK YLDFVFAVKN ENRFYLKEVN     300
ISMYLVNGSV FSIANNNLSY WDAPLGSSYM CNKEQTVSVS GAFQINTFDL RVQPFNVTQG     360
KYSTAEECSA DSDLNFLIPV AVGVALGFLI IVVFISYMIG RRKSRTGYQS V              411

SEQ ID NO: 31           moltype = DNA  length = 1347
FEATURE                 Location/Qualifiers
source                  1..1347
                        mol_type = other DNA
                        organism = Homo sapiens
CDS                     1..1347
SEQUENCE: 31
atgatcccca ccttcacggc tctgctctgc ctcgggctga gtctgggccc caggaccccac     60
atgcaggcag ggcccctccc caaacccacc tctgggctg agccaggctc tgtgatcagc     120
tggggggaact ctgtgaccat ctggtgtcag gggacccttg agctcggga gtaccgtctg     180
gataaagagg aaagcccagc accctgggac agacagaacc cactggagcc caagaacaag     240
gccagattct ccatcccatc catgacagag gactatgcag ggagatacgg ctgttactat     300
cgcagccctg taggctggtc acagcccagt gaccccctgg agctggtgat gacaggagcc     360
tacagtaaaa ccaaccccttc agccctgcgg agtcctcttt gacctcagg aaagagcgtg     420
accctgtgt gtcagtcacg gagccaatg gacacttttg ttctgatcaa ggagcgggca     480
gcccatccc tactgcatct gagatcagag cacggagctc agcagcacca ggctgaattc     540
cccatgagtc ctgtgacctc agtgcacggg gggacctaca ggtgcttcag ctcacacggc     600
ttctcccact acctgctgtc acaccccagt gaccccctgg agctcatagt ctcaggatcc     660
ttgagggtg ccaggccctc acccacaagg tccgtctcaa cagctgcagg ccctgaggac     720
cagccccctca tgcctacagg gtcagtcccc acagtggtc tgagaaggca ctgggaggta     780
```

```
ctgatcgggg tcttggtggt ctccatcctg cttctctccc tcctcctctt cctcctcctc    840
caacactggc gtcagggaaa acacaggaca ttggcccaga gacaggctga tttccaacgt    900
cctccagggg ctgccgagcc agagcccaag gacggggggcc tacagaggag gtccagccca   960
gctgctgacg tccagggaga aaacttctgt gctgccgtga agaacacaca gcctgaggac   1020
ggggtggaaa tggacactcg gcagagccca acgatgaagg accccaggc agtgacgtat    1080
gccaaggtga aacactccag acctaggaga gaaatggcct ctcctcctc cccactgtct    1140
ggggaattcc tggacacaaa ggacagacag gcagaagagg acagacagat ggacactgag   1200
gctgctgcat ctgaagcccc caggatgtg acctacgccc ggctgcacag ctttacccctc   1260
agacagaagg caactgagcc tcctccatcc caggaagggg cctctccagc tgagcccagt   1320
gtctatgcca ctctggccat ccactaa                                        1347

SEQ ID NO: 32          moltype = AA  length = 448
FEATURE                Location/Qualifiers
source                 1..448
                       mol_type = protein
                       organism = Homo sapiens
SEQUENCE: 32
MIPTFTALLC LGLSLGPRTH MQAGPLPKPT LWAEPGSVIS WGNSVTIWCQ GTLEAREYRL     60
DKEESPAPWD RQNPLEPKNK ARFSIPSMTE DYAGRYRCYY RSPVGWSQPS DPLELVMTGA    120
YSKPTLSALP SPLVTSGKSV TLLCQSRSPM DTFLLIKERA AHPLLHLRSE HGAQQHQAEF    180
PMSPVTSVHG GTYRCFSSHG FSHYLLSHPS DPLELIVSGS LEGPRPSPTR SVSTAAGPED    240
QPLMPTGSVP HSGLRRHWEV LIGVLVVSIL LLSLLLFLLL QHWRQGKHRT LAQRQADFQR    300
PPGAAEPEPK DGGLQRRSSP AADVQGENFC AAVKNTQPED GVEMDTRQSP HDEDPQAVTY    360
AKVKHSRPRR EMASPPSPLS GEFLDTKDRQ AEEDRQMDTE AAASEAPQDV TYARLHSFTL    420
RQKATEPPPS QEGASPAEPS VYATLAIH                                       448

SEQ ID NO: 33          moltype = DNA  length = 1347
FEATURE                Location/Qualifiers
source                 1..1347
                       mol_type = other DNA
                       organism = Homo sapiens
CDS                    1..1347
SEQUENCE: 33
atgatcccca ccttcacggc tctgctctgc ctcgggctga gtctgggccc caggacccac     60
atgcaggcag ggcccctccc caaacccacc ctctgggctg agccaggctc tgtgatcagc    120
tgggggaact ctgtgaccat ctggtgtcag gggaccctgg aggctcggga gtaccgtctg    180
gataaagagg aaagcccagc accctgggac agacagaacc cactgagcc caagaacaag    240
gccagattct ccatcccatc catgacagag gactatgcag ggagatatcg ctgttactat    300
cgcagccctg taggctggtc acagcccagt gacccccctgg agtcggtgat gacaggagcc    360
tacagtaaac ccacccttttc agccctgccg agtcctcttg tgacctcagg aaagagcgtg    420
accctgctgt gtcagtcacg gagcccaatg gacactttcc ttctgatcaa ggagcgggca    480
gcccatcccc tactgcatct gagatcagag cacggagctc agcagcacca ggctgaattc    540
cccatgagtc ctgtgacctc agtgcacggg gggacctaca ggtgcttcag ctcacacggc    600
ttctcccact acctgctgtc acaccccagt gaccccctgg agctcatagt ctcaggatcc    660
ttggaggatc caggccctc acccacaagg tccgtctcaa cagctgcagg ccctgaggac    720
cagcccctca tgcctacagg gtcagtcccc cacagtggtc tgaagaggca ctgggaggta    780
ctgatcgggg tcttggtggt ctccatcctg cttctctccc tcctcctctt cctcctcctc    840
caacactggc gtcagggaaa acacaggaca ttggcccaga gacaggctga tttccaacgt    900
cctccagggg ctgccgagcc agagcccaag gacggggggcc tacagaggag gtccagccca   960
gctgctgacg tccagggaga aaacttctgt gctgccgtga agaacacaca gcctgaggac   1020
ggggtggaaa tggacactcg gcagagccca acgatgaagg accccaggc agtgacgtat    1080
gccaaggtga aacactccag acctaggaga gaaatggcct ctcctcctc cccactgtct    1140
ggggaattcc tggacacaaa ggacagacag gcagaagagg acagacagat ggacactgag   1200
gctgctgcat ctgaagcccc caggatgtg acctacgccc ggctgcacag ctttacccctc   1260
agacagaagg caactgagcc tcctccatcc caggaagggg cctctccagc tgagcccagt   1320
gtctatgcca ctctggccat ccactaa                                        1347

SEQ ID NO: 34          moltype = AA  length = 448
FEATURE                Location/Qualifiers
source                 1..448
                       mol_type = protein
                       organism = Homo sapiens
SEQUENCE: 34
MIPTFTALLC LGLSLGPRTH MQAGPLPKPT LWAEPGSVIS WGNSVTIWCQ GTLEAREYRL     60
DKEESPAPWD RQNPLEPKNK ARFSIPSMTE DYAGRYRCYY RSPVGWSQPS DPLELVMTGA    120
YSKPTLSALP SPLVTSGKSV TLLCQSRSPM DTFLLIKERA AHPLLHLRSE HGAQQHQAEF    180
PMSPVTSVHG GTYRCFSSHG FSHYLLSHPS DPLELIVSGS LEGPRPSPTR SVSTAAGPED    240
QPLMPTGSVP HSGLRRHWEV LIGVLVVSIL LLSLLLFLLL QHWRQGKHRT LAQRQADFQR    300
PPGAAEPEPK DGGLQRRSSP AADVQGENFC AAVKNTQPED GVEMDTRQSP HDEDPQAVTY    360
AKVKHSRPRR EMASPPSPLS GEFLDTKDRQ AEEDRQMDTE AAASEAPQDV TYAQLHSFTL    420
RQKATEPPPS QEGASPAEPS VYATLAIH                                       448

SEQ ID NO: 35          moltype = DNA  length = 1350
FEATURE                Location/Qualifiers
source                 1..1350
                       mol_type = other DNA
                       organism = Homo sapiens
CDS                    1..1350
SEQUENCE: 35
```

```
atgatcccca ccttcacggc tctgctctgc ctcgggctga gtctgggccc caggacccac    60
atgcaggcag ggcccctccc caaacccacc ctctgggctg agccaggctc tgtgatcagc   120
tgggggaact ctgtgaccat ctggtgtcag gggaccctgg aggctcggga gtaccgtctg   180
gataaagagg aaagcccagc accctgggac agacagaacc cactggagcc caagaacaag   240
gccagattct ccatcccatc catgacagag gactatgcag ggagataccg ctgttactat   300
cgcagccctg taggctggtc acagcccagt gaccccctgg agctggtgat gacaggagcc   360
tacagtaaac ccacccttc agccctgccg agtcctcttg tgacctcagg aaagagcgtg   420
accctgctgt gtcagtcacg gagcccaatg gacactttcc ttctgatcaa ggagcgggca   480
gcccatcccc tactgcatct gagatcagag cacggagctc agcagcacca ggctgaattc   540
cccatgagtc ctgtgacctc agtgcacggg gggacctaca ggtgcttcag ctcacacgtc   600
ttctcccact acctgctgtc acaccccagt gaccccctgg agctcatagt ctcaggatcc   660
ttggaggatc ccaggccctc acccacaagg tccgtctcaa cagctgcagg ccctgaggac   720
cagcccctca tgcctacagg gtcagtcccc cacagtggtc tgagaaggca ctgggaggta   780
ctgatcgggg tcttggtggt ctccatcctg ctttctctcc tcctcctcct   840
caacactggc gtcagggaaa acacaggaca ttggcccaga gacaggctga tttccaacgt   900
cctccagggg ctgccgagcc agagcccaag gacggggggcc tacagaggag gtccagccca   960
gctgctgacg tccagggaga aaacttctca ggtgctgccg tgaagaacac acagcctgag  1020
gacggggtgg aaatggacac tcggcagagc ccacacgatg aagaccccag ggcagtgacg  1080
tatgccaagg tgaaacactc cagacctagg agagaaatgg cctctcctcc ctccccactg  1140
tctggggaat tcctggacac aaaggacaga caggcagaag gacagaca gatgacact  1200
gaggctgctg catctgaagc cccccaggat gtgacctacg cccagctgca cagctttacc  1260
ctcagacaga aggcaactga gcctcctcca tcccaggaag ggcctctcc agctgagccc  1320
agtgtctatg ccactctggc catccactaa                                    1350

SEQ ID NO: 36            moltype = AA   length = 449
FEATURE                  Location/Qualifiers
source                   1..449
                         mol_type = protein
                         organism = Homo sapiens
SEQUENCE: 36
MIPTFTALLC LGLSLGPRTH MQAGPLPKPT LWAEPGSVIS WGNSVTIWCQ GTLEAREYRL    60
DKEESPAPWD RQNPLEPKNK ARFSIPSMTE DYAGRYRCYY RSPVGWSQPS DPLELVMTGA   120
YSKPTLSALP SPLVTSGKSV TLLCQSRSPM DTFLLIKERA AHPLLHLRSE HGAQQHQAEF   180
PMSPVTSVHG GTYRCFSSHG FSHYLLSHPS DPLELIVSGS LEDPRPSPTR SVSTAAGPED   240
QPLMPTGSVP HSGLRRHWEV LIGVLVVSIL LLSLLLFLLL QHWRQGKHRT LAQRQADFQR   300
PPGAAEPEPK DGGLQRRSSP AADVQGENFS GAAVKNTQPE DGVEMDTRQS PHDEDPQAVT   360
YAKVKHSRPR REMASPPSPL SGEFLDTKDR QAEEDRQMDT EAAASEAPQD VTYAQLHSFT   420
LRQKATEPPP SQEGASPAEP SVYATLAIH                                    449

SEQ ID NO: 37            moltype = DNA   length = 1344
FEATURE                  Location/Qualifiers
source                   1..1344
                         mol_type = other DNA
                         organism = Homo sapiens
CDS                      1..1344
SEQUENCE: 37
atgatcccca ccttcacggc tctgctctgc ctcgggctga gtctgggccc caggacccac    60
atgcaggcag ggcccctccc caaacccacc ctctgggctg agccaggctc tgtgatcagc   120
tgggggaact ctgtgaccat ctggtgtcag gggaccctgg aggctcggga gtaccgtctg   180
gataaagagg aaagcccagc accctgggac agacagaacc cactggagcc caagaacaag   240
gccagattct ccatcccatc catgacagag gactatgcag ggagataccg ctgttactat   300
cgcagccctg taggctggtc acagcccagt gaccccctgg agctggtgat gacaggagcc   360
tacagtaaac ccacccttc agccctgccg agtcctcttg tgacctcagg aaagagcgtg   420
accctgctgt gtcagtcacg gagcccaatg gacactttcc ttctgatcaa ggagcgggca   480
gcccatcccc tactgcatct gagatcagag cacggagctc agcagcacca ggctgaattc   540
cccatgagtc ctgtgacctc agtgcacggg gggacctaca ggtgcttcag ctcacacgtc   600
ttctcccact acctgctgtc acaccccagt gaccccctgg agctcatagt ctcaggatcc   660
ttggaggatc ccaggccctc acccacaagg tccgtctcaa cagctgcagg ccctgaggac   720
cagcccctca tgcctacagg gtcagtcccc cacagtggtc tgagaaggca ctgggaggta   780
ctgatcgggg tcttggtggt ctccatcctg ctttctctcc tcctcctcct             840
caacactggc gtcagggaaa acacaggaca ttggcccaga gacaggctga tttccaacgt   900
cctccagggg ctgccgagcc agagcccaag gacggggggcc tacagaggag gtccagccca   960
gctgctgacg tccagggaga aaacttctgt gctgccgtga gaacacaca gcctgaggac  1020
ggggtgaaa tggacactcg gagcccacac gatgaagacc cccaggctga gacgtatgcc  1080
aaggtgaaac actccagacc taggagagaa atggcctctc ctccccaacg actgtctggg  1140
gaattcctgg acacaaagga cagacaggca agaggacaga gacgatgga cactgaggct  1200
gctgcatctg aagcccccca ggatgtgacc tacgcccagc tgcacagctt taccctcaga  1260
cagaaggcaa ctgagcctcc tccatcccag gaagggcctc tccagctgag cccagtgtc  1320
tatgccactc tggccatcca ctaa                                        1344

SEQ ID NO: 38            moltype = AA   length = 447
FEATURE                  Location/Qualifiers
source                   1..447
                         mol_type = protein
                         organism = Homo sapiens
SEQUENCE: 38
MIPTFTALLC LGLSLGPRTH MQAGPLPKPT LWAEPGSVIS WGNSVTIWCQ GTLEAREYRL    60
DKEESPAPWD RQNPLEPKNK ARFSIPSMTE DYAGRYRCYY RSPVGWSQPS DPLELVMTGA   120
YSKPTLSALP SPLVTSGKSV TLLCQSRSPM DTFLLIKERA AHPLLHLRSE HGAQQHQAEF   180
```

```
PMSPVTSVHG GTYRCFSSHG FSHYLLSHPS DPLELIVSGS LEDPRPSPTR SVSTAAGPED    240
QPLMPTGSVP HSGLRRHWEV LIGVLVVSIL LLSLLLFLLL QHWRQGKHRT LAQRQADFQR    300
PPGAAEPEPK DGGLQRRSSP AADVQGENFC AAVKNTQPED GVEMDTRSPH DEDPQAVTYA    360
KVKHSRPRRE MASPPSPLSG EFLDTKDRQA EEDRQMDTEA AASEAPQDVT YAQLHSFTLR    420
QKATEPPPSQ EGASPAEPSV YATLAIH                                       447

SEQ ID NO: 39          moltype = DNA   length = 2640
FEATURE                Location/Qualifiers
source                 1..2640
                       mol_type = other DNA
                       organism = Homo sapiens
CDS                    1..2640
SEQUENCE: 39
atggggcgcc tggcctcgag gccgctgctg ctggcgctcc tgtcgttggc tctttgccga     60
gggcgtgtgg tgagagtccc cacagcgacc ctggttcgag tggtgggcac tgagctggtc    120
atcccctgca acgtcagtga ctatgatggc cccagcgagc aaaactttga ctggagcttc    180
tcatctttgg ggagcagctt tgtggagctt gcaagcacct gggaggtggg gttcccagcc    240
cagctgtacc aggagcggct cagaggggc gagatcctgt taaggcggac tgccaacgac     300
gccgtggagc tccacataaa gaacgtccag ccttcagacc aaggccacta caatgttca     360
accccccagca cagatgccac tgtccaggga aactatgagg acacagtgca ggttaaagtg    420
ctggccgact ccctgcacgt gggccccagc gcgcggcccc cgccgagcct gagcctgcgg    480
gaggggagca ccttcgagct gcgctgcacc gccgcctccg cctcgccgct gcacacgcac    540
ctggcgctgc tgtgggaggt cgaccgcggc cggccaggc ggagcgtcct cgccctgacc      600
cacgagggca ggtccaccc gggcctgggg tacgagcagc gctaccacag tggggacgtg     660
cgcctcgaca ccgtgggcag cgacgcctac cgcctctcag tgtcccggc tctgtctgcc      720
gaccagggct cctacaggtg tatcgtcagc gagtggatcg ccgagcaggg caactggcag    780
gaaatccaag aaaaggccgt ggaagttgcc accgtggtga tccagccatc agttctgcga    840
gcagctgtgc ccaagaatgt gtctgtggct gaaggaaagg aactggacct gacctgtaac    900
atcacaacag accgagccga tgacgtccgg cccgaggtga cgtggtcctt cagcaggatg    960
cctgacagca ccctacctgg ctcccgtgt ttgaccgtga ttccctggtg                1020
cacagctcgc ctcatgttgc tttgagtcat gtggatgcac gctcctacca tttactggtt    1080
cgggatgtta gcaaagaaaa ctctggctac tattactgcc acgtgtccct gtgggcaccc    1140
ggacacaaca ggagctggca caaagtggca gaggccgtgt cttcccagc tggtgtgggt     1200
gtgacctggc tagaaccaga ctaccaggtg tacctgaatg cttccaaggt ccccgggttt    1260
gcggatgacc ccacagagct ggcatgccgg gtggtggaca cgaagagtgg ggaggcgaat    1320
gtccgattca cggtttcgtg gtactacagg atgaaccggc gcagcgacaa tgtggtgacc    1380
agcgagctgc ttgcagtcat ggacggggac tggacgctaa aatatggaga gaggagcaag    1440
cagcgggccc aggatggaga cttattttt tctaaggaac atacagacac gttcaattc     1500
cggatccaaa ggactacaga ggaagacaga ggcaattatt actgtgttgt gtctgcctgg    1560
accaaacagc ggaacaacag ctgggtgaaa agcaaggatg tcttctccaa gcctgttaac    1620
atatttgggg cattagaaga ttccgtgctt gtggtgaagg cgaggcagcc aaagcctttc    1680
tttgctgccg gaaatacatt tgagatgact tgcaaagtat cttccaagaa tattaagtcg    1740
ccacgctact ctgttctcat catggctgag aagcctggcg acctatcca cagtcccaat     1800
gaaacgaagt acatcatctc tctggaccag gattctgtgg tgaagctgga gaattggaca    1860
gatgcatcac gggtggatgg cgttgtttta gaaaaagtgc aggaggatga gttccgctat    1920
cgaatgtacc agactcaggt ctcagacgca gggctgtacc gctgcatggt gacagcctgg    1980
tctcctgtca ggggcaagcct tggcgagaa gcagcaacca gtctctccaa tcctattgag    2040
atagacttcc aaacctcagg tcctatattt aatgcttctg tgcattcaga cacaccatca    2100
gtaattcggg gagatctgat caaattgttc tgtatcatca ctgtcgaggg agcagcactg    2160
gatccagatg acatggcctt tgatgtgtcc tggtttgcgg tgcactcttt tggcctggac    2220
aaggctcctg tgctcctgtc ttccctggat cggaagggca tcgtgaccac ctcccggagg    2280
gactggaaga gcgacctcag cctggagcgc gtgagtgtgc tggaattctt gctgcaagtg    2340
catggctccg aggaccagga ctttggcaac tactactgtt ccgtgactcc atgggtgaag    2400
tcaccaacag gttcctggca gaaggaggca gagatccact ccaagcccgt ttttataact    2460
gtgaagatgg atgtgctgaa cgccttcaag tatcccttgc tgatcggcgt cggtctgtcc    2520
acggtcatcg gctcctgtc ctgtctcatc gggtactgca gctcccactg gtgttgtaag     2580
aaggaggttc aggagacacg gcgcgagcgc cgcaggctca tgtcgatgga gatggactag    2640

SEQ ID NO: 40          moltype = AA   length = 879
FEATURE                Location/Qualifiers
source                 1..879
                       mol_type = protein
                       organism = Homo sapiens
SEQUENCE: 40
MGRLASRPLL LALLSLALCR GRVVRVPTAT LVRVVGTELV IPCNVSDYDG PSEQNFDWSF     60
SSLGSSFVEL ASTWEVGFPA QLYQERLQRG EILLRRTAND AVELHIKNVQ PSDQGHYKCS    120
TPSTDATVQG NYEDTVQVKV LADSLHVGPS ARPPPSLSLR EGEPFELRCT AASASPLHTH    180
LALLWEVHRG PARRSVLALT HEGRFHPGLG YEQRYHSGDV RLDTVGSDAY RLSVSRALSA    240
DQGSYRCIVS EWIAEQGNWQ EIQEKAVEVA TVVIQPSVLR AAVPKNVSVA EGKELDLTCN    300
ITTDRADDVR PEVTWSFSRM PDSTLPGSRV LARLDRDSLV HSSPHVALSH VDARSYHLLV    360
RDVSKENSGY YYCHVSLWAP GHNRSWHKVA EAVSSPAGVG VTWLEPDYQV YLNASKVPGF    420
ADDPTELACR VVDTKSGEAN VRFTVSWYYR MNRRSDNVVT SELLAVMDGD WTLKYGERSK    480
QRAQDGDFIF SKEHTDTFNF RIQRTTEEDR GNYYCVVSAW TKQRNNSWVK SKDVFSKPVN    540
IFWALEDSVL VVKARQPKPF FAAGNTFEMT CKVSSKNIKS PRYSVLIMAE KPGDLSSPN    600
ETKYIISLDQ DSVVKLENWT DASRVDGVVL EKVQEDEFRY RMYQTQVSDA GLYRCMVTAW    660
SPVRGSLWRE AATSLSNPIE IDFQTSGPIF NASVHSDTPS VIRGDLIKLF CIITVEGAAL    720
DPDDMAFDVS WFAVHSFGLD KAPVLLSSLD RKGIVTTSRR DWKSDLSLER VSVLEFLLQV    780
HGSEDQDFGN YYCSVTPWVK SPTGSWQKEA EIHSKPVFIT VKMDVLNAFK YPLLIGVGLS    840
TVIGLLSCLI GYCSSHWCCK KEVQETRRER RRLMSMEMD                          879
```

SEQ ID NO: 41         moltype = DNA  length = 1287
FEATURE               Location/Qualifiers
source                1..1287
                      mol_type = other DNA
                      organism = Homo sapiens
CDS                   1..1287
SEQUENCE: 41
atggcagtgg gggccagtgg tctagaagga gataagatgg ctggtgccat gcctctgcaa    60
ctcctcctgt tgctgatcct actgggccct ggcaacagct tgcagctgtg ggacacctgg   120
gcagatgaag ccgagaaagc cttggtcccc ctgcttgccc gggaccggag acaggccacc   180
gaatatgagt acctagatta tgatttcctg ccagaaacgg agcctccaga aatgctgagg   240
aacagcactg acaccactcc tctgactggg cctggaaccc ctgagtctac cactgtggag   300
cctgctgcaa ggcgttctac tggcctggat gcaggaggga cagtcacaga gctgaccacg   360
gagctggcca acatggggaa cctgtccacg gattcagcag ctatggagat acagaccact   420
caaccagcag ccacggaggc acagaccact caaccagtgc ccacggaggc acagaccact   480
ccactggcag ccacagaggc acagacaact cgactgacgg ccacggaggc acagaccact   540
cctactggca ccacagaggc acagaccact ccaccggaag ccacagaggc acagaccact   600
caacccacag gcctggaggc acagaccact gcaccagcag ccatggaggc acagaccact   660
gcaccagcag ccatggaagc acagaccact ccaccagcag ccatggaggc acagaccact   720
caaaccacag ccatggaggc acagaccact gcaccagaag ccacggaggc acagaccact   780
caaccacagc ccacggaggc acagaccact ccactggcag ccatggaggc acagaccact   840
gaacccagtg ccacagaggc cctgtccatg aacctactac caaaagagg tctgttcata   900
cccttttctg tgtcctctgt tactcacaag ggcattccca tggcagccag caatttgtcc   960
gtcaactacc cagtggggc cccagaccac atctctgtga agcagtgcct gctggccatc  1020
ctaatcttgg cgctggtggc cactatcttc ttcgtgtgca ctgtggtgct ggcggtccgc  1080
ctctcccgca agggccacat gtaccccgtg cgtaattact cccccaccga gatggtctgc  1140
atctcatccc tgttgctga tgggggtgag gggccctctg ccacagccaa tgggggcctg  1200
tccaaggcca gagcccgg cctgacgcca gagcccaggg aggaccgtga ggggatgac   1260
ctcaccctg acagcttcct cccttag                                       1287

SEQ ID NO: 42         moltype = AA  length = 428
FEATURE               Location/Qualifiers
source                1..428
                      mol_type = protein
                      organism = Homo sapiens
SEQUENCE: 42
MAVGASGLEG DKMAGAMPLQ LLLLLILLGP GNSLQLWDTW ADEAEKALGP LLARDRRQAT     60
EYEYLDYDFL PETEPPEMLR NSTDTTPLTG PGTPESTTVE PAARRSTGLD AGGAVTELTT    120
ELANMGNLST DSAAMEIQTT QPAATEAQTT QPVPTEAQTT PLAATEAQTT RLTATEAQTT    180
PLAATEAQTT PPAATEAQTT QPTGLEAQTT APAAMEAQTT APAAMEAQTT PPAAMEAQTT    240
QTTAMEAQTT APEATEAQTT QPTATEAQTT PLAAMEALST EPSATEALSM EPTTKRGLFI    300
PFSVSSVTHK GIPMAASNLS VNYPVGAPDH ISVKQCLLAI LILALVATIF FVCTVVLAVR    360
LSRKGHMYPV RNYSPTEMVC ISSLLPDGGE GPSATANGGL SKAKSPGLTP EPREDREGDD    420
LTLHSFLP                                                             428

SEQ ID NO: 43         moltype = DNA  length = 1239
FEATURE               Location/Qualifiers
source                1..1239
                      mol_type = other DNA
                      organism = Homo sapiens
CDS                   1..1239
SEQUENCE: 43
atgcctctgc aactcctcct gttgctgatc ctactgggcc ctggcaacag cttgcagctg    60
tgggacacct gggcagatga agccgagaaa gccttgggtc ccctgcttgc ccgggaccgg   120
agacaggcca ccgaatatga gtacctagat tatgatttcc tgccagaaac ggagcctcca   180
gaaatgctga ggaacagcac tgacaccact cctctgactg gcctggaac ccctgagtct   240
accactgtgg agcctgctgc aaggcgttct actggcctgg atgcaggagg ggcagtcaca   300
gagctgacca cggagctggc caacatgggg aacctgtcca cggattcagc agctatggag   360
atacagacca ctcaaccagc agccacggag gcacagacca ctcaaccagt gcccacggag   420
gcacagacca ctccactggc agccacagag gcacagacaa ctcgactgac ggccacggag   480
gcacagacca ctccactggc agccacagag gcacagacca ctccaccagc agccacggaa   540
gcacagacca ctcaacccac aggcctggag gcacagacca ctgcaccagc agccatggag   600
gcacagacca ctgcaccagc agccatggaa gcacagacca ctccaccagc agccatggag   660
gcacagacca ctcaaaccac agccatggag gcacagacca ctgcaccaga agccacggag   720
gcacagacca ctcaaccaca gccacggagg cacagaccac tccactggca gccatggag   780
gccctgtcca cagaacccag tgccacagag gccctgtcca tggaacctac taccaaaaga   840
ggtctgttca taccctttc tgtgtcctct gttactcaca agggcattcc catggcagcc   900
agcaatttgt ccgtcaacta cccagtgggg gcccagacc acatctctgt gaagcagtgt   960
ctgctggcca tcctaatctt ggcgctggtg gccactatct tcttcgtgtg cactgtggtg  1020
ctggcggtcc gcctctcccg caagggccac atgtaccccg tgcgtaatta ctcccccacc  1080
gagatggtct gcatctcatc cctgttgcct gatgggggtg aggggccctc tgccacagcc  1140
aatgggggcc tgtccaaggc caagagcccg ggcctgacgc cagagcccag ggaggaccgt  1200
gagggggatg acctcacccct gcacagcttc tcccttag                         1239

SEQ ID NO: 44         moltype = AA  length = 412
FEATURE               Location/Qualifiers
source                1..412
                      mol_type = protein

```
                           organism = Homo sapiens
SEQUENCE: 44
MPLQLLLLLI  LLGPGNSLQL  WDTWADEAEK  ALGPLLARDR  RQATEYEYLD  YDFLPETEPP    60
EMLRNSTDTT  PLTGPGTPES  TTVEPAARRS  TGLDAGGAVT  ELTTELANMG  NLSTDSAAME   120
IQTTQPAATE  AQTTQPVPTE  AQTTPLAATE  AQTTRLTATE  AQTTPLAATE  AQTTPPAATE   180
AQTTQPTGLE  AQTTAPAAME  AQTTAPAAME  AQTTPPAAME  AQTTQTTAME  AQTTAPEATE   240
AQTTQPTATE  AQTTPLAAME  ALSTEPSATE  ALSMEPTTKR  GLFIPFSVSS  VTHKGIPMAA   300
SNLSVNYPVG  APDHISVKQC  LLAILILALV  ATIFFVCTVV  LAVRLSRKGH  MYPVRNYSPT   360
EMVCISSLLP  DGGEGPSATA  NGGLSKAKSP  GLTPEPREDR  EGDDLTLHSF  LP           412

SEQ ID NO: 45          moltype = DNA   length = 1341
FEATURE                Location/Qualifiers
source                 1..1341
                       mol_type = other DNA
                       organism = Homo sapiens
CDS                    1..1341
SEQUENCE: 45
atgtggtggc gtctttggtg gttgttgctt cttcttcttc tcctgtggcc catggtgtgg    60
gccgactaca aagaccatga cggagattat aaagatcatg acatcgatta caaggatgac   120
gatgacaagg gaggagggtc tggaaactct accatgggct ctggtggcgg cggcggctcc   180
ggcggcggcg gatctctcga acttaatttg accgattcag agaatgccac atgcctttat   240
gcgaaatggc agatgaattt cactgttcgg tatgaaacca caaataaaac ttataaaacc   300
gttaccataa gcgaccatgg aactgtgacc tataatggaa gcatatgtgg agatgatcag   360
aatggtccca aaattgctgt tcagttcgga cctggttttct cctggattgc taattttact   420
aaggcagcct ctaccattc catagactca gtttctttta gttacaacac aggggataac   480
acaacgtttc ctgatgccga agataaaggc atactcgtca ttgatgaact cttggccatc   540
agaataccte ttaatgacct gtttagatgc aatagcctct ccaccctgga gaagaatgat   600
gtggtacaac actactggga tgtgttggtt caagcttttg tacaaaatgg gaccgtctct   660
acaaatgagt tcctctgtga taaagacaaa accagtactg tggcaccaac catacacaca   720
acagtgccat ctccaacgac caccccctaca cccaaggaga aacctgaagc cggtacatat   780
tcagtgaata atggaaatga tacatgcctt ctggccacca tgggccttca gctcaacatc   840
actcaggata aggtcgcttc agtcattaac attaaccca atactactca ctctacaggc   900
tcttgcagga gtcacacggc gctcctgcgg ttgaatagca gcaccattaa gtatcttgac   960
tttgtctttg ctgtcaagaa tgagaacaga ttttatctga aagaggtcaa catctctatg  1020
tatttggtca atgggagtgt gttctccatt gctaataaca atctcagcta ctgggatgcc  1080
cctctgggtt cttcctatat gtgcaacaaa gagcagactg tttcagtgtc cggcgcattt  1140
cagattaata cttttgatct tcgggtgcag cctttcaatg tgacacaagg aaagtattcc  1200
accgcccaag agtgttcttt ggatgatgac accatactga tccccatcat tgtaggtgcc  1260
ggcctgagcg gccttattat cgttatcgtc attgcatacg tgattggacg cggaaatct  1320
tatgccggtt atcagacgct t                                            1341

SEQ ID NO: 46          moltype = AA   length = 447
FEATURE                Location/Qualifiers
source                 1..447
                       mol_type = protein
                       organism = Homo sapiens
SEQUENCE: 46
MWWRLWWLLL  LLLLLWPMVW  ADYKDHDGDY  KDHDIDYKDD  DDKGGGSGNS  TMGSGGGGGS    60
GGGGSLELNL  TDSENATCLY  AKWQMNFTVR  YETTNKTYKT  VTISDHGTVT  YNGSICGDDQ   120
NGPKIAVQFG  PGFSWIANFT  KAASTYSIDS  VSFSYNTGDN  TTFPDAEDKG  ILTVDELLAI   180
RIPLNDLFRC  NSLSTLEKND  VVQHYWDVLV  QAFVQNGTVS  TNEFLCDKDK  TSTVAPTIHT   240
TVPSPTTTPT  PKEKPEAGTY  SVNNGNDTCL  LATMGLQLNI  TQDKVASVIN  INPNTTHSTG   300
SCRSHTALLR  LNSSTIKYLD  FVFAVKNENR  FYLKEVNISM  YLVNGSVFSI  ANNNLSYWDA   360
PLGSSYMCNK  EQTVSVSGAF  QINTFDLRVQ  PFNVTQGKYS  TAQECSLDDD  TILIPIIVGA   420
GLSGLIIVIV  IAYVIGRRKS  YAGYQTL                                          447

SEQ ID NO: 47          moltype = DNA   length = 3090
FEATURE                Location/Qualifiers
source                 1..3090
                       mol_type = other DNA
                       organism = Homo sapiens
CDS                    1..3090
SEQUENCE: 47
atgtggtgga gattgtggtg gttgctcctt ctcttgttgt tgctttggcc aatggtatgg    60
gcgacccacc ggccgcccat gtggagccct gtgtggcccg gcggtgggtc cgactacaaa   120
gaccatgacg gagattataa agatcatgac atcgattaca aggatgacga tgacaaggga   180
aacagtacca tgggctcagg cggtggagga ggctccggag gaggtggcag cgcacgcgtg   240
aataaacata aaccgtggtt ggaaccaaca tatcatggga tcgttaccga aaatgataat   300
acagtacttc tggatccacc tctcattgct ttggacaagg acgcacccct caggttcgct   360
gaatcattcg aagttaccgt tacgaaggaa gggaaatat gccgtttcaa gatccatggt   420
caaaacgttc ctttcgacgc cgtcgtggtt gacaagagca ccggcgaagg ggttataaga   480
tctaaggaaa agctcgattg cgaacttcaa aaggattaca gctttactat acaagcgtac   540
gactgccgca aaggcccgga cggacaaat gttaagaaat cccacaaggc cacggtccac   600
atccaagtca atgatgttaa cgaatatgca cctgttttaa aagagaaaga ctataaggct   660
actgtgatag aaggaaaaca atatgatagt atcctgagag tcgaagctgt cgacgcagat   720
tgtagcccac aattttccca aatatgttcc tatgagatta taacctga tgtcccttc    780
accgtagata ggacggata catcaagaat actgaaaagc tgaattatgg taaagagcac   840
cagtacaaac tcacggtgac ggcgtacgat tgcgaaaga agcgtgcaac tgaggactta   900
cttgttaaaa ttagtatcaa accgacgtgt acaccaggct ggcagggctg gaataatcgg   960
```

```
atcgaatacg aacccggaac aggagcactg gctgtgttcc ctaacattca tctcgaaact    1020
tgcgatgaac ctgtggcaag cgtccaagct acggtagaac tggagacatc tcatattggt    1080
aagggatgtg atagagatac ttatagcgag aaaagcctto atcgcttgtg cggcgccgca    1140
gccgaacag cagaactctt gccttctccc tctggcagcc ttaattggac tatgggattg     1200
cctactgata acggtcatga ttccgatcaa gtcttcgaat ttaatggaac acaagctgta    1260
cgcattcctg acggagtggt aagtgtttct ccgaaggaac cctttacaat tagcgtatgg    1320
atgcgccacg gcccctttgg acggaagaaa gaaactatcc tgtgtagctc agacaagact    1380
gacatgaacc gccatcatta ttctttgtac gtacatggtt gtcgtcttat tttcctgttt    1440
cgccaagacc catccgaaga aaagaagtat aggcccgccg aatttcattg gaaactcaac    1500
caagtgtgcg acgaagagtg gcatcattat gttctgaacg ttgagtttcc atccgtcaca    1560
ctgtacgtcg acggtaccag ccatgaacca tttagtgtca cagaagacta tcccctgcac    1620
ccgagtaaaa tcgagacgca actggttgtc ggcgcatgtt ggcaggaatt tagtggcgtc    1680
gagaacgata acgagaccga acccgtcacc gtagcgtccg ccggcgggga tctccatatg    1740
acgcaattct ttcggggtaa cttggccggg ctgcactgac gctctggcaa gctggctgac    1800
aagaaagtta ttgattgctt gtacacgtgt aaagaaggcc ttgatctcca agttctggaa    1860
gattcaggac gaggggtcca aattcaggct catccatccc aactggtgct tacactggaa    1920
ggcgaggatc tgggagagct ggacaaagct atgcaacata tttcctatct caatagtcgc    1980
caatttccaa cacctggcat ccgacgactg aagattacgt caaccattaa atgcttcaat    2040
gaagcaacat gtatcagcgt gccacctgtg gacggatatg ttatggtact gcaacctgaa    2100
gaaccaaaga tttccctctc tggggttcat cacttcgcaa gggccgcaag tgagttcgag    2160
tcctctgagg gagtctttct cttccccgaa ctgcggataa taagtactat tacaaggaa     2220
gtcgaaccag agggagatgg agccgaagat ccaaccgtgc aggagtctct cgtatcagaa    2280
gaaattgtcc atgatcttga cacgtgcgaa gtgacagtaa aagggaaga actcaatcat     2340
gaacaagaat cattggaagt agatatggca cgattgcaac aaaagggaat cgaggtctcc    2400
tcatccgagc ttggtatgac ttttactgga gtagatacga tggcttccta tgaagaagtg    2460
ctgcatcttc tcagatacgg caattggcac gcgcgttctc tgctggacag aaaattcaaa    2520
ctgatttgta gcgaacttaa cggacggtac atatctaatg agttcaaagt agaagttaac    2580
gtgattcata ctgcaaatcc tatggagcat gcggccgctg ccgccgctca acctcaattt    2640
gtccatcccg agcataggtc attcgtggat ctctctggtc ataatttggc aaatccacat    2700
ccctttgctg tggttccatc tacagcaact gtagttattg tagtatgtgt gtcctttctc    2760
gtctttatga tcatattggg cgtcttccgc ataagagcgg cccacaggag aacaatgagg    2820
gaccaagata caggaaaaga aaatgaaatg gattgggatg atagcgcact cacaataacg    2880
gtgaatccaa tggaaacgta cgaagatcaa cattctagcg aagaagaaga agaggaagag    2940
gaagaggaag agtcagaaga tggagaagag aagacgata ttcatcagc tgaaagcgaa      3000
tcttcagaag aagaagg tgaacaaggt gatcctcaaa atgccacacg ccaacaacaa      3060
ctcgaatggg acgattctac attgtcctat                                    3090
SEQ ID NO: 48         moltype = AA  length = 1030
FEATURE               Location/Qualifiers
source                1..1030
                      mol_type = protein
                      organism = Homo sapiens
SEQUENCE: 48
MWWRLWWLLL LLLLLWPMVW ATHRPPMWSP VWPGGGSDYK DHDGDYKDHD IDYKDDDDKG    60
NSTMGSGGGG GSGGGGSARV NKHKPWLEPT YHGIVTENDN TVLLDPPLIA LDKDAPLRFA    120
ESFEVTVTKE GEICGFKIHG QNVPFDAVVV DKSTGEGVIR SKEKLDCELQ KDYSFTIQAY    180
DCGKGPDGIN VKKSHKATVH IQVNDVNEYA PVFKEKSYKA TVIEGKQYDS ILRVEAVDAD    240
CSPQFSQICS YEIITPDVPF TVDKDGYIKN TEKLNYGKEH QYKLTVTAYD CGKKRATEDV    300
LVKISIKPTC TPGWQGWNNR IEYEPGTGAL AVFPNIHLET CDEPVASVQA TVELETSHIG    360
KGCDRDTYSE KSLHRLCGAA AGTAELLPSP SGSLNWTMGL PTDNGHDSDQ VFEFNGTQAV    420
RIPDGVVSVS PKEPFTISVW MRHGPFGRKK ETILCSSDKT DMNRHHYSLY VHGCRLIFLF    480
RQDPSEEKKY RPAEFHWKLN QVCDEEWHHY VLNVEFPSVT LYVDGTSHEP FSVTEDYPLH    540
PSKIETQLVV GACWQEFSGV ENDNETEPVT VASAGGDLHM TQFFRGNLAG LTLRSGKLAD    600
KKVIDCLYTC KEGLDLQVLE DSGRGVQIQA HPSQLVLTLE GEDLGELDKA MQHISYLNSR    660
QFPTPGIRRL KITSTIKCFN EATCISVPPV DGYVMVLQPE EPKISLSGVH HFARAASEFE    720
SSEGVFLFPE LRIISTITRE VEPEGDGAED PTVQESLVSE EIVHDLDTCE VTVEGEELNH    780
EQESLEVDMA RLQQKGIEVS SSELGMTFTG VDTMASYEEV LHLLRYRNWH ARSLLDRKFK    840
LICSELNGRY ISNEFKVEVN VIHTANPMEH AAAAAAQPQF VHPEHRSFVD LSGHNLANPH    900
PFAVVPSTAT VVIVVCVSFL VFMIILGVFR IRAAHRRTMR DQDTGKENEM DWDDSALTIT    960
VNPMETYEDQ HSSEEEEEEE EEEESEDGEE EDDITSAESE SSEEEEGEQG DPQNATRQQQ    1020
LEWDDSTLSY                                                         1030

SEQ ID NO: 49        moltype = DNA  length = 1410
FEATURE              Location/Qualifiers
source               1..1410
                     mol_type = other DNA
                     organism = Homo sapiens
CDS                  1..1410
SEQUENCE: 49
atgtggtggc gattgtggtg gctccttctt cttctgctcc tgctttggcc aatggtgtgg    60
gccgactaca agaccacga cggggattat aaagatcatg acatcgatta caaggatgac    120
gatgataaga cccacgtcag cccaaaccag ggcggcctgc cttcaggtgg cggtagtgga    180
aactccacca tgggctctgg cggcggtggc ggctctggcg gaggaggctc attggaactt    240
aatttcagag attcagaaaa tgccacttgc gctttatgca atggcagat gaatttcaca     300
gtacgctatg aaactacaaa taaaactat aaaactgtaa ccatttcaga ccatggcact     360
gtgacatata atggaagcat ttgtgggat gatcagaatg gtcccaaat agcagtgcag      420
ttcggacctg gcttttcctg gattgcgaat tttaccaagg cagcatctac ttattcaatt    480
gacagcgtcc cattttccta caacactggt gataacacaa catttcctga tgctgaagat    540
aaaggaattc ttactgttga tgaactttg gccatcagaa ttccattgaa tgaccttttt    600
```

```
agatgcaata gtttatcaac tttggaaaag aatgatgttg tccaacacta ctgggatgtt   660
cttgtacaag cttttgtcca aaatggcaca gtgagcacaa atgagttcct gtgtgataaa   720
gacaaaactt caacagtggc acccaccata cacaccactg tgccatctcc tactacaaca   780
cctactccaa aggaaaaacc agaagctgga acctattcag ttaataatgg caatgatact   840
tgtctgctgg ctaccatggg gctgcagctg aacatcactc aggataaggt tgcttcagtt   900
attaacatca accccaatac aactcactcc acaggcagct gccgttctca cactgctcta   960
cttagactca atagcagcac cattaagtat ctagactttg tctttgctgt gaaaaatgaa  1020
aaccgatttt atctgaagga agtgaacatc agcatgtatt tggttaatgg ctccgttttc  1080
agcattgcaa ataacaatct cagctactgg gatgcccccc tgggaagttc ttatatgtgc  1140
aacaaagagc agactgtttc agtgtctgga gcatttcaga taaataccct tgatctaagg  1200
gttcagcctt tcaatgtgac acaaggaaag tattctacag cccaagagtg ttcgctggat  1260
gatgacacca ttcaatccc aattatagtt ggtgctggtc tttcaggctt gattatcgtt  1320
atagtgattg ctagctccca ctggtgttgt aagaaggagg ttcaggagac acggcgcgag  1380
cgccgcaggc tcatgtcgat ggagatggac                                     1410

SEQ ID NO: 50           moltype = AA  length = 470
FEATURE                 Location/Qualifiers
source                  1..470
                        mol_type = protein
                        organism = Homo sapiens
SEQUENCE: 50
MWWRLWWLLL LLLLLWPMVW ADYKDHDGDY KDHDIDYKDD DDKTHVSPNQ GGLPSGGGSG    60
NSTMGSGGGG GSGGGGSLEL NLTDSENATC LYAKWQMNFT VRYETTNKTY KTVTISDHGT   120
VTYNGSICGD DQNGPKIAVQ FGPGFSWIAN FTKAASTYSI DSVSFSYNTG DNTTFPDAED   180
KGILTVDELL AIRIPLNDLF RCNSLSTLEK NDVVQHYWDV LVQAFVQNGT VSTNEFLCDK   240
DKTSTVAPTI HTTVPSPTTT PTPKEKPEAG TYSVNNGNDT CLLATMGLQL NITQDKVASV   300
ININPNTTHS TGSCRSHTAL LRLNSSTIKY LDFVFAVKNE NRFYLKEVNI SMYLVNGSVF   360
SIANNNLSYW DAPLGSSYMC NKEQTVSVSG AFQINTFDLR VQPFNVTQGK YSTAQECSLD   420
DDTILIPIIV GAGLSGLIIV IVIASSHWCC KKEVQETRRE RRRLMSMEMD              470

SEQ ID NO: 51           moltype = DNA  length = 1443
FEATURE                 Location/Qualifiers
source                  1..1443
                        mol_type = other DNA
                        organism = Homo sapiens
CDS                     1..1443
SEQUENCE: 51
atgtggtggc gattgtggtg gctccttctt cttctgctcc tgctttggcc aatggtgtgg    60
gccgactaca aagaccacga cggggattat aaagatcatg acatcgatta caaggatgac   120
gatgataaga cccacgtcag cccaaaccag ggcggcctgc cttcaggtgg cggtagtgga   180
aactccacca tgggctctgg cggcggtggc ggctctggcg gaggaggctc attggaactt   240
aatttgacag attcagaaaa tgccacttgc ctttatgcaa aatggcagat gaatttcaca   300
gtacgctatg aaactacaaa taaaacttat ccatttcaga ccatggcact   360
gtgacatata atggaagcat ttgtggggat gatcagaatg gtcccaaaat agcagtgcag   420
ttcggacctg gcttttcctg gattgcgaat tttaccaagg cagcatctac ttattcaatt   480
gacagcgtct cattttccta caacactggt gataacacaa catttcctga tgctgaagat   540
aaaggaattc ttactgttga tgaacttttg gccatcagaa ttccattgaa tgacttttc    600
agatgcaata gtttatcaac tttggaaaag aatgatgttg tccaacacta ctgggatgtt   660
cttgtacaag cttttgtcca aaatggcaca gtgagcacaa atgagttcct gtgtgataaa   720
gacaaaactt caacagtggc acccaccata cacaccactg tgccatctcc tactacaaca   780
cctactccaa aggaaaaacc agaagctgga acctattcag ttaataatgg caatgatact   840
tgtctgctgg ctaccatggg gctgcagctg aacatcactc aggataaggt tgcttcagtt   900
attaacatca accccaatac aactcactcc acaggcagct gccgttctca cactgctcta   960
cttagactca atagcagcac cattaagtat ctagactttg tctttgctgt gaaaaatgaa  1020
aaccgatttt atctgaagga agtgaacatc agcatgtatt tggttaatgg ctccgttttc  1080
agcattgcaa ataacaatct cagctactgg gatgcccccc tgggaagttc ttatatgtgc  1140
aacaaagagc agactgtttc agtgtctgga gcatttcaga taaataccct tgatctaagg  1200
gttcagcctt tcaatgtgac acaaggaaag tattctacag cccaagagtg ttcgctggat  1260
gatgacacca ttcaatccc aattatagtt ggtgctggtc tttcaggctt gattatcgtt  1320
atagtgattg ctaagtgcgg cttcttcaag cgagcccgca ctcgcgccct gtatgaagct  1380
aagaggcaga aggcggagat gaagagccag ccgtcagaga cagagaggct gaccgacgac  1440
tac                                                                 1443

SEQ ID NO: 52           moltype = AA  length = 481
FEATURE                 Location/Qualifiers
source                  1..481
                        mol_type = protein
                        organism = Homo sapiens
SEQUENCE: 52
MWWRLWWLLL LLLLLWPMVW ADYKDHDGDY KDHDIDYKDD DDKTHVSPNQ GGLPSGGGSG    60
NSTMGSGGGG GSGGGGSLEL NLTDSENATC LYAKWQMNFT VRYETTNKTY KTVTISDHGT   120
VTYNGSICGD DQNGPKIAVQ FGPGFSWIAN FTKAASTYSI DSVSFSYNTG DNTTFPDAED   180
KGILTVDELL AIRIPLNDLF RCNSLSTLEK NDVVQHYWDV LVQAFVQNGT VSTNEFLCDK   240
DKTSTVAPTI HTTVPSPTTT PTPKEKPEAG TYSVNNGNDT CLLATMGLQL NITQDKVASV   300
ININPNTTHS TGSCRSHTAL LRLNSSTIKY LDFVFAVKNE NRFYLKEVNI SMYLVNGSVF   360
SIANNNLSYW DAPLGSSYMC NKEQTVSVSG AFQINTFDLR VQPFNVTQGK YSTAQECSLD   420
DDTILIPIIV GAGLSGLIIV IVIAKCGFFK RARTRALYEA KRQKAEMKSQ PSETERLTDD   480
Y                                                                   481
```

| SEQ ID NO: 53 | moltype = DNA   length = 1479 |
|---|---|
| FEATURE | Location/Qualifiers |
| source | 1..1479 |
| | mol_type = other DNA |
| | organism = Homo sapiens |
| CDS | 1..1479 |

SEQUENCE: 53

```
atgtggtggc gattgtggtg gctccttctt cttctgctcc tgctttggcc aatggtgtgg    60
gccgactaca aagaccacga cggggattat aaagatcatg acatcgatta caaggatgac   120
gatgataaga cccacgtcag cccaaaccag ggcggcctgc cttcaggtgg cggtagtgga   180
aactccacca tgggctctgg cggcggtggc ggctctggcg gaggaggctc attggaactt   240
aatttgacag attcagaaaa tgccacttgc ctttatgcaa aatggcagat gaatttcaca   300
gtacgctatg aaactacaaa taaaacttat aaaactgtaa ccatttcaga ccatggcact   360
gtgacatata atggaagcat ttgtggggat gatcagaatg gtcccaaaat agcagtgcag   420
ttcggacctg gcttttcctg gattgcgaat tttaccaagg cagcatctac ttattcaatt   480
gacagcgtct cattttccta aacactggt gataacacaa catttcctga tgctgaagat   540
aaaggaattc ttactgttga tgaacttttg gccatcagaa ttccattgaa tgaccttttt   600
agatgcaata gtttatcaac tttggaaaag aatgatgttg tccaacacta ctgggatgtt   660
cttgtacaag cttttgtcca aaatggcaca gtgagcacaa atgagttcct gtgtgataaa   720
gacaaaactt caacagtggc acccaccata cacaccactg tgccatctcc tactacaaca   780
cctactccaa aggaaaaacc agaagctgga acctattcag ttaataatgg caatgatact   840
tgtctgctgg ctaccatggg gctgcagctg aacatcactc aggataaggt tgcttcagtt   900
attaacatca accccaatac aactcactcc acaggcagct gccgttctca cactgctcta   960
cttagactca atagcagcac cattaagtat ctagactttg tctttgctgt gaaaaatgaa  1020
aaccgatttt atctgaagga agtgaacatc agcatgtatt tggttaatgg ctccgttttc  1080
agcattgcaa ataacaatct cagctactgg gatgcccccc tgggaagttc ttatatgtgc  1140
aacaaagagc agactgtttc agtgtctgga gcatttcaga taaataccct tgatctaagg  1200
gttcagcctt tcaatgtgac acaaggaaag tattctacag cccaagagtg ttcgctggat  1260
gatgacacca ttcaatccc aattatagtt ggtgctggtc tttcaggctt gattatcgtt  1320
atagtgattg ctgtgatgca gagactcttt ccccgcatcc ctcacatgaa agaccccatc  1380
ggtgacagct ccaaaacga caagctggtg gtctggaagg cgggcaaagc cggcctggag  1440
gagtgtctgg tgactgaagt acaggtcgtg cagaaaact                         1479
```

| SEQ ID NO: 54 | moltype = AA   length = 493 |
|---|---|
| FEATURE | Location/Qualifiers |
| source | 1..493 |
| | mol_type = protein |
| | organism = Homo sapiens |

SEQUENCE: 54

```
MWWRLWWLLL LLLLLWPMVW ADYKDHDGDY KDHDIDYKDD DDKTHVSPNQ GGLPSGGGSG    60
NSTMGSGGGG GSGGGGSLEL NLTDSENATC LYAKWQMNFT VRYETTNKTY KTVTISDHGT   120
VTYNGSICGD DQNGPKIAVQ FGPGFSWIAN FTKAASTYSI DSVSFSYNTG DNTTFPDAED   180
KGILTVDELL AIRIPLNDLF RCNSLSTLEK NDVVQHYWDV LVQAFVQNGT VSTNEFLCDK   240
DKTSTVAPTI HTTVPSPTTT PTPKEKPEAG TYSVNNGNDT CLLATMGLQL NITQDKVASV   300
ININPNTTHS TGSCRSHTAL LRLNSSTIKY LDFVFAVKNE NRFYLKEVNI SMYLVNGSVF   360
SIANNNLSYW DAPLGSSYMC NKEQTVSVSG AFQINTFDLR VQPFNVTQGK YSTAQECSLD   420
DDTILIPIIV GAGLSGLIIV IVIAVMQRLF PRIPHMKDPI GDSFQNDKLV VWEAGKAGLE   480
ECLVTEVQVV QKT                                                     493
```

| SEQ ID NO: 55 | moltype = DNA   length = 1539 |
|---|---|
| FEATURE | Location/Qualifiers |
| source | 1..1539 |
| | mol_type = other DNA |
| | organism = Homo sapiens |
| CDS | 1..1539 |

SEQUENCE: 55

```
atgtggtggc gattgtggtg gctccttctt cttctgctcc tgctttggcc aatggtgtgg    60
gccgactaca aagaccacga cggggattat aaagatcatg acatcgatta caaggatgac   120
gatgataaga cccacgtcag cccaaaccag ggcggcctgc cttcaggtgg cggtagtgga   180
aactccacca tgggctctgg cggcggtggc ggctctggcg gaggaggctc attggaactt   240
aatttgacag attcagaaaa tgccacttgc ctttatgcaa aatggcagat gaatttcaca   300
gtacgctatg aaactacaaa taaaacttat aaaactgtaa ccatttcaga ccatggcact   360
gtgacatata atggaagcat ttgtggggat gatcagaatg gtcccaaaat agcagtgcag   420
ttcggacctg gcttttcctg gattgcgaat tttaccaagg cagcatctac ttattcaatt   480
gacagcgtct cattttccta aacactggt gataacacaa catttcctga tgctgaagat   540
aaaggaattc ttactgttga tgaacttttg gccatcagaa ttccattgaa tgaccttttt   600
agatgcaata gtttatcaac tttggaaaag aatgatgttg tccaacacta ctgggatgtt   660
cttgtacaag cttttgtcca aaatggcaca gtgagcacaa atgagttcct gtgtgataaa   720
gacaaaactt caacagtggc acccaccata cacaccactg tgccatctcc tactacaaca   780
cctactccaa aggaaaaacc agaagctgga acctattcag ttaataatgg caatgatact   840
tgtctgctgg ctaccatggg gctgcagctg aacatcactc aggataaggt tgcttcagtt   900
attaacatca accccaatac aactcactcc acaggcagct gccgttctca cactgctcta   960
cttagactca atagcagcac cattaagtat ctagactttg tctttgctgt gaaaaatgaa  1020
aaccgatttt atctgaagga agtgaacatc agcatgtatt tggttaatgg ctccgttttc  1080
agcattgcaa ataacaatct cagctactgg gatgcccccc tgggaagttc ttatatgtgc  1140
aacaaagagc agactgtttc agtgtctgga gcatttcaga taaataccct tgatctaagg  1200
gttcagcctt tcaatgtgac acaaggaaag tattctacag cccaagagtg ttcgctggat  1260
gatgacacca ttcaatccc aattatagtt ggtgctggtc tttcaggctt gattatcgtt  1320
atagtgattg ctcgcctctc ccgcaagggc cacatgtacc ccgtgcgtaa ttactccccc  1380
```

```
accgagatgg tctgcatctc atccctgttg cctgatgggg gtgagggggcc ctctgccaca    1440
gccaatgggg gcctgtccaa ggccaagagc ccgggcctga cgccagagcc cagggaggac    1500
cgtgaggggg atgacctcac cctgcacagc ttcctccct                            1539

SEQ ID NO: 56          moltype = AA  length = 513
FEATURE                Location/Qualifiers
source                 1..513
                       mol_type = protein
                       organism = Homo sapiens
SEQUENCE: 56
MWWRLWWLLL LLLLLWPMVW ADYKDHDGDY KDHDIDYKDD DDKTHVSPNQ GGLPSGGGSG     60
NSTMGSGGGG GSGGGGSLEL NLTDSENATC LYAKWQMNFT VRYETTNKTY KTVTISDHGT    120
VTYNGSICGD DQNGPKIAVQ FGPGFSWIAN FTKAASTYSI DSVSFSYNTG DNTTFPDAED    180
KGILTVDELL AIRIPLNDLF RCNSLSTLEK NDVVQHYWDV LVQAFVQNGT VSTNEFLCDK    240
DKTSTVAPTI HTTVPSPTTT PTPKEKPEAG TYSVNNGNDT CLLATMGLQL NITQDKVASV    300
ININPNTTHS TGSCRSHTAL LRLNSSTIKY LDFVFAVKNE NRFYLKEVNI SMYLVNGSVF    360
SIANNNLSYW DAPLGSSYMC NKEQTVSVSG AFQINTFDLR VQPFNVTQGK YSTAQECSLD    420
DDTILIPIIV GAGLSGLIIV IVIARLSRKG HMYPVRNYSP TEMVCISSLL PDGGEGPSAT    480
ANGGLSKAKS PGLTPEPRED REGDDLTLHS FLP                                 513

SEQ ID NO: 57          moltype = DNA  length = 1470
FEATURE                Location/Qualifiers
source                 1..1470
                       mol_type = other DNA
                       organism = Homo sapiens
CDS                    1..1470
SEQUENCE: 57
atgtggtggc gattgtggtg gctccttctt cttctgctcc tgctttggcc aatggtgtgg     60
gccgactaca aagaccacga cggggattat aaagatcatg acatcgatta caaggatgac    120
gatgataaga cccacgtcag cccaaaccag ggcggcctgc cttcaggtgg cggtagtgga    180
aactccacca tgggctcagg cggcggtggc ggctctggcg gaggaggctc attggaactt    240
aatttgacag attcagaaaa tgccacttgc ctttatgcaa aatggcagat gaatttcaca    300
gtacgctatg aaactacaaa taaaacttat aaaactgtaa ccatttcaga ccatggcact    360
gtgacatata atggaagcat ttgtggggat gatcagaatg gtcccaaaat agcagtgcag    420
ttcggacctg gcttttcctg gattgcgaat tttaccaagg cagcatctac ttattcaatt    480
gacagcgtct cattttccta caacactggt gataacacaa catttcctga tgctgaagat    540
aaaggaattc ttactgttga tgaacttttg gccatcagaa ttccattgaa tgacttttt     600
agatgcaata gtttatcaac tttggaaaag aatgatgttg tccaacacta ctgggatgtt    660
cttgtacaag cttttgtcca aaatggcaca gtgagcacaa atgagttcct gtgtgataaa    720
gacaaaactt caacagtggc acccaccata cacaccactg tgccatctcc tactacaaca    780
cctactccaa aggaaaaacc agaagctgga acctattcag ttaataatgg caatgatact    840
tgtctgctgc ctaccatggg gctgcagctg aacatcactc aggataaggt tgcttcagtt    900
attaacatca accccaatac aactcactcc acaggcagct gccgttctca cactgctcta    960
cttagactca atagcagcac cattaagtat ctagactttg tctttgctgt gaaaaatgaa   1020
aaccgatttt atctgaagga agtgaacatc agcatgtatt tggttaatgg ctccgttttc   1080
agcattgcaa ataacaatct cagctactgg gatgcccccc tgggaagttc ttatatgtgc   1140
aacaaagagc agactgtttc aagtgtctgga gcatttcaga taaatacctt tgatctaagg   1200
gttcagccctt tcaatgtgac acaaggaaaa tattctacag cccaagagtg ttcgctggat   1260
gatgaccacca ttcaaatccc aattatagtt ggtgctggtc tttcaggctt gattatcgtt   1320
atagtgattg ctctttttaat gataattcat gacagaaggg agtttgctaa atttgaaaag   1380
gagaaaatga atgccaaatg ggacacgggt gaaaatccta tttataagag tgccgtaaca   1440
actgtggtca atccgaagta tgagggaaaa                                     1470

SEQ ID NO: 58          moltype = AA  length = 490
FEATURE                Location/Qualifiers
source                 1..490
                       mol_type = protein
                       organism = Homo sapiens
SEQUENCE: 58
MWWRLWWLLL LLLLLWPMVW ADYKDHDGDY KDHDIDYKDD DDKTHVSPNQ GGLPSGGGSG     60
NSTMGSGGGG GSGGGGSLEL NLTDSENATC LYAKWQMNFT VRYETTNKTY KTVTISDHGT    120
VTYNGSICGD DQNGPKIAVQ FGPGFSWIAN FTKAASTYSI DSVSFSYNTG DNTTFPDAED    180
KGILTVDELL AIRIPLNDLF RCNSLSTLEK NDVVQHYWDV LVQAFVQNGT VSTNEFLCDK    240
DKTSTVAPTI HTTVPSPTTT PTPKEKPEAG TYSVNNGNDT CLLATMGLQL NITQDKVASV    300
ININPNTTHS TGSCRSHTAL LRLNSSTIKY LDFVFAVKNE NRFYLKEVNI SMYLVNGSVF    360
SIANNNLSYW DAPLGSSYMC NKEQTVSVSG AFQINTFDLR VQPFNVTQGK YSTAQECSLD    420
DDTILIPIIV GAGLSGLIIV IVIALLMIIH DRREFAKFEK EKMNAKWDTG ENPIYKSAVT    480
TVVNPKYEGK                                                           490

SEQ ID NO: 59          moltype = DNA  length = 1635
FEATURE                Location/Qualifiers
source                 1..1635
                       mol_type = other DNA
                       organism = Homo sapiens
CDS                    1..1635
SEQUENCE: 59
atgtggtggc gattgtggtg gctccttctt cttctgctcc tgctttggcc aatggtgtgg     60
gccgactaca aagaccacga cggggattat aaagatcatg acatcgatta caaggatgac    120
gatgataaga cccacgtcag cccaaaccag ggcggcctgc cttcaggtgg cggtagtgga    180
```

```
aactccacca tgggctctgg cggcggtggc ggctctggcg gaggaggctc attggaactt    240
aatttgacag attcagaaaa tgccacttgc ctttatgcaa aatggcagat gaatttcaca    300
gtacgctatg aaactacaaa taaaacttat aaaactgtaa ccatttcaga ccatggcact    360
gtgacatata atgaagcatt tgtggggat gatcagaatg tcccaaaat agcagtgcag     420
ttcggacctg gcttttcctg gattgcgaat tttaccaagg cagcatctac ttattcaatt    480
gacagcgtct cattttccta caacactggt gataacacaa catttcctga tgctgaagat    540
aaaggaattc ttactgttga tgaacttttg gccatcagaa ttccattgaa tgacctttt    600
agatgcaata gtttatcaac tttggaaaag aatgatgttg tccaacacta ctgggatgtt    660
cttgtacaag cttttgtcca aaatggcaca gtgagcacaa atgagttcct gtgtgataaa    720
gacaaaactt caacagtggc acccaccata cacaccactg tgccatctcc tactacaaca    780
cctactccaa aggaaaaacc agaagctgga acctattcag ttaataatgg caatgatact    840
tgtctgctgg ctaccatggg gctgcagctg aacatcactc aggataaggt tgcttcagtt    900
attaacatca accccaatac aactcactcc acaggcagct gccgttctca cactgctcta    960
cttagactca atagcagcac cattaagtat ctagactttg tctttgctgt gaaaaatgaa   1020
aaccgatttt atctgaagga agtgaacatc agcatgtatt tggttaatgg ctccgttttc   1080
agcattgcaa ataacaatct cagctactgg gatgcccccc tgggaagttc ttatatgtgc   1140
aacaaagagc agactgtttc agtgtctgga gcatttcaga taaataccctt tgatctaagg   1200
gttcagcctt tcaatgtgac acaaggaaag tattctacag cccaagagtg ttcgctggat   1260
gatgacacca ttctaatccc aattatagtt ggtgctggtc tttcaggctt gattatcgtt   1320
atagtgattg ctcggatccg ggccgcacat cggcggacca tgcgggatca ggacaccggg   1380
aaggagaacg agatggactg gacgactct gccctgacca tcaccgtcaa ccccatggag   1440
acctatgagg accagcacag cagtgaggag gaggaggaga agaagagga agaggaaagc   1500
gaggacggcg aagaagagga tgacatcacc agcgccgagt cggagagcag cgaggaggag   1560
gaggggggagc agggcgaccc ccagaacgca acccggcagc agcagctgga gtgggatgac   1620
tccacccteca gctac                                                   1635

SEQ ID NO: 60          moltype = AA   length = 545
FEATURE                Location/Qualifiers
source                 1..545
                       mol_type = protein
                       organism = Homo sapiens
SEQUENCE: 60
MWWRLWWLLL LLLLLWPMVW ADYKDHDGDY KDHDIDYKDD DDKTHVSPNQ GGLPSGGGSG     60
NSTMGSGGGG GSGGGGSLEL NLTDSENATC LYAKWQMNFT VRYETTNKTY KTVTISDHGT    120
VTYNGSICGD DQNGPKIAVQ FGPGFSWIAN FTKAASTYSI DSVSFSYNTG DNTTFPDAED    180
KGILTVDELL AIRIPLNDLF RCNSLSTLEK NDVVQHYWDV LVQAFVQNGT VSTNEFLCDK    240
DKTSTVAPTI HTTVPSPTTT PTPKEKPEAG TYSVNNGNDT CLLATMGLQL NITQDKVASV    300
ININPNTTHS TGSCRSHTAL LRLNSSTIKY LDFVFAVKNE NRFYLKEVNI SMYLVNGSVF    360
SIANNNLSYW DAPLGSSYMC NKEQTVSVSG AFQINTFDLR VQPFNVTQGK YSTAQECSLD    420
DDTILIPIIV GAGLSGLIIV IVIARIRAAH RRTMRDQDTG KENEMDWDDS ALTITVNPME    480
TYEDQHSSEE EEEEEEEES EDGEEEDDIT SAESESSEEE EGEQGDPQNA TRQQQLEWDD    540
STLSY                                                                545

SEQ ID NO: 61          moltype = DNA   length = 1344
FEATURE                Location/Qualifiers
source                 1..1344
                       mol_type = other DNA
                       organism = Homo sapiens
CDS                    1..1344
SEQUENCE: 61
atgtggtggc gattgtggtg gctccttctt cttctgctcc tgctttggcc aatggtgtgg     60
gccgactaca agaccacga cggggattat aaagatcatg acatcgatta caaggatgac    120
gatgataaga cccacgtcag cccaaaccag ggcggcctgc cttcaggtgg cggtagtgga    180
aactccacca tgggctctgg cggcggtggc ggctctggcg gaggaggctc attggaactt    240
aatttgacag attcagaaaa tgccacttgc ctttatgcaa aatggcagat gaatttcaca    300
gtacgctatg aaactacaaa taaaacttat aaaactgtaa ccatttcaga ccatggcact    360
gtgacatata atgaagcatt tgtggggat gatcagaatg tcccaaaat agcagtgcag     420
ttcggacctg gcttttcctg gattgcgaat tttaccaagg cagcatctac ttattcaatt    480
gacagcgtct cattttccta caacactggt gataacacaa catttcctga tgctgaagat    540
aaaggaattc ttactgttga tgaacttttg gccatcagaa ttccattgaa tgacctttt    600
agatgcaata gtttatcaac tttggaaaag aatgatgttg tccaacacta ctgggatgtt    660
cttgtacaag cttttgtcca aaatggcaca gtgagcacaa atgagttcct gtgtgataaa    720
gacaaaactt caacagtggc acccaccata cacaccactg tgccatctcc tactacaaca    780
cctactccaa aggaaaaacc agaagctgga acctattcag ttaataatgg caatgatact    840
tgtctgctgg ctaccatggg gctgcagctg aacatcactc aggataaggt tgcttcagtt    900
attaacatca accccaatac aactcactcc acaggcagct gccgttctca cactgctcta    960
cttagactca atagcagcac cattaagtat ctagactttg tctttgctgt gaaaaatgaa   1020
aaccgatttt atctgaagga agtgaacatc agcatgtatt tggttaatgg ctccgttttc   1080
agcattgcaa ataacaatct cagctactgg gatgcccccc tgggaagttc ttatatgtgc   1140
aacaaagagc agactgtttc agtgtctgga gcatttcaga taaataccctt tgatctaagg   1200
gttcagcctt tcaatgtgac acaaggaaag tattctacag cccaagagtg ttcgctggat   1260
gatgacacca ttctaatccc aattatagtt ggtgctggtc tttcaggctt gattatcgtt   1320
atagtgattg ctaagaagcc acgt                                           1344

SEQ ID NO: 62          moltype = AA   length = 448
FEATURE                Location/Qualifiers
source                 1..448
                       mol_type = protein
                       organism = Homo sapiens
```

```
SEQUENCE: 62
MWWRLWWLLL LLLLLWPMVW ADYKDHDGDY KDHDIDYKDD DDKTHVSPNQ GGLPSGGGSG    60
NSTMGSGGGG GSGGGGSLEL NLTDSENATC LYAKWQMNFT VRYETTNKTY KTVTISDHGT   120
VTYNGSICGD DQNGPKIAVQ FGPGFSWIAN FTKAASTYSI DSVSFSYNTG DNTTFPDAED   180
KGILTVDELL AIRIPLNDLF RCNSLSTLEK NDVVQHYWDV LVQAFVQNGT VSTNEFLCDK   240
DKTSTVAPTI HTTVPSPTTT PTPKEKPEAG TYSVNNGNDT CLLATMGLQL NITQDKVASV   300
ININPNTTHS TGSCRSHTAL LRLNSSTIKY LDFVFAVKNE NRFYLKEVNI SMYLVNGSVF   360
SIANNNLSYW DAPLGSSYMC NKEQTVSVSG AFQINTFDLR VQPFNVTQGK YSTAQECSLD   420
DDTILIPIIV GAGLSGLIIV IVIAKKPR                                     448

SEQ ID NO: 63         moltype = DNA  length = 36
FEATURE               Location/Qualifiers
source                1..36
                      mol_type = other DNA
                      organism = Homo sapiens
CDS                   1..36
SEQUENCE: 63
acccaccggc cgcccatgtg gagccctgtg tggccc                              36

SEQ ID NO: 64         moltype = AA   length = 12
FEATURE               Location/Qualifiers
source                1..12
                      mol_type = protein
                      organism = Homo sapiens
SEQUENCE: 64
THRPPMWSPV WP                                                        12

SEQ ID NO: 65         moltype = DNA  length = 36
FEATURE               Location/Qualifiers
source                1..36
                      mol_type = other DNA
                      organism = Homo sapiens
CDS                   1..36
SEQUENCE: 65
acccacgtca gcccaaacca gggcggcctg ccttca                              36

SEQ ID NO: 66         moltype = AA   length = 12
FEATURE               Location/Qualifiers
source                1..12
                      mol_type = protein
                      organism = Homo sapiens
SEQUENCE: 66
THVSPNQGGL PS                                                        12

SEQ ID NO: 67         moltype = DNA  length = 1146
FEATURE               Location/Qualifiers
source                1..1146
                      mol_type = other DNA
                      organism = Homo sapiens
CDS                   1..1146
SEQUENCE: 67
ctcgaactta atttgaccga ttcagagaat gccacatgcc tttatgcgaa atggcagatg    60
aatttcactg ttcggtatga aaccacaaat aaaacttata aaaccgttac cataagcgac   120
catgaaactg tgacctataa tggaagcata tgtggagatg atcagaatgg tcccaaaatt   180
gctgttcagt tcggacctgg tttctcctgg attgctaatt ttactaaggc agcctctacc   240
tattccatag actcagtttc ttttagttac aacacagggg ataacacaac gtttcctgat   300
gccgaagata aaggcatact caccgttgat gaactcttgg ccatcagaat acctcttaat   360
gacctgtttc gatgcaatag cctctccacc ctggagaaga atgatgtggt acaacactac   420
tgggatgtgt tggttcaagc tttttgtacaa aatgggaccg tctctacaaa tgagttcctc   480
tgtgataaag acaaaaccag tactgtggca ccaaccatac acacaacagt gccatctcca   540
acgaccaccc ctacacccaa ggagaaacct gaagccggta catattcagt gaataatgga   600
aatgatacat gccttctggc caccatgggc cttcagctca acatcactca ggataaggtc   660
gcttcagtca ttaacattaa ccccaatact actcactcta caggctcttg caggagtcac   720
acggcgctcc tgcggttgaa tagcagcacc attaagtatc ttgactttgt ctttgctgtc   780
aagaatgaga acagattttta tctgaaagag tcaacatctc tatgtatttt ggtcaatggg   840
agtgtgttct ccattgctaa taacaatctc agctactggg atgcccctct ggttcttcc    900
tatatgtgca acaagagca gactgtttca gtgtccggcg catttcagat taatactttt   960
gatcttcggg tgcagccttt caatgtgaca caaggaaagt attccaccgc caagagtgt   1020
tctttggatg atgacaccat actgatcccc atcattgtag tgccggcct gagcggcctt   1080
attatcgtta tcgtcattgc atacgtgatt ggacggcgga aatcttatgc cggttatcag   1140
acgctt                                                             1146

SEQ ID NO: 68         moltype = AA   length = 382
FEATURE               Location/Qualifiers
source                1..382
                      mol_type = protein
                      organism = Homo sapiens
SEQUENCE: 68
LELNLTDSEN ATCLYAKWQM NFTVRYETTN KTYKTVTISD HGTVTYNGSI CGDDQNGPKI    60
```

```
AVQFGPGFSW  IANFTKAAST  YSIDSVSFSY  NTGDNTTFPD  AEDKGILTVD  ELLAIRIPLN   120
DLFRCNSLST  LEKNDVVQHY  WDVLVQAFVQ  NGTVSTNEFL  CDKDKTSTVA  PTIHTTVPSP   180
TTTPTPKEKP  EAGTYSVNNG  NDTCLLATMG  LQLNITQDKV  ASVININPNT  THSTGSCRSH   240
TALLRLNSST  IKYLDFVFAV  KNENRFYLKE  VNISMYLVNG  SVFSIANNNL  SYWDAPLGSS   300
YMCNKEQTVS  VSGAFQINTF  DLRVQPFNVT  QGKYSTAQEC  SLDDDTILIP  IIVGAGLSGL   360
IIVIVIAYVI  GRRKSYAGYQ  TL                                              382

SEQ ID NO: 69           moltype = DNA  length = 2859
FEATURE                 Location/Qualifiers
source                  1..2859
                        mol_type = other DNA
                        organism = Homo sapiens
CDS                     1..2859
SEQUENCE: 69
gcacgcgtga ataaacataa accgtggttg gaaccaacat atcatgggat cgttaccgaa          60
aatgataata cagtacttct ggatccacct ctcattgctt tggacaagga cgcacccctc         120
aggttcgctg aatcattcga agttaccgtt acgaaggaag gggaaatatg cggtttcaag         180
atccatggtc aaaacgttcc tttcgacgcc gtcgtggttg acaagagcac cggcgaaggg         240
gttataagat ctaaggaaaa gctcgattgc gaacttcaaa aggattacag ctttactata         300
caagcgtacg actgcggcaa agggcccgac gggacaaatg ttaagaaatc ccacaaggcc         360
acggtccaca tccaagtcaa tgatgttaac gaatatgcac tgttttcaa agagaaaagc          420
tataaggcta ctgtgataga aggaaaacaa tatgatagta tcctgagagt cgaagctgtt         480
gacgcagatt gtagcccaca attttcccaa atatgttcct atgagattat aacacctgat         540
gtcccttttca ccgtagataa ggacggatac atcaagaata ctgaaaagct gaattatggt        600
aaagagcacc agtacaaact cacggtgacg gcgtacgatt gcggaaagaa gcgtgcaact         660
gaggacgtac ttgttaaaat tagtatcaaa ccgacgtgta caccaggctg gacgggctgg         720
aataatcgga tcgaatacga acccggaaca ggagcactgg ctgtgtttcc taacattcat         780
ctcgaaactt gcgatgaacc tgtggcaagc gtccaagcta cggtagaact ggagacatct         840
catattggta agggatgtga tagagatact atagcgaga aaagccttca tcgcttgtgc          900
ggcgccgcag ccggaacagc agaactcttg ccttctccct ctggcagcct taattggact         960
atgggattgc ctactgataa cggtcatgat tccgatcaag tcttcgaatt taatgaaaca        1020
caagctgtac gcattcctga cggagtggta agtgtttctc cgaaggaacc ctttacaatt        1080
agcgtatgga tgcgccacgg cccctttgga cggaagaaag aaactatcct gtgtagctca        1140
gacaagactg acatgaaccg ccatcattat tcctttatga tcatggtttg tcgtcttatt        1200
ttcctgtttc gccaagaccc atccgaagaa aagaagtata ggcccgccga atttcattgg        1260
aaactcaacc aagtgtgcga cgaagagtgg catcattatg ttctgaacgt tgagtttcca        1320
tccgtcacac tgtacgtcga cggtaccagc catgaaccat ttagtgtcac agaagactat        1380
cccctgcacc cgagtaaaat cgagacgcaa ctggttgtcg gcgcatgttg gcaggaattt        1440
agtggcgtcg agaacgataa cgagaccgaa cccgtcaccg tagcgtccgc cggcggggat        1500
ctccatatga cgcaattctt tcggggtaac ttggccgggc tgacactgcg ctctggcaag        1560
ctggctgaca gaaagttat tgattgcttg tacacgtgta agaaggcct tgatctccaa          1620
gttctggaag attcaggacg aggggtccaa attcaggctc atccatccca actggtgctt        1680
acactggaag gcgaggatct gggagagctg gacaaagcta tgcaacatat ttcctatctc        1740
aatagtcgcc aatttccaac acctggcatc cgacgactga gattacgtc aaccattaaa        1800
tgcttcaatg aagcaacatg tatcagcgtg ccacctgtgg acggatatgt tatggtactg        1860
caacctgaag aaccaaagat ttccctctct ggggttcatc acttcgcaag ggccgcaagt        1920
gagttcgagt cctctgaggg agtctttctc ttttcccgaac tcgggataat aagtactatt        1980
acaagggaag tcgaaccaga gggagatgga gccgaagatc caaccgtgca ggagtctctc        2040
gtatcagaag aaattgtcca tgatcttgac acgtgcgaag tgacagtaga aggggaagaa        2100
ctcaatcatg aacaagaatc attggaagta gatatgcac gattgcaaca aaagggaatc         2160
gaggtctcct catccgagct tggtatgact tttactgaag tagatacgat ggcttcctat        2220
gaagaagtgc tgcatcttct cagataccgc aattggcacg cgcgttctct gctggacaga        2280
aaattcaaac tgatttgtag cgaacttaac ggacggtaca tatctaatga gttcaaagta        2340
gaagttaacg tgattcatac tgcaaatcct atggagcatg cggccgctgc cgccgctcaa        2400
cctcaatttg tccatcccga tcataggtca ttcgtgagtc tctctggtca taatttggca        2460
aatccacatc cctttgctgt ggttccatct acagcaactg tagttattgt agtatgtgtg        2520
tcctttctcg tctttatgat catattgggc gtcttccgca aagagcggc ccacaggaga         2580
acaatgaggg accaagatac aggaaaagaa atgaaatgg attgggatga tagcgcactc         2640
acaataacgg tgaatccaat ggaaacgtac gaagatcaac attctagcga agaagaagaa        2700
gaggaagagg aagaggaaga gtcagaagat gagaagagg aagacaggat tacatcagct         2760
gaaagcgaat cttcagaaga agaagaaggt gaacaaggtg atcctcaaaa tgccacacgc        2820
caacaacaac tcgaatggga cgattctaca ttgtcctat                              2859

SEQ ID NO: 70           moltype = AA  length = 953
FEATURE                 Location/Qualifiers
source                  1..953
                        mol_type = protein
                        organism = Homo sapiens
SEQUENCE: 70
ARVNKHKPWL  EPTYHGIVTE  NDTVLLDPP   LIALDKDAPL  RFAESFEVTV  TKEGEICGFK    60
IHGQNVPFDA  VVVDKSTGEG  VIRSKEKLDC  ELQKDYSFTI  QAYDCGKGPD  GTNVKKSHKA   120
TVHIQVNDVN  EYAPVFKEKS  YKATVIEGKQ  YDSILRVEAV  DADCSPQFSQ  ICSYEIITPD   180
VPFTVDKGY   IKNTEKLNYG  KEHQYKLTVT  AYDCGKKRAT  EDVLVKISIK  PTCTPGWQGW   240
NNRIEYEPGT  GALAVFPNIH  LETCDEPVAS  VQATVELETS  HIGKGCDSIK  YSEKSLHRLC   300
GAAAGTAELL  PSPSGSLNWT  MGLPTDNGHD  SDQVFEFNGT  QAVRIPDGVV  SVSPKEPFTI   360
SVWMRHGPFG  RKKETILCSS  DKTDMNRHHY  SLYVHGCRLI  FLFRQDPSEE  KKYRPAEFHW   420
KLNQVCDEEW  HHYVLNVEFP  SVTLYVDGTS  HEPFSVTEDY  PLHPSKIETQ  LVVGACWQEF   480
SGVENDNETE  PVTVASAGGD  LHMTQFFRGN  LAGLTLRSGK  LADKKVIDCL  YTCKEGLDLQ   540
VLEDSGRGVQ  IQAHPSQLVL  TLEGEDLGEL  DKAMQHISYL  NSRQFPTPGI  RRLKITSTIK   600
```

```
CFNEATCISV PPVDGYVMVL QPEEPKISLS GVHHFARAAS EFESSEGVFL PPELRIISTI    660
TREVEPEGDG AEDPTVQESL VSEEIVHDLD TCEVTVEGEE LNHEQESLEV DMARLQQKGI    720
EVSSSELGMT FTGVDTMASY EEVLHLLRYR NWHARSLLDR KFKLICSELN GRYISNEFKV    780
EVNVIHTANP MEHAAAAAAQ PQFVHPEHRS FVDLSGHNLA NPHPFAVVPS TATVVIVVCV    840
SPLVFMIILG VFRIRAAHRR TMRDQDTGKE NEMDWDDSAL TITVNPMETY EDQHSSEEEE    900
EEEEEEESED GEEEDDITSA ESESSEEEEG EQGDPQNATR QQQLEWDDST LSY           953

SEQ ID NO: 71           moltype = DNA  length = 1179
FEATURE                 Location/Qualifiers
source                  1..1179
                        mol_type = other DNA
                        organism = Homo sapiens
CDS                     1..1179
SEQUENCE: 71
ttggaactta atttgacaga ttcagaaaat gccacttgcc tttatgcaaa atggcagatg     60
aatttcacag tacgctatga aactacaaat aaaacttata aaactgtaac catttcagac    120
catggcactg tgacatataa tggaagcatt tgtggggatg atcagaatgg tcccaaaata    180
gcagtgcagt tcggacctgg cttttcctgg attgcgaatt ttaccaaggc agcatctact    240
tattcaattg acagcgtctc attttcctac aacactggtg ataacacaac atttcctgat    300
gctgaagata aggaattct tactgttgat gaacttttgg ccatcagaat tccattgaat     360
gaccttttta gatgcaatag tttatcaact ttggaaaaga atgatgttgt ccaacactac    420
tgggatgttc ttgtacaagc ttttgtccaa aatggcacag tgagcacaaa tgagttcctg    480
tgtgataaag acaaaacttc aacagtggca cccaccatac acaccactgt gccatctcct    540
actacaacac ctactccaaa ggaaaaacca gaagctggaa cctattcagt taataatggc    600
aatgatactt gtctgctggc taccatgggg ctgcagctga acatcactca ggataaggtt    660
gcttcagtta ttaacatcaa ccccaataca actcactcca caggcagctg ccgttctcac    720
actgctctac ttagactcaa tagcagcacc attaagtatc tagactttgt ctttgctgtg    780
aaaaatgaaa accgatttta tctgaaggaa gtgaacatca gcatgtattt ggttaatggc    840
tccgtttca gcattgcaaa taacaatctc agctactggg atgccccct gggaagttct     900
tatatgtgca acaaagagca gactgtttca gtgtctggag catttcagat aaataccttt    960
gatctaaggg ttcagccttt caatgtgaca caaggaaagt attctacagc ccaagagtgt   1020
tcgctggatg atgacaccat tctaatccca attatagttg gtgctggtct ttcaggcttg   1080
attatcgtta tagtgattgc tagctcccac tggtgttgta agaaggaggt tcaggagaca   1140
cggcgcgagc gccgcaggct catgtcgatg gagatggac                          1179

SEQ ID NO: 72           moltype = AA  length = 393
FEATURE                 Location/Qualifiers
source                  1..393
                        mol_type = protein
                        organism = Homo sapiens
SEQUENCE: 72
LELNLTDSEN ATCLYAKWQM NFTVRYETTN KTYKTVTISD HGTVTYNGSI CGDDQNGPKI     60
AVQFGPGFSW IANFTKAAST YSIDSVSFSY NTGDNTTFPD AEDKGILTVD ELLAIRIPLN    120
DLFRCNSLST LEKNDVVQHY WDVLVQAFVQ NGTVSTNEFL CDKDKTSTVA PTIHTTVPSP    180
TTTPTPKEKP EAGTYSVNNG NDTCLLATMG LQLNITQDKV ASVININPNT THSTGSCRSH    240
TALLRLNSST IKYLDFVFAV KNENRFYLKE VNISMYLVNG SVFSIANNNL SYWDAPLGSS    300
YMCNKEQTVS VSGAFQINTF DLRVQPFNVT QGKYSTAQEC SLDDDTILIP IIVGAGLSGL    360
IIVIVIASSH WCCKKEVQET RRERRRLMSM EMD                                 393

SEQ ID NO: 73           moltype = DNA  length = 1212
FEATURE                 Location/Qualifiers
source                  1..1212
                        mol_type = other DNA
                        organism = Homo sapiens
CDS                     1..1212
SEQUENCE: 73
ttggaactta atttgacaga ttcagaaaat gccacttgcc tttatgcaaa atggcagatg     60
aatttcacag tacgctatga aactacaaat aaaacttata aaactgtaac catttcagac    120
catggcactg tgacatataa tggaagcatt tgtggggatg atcagaatgg tcccaaaata    180
gcagtgcagt tcggacctgg cttttcctgg attgcgaatt ttaccaaggc agcatctact    240
tattcaattg acagcgtctc attttcctac aacactggtg ataacacaac atttcctgat    300
gctgaagata aggaattct tactgttgat gaacttttgg ccatcagaat tccattgaat     360
gaccttttta gatgcaatag tttatcaact ttggaaaaga atgatgttgt ccaacactac    420
tgggatgttc ttgtacaagc ttttgtccaa aatggcacag tgagcacaaa tgagttcctg    480
tgtgataaag acaaaacttc aacagtggca cccaccatac acaccactgt gccatctcct    540
actacaacac ctactccaaa ggaaaaacca gaagctggaa cctattcagt taataatggc    600
aatgatactt gtctgctggc taccatgggg ctgcagctga acatcactca ggataaggtt    660
gcttcagtta ttaacatcaa ccccaataca actcactcca caggcagctg ccgttctcac    720
actgctctac ttagactcaa tagcagcacc attaagtatc tagactttgt ctttgctgtg    780
aaaaatgaaa accgatttta tctgaaggaa gtgaacatca gcatgtattt ggttaatggc    840
tccgtttca gcattgcaaa taacaatctc agctactggg atgccccct gggaagttct     900
tatatgtgca acaaagagca gactgtttca gtgtctggag catttcagat aaataccttt    960
gatctaaggg ttcagccttt caatgtgaca caaggaaagt attctacagc ccaagagtgt   1020
tcgctggatg atgacaccat tctaatccca attatagttg gtgctggtct ttcaggcttg   1080
attatcgtta tagtgattgc taagtgcggc ttcttcaagc gagcccgcac tcgcgccctg   1140
tatgaagcta gaggcagaa ggcggagatg aagagccagc cgtcagagac agagaggctg    1200
accgacgact ac                                                       1212

SEQ ID NO: 74           moltype = AA  length = 404
```

```
FEATURE                 Location/Qualifiers
source                  1..404
                        mol_type = protein
                        organism = Homo sapiens
SEQUENCE: 74
LELNLTDSEN ATCLYAKWQM NFTVRYETTN KTYKTVTISD HGTVTYNGSI CGDDQNGPKI    60
AVQFGPGFSW IANFTKAAST YSIDSVSFSY NTGDNTTFPD AEDKGILTVD ELLAIRIPLN   120
DLFRCNSLST LEKNDVVQHY WDVLVQAFVQ NGTVSTNEFL CDKDKTSTVA PTIHTTVPSP   180
TTTPTPKEKP EAGTYSVNNG NDTCLLATMG LQLNITQDKV ASVININPNT THSTGSCRSH   240
TALLRLNSST IKYLDFVFAV KNENRFYLKE VNISMYLVNG SVFSIANNNL SYWDAPLGSS   300
YMCNKEQTVS VSGAFQINTF DLRVQPFNVT QGKYSTAQEC SLDDDTILIP IIVGAGLSGL   360
IIVIVIAKCG FFKRARTRAL YEAKRQKAEM KSQPSETERL TDDY                    404

SEQ ID NO: 75           moltype = DNA  length = 1248
FEATURE                 Location/Qualifiers
source                  1..1248
                        mol_type = other DNA
                        organism = Homo sapiens
CDS                     1..1248
SEQUENCE: 75
ttggaactta atttgacaga ttcagaaaat gccacttgcc tttatgcaaa atggcagatg    60
aatttcacag tacgctatga aactacaaat aaaacttata aactgtaac catttcagac   120
catggcactg tgacatataa tggaagcatt tgtggggatg atcagaatgg tcccaaaata   180
gcagtgcagt tcggacctgg cttttcctgg attgcgaatt ttaccaaggc agcatctact   240
tattcaattg acagcgtctc attttcctac aacactggtg ataacacaac atttcctgat   300
gctgaagata aaggaattct tactgttgat gaactttttg ccatcagaat tccattgaat   360
gaccttttta gatgcaatag tttatcaact ttggaaaaga atgatgttgt ccaacactac   420
tgggatgttc ttgtacaagc ttttgtccaa aatggcacag tgagcacaaa tgagttcctg   480
tgtgataaag acaaaacttc aacagtggca cccaccatac acaccactgt gccatctcct   540
actacaacac ctactccaaa ggaaaaacca gaagctggaa cctattcagt taataatggc   600
aatgatactt gtctgctggc taccatgggg ctgcagctga acatcactca ggataaggtt   660
gcttcagtta ttaacatcaa ccccaataca actcactcca caggcagctg ccgttctcac   720
actgctctac ttagactcaa tagcagcacc attaagtatc tagactttgt ctttgctgtg   780
aaaaatgaaa accgatttta tctgaaggaa gtgaacatca gcatgtattt ggttaatggc   840
tccgttttca gcattgcaaa taacaatctc agctactggg atgcccccct gggaagttct   900
tatatgtgca acaaagagca gactgtttca gtgtctggag catttcagat aaatacctttt   960
gatctaaggt ttcagccttt caatgtgaca caaggaaagt attctacagc caagagtgt   1020
tcgctggatg atgacaccat tctaatccca attatagttg gtgctggtct ttcaggcttg  1080
attatcgtta tagtgattgc tgtgatgcag agactctttc cccgcatccc tcacatgaaa  1140
gaccccatcg gtgacagctt ccaaaacgac aagctggtgg tctggaggc gggcaaagcc   1200
ggcctggagg agtgtctggt gactgaagta caggtcgtgc agaaaact              1248

SEQ ID NO: 76           moltype = AA  length = 416
FEATURE                 Location/Qualifiers
source                  1..416
                        mol_type = protein
                        organism = Homo sapiens
SEQUENCE: 76
LELNLTDSEN ATCLYAKWQM NFTVRYETTN KTYKTVTISD HGTVTYNGSI CGDDQNGPKI    60
AVQFGPGFSW IANFTKAAST YSIDSVSFSY NTGDNTTFPD AEDKGILTVD ELLAIRIPLN   120
DLFRCNSLST LEKNDVVQHY WDVLVQAFVQ NGTVSTNEFL CDKDKTSTVA PTIHTTVPSP   180
TTTPTPKEKP EAGTYSVNNG NDTCLLATMG LQLNITQDKV ASVININPNT THSTGSCRSH   240
TALLRLNSST IKYLDFVFAV KNENRFYLKE VNISMYLVNG SVFSIANNNL SYWDAPLGSS   300
YMCNKEQTVS VSGAFQINTF DLRVQPFNVT QGKYSTAQEC SLDDDTILIP IIVGAGLSGL   360
IIVIVIAVMQ RLFPRIPHMK DPIGDSFQND KLVVWEAGKA GLEECLVTEV QVVQKT       416

SEQ ID NO: 77           moltype = DNA  length = 1308
FEATURE                 Location/Qualifiers
source                  1..1308
                        mol_type = other DNA
                        organism = Homo sapiens
CDS                     1..1308
SEQUENCE: 77
ttggaactta atttgacaga ttcagaaaat gccacttgcc tttatgcaaa atggcagatg    60
aatttcacag tacgctatga aactacaaat aaaacttata aactgtaac catttcagac   120
catggcactg tgacatataa tggaagcatt tgtggggatg atcagaatgg tcccaaaata   180
gcagtgcagt tcggacctgg cttttcctgg attgcgaatt ttaccaaggc agcatctact   240
tattcaattg acagcgtctc attttcctac aacactggtg ataacacaac atttcctgat   300
gctgaagata aaggaattct tactgttgat gaactttttg ccatcagaat tccattgaat   360
gaccttttta gatgcaatag tttatcaact ttggaaaaga atgatgttgt ccaacactac   420
tgggatgttc ttgtacaagc ttttgtccaa aatggcacag tgagcacaaa tgagttcctg   480
tgtgataaag acaaaacttc aacagtggca cccaccatac acaccactgt gccatctcct   540
actacaacac ctactccaaa ggaaaaacca gaagctggaa cctattcagt taataatggc   600
aatgatactt gtctgctggc taccatgggg ctgcagctga acatcactca ggataaggtt   660
gcttcagtta ttaacatcaa ccccaataca actcactcca caggcagctg ccgttctcac   720
actgctctac ttagactcaa tagcagcacc attaagtatc tagactttgt ctttgctgtg   780
aaaaatgaaa accgatttta tctgaaggaa gtgaacatca gcatgtattt ggttaatggc   840
tccgttttca gcattgcaaa taacaatctc agctactggg atgcccccct gggaagttct   900
tatatgtgca acaaagagca gactgtttca gtgtctggag catttcagat aaatacctttt   960
```

```
gatctaaggg ttcagccttt caatgtgaca caaggaaagt attctacagc ccaagagtgt   1020
tcgctggatg atgacaccat tctaatccca attatagttg gtgctggtct ttcaggcttg   1080
attatcgtta tagtgattgc tcgcctctcc cgcaagggcc acatgtaccc cgtgcgtaat   1140
tactccccca ccgagatggt ctgcatctca tccctgttgc ctgatggggg tgaggggccc   1200
tctgccacag ccaatggggg cctgtccaag gccaagagcc cgggcctgac gccagagccc   1260
agggaggacc gtgaggggga tgacctcacc ctgcacagct cctccct                 1308

SEQ ID NO: 78           moltype = AA   length = 436
FEATURE                 Location/Qualifiers
source                  1..436
                        mol_type = protein
                        organism = Homo sapiens
SEQUENCE: 78
LELNLTDSEN ATCLYAKWQM NFTVRYETTN KTYKTVTISD HGTVTYNGSI CGDDQNGPKI    60
AVQFGPGFSW IANFTKAAST YSIDSVSFSY NTGDNTTFPD AEDKGILTVD ELLAIRIPLN   120
DLFRCNSLST LEKNDVVQHY WDVLVQAFVQ NGTVSTNEFL CDKDKTSTVA PTIHTTVPSP   180
TTTPTPKEKP EAGTYSVNNG NDTCLLATMG LQLNITQDKV ASVININPNT THSTGSCRSH   240
TALLRLNSST IKYLDFVFAV KNENRFYLKE VNISMYLVNG SVFSIANNNL SYWDAPLGSS   300
YMCNKEQTVS VSGAFQINTF DLRVQPFNVT QGKYSTAQEC SLDDDTILIP IIVGAGLSGL   360
IIVIVIARLS RKGHMYPVRN YSPTEMVCIS SLLPDGGEGP SATANGGLSK AKSPGLTPEP   420
REDREGDDLT LHSFLP                                                   436

SEQ ID NO: 79           moltype = DNA   length = 1239
FEATURE                 Location/Qualifiers
source                  1..1239
                        mol_type = other DNA
                        organism = Homo sapiens
CDS                     1..1239
SEQUENCE: 79
ttggaactta atttgacaga ttcagaaaat gccacttgcc tttatgcaaa atggcagatg    60
aatttcacag tacgctatga aactacaaat aaaacttata aaactgtaac catttcagac   120
catggcactg tgacatataa tggaagcatt tgtggggatg atcagaatgg tcccaaaata   180
gcagtgcagt tcggacctgg cttttcctgg attgcgaatt ttaccaaggc agcatctact   240
tattcaattg acagcgtctc attttcctac aacactggtg ataacacaac atttcctgat   300
gctgaagata aggaattct tactgttgat gaacttttgg ccatcagaat tccattgaat   360
gaccttttta gatgcaatag tttatcaact ttggaaaaga atgatgttgt ccaacactac   420
tgggatgttc ttgtacaagc ttttgtccaa aatggcacag tgagcacaaa tgagttcctg   480
tgtgataaag acaaaacttc aacagtggca cccaccatac acaccactgt gccatctcct   540
actacaacac ctactccaaa ggaaaaacca gaagctgaa cctattcagt taataatgac   600
aatgatactt gtctgctggc taccatgggg ctgcagctga acatcactca ggataaggtt   660
gcttcagtta ttaacatcaa ccccaataca actcactcca caggcagctg ccgttctcac   720
actgctctac ttagactcaa tagcagcacc attaagtatc tagactttgt ctttgctgtg   780
aaaaatgaaa accgattttta tctgaaggaa gtgaacatca gcatgtattt ggttaatggc   840
tccgttttca gcattgcaaa taacaatctc agctactggg atgcccccct gggaagttct   900
tatatgtgca acaaagagca gactgtttca gtgtctggag catttcagat aaataccttt   960
gatctaaggg ttcagccttt caatgtgaca caaggaaagt attctacagc ccaagagtgt  1020
tcgctggatg atgacaccat tctaatccca attatagttg gtgctggtct ttcaggcttg  1080
attatcgtta tagtgattgc tcttttaatg ataattcatg acagaaggga gtttgctaaa  1140
tttgaaaagg agaaaatgaa tgccaaatgg gacacgggtg aaaatcctat ttataagagt  1200
gccgtaacaa ctgtggtcaa tccgaagtat gagggaaaa                         1239

SEQ ID NO: 80           moltype = AA   length = 413
FEATURE                 Location/Qualifiers
source                  1..413
                        mol_type = protein
                        organism = Homo sapiens
SEQUENCE: 80
LELNLTDSEN ATCLYAKWQM NFTVRYETTN KTYKTVTISD HGTVTYNGSI CGDDQNGPKI    60
AVQFGPGFSW IANFTKAAST YSIDSVSFSY NTGDNTTFPD AEDKGILTVD ELLAIRIPLN   120
DLFRCNSLST LEKNDVVQHY WDVLVQAFVQ NGTVSTNEFL CDKDKTSTVA PTIHTTVPSP   180
TTTPTPKEKP EAGTYSVNNG NDTCLLATMG LQLNITQDKV ASVININPNT THSTGSCRSH   240
TALLRLNSST IKYLDFVFAV KNENRFYLKE VNISMYLVNG SVFSIANNNL SYWDAPLGSS   300
YMCNKEQTVS VSGAFQINTF DLRVQPFNVT QGKYSTAQEC SLDDDTILIP IIVGAGLSGL   360
IIVIVIALLM IIHDRREFAK FEKEKMNAKW DTGENPIYKS AVTTVVNPKY EGK          413

SEQ ID NO: 81           moltype = DNA   length = 1404
FEATURE                 Location/Qualifiers
source                  1..1404
                        mol_type = other DNA
                        organism = Homo sapiens
CDS                     1..1404
SEQUENCE: 81
ttggaactta atttgacaga ttcagaaaat gccacttgcc tttatgcaaa atggcagatg    60
aatttcacag tacgctatga aactacaaat aaaacttata aaactgtaac catttcagac   120
catggcactg tgacatataa tggaagcatt tgtggggatg atcagaatgg tcccaaaata   180
gcagtgcagt tcggacctgg cttttcctgg attgcgaatt ttaccaaggc agcatctact   240
tattcaattg acagcgtctc attttcctac aacactggtg ataacacaac atttcctgat   300
gctgaagata aggaattct tactgttgat gaacttttgg ccatcagaat tccattgaat   360
gaccttttta gatgcaatag tttatcaact ttggaaaaga atgatgttgt ccaacactac   420
```

```
tgggatgttc ttgtacaagc ttttgtccaa aatggcacag tgagcacaaa tgagttcctg    480
tgtgataaag acaaaacttc aacagtggca cccaccatac acaccactgt gccatctcct    540
actacaacac ctactccaaa ggaaaaacca gaagctggaa cctattcagt taataatggc    600
aatgatactt gtctgctggc taccatgggg ctgcagctga acatcactca ggataaggtt    660
gcttcagtta ttaacatcaa ccccaataca actcactcca caggcagctg ccgttctcac    720
actgctctac ttagactcaa tagcagcacc attaagtatc tagactttgt ctttgctgtg    780
aaaaatgaaa accgatttta tctgaaggaa gtgaacatca gcatgtattt ggttaatggc    840
tccgttttca gcattgcaaa taacaatctc agctactggg atgccccct gggaagttct     900
tatatgtgca acaaagagca gactgtttca gtgtctggag catttcagat aaataccttt    960
gatctaaggg ttcagccttt caatgtgaca caaggaaagt attctacagc caagagtgt    1020
tcgctggatg atgacaccat tctaatccca attatagttg gtgctggtct ttcaggcttg   1080
attatcgtta tagtgattgc tcggatccgg gccgcacatc ggcggaccat gcgggatcag   1140
gacaccggga aggagaacga gatggactgg gacgactctg ccctgaccat caccgtcaac   1200
cccatggaga cctatgagga ccagcacagc agtgaggagg aggaggaaga ggaagaggaa   1260
gaggaaagcg aggacggcga agaagaggat gacatcacca gcgccgagtc ggagagcagc   1320
gaggaggagg aggggagca gggcgacccc cagaacgcaa cccggcagca gcagctggag   1380
tgggatgact ccaccctcag ctac                                          1404

SEQ ID NO: 82          moltype = AA   length = 468
FEATURE                Location/Qualifiers
source                 1..468
                       mol_type = protein
                       organism = Homo sapiens
SEQUENCE: 82
LELNLTDSEN ATCLYAKWQM NFTVRYETTN KTYKTVTISD HGTVTYNGSI CGDDQNGPKI   60
AVQFGPGFSW IANFTKAAST YSIDSVSFSY NTGDNTTFPD AEDKGILTVD ELLAIRIPLN  120
DLFRCNSLST LEKNDVVQHY WDVLVQAFVQ NGTVSTNEFL CDKDKTSTVA PTIHTTVPSP  180
TTTPTPKEKP EAGTYSVNNG NDTCLLATMG LQLNITQDKV ASVININPNT THSTGSCRSH  240
TALLRLNSST IKYLDFVFAV KNENRFYLKE VNISMYLVNG SVFSIANNNL SYWDAPLGSS  300
YMCNKEQTVS VSGAFQINTF DLRVQPFNVT QGKYSTAQEC SLDDDTILIP IIVGAGLSGL  360
IIVIVIARIR AAHRRTMRDQ DTGKENEMDW DDSALTITVN PMETYEDQHS SEEEEEEEE   420
EESEDGEEED DITSAESESS EEEEGEQGDP QNATRQQQLE WDDSTLSY               468

SEQ ID NO: 83          moltype = DNA   length = 1113
FEATURE                Location/Qualifiers
source                 1..1113
                       mol_type = other DNA
                       organism = Homo sapiens
CDS                    1..1113
SEQUENCE: 83
ttggaactta atttgacaga ttcagaaaat gccacttgcc tttatgcaaa atggcagatg    60
aatttcacag tacgctatga aactacaaat aaaacttata aaactgtaac catttcagac   120
catggcactg tgacatataa tggaagcatt tgtggggatg atcagaatgg tcccaaaata   180
gcagtgcagt tcggacctgg cttttcctgg attgcgaatt ttaccaaggc agcatctact   240
tattcaattg acagcgtctc attttcctac aacactggtg ataacacaac atttcctgat   300
gctgaagata aaggaattct tactgttgat gaacttttgg ccatcagaat tccattgaat   360
gacctttta gatgcaatag tttatcaact ttggaaaaga tgatgttgt ccaacactac    420
tgggatgttc ttgtacaagc ttttgtccaa aatggcacag tgagcacaaa tgagttcctg   480
tgtgataaag acaaaacttc aacagtggca cccaccatac acaccactgt gccatctcct   540
actacaacac ctactccaaa ggaaaaacca gaagctggaa cctattcagt taataatggc   600
aatgatactt gtctgctggc taccatgggg ctgcagctga acatcactca ggataaggtt   660
gcttcagtta ttaacatcaa ccccaataca actcactcca caggcagctg ccgttctcac   720
actgctctac ttagactcaa tagcagcacc attaagtatc tagactttgt ctttgctgtg   780
aaaaatgaaa accgatttta tctgaaggaa gtgaacatca gcatgtattt ggttaatggc   840
tccgttttca gcattgcaaa taacaatctc agctactggg atgccccct gggaagttct    900
tatatgtgca acaaagagca gactgtttca gtgtctggag catttcagat aaataccttt   960
gatctaaggg ttcagccttt caatgtgaca caaggaaagt attctacagc caagagtgt   1020
tcgctggatg atgacaccat tctaatccca attatagttg gtgctggtct ttcaggcttg  1080
attatcgtta tagtgattgc taagaagcca cgt                               1113

SEQ ID NO: 84          moltype = AA   length = 371
FEATURE                Location/Qualifiers
source                 1..371
                       mol_type = protein
                       organism = Homo sapiens
SEQUENCE: 84
LELNLTDSEN ATCLYAKWQM NFTVRYETTN KTYKTVTISD HGTVTYNGSI CGDDQNGPKI   60
AVQFGPGFSW IANFTKAAST YSIDSVSFSY NTGDNTTFPD AEDKGILTVD ELLAIRIPLN  120
DLFRCNSLST LEKNDVVQHY WDVLVQAFVQ NGTVSTNEFL CDKDKTSTVA PTIHTTVPSP  180
TTTPTPKEKP EAGTYSVNNG NDTCLLATMG LQLNITQDKV ASVININPNT THSTGSCRSH  240
TALLRLNSST IKYLDFVFAV KNENRFYLKE VNISMYLVNG SVFSIANNNL SYWDAPLGSS  300
YMCNKEQTVS VSGAFQINTF DLRVQPFNVT QGKYSTAQEC SLDDDTILIP IIVGAGLSGL  360
IIVIVIAKKP R                                                       371
```

NON-NATURALLY OCCURRING VESICLES COMPRISING A CHIMERIC VESICLE LOCALIZATION MOIETY, METHODS OF MAKING AND USES THEREOF

This application is a 111 application of and claims priority to U.S. Ser. No. 17/795,857, filed Jul. 27, 2022, which claims priority to PCT application No. PCT/US2021/015334, filed Jan. 27, 2021, which claims the benefit under 35 U.S.C. § 119(e) to U.S. Provisional Application No. 62/966,487, filed on Jan. 27, 2020, the contents of which is incorporated herein by reference in its entirely for all purposes. All publications, gene transcript identifiers, patents, and patent applications mentioned in this specification tire herein incorporated by reference to the same extent as if each individual publication, gene transcript identifiers, patent, or patent application was specifically and individually indicated to be incorporated by reference.

The present application contains a Sequence Listing XML that has been filed in electronic format in the form of a XML file, created Mar. 28, 2023, and named 20230328 VLM sequence listing.XML (164 KB). The information in the electronic format of the Sequence Listing XML is incorporated by reference in its entirety.

BACKGROUND

There are many different types of vesicles. Extracellular vesicles (EVs) can be membrane-based structures. In nature, EVs can serve as vehicles that carry different types of cellular cargo—such as lipids, proteins, receptors and effector molecules—to the recipient cells. Exosomes are a type of EV that can be released into the extracellular environment following fusion of multivesicular bodies with the plasma membrane. Exosome production has been described in cells, including B cells, T cells, and dendritic cells (DCs). However, there remains a need for more efficient EV biogenesis or localization and this invention addresses that need.

SUMMARY OF THE INVENTION

Provided herein are non-naturally occurring vesicles comprising a chimeric vesicle localization moiety for efficient EV biogenesis or localization. Merely by way of example, the chimeric vesicle localization moiety may comprise a surface-and-transmembrane domain of a first vesicle localization moiety and a cytosolic domain of a second vesicle localization moiety. Such chimeric vesicle localization moiety may additionally comprise one or more tissue or cell targeting moieties for targeting exosomes to a tissue or a specific cell type. Also, the invention provides fusion proteins containing chimeric vesicle localization moieties, vectors comprising nucleic acid sequences encoding such fusion proteins, genetically modified cells comprising such vectors, methods of making the non-naturally occurring vesicles of the invention, pharmaceutical compositions and kits containing same.

BRIEF DESCRIPTION OF FIGURES OF THE INVENTION

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1 is a map of EV-localizing fusion proteins produced from expression vectors 91, 112, 135, 140 and 141. Numbers represent length in nucleotides for the marks on the line above, Arrangement of notable biological sequences are indicated by various arrows used to represent signal sequence, epitope sequence, affinity peptide, linkers, glycosylation site, and a vesicle localization moiety (vector #91 for LAMP2; vector #112 for CLSTN1) or a chimeric vesicle localization moiety comprising LAMP2 surface-and-transmembrane domain and cytosolic domain of PTGFRN or Prostaglandin F2 Receptor Inhibitor (vector #135). ITGA3 or Integrin Alpha 3 (vector #140), or IL3RA or interleukin 3 Receptor Subunit Alpha (vector #141). Note that the coding sequence for LAMP2 in vector #91 and that for CLSTN1 in vector #121 are for the respective nature protein which lacks the signal sequence (first 28 amino acid) present in the native LAMP2 nascent protein and native CLSTN1 nascent protein, respectively.

FIG. 2 is a map of EV-localizing fusion proteins produced from expression vectors 142, 141, 144 and 145. Numbers represent length in nucleotides for the marks on the line above. Arrangement of notable biological sequences are indicated by various arrows used to represent signal sequence, epitope sequence, affinity peptide, linkers, glycosylation site, and a chimeric vesicle localization moiety comprising LAMP2 surface-and-transmembrane domain and cytosolic domain of SELPLG or P-Selectin Glycoprotein Ligand 1 (vector #142). ITGB1 or Integrin Beta-1 (vector #143), or CLSTN1 or Calsyntenin-1 (vector #144). An expression vector (vector #145) serves as a control for ability for a truncated LAMP2 vesicle localization moiety retaining LAMP2 surface-and-transmembrane domain but lacking LAMP2 cytosolic domain to localize at an EV; the LAMP2 cytosolic domain has been replaced with a highly positive charged 4-amino acid peptide, KKPR (vector #145).

FIG. 3 provides the amino acid sequence of EV-localizing fusion proteins encoded by expression vector 91 (LAMP2) and produced when the expression vector is introduced into HEK293F cells along with the location of notable biological sequences. The bold, regular text signifies a signal sequence ta portion of the translated sequence that helps the polypeptide be synthesized by the cell and inserted into a membrane, but is not present in the mature protein that gets incorporated into an EV). The lowercase text signifies a glycosylation site. The underlined text signifies an epitope sequence. The boxed text signifies linker sequence. The italicized text signifies a surface domain. The italicized, hold text signifies a transmembrane domain. The italicized, underlined text signifies a cytosolic domain (also considered to be lumenal domain when at an EV), The highlighted text signifies an affinity peptide. The signal sequence used here is a signal peptide sequence for optimal expression and secretion in human cells, and the epitope tag used here is 3×FLAG epitope tag.

FIG. 4 provides the amino acid sequence of EV-localizing fusion proteins encoded by expression vector 112 (CLSTN1) and produced when the expression vector is introduced into HEK293F cells along with the location of notable biological sequences. The bold text signifies a signal sequence (a portion of the translated sequence that helps the polypeptide be synthesized by the cell and insert into a membrane, but is not present in the mature protein that gets incorporated into an EV). The lowercase text signifies a glycosylation site. The underlined text signifies an epitope sequence. The boxed text signifies linker sequence. The italicized text signifies a surface domain. The italicized, hold text signifies a transmembrane domain. The italicized, underlined text signifies a cytosolic domain (also considered to be lumenal domain when at an EV). The highlighted text signifies an affinity peptide: THRPPMWSPVWP (SEQ ID NO.: 64). The signal sequence used here is a signal peptide sequence for optimal expression and secretion in human cells, and the epitope tag used here is 3×FLAG epitope tag.

FIG. 5 provides the amino acid sequence of EV-localizing fusion proteins encoded by expression vector 135 (a chimeric vesicle localization moiety comprising LAMP2 surface-and-transmembrane domain and cytosolic domain of PTGFRN) and vector 140 (a chimeric localization moiety comprising LAMP2 surface-and-transmembrane domain and cytosolic domain of ITGA31 and produced when the expression vector is introduced into HEK293F cells along with the location of notable biological sequences. The bold text signifies a signal sequence (a portion of the translated sequence that helps the polypeptide be synthesized by the cell and insert into a membrane, but is not present in the mature protein that gets incorporated into an EV). The lowercase text signifies a glycosylation site. The underlined text signifies an epitope sequence. The boxed text signifies linker sequence. The italicized text signifies a surface domain. The italicized, bold text signifies a transmembrane domain. The italicized, underlined text signifies a cytosolic domain (also considered to be lumenal domain when at an EV). The highlighted text signifies an affinity peptide: THVSPNQGGLPS (SEQ ID NO.: 66). The signal sequence used here is a signal peptide sequence for optimal expression and secretion in human cells, and the epitope tag used here is 3×FLAG epitope tag.

FIG. 6 provides the amino acid sequence of EV-localizing fusion proteins encoded by expression vector 141 (a chimeric vesicle localization moiety comprising LAMP2 surface-and-transmembrane domain and cytosolic domain of IL3RA) and vector 142 (a chimeric vesicle localization moiety comprising LAMP2 surface-and-transmembrane domain and cytosolic domain of SELPLG) and produced when the expression vector is introduced into HEK293F cells along with the location of notable biological sequences. The bold text signifies a signal sequence (a portion of the translated sequence that helps the polypeptide be synthesized by the cell and insert into a membrane, but is not present in the mature protein that gets incorporated into an EV). The lowercase text signifies a glycosylation site. The underlined text signifies an epitope sequence. The boxed text signifies linker sequence. The italicized caps text a surface domain. The italicized, bold text signifies a transmembrane domain. The italicized, underlined text signifies a cytosolic domain (also considered to be lumenal domain when at an EV). The highlighted text signifies an affinity peptide: THVSPNQGGLPS (SEQ ID NO.: 66). The signal sequenced used here is a signal peptide sequence for optimal expression and secretion in human cells, and the epitope tag used here is 3×FLAG epitope tag.

FIG. 7 provides the amino acid sequence of EV-localizing fusion proteins encoded by expression vector 143 (a chimeric vesicle localization moiety comprising LAMP2 surface-and-transmembrane domain and cytosolic domain of ITGB1) and vector 144 (a chimeric vesicle localization moiety comprising LAMP2 surface-and-transmembrane domain and cytosolic domain of CLSTN1) and produced when the expression vector is introduced into HEK293F cells along with the location of notable biological sequences. The hold text signifies a signal sequence (a portion of the translated sequence that helps the polypeptide be synthesized by the cell and insert into a membrane, but is not present in the mature protein that gets incorporated into an EV). The lowercase text signifies a glycosylation site. The underlined text signifies an epitope sequence. The boxed text signifies linker sequence. The italicized text signifies a surface domain. The italicized, bold text signifies a transmembrane domain. The italicized, underlined text signifies a cytosolic domain (also considered to be lumenal domain when at an EV). The highlighted text signifies an affinity peptide: THVSPNQGGLPS (SEQ ID NO.: 66), The signal sequence used here is a signal peptide sequence for optimal expression and secretion in human cells, and the epitope tag used here is 3×FLAG epitope tag.

FIG. 8 provides the amino acid sequence of EV-localizing fusion proteins encoded by expression vector 145 (truncated LAMP2 having surface-and-transmembrane domain but lacking LAMP2 cytosolic domain, which has been replaced with a positively charged 4-amino acid peptide, KKPR) and produced when the expression vector is introduced into HEK293F cells along with the location of notable biological sequences. The bold text signifies a signal sequence (a portion of the translated sequence that helps the polypeptide be synthesized by the cell and insert into a membrane, but is not present in the nature protein that gets incorporated into an EV). The lowercase text signifies a glycosylation site. The underlined text signifies an epitope sequence. The boxed text signifies linker sequence. The italicized text signifies a surface domain. The italicized, bold text signifies a transmembrane domain. The italicized, underlined text signifies a cytosolic domain (also considered to be lumenal domain when at an EV). The highlighted text signifies an affinity peptide: THVSPNQGGLPS (SEQ ID NO.: 66) in vector 145. The signal sequence used here is a signal peptide sequence for optimal expression and secretion in human cells for vector 145. The epitope tag used here is a 3×FLAG epitope tag, FIG. 9 provides the amino acid sequences for the mature LAMP2 and CLSTN1 vesicle localization moieties in the fusion proteins produced from expression vectors #91 and #112, respectively. The italicized text signifies a surface domain, topologically equivalent to an extracellular domain and is sometimes referred to as an extracellular domain of a transmembrane protein. The three contiguous domains (surface, transmembrane and cytosolic domains) are indicated. The italicized text signifies a surface domain, topologically equivalent to an extracellular domain and is sometimes referred to as an extracellular domain of a transmembrane protein. The italicized, hold text signifies a transmembrane domain. The italicized, underlined text signifies a cytosolic domain (also referred to as a lumenal domain when at an EV)

FIG. 10 provides the amino acid sequences of the mature chimeric vesicle localization moieties in the fusion proteins produced from expression vectors #135, #140 and #141. The chimeric vesicle localization moieties share an amino acid sequence of the surface-and-transmembrane domain of LAMP2 at the amino-terminal end (indicated by italicized text for surface domain and italicized, bold text for a transmembrane domain) and amino acid sequences for the cytosolic domain of PTGFRN or Prostaglandin F2 Receptor Inhibitor (vector #135), ITGA3 or Integrin Alpha 3 (vector #140), IL3RA or interleukin 3 Receptor Alpha (vector #141), indicated by italicized, underlined text and at the carboxyl-terminal end. Note that the cytosolic domain of LAMP2 has been replaced in these chimeric vesicle localization moieties.

FIG. 11 provides the amino acid sequences of the mature chimeric vesicle localization moieties in the fusion proteins produced from expression vectors #142 and #143. The chimeric vesicle localization moieties share an amino acid sequence of the surface-and-transmembrane domain of LAMP2 at the amino-terminal end (indicated by italicized text for surface domain and italicized, bold text for a transmembrane domain) and amino acid sequences for the cytosolic domain of SELPLG or P-Selectin Glycoprotein Ligand 1 (vector #142) and ITGB1 or Integrin Beta-1 (vector #143), indicated by italicized, underlined text and at the carboxyl-terminal end. Note that the cytosolic domain of LAMP2 has been replaced in these chimeric vesicle localization moieties.

FIG. 12 provides the amino acid sequences of the mature chimeric vesicle localization moiety in the fusion protein produced from expression vector #144 and a mature truncated LAMP2 protein in the fusion protein produced from expression vector #145. The amino acid sequences corresponding to the surface-and-transmembrane domain of LAMP2 is indicated by indicated by italicized text for surface domain and italicized, bold text for a transmembrane domain. The cytosolic domain of LAMP2 has been replaced with the cytosolic domain of CLSTN1 or Calsyntenin-1 (vector #144) or a high positively charged tetrapeptide sequence, KKPR (vector #145), indicated by italicized, underlined text.

FIGS. 13 and 14 provide mean abundance of a recombinant or fusion protein on an EV, and fraction (or percent) of total EVs positive for the recombinant or fusion protein produced by the expression vector constructs of FIGS. 1 and 2 following transfection into HEK293F cells, respectively. FIG. 13 shows IN populations isolated from cells transfected with the indicated vector number. Isolated EVs were stained with a mouse monoclonal antibody specific to an epitope sequence encoded in the EV surface domain of each recombinant or fusion protein. The Y-axis (mean recombinant protein density per exosome) represents the relative amount (on average) of antibody bound to each EV positively identified to comprise the recombinant or fusion protein and excludes those EVs not stained by the antibody, serving as an indirect measure of the abundance of recombinant or fusion protein incorporated into each EV which contains the recombinant or fusion protein. The background signal associated with EVs from mock transfected cells has been subtracted from these values. FIG. 14 shows the fraction of the total EV population displaying a detectable amount of the recombinant or fusion protein.

FIGS. 15 and 16 show fold increase in mean fusion protein abundance on EV surface, and fold increase in fraction (or percent) of total EVs positive for the recombinant or fusion protein relative to fusion protein produced by vector #91 construct (fusion protein with LAMP2 vesicle localization moiety lacking signal sequence following incorporation into an EV), respectively. FIG. 15 shows enrichment of recombinant proteins in EVs: A) EV populations were isolated from cells transfected with the indicated vector numbers. Isolated EVs were stained with a mouse monoclonal antibody specific to an epitope sequence encoded in the IN surface domain of each recombinant protein. The Y-axis represents the relative amount (on average) of antibody bound to each EV, serving as an indirect measure of the abundance of recombinant protein incorporated into each UV, relative to vector #91. The background signal associated with UVs from mock transfected cells has been subtracted from these values. FIG. 16 shows enrichment of recombinant proteins in EVs: EV populations were isolated from cells transfected with the indicated vector numbers, Isolated EVs were stained with a mouse monoclonal antibody specific to an epitope sequence encoded in the EV surface domain of each recombinant protein. The Y-axis represents the fraction of the total EV population displaying a detectable amount of the recombinant protein on the EV surface, relative to vector #91. The background signal associated with EVs from mock transfected cells has been subtracted from these values. Compared to the fusion protein produced by vector #91, the fusion protein produced by vector #112 (fusion protein with CLSTN1 vesicle localization moiety having CLSTN1 surface-transmembrane-and-cytosolic domain but no CLSTN1 signal sequence) concentrates at a much lower level, about 25% the abundance of the LAMP2-vesicle localization moiety (compare values of #91 and #112 in FIG. 15). Surprisingly, when the cytosolic domain LAMP2 is replaced with the cytosolic domain of the CLSTN1, the new chimeric vesicle localization moiety increases by about 2-fold the abundance of the fusion protein over its parental LAMP2 (compare values of #91 and #144) or over 8-fold the abundance of the fusion protein over its parental CLSTN1 (compare values of #112 and #144), indicative of synergistic interaction involving the surface-and-transmembrane domain of LAMP2 and the cytosolic domain of CLSTN1 that leads to increased EV localization.

DETAILED DESCRIPTION OF THE INVENTION

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present teachings, some exemplary methods and materials are now described. References to exemplary nucleic acid and amino acid sequences and, when applicable their respective SEQ ID Nos, are provided in the Tables herein.

Modified extracellular vesicles are provided which comprise chimeric vesicle localization moieties (also referred to as "chimeric vesicle targeting moiety(ies)") that enhance the efficient EV biogenesis or localization. Also provided are chimeric vesicle localization moieties that enhance the efficient EV biogenesis or localization. Recombinant plasmids that express chimeric vesicle localization moieties may be used to genetically modify mammalian cells with enhanced properties for enriching in extracellular vesicles, based on the nucleic acid encoding the chimeric vesicle localization moieties, disclosed herein. The chimeric vesicle localization moieties may be produced in vitro or isolated from a cell and later introduced into an extracellular vesicle from an EV producer cell. Such chimeric vesicle localization moieties may additionally comprise one or more targeting moieties. Such targeting moiety(ies) can be engineered to be included on the vesicle surface. The vesicles contemplated herein can include a payload. Such payload can preferably be one that is nut naturally present in the vesicle. Such payload cart be a natural or synthetic bioactive molecule for eliciting a phenotypic modification in the target cell or tissue of interest. In some instances, a payload is useful for the treatment of a condition. In some instances, a payload is a reporter for screening, detecting, and/or diagnosing a condition in a cell or a subject.

The targeting moieties provided herein can allow selective targeting or focused delivery of appropriate payloads to the cells of interest. This selective targeting or focused delivery can reduce delivery of therapeutics to oft-target tissue and cell types, and/or reduce toxicity of the treatment.

Extracellular Vesicles

An extracellular vesicle can be a membrane that encloses an internal space. Extracellular vesicles can be cell-derived bubbles or vesicles made of the same material as cell membranes, such as phospholipids. Cell-derived extracellular vesicles can be smaller than the cell from which they are derived and range in diameter from about 20 nm to 1000 nm (e.g., 20 nm to 1000 nm; 20 nm to 200 nm; 90 nm to 150 nm). Such vesicles can be created through the outward budding and fission from plasma membranes, assembled at and released from an endomembrane compartment, or derived from cells or vesiculated organelles having undergone apoptosis, and can contain organelles. They can be produced in an endosome by inward budding into the endosomal lumen resulting in intraluminal vesicles of a multivesicular body (MVB) and released extracellularly as exosomes upon fusion of the multivesicular body (MVB) with the plasma membrane. They can be derived from cells by direct and indirect manipulation that may involve the destruction of said cells. They can also be derived from a living or dead organism, an explanted tissue or organ, and/or a cultured cell.

Examples of extracellular vesicles include exosomes, ectosome, microvesicle, microsome or other cell-derived membrane vesicles. Other cell-derived membrane vesicles include a shedding vesicle, a plasma membrane-derived vesicle, and/or an exovesicle.

An "extracellular vesicle" used here is produced by cells, and may comprise a phospholipid membrane bilayer enclosing a luminal space. The membrane bilayer incorporates proteins and other macromolecules derived from the cell of origin. The luminal space encapsulates lipids, proteins, organic molecules and macromolecules including nucleic acids and polypeptides.

Exosomes can be secreted membrane-enclosed vesicles that originate from the endosome compartment in cells. The endosome compartment, or the multi-vesicular body, can fuse with the plasma membrane of the cell, with ensuing release to the extracellular space of their vesicles as exosomes. Further, an exosomes can comprise a bilayer membrane, and can comprise various macromolecular cargo either within the internal space, displayed on the external surface of the extracellular vesicle, and/or spanning the membrane. Cargo can comprise nucleic acids, proteins, carbohydrates, lipids, small molecules, and/or combinations thereof. Exosomes can range in size from about 20 nm to about 300 nm. Additionally, the exosome may have an average diameter in the range of about 50 nm to about 220 nm. Preferably, in a specific embodiment, the exosome has an average diameter of about 120 nm±20 nm.

In some instances, exosomes and other extracellular vesicles can be characterized and marked based on their protein compositions, such as integrins and tetraspanins. Other protein markers that are used to characterize exosomes and other extracellular vesicles (EVs) include TSG101, ALG-2 interacting protein X (ALIX), flotillin I, and cell adhesion molecules which are derived from the parent cells in which the exosome and/or UV is formed. Similar to proteins, lipids can be major components of exosomes and EVs and can be utilized to characterize them.

Further, naturally occurring exosomes can originate from the endosome and can contain proteins such as heat shock proteins Hsp70 and Hsp90), membrane transport and fusion proteins (GTPases, Annexins and flotillin), tetraspanins (CD9, CD63, CD81, and CD82) and proteins such as CD47. Among these proteins, heat shock proteins, annexins, and proteins of the Rab family can abundantly be detected in exosomes and can be involved in their intracellular assembly and trafficking. Tetraspanins, a family of transmembrane proteins, can also be detected in exosomes. In a cell, tetraspanins can mediate fusion, cell migration, cell-cell adhesion, and signaling. Other abundant proteins found in exosomes can be the integrins, which can be adhesion molecules that can facilitate cell binding to the extracellular matrix. Integrins can be involved in adhering the vesicles to their target cells. Certain proteins that can be found on the surface of exosomes, such as CD55 and CD59, can protect exosomes from lysis by circulating immune cells, while CD47 on exosomes can act as an anti-phagocytic signal that blocks the uptake of exosomes by immune cells. Other proteins that can be associated with exosomes include thrombospondin, lactadherin, ALIX (also known as PDCD61P), TSG1012, and SDCB1. Classes of membrane proteins that can naturally occur on the surface of exosomes and other extracellular vesicles include ICAMs, MHC Class 1, LAMP2, lactadherin (C1C2 domain), tetraspanins (CD63, CD81, CD82, CD53, and CD37), Tsg101, Rab proteins, integrins, Alix, and lipid raft-associated proteins such as glycosylphosphatidylinositol (GPI)-modified proteins and flotillin.

Besides proteins, exosomes can also be rich in lipids, with different types of exosomes containing different types of lipids. The lipid bilayer of exosomes can be constituted of cell plasma membrane types of lipids such as sphingomyelin, phosphatidylcholine, phosphatidylethanolamine, phosphatidylserine, monosialotetrahexosylganglioside (GM3), and phosphatidylinositol. Other types of lipids that can be found in exosomes are cholesterol, ceramide, and phosphoglycerides, along with saturated fatty-acid chains. Additional optional constituents of exosomes can include nucleic acids such as micro RNA (miRNA), messenger RNA (mRNA), and non-coding RNAs. Exosomes can also contain a sugar (e.g., a simple sugar, polysaccharide, or glycan) or other molecules.

An extracellular vesicle can have a longest dimension, such as a cross-sectional diameter, of at least about 10, 20, 30, 40, 50, 60, 70, 80, 90, 100, 200, 300, 400, or 500 nm and/or at most about 1000, 500, 400, 300, 200, 100, 90, 80, 70, 60, or 50 nm. In some instances, a longest dimension of a vesicle can range from about 10 nm to about 1000 nm, about 20 nm to about 1000 nm, about 30 nm to about 1000 nm, about 10 nm to about 100 nm, about 20 nm to about 100 nm, about 30 nm to about 100 nm, about 40 nm to about 100 nm, about 10 nm to about 200 nm, about 20 nm to about 200 nm, about 30 nm to about 200 nm, about 40 nm to about 200 nm, about 10 nm to about 120 nm, about 20 nm to about 120 nm, such as about 30 nm to about 120 nm, about 40 nm to about 120 nm, about 10 nm to about 300 nm, about 20 nm to about 300 nm, about 30 nm to about 300 nm, about 40 nm to about 300 nm, about 50 nm to about 1000 nm, about 500 nm to about 2000 nm, about 100 nm to about 500 nm, about 500 nm to about 1000 nm, and such as about 40 nm to about 500 nm, each range inclusive. When referring to a plurality of vesicles, such ranges can represent the average of all vesicles, including naturally occurring and modified vesicles in the mix.

As used herein, the term "average" may be mean, node or medium for a group of measurements.

As used herein, the term "about" when used before a numerical designation, e.g., diameter, size, temperature, time, amount, concentration, and such other, including a range, indicates approximations which may vary by (+) or (−) 10%, 5% or 10%.

As used herein the singular forms "a", "and", and "the" include plural referents unless the context clearly dictates otherwise. Thus, for example, reference to "a cell" includes a plurality of such cells and reference to "the culture" includes reference to one or more cultures and equivalents thereof known to those skilled in the art, and so forth.

Without being bound by any theory, a "vesicle localization moiety" (also referred to as a vesicle targeting moiety) may be a macromolecule that localizes at an extracellular vesicle. In an embodiment, the vesicle localization moiety is a polypeptide. In an embodiment, the vesicle localization moiety is a protein. In an embodiment, the protein is a single polypeptide chain. In an embodiment, the vesicle localization moiety is a protein that localizes at an extracellular vesicle. In an embodiment, the vesicle localization moiety is a membrane protein. In a preferred embodiment, the vesicle localization moiety is a transmembrane protein comprising a surface domain, a transmembrane domain and a cytosolic domain. Localization of such a transmembrane protein at an extracellular vesicle results in the surface domain at the outer surface of the vesicle, the transmembrane domain with the lipid bilayer of the vesicle and the cytosolic domain in the lumen of the vesicle. Because of topological equivalence, a surface domain may also be referred to as an extracellular domain, since the surface domain on the surface of an exosome shares the same topological state as plasma membrane bound transmembrane protein on the surface of a cell; similarly, a cytosolic domain may be referred to as a lumenal domain, since part of the cytoplasm where the cytosolic domain initially resides is incorporated into the lumen of a vesicle produced by inward budding of an endosomal membrane to eventually produce multiple intraluminal vesicles of a multivesicular body (MVB) prior to secretion of the vesicles as exosomes upon fusion of the MVB with the plasma membrane of an EV producer cell.

In an embodiment, the vesicle localization moiety may be a single pass transmembrane protein. Merely by way of example, the single pass transmembrane protein may comprise an amino-terminal surface domain and a carboxyl-terminal cytosolic domain (lumenal domain) joined by a transmembrane domain. For example, nascent or newly synthesized single pass transmembrane protein may additionally comprise a signal peptide preceding the surface domain, which is cleaved by a signal peptidase upon translocation of the nascent protein into a membrane, such as endoplasmic reticulum in eukaryotes or plasma membrane in prokaryotes. In another embodiment, the nascent or newly synthesized transmembrane protein may be processed to a mature transmembrane protein which lacks a signal peptide of the nascent or newly synthesized transmembrane protein.

In one example, the single pass transmembrane protein is a type I transmembrane protein. In an embodiment, the single pass, Type I transmembrane protein comprises an amino-terminal surface domain and a carboxyl-terminal cytosolic domain (lumenal domain) joined by a transmembrane domain. In another embodiment, nascent or newly synthesized single pass, type I transmembrane protein additionally comprises a signal peptide preceding the surface domain, which is cleaved by a signal peptidase upon translocation of the nascent protein into a membrane, such as endoplasmic reticulum in eukaryotes or plasma membrane in prokaryotes. In yet another embodiment, the nascent or newly synthesized single pass, type I transmembrane protein is processed to a mature single pass, type I transmembrane protein which lacks a signal peptide of the nascent or newly synthesized single pass, type I transmembrane protein. In a preferred embodiment, the nascent or newly synthesized single pass, type I transmembrane protein may be processed to a mature single pass, type I transmembrane protein which lacks a signal peptide of the nascent or newly synthesized single pass, type I transmembrane protein.

The vesicle localization moiety may have a surface domain, a transmembrane domain and a cytosolic domain. Such protein domains are known in the art and are well annotated and defined for the proteins described, herein, in the figures and in annotations associated with Accession Numbers from publicly available databases, referred herein, such as UniProtKB (UniProt Release 2019_11 (11 Dec. 2019); The UniProt Consortium (2019) UniProt: a worldwide hub of protein knowledge. Nucleic Acids Res. 47:0506-515) and Genome Reference Consortium Human Build 38 patch release 13 (GRCh38.p13; GenBaank assembly accession GCA_000001405.28 and RelSeq assembly accession GCF_000001405.39).

In an embodiment of the invention, the vesicle localization moiety is produced in a eukaryotic cell, preferably a mammal and most preferably a human, in another embodiment, a vesicle localization moiety may be linked to a targeting moiety either covalently in a fusion protein comprising the vesicle localization moiety and a targeting moiety or non-covalently through a pair of interacting domains or surfaces shared between a polypeptide comprising the vesicle localization moiety and a second polypeptide comprising a targeting moiety.

A "chimeric vesicle localization moiety" is a vesicle localization moiety which may be produced by substituting one vesicle localization domain with another vesicle localization domain, so as to produce a chimeric vesicle localization moiety. A chimeric vesicle localization moiety may be obtained by combining one or more functional domains of one vesicle localization moiety with one or more functional domains of another, different vesicle localization moiety. The combination comprises portion(s) of at least two vesicle localization moieties, so as to obtain a chimeric vesicle localization moiety which is superior in its association with an EV than either of the parental vesicle localization moiety, as quantified by mean recombinant protein density on EV surface and/or traction (or percent) of total EVs positive for the recombinant protein. In an embodiment, the chimeric vesicle localization moiety comprises a surface domain, a transmembrane domain and a lumenal or cytosolic domain of a transmembrane protein or the two parental transmembrane proteins from which it is derived. In an embodiment, the chimeric vesicle localization moiety has the same arrangement of surface domain, transmembrane domain and lumenal or cytosolic domain as described for the vesicle localization moiety, described above. Merely by way of example, a chimeric vesicle localization moiety comprising a surface-and-transmembrane domain of a first vesicle localization moiety and a cytosolic domain of a second vesicle localization moiety may interact synergistically to increase accumulation at an extracellular vesicle. This not only may improve FN localization but may also change the composition of EVs.

The chimeric vesicle localization moiety can be a single pass transmembrane protein. The chimeric vesicle localization moiety can be a type I transmembrane protein, albeit a chimeric type I transmembrane protein. The chimeric vesicle localization moiety can be a single pass, type I transmembrane protein, albeit a chimeric single pass, type I transmembrane protein. In an embodiment, the chimeric vesicle localization moiety comprises an amino-terminal surface domain and a carboxyl-terminal cytosolic domain (lumenal domain) joined by a transmembrane domain. In an embodiment, nascent or newly synthesized chimeric vesicle localization moiety additionally comprises a signal peptide preceding the surface domain, which is cleaved by a signal peptidase upon translocation of the nascent protein into a membrane, such as endoplasmic reticulum in eukaryotes or plasma membrane in prokaryotes. In an embodiment, the nascent or newly synthesized chimeric vesicle localization moiety is processed to a mature form which lacks a signal peptide of the nascent or newly synthesized transmembrane protein. In an embodiment, the nascent or newly synthesized chimeric vesicle localization moiety is processed to a mature transmembrane protein which lacks a signal peptide of the nascent or newly synthesized transmembrane protein. In an embodiment, the extracellular vesicle comprises a chimeric vesicle localization moiety which has been processed to a mature form lacking a signal peptide of a nascent or newly synthesized chimeric vesicle localization moiety, a transmembrane protein. In an embodiment, the chimeric vesicle localization moiety lacking a signal peptide or nature form may be any of the chimeric vesicle localization moiety as provided in FIGS. 10-12 or Table 5, corresponding to the chimeric vesicle localization moiety in vector #135, #140, #141, #142, #143 and #144. In an embodiment, nucleic acid sequences provided in Table 5 for chimeric vesicle localization moieties may be used to produce polypeptides comprising a chimeric vesicle localization moiety. Furthermore, a nucleic acid comprising a coding sequence for a targeting moiety of interest may be fused in-frame with a coding sequence for a chimeric vesicle localization moiety as provided in Table 5 to encode for a polypeptide comprising a targeting moiety and a chimeric vesicle localization moiety. Examples of such nucleic acids encoding a polypeptide comprising an affinity peptide as a targeting moiety and a chimeric vesicle localization moiety can be seen in Table 3 for vector #135, #140, #141, #142, #143 and #144 as well as the amino acid sequence of said polypeptide in Table 3 and also in FIGS. 5-8.

In a preferred embodiment, the cytosolic domain of one vesicle localization moiety is used to replace that of another so as to obtain a chimeric vesicle localization moiety with a surface-and-transmembrane domain of one vesicle localization moiety and a cytosolic domain of a second vesicle localization moiety. Other types of domain swapping between different vesicle localization moieties are contemplated, including chimeric vesicle localization moieties having the arrangement of ABc, AbC, Abc, aBC, aBc and abC, where A, B and C correspond to the surface domain, transmembrane domain and cytosolic domain, respectively, of a first vesicle localization moiety and a, b, and c correspond to the surface domain, transmembrane domain and cytosolic domain, respectively, of a second vesicle localization moiety. Similarly, for any chimeric vesicle localization moiety with surface domain, transmembrane domain and cytosolic domain, obtained by combining domains from about 3 or 4 distinct vesicle localization moieties, the possible number of chimeric vesicle localization moieties contemplated are about 24 and 60, respectively.

While the desired chimeric vesicle localization moieties are ones with superior localization to EVs (over parental vesicle localization moieties contributing to the chimeric vesicle localization moiety), it is also contemplated that some of these chimeric vesicle localization moieties may have desirable qualities other than ability to associate with or be incorporated as part of an EV. In a preferred embodiment, the chimeric vesicle localization moiety comprises a surface-and-transmembrane domain of a first ($1^{st}$) vesicle localization moiety and a cytosolic domain of a second ($2^{nd}$) vesicle localization moiety, which is a full-length surface-and-transmembrane domain of the $1^{st}$ vesicle localization moiety and a full-length cytosolic domain of a $2^{nd}$ vesicle localization moiety. In a preferred embodiment, the surface domain and transmembrane domain are contiguous derived from a $1^{st}$ vesicle localization moiety and a cytosolic domain from a $2^{nd}$ vesicle localization moiety.

In a separate embodiment, the chimeric vesicle localization moiety comprises a surface domain or portion thereof and a transmembrane domain or portion thereof of a $1^{st}$ vesicle localization moiety and a cytosolic domain or portion thereof of a $2^{nd}$ vesicle localization moiety. In a separate embodiment, the chimeric vesicle localization moiety comprises a surface domain or portion thereof, a transmembrane domain or portion thereof, and a cytosolic domain or portion thereof, where each domain is chosen from two or more vesicle localization moieties.

In an embodiment, the chimeric vesicle localization moiety additionally comprises a signal peptide. In an embodiment, the nascent or newly synthesized polypeptide of the chimeric vesicle localization moiety comprises a signal peptide sequence at the N-terminus. In an embodiment, the nascent polypeptide or newly synthesized polypeptide is a polypeptide being produced or initially produced by ribosome translation of a mRNA encoding the chimeric vesicle localization moiety. In an embodiment, the nascent or newly synthesized polypeptide of the chimeric vesicle localization moiety comprises from amino-to-carboxyl terminus in the order: signal peptide, surface domain, transmembrane domain and cytosolic domain. In an embodiment, the nascent or newly synthesized polypeptide of the chimeric vesicle localization moiety may additionally comprise any one or more linkers, affinity peptides, epitope tags and/or glycosylation sites. In an embodiment, the signal peptide sequence may be a naturally occurring sequence or an engineered (not naturally occurring) sequence. In an embodiment, the engineered signal peptide sequence may be an artificial signal peptide sequence which directs strong protein secretion and expression in human cells. In an embodiment, the engineered signal peptide may be MWWRLWWLLLLLLLLWPMVWA.

Examples of suitable affinity peptides include, but are not limited to, those shown in Table 3: THRPPMWSPVWP (SEQ ID NO.: 64), a targeting moiety(ies) or peptide for transferrin receptor (TfR), and THVSPNQGGLPS (SEQ ID NO.: 66), a targeting moiety(ies) or peptide for glypican-3 (GPC3). Examples of suitable linkers include, but are not limited to, any of $(Gly)_8$, $(Gly)_6$, $(GS)_n$ (n=1-5), $(GGGS)_n$ (n=1-5), $(GGGS)_n$ (n=1-5), $(GGGGS)_n$ (n=1-5), $(GGGGGS)_n$ (n=1-5) $(EAAAK)_n$ (n=1-3), $A(EAAAK)_4ALEA(EAAAK)_4A$, $(GGGGS)_n$ (n=1-4), $(Ala-Pro)_n$ (10-34 aa), cleavable linkers such as VSQTSKLTRAETVFPDV, PLGLWA, RVLAEA; EDVVCCSMSY; GGIEGRGS, TRHRQPRGWE, AGNRVRRSVG, RRRRRRRR, GLFG, and LE. Examples of suitable epitope tags include, but are not limited to, FLAG tags such as single or 3×FLAG tags, Myc tags, V5 tags, S-tags, HA tags, 6×His tag, or a combination thereof.

In a separate embodiment, the chimeric vesicle localization moiety lacks a signal peptide. In an embodiment, the chimeric vesicle localization moiety is a mature or processed polypeptide. In an embodiment, the mature or processed polypeptide lacks the signal peptide sequence of the nascent polypeptide. In an embodiment, the mature or processed polypeptide comprises a glycosylation site. In un embodiment, the mature or processed polypeptide is a glycoprotein. In an embodiment, the glycoprotein comprises glycans. In an embodiment, the glycoprotein comprises N-linked glycan, O-linked glycan, phosphoglycan, C-linked glycan and/or GPI anchor. In an embodiment, the chimeric vesicle localization moiety is a mature or processed vesicle localizing polypeptide found in association or incorporated by an EV and lacks a signal peptide sequence present in the nascent polypeptide prior to maturation or processing.

"Surface domain" is a subset of the protein or polypeptide primary sequence that is exposed to the extra-EV environment. The surface domain may be a loop between two transmembrane domains or it can contain one of the termini (amino or carboxy) of the protein. Protein domain topology relative to the membrane bi-layer can be determined empirically by assessing what portions of the protein are digested by an external protease. More recently, characteristic amino acid patterns, such as basic or acidic residues in the juxtamembrane regions of the protein have been used to algorithmically assign probable topologies (extracellular versus cytosolic) to integral membrane proteins. Since EVs have the same membrane topology orientation as the plasma membrane of the whole cell (the outer leaflet of the membrane is the same between cells and EVs), these algorithms can be applied to EV resident proteins as well. As such, the surface domain of an EV localizing transmembrane protein may sometimes be referred to as an extracellular domain due to the same membrane topology of an EV and plasma membrane. For example, the "surface domain" may be a short peptide of approximately 10-15 amino acids. In one embodiment, the "surface domain" may be an unstructured polypeptide. In another embodiment, the "surface domain" is the entire surface domain of an integral membrane protein. In yet another embodiment, the "surface domain" is part or portion of the surface domain of an integral membrane protein. In an embodiment, the surface domain is amino terminal to the transmembrane domain and cytosolic domain. In an embodiment, the surface domain is at the N-terminus of the vesicle localization moiety or the chimeric vesicle localization moiety and is on the external surface of an extracellular vesicle, such as an exosome.

"Transmembrane domain" may be a span of about 18-40 aliphatic, apolar and hydrophobic amino acids that assembles into an alpha-helical secondary structure and spans from one face of a membrane bilayer to the other face, meaning that the N-terminus of the helix extends at least to and in many cases beyond the phospholipid headgroups of one membrane leaflet while the C-terminus extends to the phospholipid headgroups of the other leaflet. In an embodiment, the transmembrane domain connects an amino terminal surface domain with a carboxyl terminal cytosolic domain.

"Cytosolic domain" is a subset of the protein or polypeptide primary sequence that is exposed to the intra-EV or intracellular environment. The cytosolic domain can be a loop between two transmembrane domains or it can contain one of the termini (amino or carboxy) of the protein. Its topology is distinct from that of the transmembrane and the surface domains. In an embodiment, the cytosolic domain is in the cytoplasmic side of a cell. In another embodiment, the cytosolic domain is in the lumen of a vesicle. In an embodiment, the cytosolic domain is at the C-terminus of the vesicle localization moiety or the chimeric vesicle localization moiety.

Merely by way of example, sequences corresponding to "surface domain," "transmembrane domain" and "cytosolic domain" for the proteins disclosed herein may be found within the description under protein accession numbers provided herein. Particularly useful examples are the proteins cataloged within UniProtKB (UniProt Release 2019_11 (11 Dec. 2019)) where under each accession number amino acid sequence along with features and functional domains are provided. For example, topological domains associated with each of the transmembrane vesicle localization moiety provided herein may be found in UniProKB accession number with the description of "extracellular" for the "surface domain," "helical" for the "transmembrane domain" and "cytoplasmic" for the "cytosolic domain." Amino acid sequences corresponding to "signal peptide" are also indicated as being processed out of the mature transmembrane protein. In addition, at number of other publicly available databases may also be used to identify the surface (extracellular), transmembrane and cytosolic (lumenal or cytoplasmic) domain, such as Membranome: membrane proteome of single-helix transmembrane proteins (membranome.org; Lomize, A. L. et al. (2017) Membranome: a database for proteome-wide analysis of single-pass membrane proteins. Nucleic Acids Res. 45:D250-D255 and Lomize, A. L. et al. (2018) Membranome 2.0: database for proteome-wide profiling of bitopic proteins and their dimers. Biointformatics 34:1061-1062) and PDBTM: Protein Data Bank of Transmembrane Proteins (pdbtm.enzim.bu; PDBTM version 2021-01-08) (Kozma, D. et al. (2013) Nucleic Acids Res. 41:D524-D529) Outside of these curated publicly available databases, the classification of transimembrane proteins and identification of surface, transmembrane and cytosolic domains are reviewed in Goder. V. and Spiess, M. (2001) Topogenesis of membrane proteins: determinants and dynamics. FEBS Lett. 504:87-93; Tusnady. G. et al. (2004) Transmembrane proteins in the Protein Data Bank, identification and classification. Bioinformatics 20:2964-2972; Chou. K.-C. and Shen, H-B. 12007) MemType-2L: A Web server for predicting membrane proteins and their types by incorporating evolution information through Pse-PSSM. Biochem. Biophys. Res. Comm. 360:330-345; Casadio R., Martelli P. L., Bartoli L., Fariselli P. (2010) Topology prediction of membrane proteins: how distantly related homologs come into play. In: Structural Bioinformatics of Membrane Proteins, Springer, Vienna.

In a preferred embodiment, a "chimeric vesicle localization moiety" comprises the "surface-and-transmembrane domain" of one vesicle localization moiety and the "cytosolic domain" of a second vesicle localization moiety, wherein the two vesicle localization moieties are different and distinct proteins and are not isoforms. In an embodiment, the "chimeric vesicle localization moiety" comprises the "surface-and-transmembrane domain" of one vesicle localization moiety and the "cytosolic domain" of a second vesicle localization moiety, wherein the two vesicle focalization moieties are different and distinct proteins and are not isoforms and wherein the "surface-and-transmembrane domain" may have a mutation. The mutation may be a deletion, insertion or a substitution, so long as the resulting mutant retains at least 80% or at least about 90% of the EV association activity of the unmutated counterpart. In an embodiment, the "chimeric vesicle localization moiety" is derived from combining domains of two proteins encoded by two distinct genes which are not allelic or homologs. In an embodiment, the "chimeric vesicle localization moiety" is derived from combining domains of two proteins encoded by two distinct genes which are not orthologs. In an embodiment, the "chimeric vesicle localization moiety" is derived from combining domains of two proteins encoded by two distinct genes which are not paralogs. In an embodiment, the "chimeric vesicle localization moiety" is derived from combining domains of two proteins encoded by two distinct genes which are paralogs. In an embodiment, the "chimeric vesicle localization moiety" is derived from combining domains of two proteins encoded by two nonhomologous genes. In an embodiment, the "chimeric vesical localization moiety" is derived fro combining domains of two or more proteins encoded by two or more nonhomologous genes. In an embodiment, the "chimeric vesicle localization moiety" is derived from combining domains of two or more proteins encoded by two or more nonhomologous human genes. In an embodiment, the "chimeric vesicle localization moiety" is produced from combining domains of two or more human genes encoding transmembrane proteins. In a preferred embodiment, the "chimeric vesicle localization moiety" is produced from combining two nonhomologous human genes or two human genes not placed within the same gene family, wherein the genes encode transmembrane proteins.

An "isoform" of a protein can be, e.g., a protein resulting from alternative splicing of a gene expressing the protein, a protein resulting from alternative promoter usage of a gene expressing the protein, or a degradation product of the protein.

"Surface-and-transmembrane domain" is a contiguous polypeptide containing both a domain that is exposed to extracellular or extra-EV solvent and a transmembrane domain as described above.

A "linker" may be a peptide or polypeptide with 3 to 1000 amino acids that are generally non-hydrophobic and encode no secondary structural elements such as helices or beta-sheets. Suitable examples include, but are not limited to, any of $(Gly)_8$, $(Gly)_6$, $(GS)_n$ (n=1-5), $(GGS)_n$ (n=1-5), $(GGGS)_n$ (n=1-5), $(GGGGS)_n$ (n=1-5), $(GGGGGS)_n$ (n=1-5) $(EAAAK)_n$ (n=1-3), $A(EAAAK)_4ALEA(EAAAK)_4A$, $(GGGGS)_n$ (n=1-4), $(Ala-Pro)_n$ (10-34 aa), cleavable linkers such as VSQTSKLTRAETVFPDV, PLGLWA, RVLAEA; EDVVCCSMSY; GGIEGRGS, TRHRQPRGWE, AGNRVRRSVG, RRRRRRRRR, GLFG, and LE.

As used herein "isolated" means a state following one or more purifying steps but does not require absolute purity. "Isolated" extracellular vesicle (e.g., exosome) or composition thereof means a extracellular vesicle, exosome or composition thereof passed through one or more purifying steps that separate the vesicle, extracellular vesicle, exosome or composition from other molecules, materials or cellular components found in a mixture or outside of the vesicle, extracellular vesicle or exosome or found as part of the composition prior to purification or separation. Isolation and purification may be achieved in accordance with conventional methods of recombinant synthesis or cell free protein synthesis. Separation procedures of interest include affinity chromatography. Affinity chromatography makes use of the highly specific binding sites usually present in biological macromolecules, separating molecules on their ability to bind a particular ligand. For example, covalent bonds attach the ligand to an insoluble, porous support medium in a manner that overtly presents the ligand to the protein sample, thereby using natural biospecific binding of one molecular species to separate and purify a second species from a mixture. Antibodies may be used in affinity chromatography. Preferably a microsphere or matrix is used as the support for affinity chromatography. Such supports are known in the art and are commercially available, and include activated supports that can be combined to the linker molecules. For example, Affi-Gel supports, based on agarose or polyacrylamide are low pressure gels suitable for most laboratory-scale purifications with a peristaltic pump or gravity flow elution. Affi-Prep supports, based on a pressure-stable macroporous polymer, may be suitable for preparative and process scale applications. Isolation may also be performed using methods involving centrifugation, filtration, size exclusion chromatography and vesicle low cytometry.

In some embodiments, a composition herein comprises an isolated or enriched set of vesicles that selectively target a tissue or cell of interest. Such vesicles can be loaded with a payload as described herein to be delivered to the cell or tissue of interest.

In one embodiment of the invention, the chimeric vesicle localization moiety may comprise a surface-and-transmembrane domain of a first vesicle localization moiety and a cytosolic domain of a second vesicle localization moiety. In a preferred embodiment, the first and second vesicle localization moieties are distinct/different proteins and not isoforms, in a preferred embodiment, the first and second vesicle localization moieties are distinct/different proteins and not an allelic variant. In a preferred embodiment, the first and second vesicle localization moieties are distinct/different proteins and not a homolog. In a preferred embodiment, the first and second vesicle localization moieties are distinct/different proteins and not an ortholog. In an embodiment, the first and second vesicle localization moieties are distinct/different proteins but are paralogs. In a preferred embodiment, the first and second vesicle localization moieties are distinct/different proteins and are not paralogs.

In an embodiment, the first and second vesicle localization moieties are distinct/different proteins from a eukaryote or of eukaryotic origin. The eukaryote may include any an of animal, plant, fungi, and protist. In an embodiment, the first and second vesicle localization moieties are distinct/different proteins from a mammal or of mammalian origin. The mammal may include, but is not limited to, a human, monkey, chimpanzee, ape, gorilla, cattle, pig, sheep, horse, donkey, kangaroo, rat, mouse, guinea pig, hamster, cat, dog, rabbit and squirrel. In an embodiment, the first and second vesicle localization moieties are distinct/different proteins from a human or of human origin.

In an embodiment, the chimeric vesicle localization moiety is obtained using recombinant DNA methods. The chimeric vesicle localization moiety can be produced from expression of a nucleic acid encoding amino acid sequence of the $1^{st}$ vesicle localization moiety and the $2^{nd}$ vesicle localization moiety. The nucleic acid encoding the chimeric vesicle localization moiety can be introduced into an expression vector or system. Examples of nucleic acid sequences are provided in the Tables herein and the Sequence Listing provided herewith. The expression vector or system may be introduced into a cell which expresses the chimeric localization moiety as a polypeptide. In an embodiment, preferably the cell is a mammalian cell, more preferably a human cell. In an embodiment, the expression vector or system may be introduced into a producer cell, which produces extracellular vesicles, preferably exosomes. In an embodiment, the producer cell is a mammalian cell, in a preferred embodiment, the producer cell is a human cell. Alternatively, the expression vector or system may be used in an in vitro transcription and translation system to produce a chimeric vesicle localization moiety as a polypeptide. In an embodiment, the in vitro produced chimeric vesicle localization moiety may be isolated. In an embodiment, an isolated chimeric vesicle localization moiety may be introduced into an extracellular vesicle or exosome isolated from cells.

Examples of suitable first vesicle localization moieties include, but are not limited to, ADAM10, ALCAM, CLSTN1, IGSF8, IL3RA, ITGA3, ITGB1, LAMP2, LILRB4, PTGFRN, and SELPLG. Further examples of suitable vesicle localization moieties may include, but are not limited to, a growth factor receptor, Fc receptor, interleukin receptor, immunoglobulin, MHC-1 or MHC-II component, CD antigen, and escort protein. Examples of suitable second vesicle localization moieties include, but are not limited to, the same examples as described for the first vesicle localization moieties.

The vesicle-localization moiety may further comprise a peptide or protein with a modified amino acid. The modified amino acid may result from an attachment of a hydrophobic group. The attachment of a hydrophobic group may be myristoylation for attachment of myristate, palmitoylation for attachment of palmitate, prenylation for attachment of a prenyl group, farnesylation for attachment of a farnesyl group, geranylgeranylation for attachment of a geranylgeranyl group or glycosylphosphatidylinositol (GPI) anchor formation for attachment of a glycosylphosphatidylinositol comprising a phosphoethanolamine linker, glycan core and phospholipid tail. The attachment of a hydrophobic group may be performed by chemical synthesis in vitro or is performed enzymatically in a post-translational modification reaction.

Example, of the first and second vesicle localization moieties include, but are not limited to, any of ACE, ADAM10, ADAM15, ADAM9, AGRN, ALCAM, ANPEP, ANTXR2, ATP1A1, ATP1B3, BSG, BTN2A1, CALM1, CANX, CD151, CD19, CD1A, CD1B, CD1C, CD2, CD200, CD200R1, CD226, CD247, CD274, CD276, CD33, CD34, CD36, CD37, CD3E, CD40, CD40LG, CD44, CD47, CD53, CD58, CD63, CD81, CD82, CD84, CD86, CD9, CHMP1A, CHMP1B, CHMP2A, CHMP3, CHMP4A, CHMP4B, CHMP5, CHMP6, CLSTN1, COL6A1, CR1, CSF1R, CXCR4, DDOST, DLL1, DLL4, DSG1, EMB, ENG, EV12B, FIIR, FASN, FCER1G. FCGR2C, FLOT1, FLOT2, FLT3, FN1, GAPDH, GLG1, GRIA2, GRIA3, GYPA, HSPG2, ICAM1, ICAM2, ICAM3, IGSF8, IL1RAP, IL3RA, IL5RA, IST1, ITGA2, ITGA2B, ITGA3, ITGA4. ITGA5, ITGA6, ITGAL, ITGAM, ITGAV, ITGAX, ITGB1, ITGB2, ITGB3, ITGB4, ITGB5, ITGB6, ITGB7, JAG1, JAG2, KIT, LAMP2, LGALS3BP, LILRA6, LILRB1, LILRB2, LILRB3, LILRB4, LMAN2, LRRC25, LY75, M6PR, MFGE8, MMP14, MPL, MRC1, MVB12B, NECTIN1, NOMO1, NOTCH1, NOTCH2, NOTCH3, NOTCH4, NPTN, NRP1, PDCD1, PDCD1LG2, PDCD6IP, PDGFRB, PECAM1, PLXNB2, PLXND1, PROM1, PTGES2, PTGFRN, PTPRA, PTPRC, PTPRJ, PTPRO, RPN1, SDC1, SDC2, SDC3, SDC4, SDCBP, SDCBP2, SELPLG, SIGLEC7, SIGLEC9, SIRPA, SLIT2, SNF8, SPN, STX3, TACSTD2, TFRC, TLR2, TMED10, TNFRSF8, TRAC, TSG101, TSPAN14, TSPAN7, TSPAN8, TYROBP, VPS25, VPS28, VPS36, VPS37A, VPS37B, VPS37C, VPS37D, VPS4A, VPS4B, VT1A, and VT1B or a homologue thereof; or a combination thereof. Amino acid sequences and associated nucleic acid encoding sequences for the vesicle localization moieties (above) may be obtained in Tables 1 and 2; where the sequences are not directly provided in the table, the sequences may be obtained from provided Accession Number and database referred to in the tables.

In an embodiment, the first and second vesicle localization moieties from which a chimeric vesicle localization moiety is derived may be from any of the transmembrane proteins listed in Table 1 and 2 or a homologue thereof. In an embodiment, the chimeric vesicle localization moiety comprises a surface-and-transmembrane domain of a $1^{st}$ vesicle localization moiety selected from any of the transmembrane protein listed in Table 1 or a homologue thereof and a cytosolic domain of a $2^{nd}$ a vesicle localization moiety selected from any of the transmembrane protein listed in Table 2 of a homologue thereof. In a separate embodiment, the chimeric vesicle localization moiety comprises a surface-and-transmembrane domain of a $1^{st}$ vesicle localization moiety selected from any of the transmembrane protein listed in Table 2 or a homologue thereof and a cytosolic domain of a $2^{nd}$ vesicle localization moiety selected from any of theca transmembrane protein listed in Table 1 or a homologue thereof. In a preferred embodiment, the chimeric vesicle localization moiety comprises a surface-and-transmembrane domain of a $1^{st}$ vesicle localization moiety selected from any of the transmembrane protein listed in Table 1 or a homologue thereof and a cytosolic domain of a $2^{nd}$ vesicle localization moiety from any of the transmembrane protein listed in Table 1 or a homologue thereof, but not selected for the $1^{st}$ vesicle localization domain.

In an embodiment, nucleic acid sequences as provided in Tables 1 and 2 may be used to produce a chimeric vesicle localization moiety through recombinant DNA method. In an embodiment, the next adjacent amino acid of a surface domain is followed and joined to first amino acid of a transmembrane domain and the last amino acid of the transmembrane domain is joined to the first amino acid of a cytosolic domain. In an embodiment, a vesicle localization moiety in Tables 1 and 2 comprises a transmembrane protein in which from amino-to-carboxyl terminal direction, last amino acid of a surface domain is joined to first amino acid of a transmembrane domain, and further, last amino acid of the transmembrane domain is joined to first amino acid of a cytosolic domain. Note additional presence of a signal peptide sequence with its last amino acid joined to the first amino acid of the surface domain for the amino acid sequences in Table 1 and the nucleic acid sequences in Table 1 or the vesicle localization moiety coding sequences associated with each ENST number in Table 2. During cellular expression, the signal peptide is cleaved from the nascent protein to produce a mature vesicle localization moiety round associated with an EV. As such, Tables 1 and 2 provide full-length vesicle localization moieties with signal peptides and nucleic acid coding sequences. Amino acid sequences of vesicle localization moieties and amino acid sequences for signal peptide, surface domain, transmembrane domain and cytosolic domain along with nucleic acid coding sequences may additionally be accessed through accession numbers associated with the UniProtKB and Ensembl ENSP and ENST identifiers.

In an embodiment, the chimeric vesicle localization moiety comprises a surface-and-transmembrane domain of a $1^{st}$ vesicle localization moiety and a cytosolic domain of a $2^{nd}$ vesicle localization moiety. The $1^{st}$ vesicle localization moiety may include any of ADAM10, ALCAM, CLSTN1, IGSF8, IL3RA, ITGA3, ITGB1, LAMP2, LILRB4, PTGFRN, and SELPLG or a homologue thereof. The $2^{nd}$ vesicle localization moiety may be selected from the same group of transmembrane proteins so long as the first and second vesicle localization moieties are from different or non-homologus proteins. Amino acid sequences and nucleic acid sequences encoding ADAM10, ALCAM, CLSTN1, IGSF8, IL3RA, ITGA3, ITGB1, LAMP2, LILRB4, PTGFRN, and SELPLG are provided in Table 1 along with Ensembl ENSP and ENST identifiers (Hunt, S. E. et al, (2018) Database, 2018, 1-12; doi: 10.1093/database/bay119; Yates. A. D. et al., (2019) Nucleic Acids Res, 48:D682-D688).

In a preferred embodiment, the chimeric vesicle localization moiety comprises a LAMP2 surface-and-transmembrane domain and has an amino sequence as provided in FIG. 9 or a LAMP2 protein with Accession Number ENSP00000360386 encoded by Transcript ID ENST00000371335 from Gene ID ENSP300000005893, based on assembled sequence in Genome Reference Consortium Human Build 38 patch release 13 (GRCh38.p1:3: GenBank assembly accession GCA_000001405.28 and RefSeq assembly accession GCF_000001405.39). In a preferred embodiment, LAMP2 protein with Accession Number ENSP00000360386 encoded by Transcript ID ENST00000371335 is LAMP2B. The chimeric vesicle localization moiety comprising a LAMP2 surface-and-transmembrane domain additionally comprises a cytosolic domain of ADAM10, ALCAM, CLSTN1, IGSF8, IL3RA, ITGA3, ITGB1, LILRB4, PTGPRN, or SELPLG or a homologue or portion thereof. In a preferred embodiment, the chimeric vesicle localization moiety comprising a LAMP2 surface-and-transmembrane domain additionally comprises a cytosolic domain of PTGFRN, ITGA3, IL3RA, SELPLG, ITGB1, or CLSTN1 or a homologue or portion thereof.

In one embodiment of the invention, the cytosolic domain of PTGFRN has an amino acid sequence as provided in FIG. 5 or FIG. 10 or a homologue or portion thereof. Merely by way of example, the homologue or portion may retain at least about 80% or at least about 90% of cytosolic domain activity of PTGFRN which may be determined by detecting its accumulation at an extracellular vesicle. Accumulation may be assessed for a chimeric vesicle localization moiety on the basis of the percent of extracellular vesicle positive for the chimeric vesicle localization moiety, and/or the mean abundance of localization moiety in an extracellular vesicle positive for the localization moiety and ignoring extracellular vesicles lacking the localization moiety, as measured by vesicle flow cytometry. The mean abundance of localization moiety in an extracellular vesicle may be the mean concentration, density or amount of localization moiety in an extracellular vesicle positive for the localization moiety. In an embodiment, an alternative measure can also be used, including total number of extracellular vesicles positive for the localization moiety.

In another embodiment, the cytosolic domain of ITGA3 has an amino acid sequence as provided in FIG. 5 or FIG. 10 or a homologue or portion thereof. Merely by way of example, the homologue or portion may retain at least 80% or at least about 90% of cytosolic domain activity of ITGA3 which may be determined by detecting its accumulation at an extracellular vesicle.

In yet another embodiment, the cytosolic domain of IL3RA hits an amino acid sequence as provided in FIG. 6 or FIG. 10 or a homologue or portion thereof. As an example, the homologue or portion may retain at least about 80% or at least about 90% of cytosolic domain activity of IL3RA which may be determined by detecting its accumulation at an extracellular vesicle.

Additionally, in a further embodiment, the cytosolic domain of SELPLG has an amino acid sequence as provided in FIG. 6 or FIG. 11 or a homologue or portion thereof. In an example of the invention, the homologue or portion retains at least about 80% or at least about 90% of cytosolic domain activity of SELPLG which may be determined by detecting its accumulation at an extracellular vesicle.

Further, in one embodiment of the invention, the cytosolic domain of ITGB1 may have an amino acid sequence as provided in FIG. 7 or FIG. 11 or a homologue or portion thereof, wherein the homologue or portion retains at least 80% or at least about 90% of cytosolic domain activity of ITGB1 which may be determined by detecting its accumulation at an extracellular vesicle.

Further, the cytosolic domain of CLSTN1 may have an amino acid sequence as provided in FIG. 7 or FIG. 12 or a homologue or portion thereof, wherein the homologue or portion retains at least 80% or at least about 90% of cytosolic domain activity of CLSTN1 which may be determined by detecting its accumulation at an extracellular vesicle.

In an embodiment, a homologue is an ortholog derived from a common ancestral gene and encodes a protein with the same function in different species. In an embodiment, a homologue is a paralog derived from a homologous gene that has evolved by gene duplication and encodes for a protein with similar but not identical function. Homologous proteins, including orthologs and paralogs, may be identified based on amino acid sequences, curated, grouped and aligned in publicly available databases, such as Homolo-Gene at the National Center for Biotechnology Information of the National Institutes of Health (NCBI Resource Coordinators (22016) Database resources of the National Center for Biotechnology Information. Nucleic Acids Res. 44:D7-D9). OrthoDB (Waterhouse. R. M. et al. (2011) OrthoDB: the hierarchical catalog of eukaryotic orthologs in 2011, Nucleic Acids Res. 39:D283-8), HOGENOM (Penel, S. et al. (2009) Databases of homologous gene families for comparative genomics, BMC Bioinformatics 10:S3. TreeFam (Ruan. J. et al. (2008) TreeFam; 2008 Update. Nucleic Acids Res. 36: D735-D740), Gene Sorter (Kent, W. J. et al. (2005) Exploring relationships and mining data with the UCSC Gene Sorter. Genome Res. 15:737-41), and InParanoid (Sonnhammer, E. L. L. and Östlund. G. (2015) InParanoid 8: orthology analysis between 273 proteomes, mostly eukaryotic. Nucleic Acids Res. 43:D234-D239).

Engineered Extracellular Vesicles

In some instances, an extracellular vesicle herein is engineered for enhanced targeting to a cell or tissue of interest. Such engineered vesicles can be non-naturally occurring. Such engineered vesicles can be 'targeted' or 'guided' via a functionalized moiety (a targeting moiety) for increased affinity to a cell, tissue, or organ of interest. A vesicle can be engineered to include a heterologous expression of one or more targeting moieties.

Vesicle functionalization can occur by modification of vesicles such as exosomes, to display an exogenous protein or nucleic acid. As used herein, a "targeting moiety" can include, but is not limited to, a small molecule, glycoprotein, protein, peptide, lipid, carbohydrate, nucleic acid, or other molecules involved in EV trafficking, and/or EV interaction with target cells. The targeting moiety may be displayed inside or on the outside of a vesicle membrane or may span the inner membrane, outer membrane, or both inner and other membranes. For targeting cell surface receptor, ligand, or moiety on the outside of a cell or tissue, the targeting moiety is similarly displayed oi the outside of a vesicle membrane, so as to be able to hind to the targeted cell surface receptor, ligand or moiety. The targeting moiety may be expressed in exosomes that are "emptied" of natural cargo, "carry" a naturally occurring cargo or loaded with a payload for delivery to such as target cells or tissues.

In one instance, an engineered vesicle is one that is functionalized or is engineered to express a targeting moiety (e.g., a protein, peptide or nucleic acid) that selectively targets a cell or tissue of interest. Such engineered vesicle can be an exosome. In some embodiments, such engineered vesicle is an extracellular vesicle. In a preferred embodiment, the engineered vesicle is an exosome. In an embodiment, an engineered vesicle comprises a chimeric vesicle localization moiety attached to a targeting moiety. In a preferred embodiment, an engineered vesicle comprises a chimeric vesicle localization moiety attached to a targeting moiety, displayed outside the vesicle. In another preferred embodiment, an engineered vesicle is an engineered extracellular vesicle comprising a chimeric vesicle localization moiety attached to a targeting moiety, displayed outside the EV. In a more preferred embodiment, an engineered vesicle is an engineered exosome comprising a chimeric vesicle localization moiety attached to a targeting moiety, displayed outside the exosome.

Target Cells

The vesicles described herein can be used to selectively target a cell, tissue, or organ of interest. In some embodiments, the target cell is an eukaryotic cell. A target cell can be a cell from an animal such as a mouse, rat, rabbit, hamster, porcine, bovine, feline, or canine. The target cells can be a cell of primates, including but not limited to, monkeys, chimpanzees, gorillas, and humans.

Targeting Moieties of Interest

Any of the extracellular vesicles disclosed herein may include one or more targeting moieties of interest. They can be embedded in or displayed on vesicle membranes. The extracellular vesicle can be an exosome, and the targeting moiety can be displayed on the outer surface of the exosome. For example, the targeting moiety may be displayed/joined/attached to the surf Ice domain of the chimeric localization moiety.

In a preferred example, the invention provides an extracellular vesicle of the invention comprising a chimeric vesicle localization moiety comprising a surface and transmembrane domain of a first vesicle localization moiety and a cytosolic domain of a second vesicle localization moiety, wherein a targeting moiety is attached or joined covalently or noncovalently to, the surface domain of the first vesicle localization moiety. However, the invention contemplates other types of domain swapping between different vesicle localization moieties including chimeric vesicle localization moieties having the arrangement of ABc, AbC, Abe, aBC, aBc and abC, where A, B and C correspond to the surface domain, transmembrane domain and cytosolic domain, respectively, of a first vesicle localization moiety and a, b, and c correspond to the surface domain, transmembrane domain and cytosolic domain, respectively, of a second vesicle localization moiety. In those embodiments, the targeting moiety can be displayed on a surface domain.

Targeting moieties (such as tissue specific targeting moieties) can comprise a small molecule, glycoprotein, polypeptides, peptide, oligopeptide, protein, lipid, carbohydrate, nucleic acid polysaccharides, therapeutic drugs, imaging moieties or other molecules that facilitates the targeting of the vesicle to a cell or tissue of interest. The term "polypeptide," "peptide," "oligopeptide," and "protein," are used interchangeably herein, and refer to a polymeric form of amino acids of any length, which can include coded and non-coded amino acids, chemically, or biochemically modified or derivatized amino acids, and polypeptides having modified peptide backbones.

In one embodiment of the invention, a targeting moiety may be an antibody, a ligand or a functional epitope thereof that binds to a cell or tissue marker, for example, a cell surface receptor.

As used herein, the term antibody can be a protein or polypeptide functionally defined as a binding protein and structurally defined as comprising an amino acid sequence that is recognized by one of skill in the art as being derived from a variable region or an immunoglobulin. An antibody can comprise one or more polypeptides substantially encoded by immunoglobulin genes, fragments of immunoglobulin genes, hybrid immunoglobulin genes (made by combining the genetic information from different animals), or synthetic immunoglobulin genes. The recognized, native, immunoglobulin genes can include the kappa, lambda, alpha, gamma, delta, epsilon and mu constant region genes, as well as myriad immunoglobulin variable region genes and multiple D-segments and D-segments, Light chains can be classified as either kappa or lambda. Heavy chains can be classified as gamma, mu, alpha, delta, or epsilon, which in turn define the immunoglobulin classes, IgG, IgM, IgA, IgD and IgE, respectively.

Antibodies may exist as intact immunoglobulins, as a number of well characterized fragments produced by digestion with various peptidases to produce, for example, antigen-binding fragments $F(ab')_2$, Fab and Fab', or as a variety of fragments made by recombinant DNA technology, such as variable fragment (Fv), single chain variable fragment (scFv), diabodies, taseFv, bis-scFv, nanobody (e.g., $V_HH$ or $V_{NAR}$ fragment), and miniaturized "3G" fragment (Nelson. A. L. (2010) Antibody fragments, MAbs 2: 77-83; and Muyldermans, S. (2103) Nanobodies: natural single-domain antibodies. Ann. Rev. Biochem, 82:775-797). Antibodies can derive from many different species (e.g., rabbit, sheep, camel, human, or rodent, such as mouse or rat), or can be synthetic. Antibodies can be chimeric, humanized, or human, Antibodies can be monoclonal or polyclonal, multiple or single chained, fragments or intact immunoglobulins. In a preferred embodiment, the antibody is a scFv.

In an embodiment of the invention, the targeting moiety is a peptide (e.g., an affinity peptide). In another embodiment, the targeting moiety may be an antibody fragment. In yet another embodiment, the antibody fragment may be any of $F(ab')_2$, Fab, Fab', Fv, sFv, diabodies, taseFv, bis-scFv, nanobody and miniaturized "3G" fragment. In a preferred embodiment, the antibody fragment is single chain Fv (scFv), wherein variable region of heavy chain ($V_H$) and variable region of light chain (Vt.) are joined together by a flexible linker. The variable region of heavy chain fragment can precede the variable region of light chain fragment, or vice versa. The flexible linker is often glycine-serine rich, such as a $(GGGGS)_{14}$ linker. In one embodiment, the scFv binds a target on the surface of a cell or tissue. In a preferred embodiment, the scFv is attached to a chimeric vesicle localization moiety incorporated in an extracellular vesicle (such as an exosome) and displayed outside the extracellular vesicle (e.g., exosome). In a more preferred embodiment, the scFv is attached to a chimeric vesicle localization moiety and displayed outside an extracellular vesicle (e.g., exosome) preferentially or selectively targets a specific cell type or tissue. Merely by way of example, the antibody fragment may be monospecific or bispecific. In an embodiment of the invention, the antibody fragment may be multivalent.

Examples of suitable antibodies particularly single chain Fv antibodies; and fragments, include antibodies directed against any of Thy1, MHC class II, C3d-binding region of complement receptor type 2 (CR2), VCAM-1, E-selectin, alpha 8 integrin, integrin alpha-M (CD11b) and CD163. Exemplary antibodies from which Fab and/or scFv antibodies may be prepared include OX7 antibody against Thy1 protein (Suana, A. J. et al., J. Pharmacol. Exp. Ther. 2011: 337:411-422; RT1 antibody against MHC class II protein (Hultmaan, K. L. et al., ACS Nano. 2008: 2:477-484); monoclonal antibody to C3d binding region of CR2 (Serkova, N. J. et al., Radiology. 2010; 255:517-526): monoclonal antibody to VCAM-1 (clone M/K2, Cambridge Bioscience) (Akhtar, A. M., PLoS One. 2010: 5:e12800): monoclonal antibody, MES-1, directed to E-selectin (Asgeirsdottir, S. A. et al., Mol. Pharmacol. 2007; 72:121-131); anti-α8 integrin antibody (Santa Cruz Biotechnologies) (Scindia, Y. et al., Arthritis Rheum, 2008; 58:3884-3891); monoclonal antibody against CD11b (Shirai, T. Ct al., Drug Targeting. 2012; 20:535-543); and anti-CD163 monoclonal antibody (ED2; sc-58965, Santa Cruz Biotechnology) (Sawano, T. et al. 2015. Oncology reports. 33: 2151-60).

Any of the targeting moieties described herein can enhance the selectivity of the vesicles towards the target cell of interest as compared to one or more other tissues or cells. The one or more selective targeting moities can be expressed on modified vesicles in a way that allows such modified vesicles to bind to intended targets. The one or more targeting moieties can expose sufficient amount of amino acids to allow such binding.

The modified vesicles provided herein can comprise one or more targeting moieties that selectively target the vesicles to cells or tissue of interest by binding or physically interacting with markers expressed on such cells.

The term "selective" or "selectively" as used herein in the context of selective targeting or selective binding or selective interaction can refer to a preferential targeting, binding or interaction to a cell, tissue, or organ of interest as compared to at least one other type of cell, tissue or organ.

A "functional fragment" of a protein can mean a fragment of the protein which retains a function of a full-length protein lion which it is derived. e.g., a targeting or binding function identical or similar to that of the full-length protein, A "functional fragment" of an antibody can be its antigen binding portion or fragment, which confers binding specificity for the intact antibody. A function can be similar to a function of a full-length protein if it retains at least 75%, 80%, 85%. 90%, 95%, 99%, or 100% of that function of the full-length protein. The function can be measured e.g., using an assay, e.g., an in vivo binding assay, a binding assay in a cell, or an in vitro binding assay.

In general, "sequence identity" or "sequence homology", refer to a nucleotide-to-nucleotide or amino acid-to-amino acid correspondence of two polynucleotides or polypeptide sequences, respectively. As used herein. "sequence identity" or "identity" refers, in the context of two nucleic acid sequence, or amino acid sequences, to the residues in the two sequences that are the same when aligned for maximum correspondence over a specified comparison window.

As used herein. "percent sequence identity" means the value determined by comparing two optimally aligned sequences over a comparison window, wherein (the portion of the polynucleotide or polypeptide sequence in the comparison window may comprise additions or deletions (i.e., gaps) compared to the reference sequence which does not comprise additions or deletions comprises) can for optimal alignment of the two sequences. The percentage can be calculated by determining the number of positions at which the identical nucleotide or amino acid occurs in both sequences to yield the number of matched positions, dividing the number of matched positions by the total number of positions in the comparison window and multiplying the result by 100 to determine the percentage of sequence identity.

Sequence comparisons, such as for the purpose of assessing identities, may be performed by any suitable alignment algorithm, including but not limited to the Needleman-Wunsch algorithm (see, e.g., the EMBOSS Needle aligner available at www.ebi.ac.uk/Tools/psa/emboss_needle/, optionally with default settings; Needleman, S. B. and Wunsch, C. D, (1970) A general method applicable to the search for similarities in the amino acid sequence of two proteins. J. Mol. Biol. 48:443-53), the BLAST algorithm (see, e.g., the BLAST alignment tool available at blast.ncbi.nlm.nih.gov/Blast.cgi, optionally with default settings; Altschul, S. F. et al. (1990) Basic local alignment search tool. J. Mol. Biol. 215:403-410; and Altschul, S. F. et al. (1997) Gapped BLAST and PSI-BLAST: a new generation of protein database search programs. Nucleic Acids Res, 25:3389-3402), and the Smith-Waterman algorithm (see, e.g., the EMBOSS Water aligner available at www.ebi.ac.uk/Tools/psa/emboss_water/, optionally with default settings; Smith. T. F. and Waterman, M. S. (1981) Identification of common molecular subsequences. J. Mol. Biol. 147:195-7). Optimal alignment may be assessed using any suitable parameters of a chosen algorithm, including default parameters.

The "percent identity" between two sequences may be calculated as the number of exact matches between two optimally aligned sequences divided by the length of the reference sequence and multiplied by 100. Percent identity may also be determined, for example, by comparing sequence information using the advanced BLAST computer program, including version 2.2.9, available from the National Institutes of Health. The BLAST program can be based on the alignment method of Karlin and Altschul. Proc. Natl. Acad. Sci. USA 87:2264-2268 (1990) and as discussed in Altshul, et al., J. Mol. Biol. 215; 403-410 (1990): Karlin and Altschul. Proc. Natl. Acad. Sci, USA 90:5873-5877 (1993); and Altschul et al., Nucleic Acids Res. 25:3389-3402 (1997). Briefly, the BLAST program can define identity as the number of identical aligned symbols (i.e., nucleotides or amino acids), divided by the total number of symbols in the shorter of the two sequences. The program may be used to determine percent identity over the entire length of the sequences being compared. Default parameters can be provided to optimize searches with short query sequences, for example, with the BLASTP program. The program can also allow use of an SEG filter to mask-off segments of the query sequences as determined by the SEG program of Wootton, J. C., and Federhen, S. (1993) Computers Chem. 17:149-163. High sequence identity con include sequence identity in ranges of sequence identity of approximately 80% to 99% and integer values there between.

A "homolog" or "homologue" can refer to any sequence that has at least about 90%, 95%, 96%, 97%, 98%, 99%, or 99.5% sequence homology to another sequence. Preferably, a homolog or homologue refers to any sequence that has at least about 98%, 99%, or 99.5% sequence homology to another sequence. In some cases, the homolog can have a functional or structural equivalence with the native or naturally occurring sequence. In some cases, the homolog can have a functional or structural equivalence with a domain, a motif or a part of the protein, that is encoded by the native sequence or naturally occurring sequence.

Homology comparisons may be conducted with sequence comparison programs. Computer programs may calculate percent (%) homology between two or more sequences and may also calculate the sequence identity shared by two or more amino acid or nucleic acid sequences. Sequence homologies may be generated by any of a number of computer programs, for example BLAST or FASTA, etc. A suitable computer program for carrying out such an alignment is the (GCG Wisconsin Bestfit package (University of Wisconsin, U.S.A; Devereux. J. et al. (1984) Nucleic Acids Res. 12:387). Examples of other software than may perform sequence comparisons include, but are not limited to, the BLAST package (see Ausubel, F. M. et al, (1999) Short Protocols in Molecular Biology, 4$^{th}$ Ed.—Chapter 18), PASTA (Atschul, S. F. et al. (1990) J. Mol. Biol. 215:403-410) and the GENEWORKS suite of comparison tools.

Percent homology may be calculated over contiguous sequences, i.e., one sequence is aligned with the other sequence and each amino acid or nucleotide in one sequence is directly compared with the corresponding amino acid or nucleotide in the other sequence, one residue at a time. This is called an "ungapped" alignment. Typically, such ungapped alignments can be performed over a relatively short number of residues.

In an otherwise identical pair of sequences, one insertion or deletion may cause the following amino acid or nucleotide residues to be put out of alignment, thus potentially resulting in a large reduction in % homology when a global alignment is performed. Consequently, the sequence comparison method can be designed to produce optimal alignments that take into consideration possible insertions and deletions without unduly penalizing the overall homology or identity score. This can be achieved by inserting "gaps" in the sequence alignment to try to maximize local homology or identity.

BLAST 2 Sequences is another tool that can be used for comparing protein and nucleotide sequences (see FEMS Microbiol Lett. 1999 174(2): 247-50; FEMS Microbiol Lett. 1999 177(1); 187-8 and the website of the National Center for Biotechnology information at the website of the National Institutes for Health).

Homologous sequences can also have deletions, insertions or substitutions of amino acid residues which result in a functionally equivalent substance. Deliberate amino acid substitutions may be made on the basis of similarity in amino acid properties (such as polarity, charge, solubility, hydrophobicity, hydrophilicity, and/or the amphipathic nature of the residues) and it is therefore useful to group amino acids together in Functional groups. Amino acids may be grouped together based on the properties of their side chains alone.

Substantially homologous sequences of the present invention include variants of the disclosed sequences, e.g., those resulting from site-directed mutagenesis, as well as synthetically generated sequences, in some cases, the variants may be allelic variants due to different alleles. In some cases, the variants may be derived from the same gene or allele due to alternative transcription start site or alternative splicing, resulting in variants which are isoforms.

An extracellular vesicle of the present disclosure can be one that comprises (e.g., on its surface) one or more targeting moiety(ies) to a marker of interest. A marker of interest may be a cell surface marker of a target cell of interest to which a vesicle of the present invention is intended to target or hind. In some embodiments, a vesicle of the present disclosure is one that comprises e.g., on its surface) targeting moiety(ies) to a marker of interest or a homologue(s) of a marker of interest. In some instance, a vesicle comprises at least 2, 3, 4, 5, 6, 7, 8, 9 or 10 different targeting moiety(ies). In an embodiment, a vesicle comprises a chimeric vesicle localization moiety attached to one or more targeting moiety(ies) to a marker of interest. The marker of interest may be a cell surface marker. In an embodiment, a vesicle comprises two or more chimeric vesicle localization moieties, wherein each chimeric vesicle localization moiety comprises a different targeting moiety(ies) targeted to the same marker of interest. In an embodiment, a vesicle comprises two or more chimeric vesicle localization moieties, wherein each chimeric vesicle localization moiety comprises a different targeting moiety(ies) targeted to the different markers of interest. In an embodiment, a vesicle comprises two or more chimeric vesicle localization moieties, wherein each chimeric vesicle localization moiety comprises a different targeting moiety(ies) targeted to the different markers of interest present on the same cell. In an embodiment, a vesicle comprises two or more chimeric vesicle localization moieties, wherein each chimeric vesicle localization moiety comprises a different targeting moiety(ies) targeted to the different markers of interest present on different cell types. In an embodiment, a vesicle comprises two or more chimeric vesicle localization moieties, wherein each chimeric vesicle localization moiety comprises a different targeting moiety(ies) targeted to the different markers of interest present in a tissue. In an embodiment, a vesicle comprises two or more chimeric vesicle localization moieties, wherein each chimeric vesicle localization moiety comprises a different targeting moiety(ies) targeted to the different markers of interest present in different tissues. In some instance, a vesicle comprises a sufficient number of targeting moiety(ies) to selectively target cells of interest over other cells. In some instance, a vesicle comprises a sufficient number of targeting moiety(ies) to selectively target a tissue of interest over other tissues.

In some cases, the vesicle comprises a concentration of a targeting moiety of interest that is 2, 3, 4, 5, 6, 8, 10, 12, 14, 17, 18, 20, 22, 25, 28, 30, 33, 35, 38, 40, 43, 44, 46, 47, 48, 50, 52, 55, 57, 59, 62, 65, 68, 70, 72, 75, 78, 80, 82, 85, 89, 91, 92, 95, 100, 110, 120, 125, 130, 135, 145, 150, 155, 160, 170, 180, 185, 200, 210, 220, 230, 250, 270, 280, 290, 300, 310, 320, 330, 340, 350, 380, 400, 410, 430, 440, 450, 470, 490, 500, 510, 525, 540, 560, 580, 590, 600, 620, 650, 670, 680, 690, 700, 720, 740, 760, 780, 800, 820, 840, 860, 880, 890, 900, 920, 940, 960, 980 or 1000 times higher than the concentration of the targeting moiety on the surface of a naturally occurring vesicle. In some cases, the vesicle comprises a targeting moiety which is not naturally associated with a vesicle or an extracellular vesicle. In a preferred embodiment, the vesicle comprises a targeting moiety of interest fused to a Chimeric vesicle localization moiety. In a separate preferred embodiment, the vesicle comprises two or more targeting moiety of interest fused to one or more chimeric vesicle localization moiety.

Fusion Proteins

The "fusion protein" can be a single polypeptide derived from two separate polypeptides or portions of two separate polypeptides. As such, a chimeric vesicle localization may be considered a fusion protein. The one or more targeting moieties of interest can be operably linked (directly or indirectly) to a chimeric vesicle localization moiety (e.g., as a fusion protein). In an embodiment, a targeting moiety may be linked non-covalently to a chimeric vesicle localization moiety mediated by interacting surfaces or partners in separate polypeptides comprising the targeting moiety and another polypeptide comprising the chimeric vesicle localization moiety. Such interacting surfaces or partners may be inherently present on or be covalently attached to the targeting moiety and/or chimeric vesicle localization moiety, Molecular forces maintaining non-covalent linkages or interactions include hydrogen bond, ionic bond, van der Waals interaction and hydrophobic bond.

Alternatively, in a separate embodiment, a targeting moiety may be covalently linked to a chimeric vesicle localization moiety, and together the two can be referred to as a fusion protein comprising a targeting moiety and a chimeric vesicle localization moiety. The chimeric vesicle localization moiety of the fusion protein can target the targeting moieties of interest for other fused molecule) to a vesicle. In some embodiments, a chimeric vesicle localization moiety targets the targeting moieties of interest (or other fused molecule) to the membrane of a vesicle. Preferably the chimeric vesicle localization moiety targets to the membrane of an exosome. In some instances, fusion proteins can be made with a chimeric vesicle localization moiety and a ligand (targeting moiety of interest) that binds a cell receptor of interest. The ligand can be surface exposed and can selectively hind to ta receptor or receptors on the surface of the target cell. These fusion proteins of such targeting moieties can be loaded onto vesicles (e.g., exosomes and EVs) endogenously or exogenously. Alternatively, nucleic acids encoding fusion proteins or such targeting moieties and chimeric vesicle localization moieties separately can be used to express the exosome localization moiety and targeting moieties.

Examples of vesicle localization moieties from which chimeric vesicle localization moieties may be produced by domain swapping include any of the following: ACE, ADAM10, ADAM15, ADAM9, AGRN, ALCAM, ANPEP, ANTXR2, ATP1A1, ATP1B3, BSG, BTN2A1, CALM1, CANX, CD151, CD19, CD1A, CD1B, CD1C, CD2, CD200, CD200R1, CD226, CD247, CD274, CD276, CD33, CD34, CD36, CD37, CD3E, CD40, CD40LG, CD44, CD47, CD53, CD58, CD63, CD81, CD82, CD84, CD86, CD9, CHMP1A, CHMP1B, CHMP2A, CHMP3, CHMP4A, CHMP4B, CHMP5, CHMP6, CLSTN1, COL6A1, CR1, CSF1R, CXCR4, DDOST, DLL1, DLL4, DSG1, EMB, ENG, EV12B, FIIR, FASN, FCER1G, FCGR2C, FLOT1, FLOT2, FLT3, FN1, GAPDH, GLG1, GRIA2, GRIA3, GYPA, HSPG2, ICAM1, ICAM2, ICAM3, IGSF8, IL1RAP, IL3RA, IL5RA, IST1, ITGA2, ITGA2B, ITGA3, ITGA4, ITGA5, ITGA6, ITGAL, ITGAM, ITGAV, ITGAX, ITGB1, ITGB2, ITGB3, ITGB4, ITGB5, ITGB6, ITGB7, JAG1, JAG2, KIT, LAMP2, LGALS3BP, LILRA6, LILRB1, LILRB2, LILRB3, LILRB4, LMAN2, LRRC25, LY75, M6PR, MFGE8, MMP14, MPL, MRC1, MVB12B, NECTIN1, NOMO1, NOTCH1, NOTCH2, NOTCH3, NOTCH4, NPTN, NRP1, PDCD1, PDCD1LG2, PDCD6IP, PDGFRB, PECAM1, PLXNB2, PLXND1, PROM1, PTGES2, PTGFRN, PTPRA, PTPRC, PTPRJ, PTPRO, RPN1, SDC1, SDC2, SDC3, SDC4, SDCBP, SDCBP2, SELPLG, SIGLEC7, SIGLEC9, SIRPA, SLIT2, SNF8, SPN, STX3, TACSTD2, TFRC, TLR2, TMED10, TNFRSF8, TRAC, TSG101, TSPAN14, TSPAN7, TSPAN8, TYROBP, VPS25, VPS28, VPS36, VPS37A, VPS37B, VPS37C, VPS37D, VPS4A, VPS4B, VT1A, and VT1B or an isoform thereof, or a homologue thereof, or a functional fragment thereof, or an exosomal polypeptide. In a preferred embodiment, the chimeric vesicle localization moieties may be produced by domain swapping include any of the following: ADAM10, ALCAM, CLSTN1, IGSF8, IL3RA, ITGA3, ITGB1, LAMP2, LILRB4, PTGFRN, and SELPLG or an isoform thereof, or a homologue thereof, or a functional fragment thereof. Domain swapping is most easily achieved through recombinant DNA methods using coding sequence provided or referred to in Tables 1 and 2 to precisely dissect and fuse two different coding sequences in-frame with each other to obtain a single nucleic acid encoding a chimeric vesicle localization moiety. Nucleic acid sequences encoding exemplary chimeric vesicle localization moieties may be obtained in Tables 3 and 5.

In an embodiment, a chimeric vesicle localization moiety may be produced by domain swapping two non-homologous vesicle localization moieties. In an embodiment, a chimeric vesicle localization moiety may be produced by domain swapping two vesicle localization moieties which are not orthologs. In an embodiment, a chimeric vesicle localization moiety may be produced by domain swapping two vesicle localization moieties which are not paralogs. In an embodiment, a chimeric vesicle localization moiety may be produced by domain swapping two vesicle localization moieties which are paralogs. In an embodiment, a chimeric vesicle localization moiety may be produced by domain swapping two vesicle localization moieties which are not allelic variants. In an embodiment, a chimeric vesicle localization moiety may be produced by domain swapping two vesicle localization moieties which are not isoforms. In an embodiment, a chimeric vesicle localizations moiety may be produced by domain swapping two vesicle localization moieties which are not related by an ancestral gene or gene duplication. In an embodiment, a chimeric vesicle localization moiety may be produced by domain swapping two vesicle localization moieties which are related by gene duplication and have evolved to be paralogs encoded by homologous genes at a different genetic locus (not allelic). In an embodiment, a chimeric vesicle localization moiety may be produced by domain swapping two vesicle localization moieties which are distinct and non-homologous proteins. In an embodiment, a chimeric vesicle localization moiety may be produced by domain swapping two vesicle localization moieties, wherein the domains being swapped share less than about 95%, 90%, 70%, 50% or preferably less than about 30% amino acid sequence identity with gaps allowed in the sequence alignment to maximize sequence identity. In an embodiment, a chimeric vesicle localization moiety may be produced by domain swapping two vesicle localization moieties, wherein the domains being swapped differ in the length of the primary amino acid sequence by more than about 1.3-fold, 1.5-fold, 1.7-fold, 1.9-fold, 2.3-fold, 2.7-fold or more preferably about 3-fold compared to the shorter domain. The domains of a vesicle localization moiety may be determined in relation to membrane of a vesicle and may be described as surface domain (outside of the vesicle: also referred to sometimes as extracellular domain, which is topologically equivalent), transmembrane domain (spanning the lipid bilayer of the vesicle) and lumenal domain (in the interior of the vesicle; also referred to as a cytosolic domain prior to formation of a vesicle, which is topologically equivalent). In an embodiment, the three domains present in a vesicle localization moiety may be swapped with one or more domains from one or more other vesicle localization moiety. In a preferred embodiment, the cytosolic domain or lumenal domain of a vesicle localization moiety is swapped with a cytosolic domain or lumenal domain of a second vesicle localization moiety so as to produce a chimeric vesicle localization moiety with a surface-and-transmembrane domain of a $1^{st}$ vesicle localization moiety and a cytosolic domain of a $2^{nd}$ vesicle localization moiety.

Methods for making such fusion proteins and for targeting/localizing fusion proteins to exosomes can be as described, e.g., in Limoni S K, et al. Appl Biochem Biotechnol. 2018 Jun. 28. doi: 10.1007/s12010-018-2813-4.

Nucleic Acids

The production of engineered vesicles can involve generation of nucleic acids that encode, at least, in part, one or more of the cell-type specific or selective targeting moieties described herein, one or more of the targeting moiety(ies) described herein, one or more of the vesicle localization moieties including chimeric vesicle localization moieties described herein, one or more fusion proteins described herein, or a combination thereof.

The disclosure includes vectors. Methods which are well known to those skilled in the art can be used to construct expression vectors containing coding sequences and appropriate transcriptional/translational control signals. Generally, expression vectors include transcriptional and translational regulatory nucleic acid operably linked to the nucleic acid encoding the protein. The term "control sequences" refers to DNA sequences necessary for the expression of an operably linked coding sequence in a particular expression system, e.g. mammalian cell, bacterial cell, cell-free synthesis, etc. The control sequences that are suitable for prokaryote systems, for example, include a promoter, optionally an operator sequence, and a ribosome binding site. Eukaryotic cell Systems may utilize promoters, polyadenylation signals, and enhancers.

These methods include, for example, in vitro recombinant DNA techniques, synthetic techniques and in vivo recombination/genetic recombination. Alternatively, RNA capable of encoding the polypeptides of interest may be chemically synthesized. One of skill in the art can readily utilize well-known codon usage tables and synthetic methods to provide a suitable coding sequence for any of the polypeptides of the invention.

In some embodiments, a vector comprises nucleic acids encoding one or more cell-type specific or selective targeting moieties operably linked to nucleic acids that encode one or more vesicle localization moieties, preferably chimeric vesicle localization moieties A nucleic acid is "operably linked" when it is placed into a functional relationship with another nucleic acid sequence. For example, a promoter or enhancer is operably linked to a coding sequence if it affects the transcription of the sequence; or a ribosome binding site is operably linked to a coding sequence if it is positioned so as to facilitate the initiation of translation. Generally, "operably linked" means that the DNA sequences being linked are contiguous, and, in the case of a secretory leader, contiguous and in reading phase. Linking is accomplished by ligation or through amplification reactions. Synthetic oligonucleotide adaptors or linkers may be used for linking sequences in accordance with conventional practice.

In some embodiment, a vector comprises nucleic acids encoding the amino acid sequences set forth in Table 3 or the figures. In an embodiment, a vector comprises nucleic acids encoding the chimeric vesicle localization moiety produced from the vesicle localization moieties disclosed herein or in Table 3 or the figures. In one example, a vector comprises nucleic acids encoding a chimeric vesicle localization moiety operably linked to nucleic acids encoding any one or more of a targeting moiety(ies) of interest or cell-type specific or selective targeting moieties. In an embodiment, a cell-type specific or selective targeting moiety is a peptide. In an embodiment, a cell-type specific or selective targeting moiety is an antibody or an antibody fragment. In an embodiment, a cell-type specific or selective targeting moiety is a F(ab')$_2$, Fab or Fab'. In a preferred embodiment, a cell-type specific or selective targeting moiety is a scFv.

The nucleic acids may be natural, synthetic or a combination thereof. The nucleic acids may be RNA, mRNA, DNA or cDNA. Nucleic acid encoding the protein may be produced using known synthetic techniques, incorporated into a suitable expression vector using well established methods to form a protein-encoding expression vector which is introduced into a cell for protein expression using known techniques, such as transfection, lipofection, transduction and electroporation. The nucleic acids may be isolated and obtained in substantial purity. Usually, the nucleic acids, either as DNA or RNA, will be obtained substantially free other naturally-occurring nucleic; acid sequences, generally being at least about 50%, usually at least about 90% pure and are typically "recombinant," e.g., flanked by one or more nucleotides with which it is not normally associated on a naturally occurring chromosome.

Expression of the nucleic acids van be regulated by their own or by other regulatory sequences known in the art. The nucleic acids of the invention can be introduced into suitable host cells using a variety of techniques available in the art. The expressed protein may localize or form an exosome or extracellular vesicle and released from the producing cell. Such exosomes or extracellular vesicles may be harvested from the culture medium. Similarly, the selected protein may be produced using recombinant techniques, or may be otherwise obtained, and then may be introduced directly into isolated exosomes by electroporation or transfection e.g. electroporation, transfection using cationic lipid-based transfection reagents, and the like.

The nucleic acids can also include expression vectors, such as plasmids, or viral vectors, or linear vectors, or vectors that integrate into chromosomal DNA. Expression vectors can contain a nucleic acid sequence that enables the vector to replicate in one or more selected host cells. Such sequences are well known for a variety of cells. The origin of replication from the plasmid pBR322 is suitable for most Gram-negative bacteria. In eukaryotic host cells, mammalian cells, the expression vector can be integrated into the host cell chromosome and then replicate with the host chromosome or the expression vector may be an episome and replicate autonomously independent of the host chromosome.

Expression vectors also can contain a selection gene, also termed a selectable marker. The selection gene can encode a protein necessary for the survival or growth of transformed host cells grown in a selective culture medium. Host cells not transformed with the vector containing the selection gene will not survive in the selective culture medium. Selection genes can encode proteins that (a) confer resistance to antibiotics or other toxins, e.g., ampicillin, neomycin, G418, puromycin, hygromycin, methotrexate, or tetracycline, (b) complement auxotrophic deficiencies, or (c) supply critical nutrients not available from complex media, e.g., the gene encoding D-alanine racemase for Bacilli. An exemplary selection scheme can utilize a drug to arrest growth of a host cell. Those cells that are successfully transformed with a heterologous gene can produce a protein conferring drug resistance and thus survive the selection regimen. Other selectable markers for use in bacterial or eukaryotic (including mammalian) systems are well-known in the art.

An example of a promoter that is capable of expressing a transgene in a mammalian nervous system cell is the EF1a promoter. Another example of a promoter is the immediate curly cytomegalovirus (CMV) promoter sequence. Other constitutive promoter sequences may also be used, including, but not limited to the simian virus 40 (SV40) early promoter, mouse mammary tumor virus promoter (MMTV), human immunodeficiency virus (HIV) long terminal repeat (LTR) promoter. MoMuLV promoter, phosphoglycerate kinase (PGK) promoter, MND promoter (a synthetic promoter that contains the U3 region of a modified MoMuLV LTR with myeloproliferative sarcoma virus enhancer, an avian leukemia virus promoter, an Epstein-Barr virus immediate early promoter, a Rous sarcoma virus promoter, as well as human gene promoters such as, but not limited to, the actin promoter, the myosin promoter, the elongation factor-1a promoter, the hemoglobin promoter, and the creatine kinase promoter. The promoter can be a non-constitutive promoter.

Inducible or repressible promoters are also contemplated for use in this disclosure. Examples of inducible promoters include a metallothionein promoter, a glucocorticoid promoter, a progesterone promoter, a tetracycline promoter, a c-fos promoter, the TREx system of ThermoFisher which places expression from the human cytomegalovirus immediate-early promoter under the control of tetracycline operator(s), and RheoSwitch promoters of Intrexon.

Expression vectors typically have promoter elements, e.g., enhancers, to regulate the frequency of transcriptional initiation. These can be located in the region 30-110 bp upstream of the start site, although a number of promoters have been shown to contain functional elements downstream of the start site as well. The spacing between promoter elements can frequently be flexible, so that promoter function can be preserved when elements are inverted or moved relative to one another. The expression vector may be a mono-cistronic construct, a bi-cistronic construct or multiple cistronic construct. For a bi-cistronic construct, the two cistrons can be oriented in opposite directions with the control regions for the cistrons located in between the two cistrons. When the construct has more than two cistrons, the cistrons can be arranged in two groups with the two groups oriented in opposite directions for transcription.

It can be desirable to modify the polypeptides described herein. There can be many ways of generating alterations in a given nucleic acid construct to generate variant polypeptides. Such methods can include site-directed mutagenesis. PCR amplification using degenerate oligonucleotides, exposure of cells containing the nucleic acid to mutagenic agents or radiation, chemical synthesis of a desired oligonucleotide (e.g., in conjunction with ligation and/or cloning to generate large nucleic acids) and other techniques (see, e.g., Gillam and Smith, *Gene* 8:81-97, 1979; Roberts el al., *Nature* 328:731-734, 1987, which is incorporated by reference in its entirely for all purposes). The recombinant nucleic acids encoding the polypeptides described herein can be modified to provide preferred codons which can enhance translation of the nucleic acid in a selected organism or cell line.

The polynucleotides can also include nucleotide sequences that are substantially equivalent (homologues) to other polynucleotides described herein. Polynucleotides can have at least about 80%, more typically at least about 90%, and even more typically at least about 95%, sequence identity to another polynucleotide. In an embodiment, a polynucleotide encoding a protein may be considered equivalent to a second polynucleotide encoding the same protein due to degeneracy of the genetic codon. Such polynucleotides are anticipated herein.

The nucleic acids can also provide the complement of the polynucleotides including a nucleotide sequence that has at least about 80%, more typically at least about 90%, and even more typically at least about 95%, sequence identity to a polynucleotide encoding a polypeptide recited herein. The polynucleotide can be DNA (genomic, cDNA, amplified, or synthetic) or RNA. Nucleic acids which encode protein analogs or variants (i.e., wherein one or more amino acids are designed to differ from the wild type polypeptide) may be produced using site directed mutagenesis or PCR amplification in which the primer(s) have the desired point mutations. For a detailed description of suitable mutagenesis techniques, see Sambrook el al., Molecular Cloning: A Laboratory Manual, Cold Spring Harbor Laboratory Press, Cold Spring Harbor. N.Y. (1989) and/or Current Protocols in Molecular Biology, Ausubel et al., eds, Green Publishers Inc. and Wiley and Sons, N.Y (1994), each of which is incorporated by reference in its entirely for all purposes. Chemical synthesis using methods well known in the art, such as that described by Engels et al., *Angew Chem Intl Ed* 28:716-34, 1989 (which is incorporated by reference in its entirety for all purposes), may also be used to prepare such nucleic acids.

Amino acid "substitutions" for creating variants can result from replacing one amino acid with another amino acid having similar structural and/or chemical properties, i.e., conservative amino acid replacements. Amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

When the nucleic acid is introduced into a cell ex vivo, the nucleic acid may be combined with a substance that promotes transference of a nucleic acid into a cell, for example, a reagent for introducing a nucleic acid such as a liposome or a cationic lipid, in addition to any additional excipients. Electroporation applying voltages in the range of about 20-1000 V/cm may be used to introduce nucleic acid or protein into exosomes. Transfection using cationic lipid-based transfection reagents such as, but not limited to, Lipofectamine® MessengerMAX™, Transfection Reagent. Lipofectamine® RNAiMAX Transfection Reagent, Lipofectaminc® 3000 Transfection Reagent, or Lipofectamine® LTX Reagent with PLUS™ Reagent, may also be used. The amount of transfection reagent used may vary with the reagent, the sample and the cargo to be introduced. Alternatively, a vector carrying the nucleic acid of the present invention can also be used. Particularly, a composition in a form suitable for administration to a living body which contains the nucleic acid of the present invention carried by a suitable vector can be suitable for in vivo gene therapy.

The nucleic acid constructs can include linker peptides. The linker peptides can adopt a helical, β-strand, coil-bend or turn conformations. The linker motif can be flexible linkers, rigid linkers or cleavable linkers. The linker peptides can be used for increasing the stability or folding of the peptide, avoid steric clash, increase expression, improve biological activity, enable targeting to specific sites in vivo, or alter the pharmacokinetics of the resulting fusion peptide by increasing the binding affinity of the targeting domain for its receptor. Folding, as used herein, refers to the process of forming the three-dimensional structure of polypeptides and proteins, where interactions between amino acid residues act to stabilize the structure. Non-covalent interactions are important in determining structure, and the effect of membrane contacts with the protein may be important for the correct structure. For naturally occurring proteins and polypeptides or derivatives and variants thereof, the result of proper folding is typically the arrangement that results in optimal biological activity, and can conveniently be monitored by assays for activity, e.g. ligand binding, enzymatic activity, etc.

The linker peptides can generally be composed of small non-polar (Gly) or non-polar (Ser) amino acids. The linker peptides can have sequences consisting primarily of stretches of glycine and/or serine residues. But can contain additional amino acids, such as Thr and Ala to maintain flexibility, as well as polar amino acids, such as Lys and Glu to improve solubility. In other cases, rigid linkers can have a Proline-rich sequence, such as $(XP)_n$, with X designating any amino acid, preferably Ala, Lys or Glu. In other cases, cleavable linkers can be used susceptibly to reductive or enzymatic cleavage, such as disulfide or protease sensitive sequences, respectively. In some cases, the linker peptides can be linked to a reporter moiety, such as a fluorescent protein. Examples of linker sequences include but are not limited to, any of $(Gly)_8$, $(Gly)_6$, $(GS)_n$ (n=1-5), $(GGGS)_n$ (n=1-5), $(GGGS)_n$ (n=1-5), $(GGGGS)_n$ (n=1-5), $(GGGGGS)_n$ (n=1-5) $(EAAAK)_n$ (n=1-3), $A(EAAAK)_4ALEA(EAAAK)_4A$, $(GGGGS)_n$ (n=1-4), (Ala-Pro)$_n$ (10-34 aa), cleavable linkers such as VSQTSKLTRA-ETVFPDV, PLGLWA, RVLAEA; EDVVCCSMSY; GGIEGRGS, TRHRQPRGWE, AGNRVRRSVG, RRRRRRRR, GLFG, and LE.

The nucleic acid sequence can also contain signal sequences that encode for signal peptides that function as recognition sequences for sorting of the resulting fusion protein to the vesicular surface. The signal sequence can comprise a tyrosine-based sorting signal and can contain the NPXY where N stands for asparagine, P stands for proline, Y stands for tyrosine and X stands for any amino acid (alanine, cysteine, aspartic acid, glutamic acid, phenylalanine, glycine, histidine, isoleucine, lysine, leucine, methionine, asparagine, proline, glutamine, arginine, serine, threonine, valine, tryptophan or tyrosine). In some cases, the signal sorting motif can comprise a YXXO consensus motif, where O stands for an amino acid residue with a bulky hydrophobic side chain. In some vases, the sorting signal can comprise a (DE)XXXI(LI) consensus motif where D stands for aspartic acid. E stands for glutamic acid, X stands for any amino acid, L stands for leucine and 1 stands for isoleucine. In some cases, the signal sequence can comprise a di-leucine-based signal sequence motif such as (DE)XXXL(LI) or DXXLL consensus motifs, where D stands for aspartic acid, E stands for glutamic acid, X stands for any amino acid, L stands for leucine and I stands for isoleucine. In some cases, the signal peptic can comprise an acidic cluster. In some cases, the signal peptide can comprise a FW-rich consensus motif, where F stands for phenylalanine and W stands for tryptophan. In some cases, the signal peptide can comprise a proline-rich domain. In some cases, the sorting signal comprises the consensus motif NPFX (1.2) D, where N stands for asparagine, P stands for proline, F stands for phenylalanine, D stands for aspartic acid and X stands for any amino acids. In some cases, the encoded signal peptides can be recognized by adaptor protein complexes AP-1, AP-2, AP-3 and AP-4. In some cases, the DXXLL signals are recognized by another family of adaptors known as GGAs. In some cases, the signal peptides can be ubiquitinated, in an embodiment of the invention, the signal peptide is an immunoglobulin K-chain signal peptide sequence, METDTLLLWVLLLWVPGSTGD. In another embodiment, the signal peptide is a human signal sequence. In a preferred embodiment, the signal peptide is a computationally designed signal peptide. In a preferred embodiment, the signal peptide sequence is MWWRLWWLLLLLLLLWPMVWA.

Production of Extracellular Vesicles

Any of the nucleic acids herein can be used for heterologous expression in a cell of a fusion protein comprising one or more chimeric vesicle localization moiety and one or more targeting moiety of interest, wherein the fusion protein localizes or is an integral part of an extracellular vesicle produced by the cell. In an embodiment, the vesicle is an extracellular vesicle or an exosome. Additionally, one or more nucleic acid encoding a chimeric vesicle localization moieties and one or more nucleic acid encoding a targeting moieties of interest can be used for heterologous expression in a cell to produce operably linked one or more chimeric vesicle localization moieties and one or more targeting moieties of interest wherein a targeting moiety associates with a chimeric vesicle localization moiety by non-covalent interaction through interacting partners or surfaces inherently present in or covalently attached to the targeting moiety of interest or chimeric vesicle localization moiety and wherein both the targeting moiety of interest and the chimeric vesicle localization are present at or associate with a vesicle, preferably an extracellular vesicle or exosome, produced by the cell.

Common GMP-grade cells used in such heterologous expression and from which vesicles may be isolated, including extracellular vesicles and exosomes, include HEK293 (human embryonic kidney cell line), variants of HEK293, such as HEK293T, HEK 293-F, HEK 293T, and HEK 293-H, dendritic cells, mesenchymal stem cell (MSCs), HT-1080, PER.C6, HeLa, C127, BHK, Sp2/0, NS0 and any variants thereof, and any of the following types of allogeneic stem cell lines: Hematopoietic Stem Cells, such as bone marrow HSC, Mesenchymal Stem Cells, such as bone marrow MSC or placenta MSC, human Embryonic Stem Cells or its more differentiated progeny, such as hESC-derived dendritic cell or hESC-derived oligodendrocyte progenitor cell, Neural Stem Cells (NSC's), endothelial progenitor cells (EPCs), or induced Pluripotent Stem Cells (iPSCs). In an embodiment, any of the cells used for heterologous expression may serve as a source for vesicles, especially extracellular vesicles comprising one or more chimeric vesicle localization moiety(ies) operably linked to one or more targeting moiety(ies) of interest. In a preferred embodiment, any of the cell used for heterologous expression may serve as a source for vesicles, especially extracellular vesicles comprising one or more chimeric vesicle localization moieties covalently linked to one or more targeting moieties of interest or a fusion protein comprising one or more chimeric vesicle localization moieties and to one or more targeting moieties of interest.

Any of the polypeptides herein can be produced by a cell (or cell line) generating vesicles which contain the polypeptide. Alternatively, the targeting moiety can be heterologously expressed by the cell producing the vesicle. In an embodiment, the cell producing the vesicle expresses a chimeric vesicle localization moiety and a targeting moiety wherein the targeting moiety associates with the chimeric vesicle localization moiety by a non-covalent linkage and wherein both the targeting moiety and the chimeric vesicle localization moiety associate with the vesicle. In an embodiment, the targeting moiety is displayed on the external surface or outside the vesicle. In an embodiment, the non-covalent linkage of a targeting moiety and a chimeric vesicle localization is mediated by interacting surfaces or partners between a polypeptide comprising the targeting moiety and a $2^{nd}$ polypeptide comprising the chimeric vesicle localization moiety, Such interacting surfaces or partners may be inherently present on or is introduced to the polypeptide comprising the targeting moiety and the $2^{nd}$ polypeptide comprising the chimeric vesicle localization moiety. Molecular forces maintaining non-covalent linkages or interactions include hydrogen bond, ionic bond, van der Waals interaction and hydrophobic bond.

In a preferred embodiment, the cell producing the vesicle also expresses a fusion protein comprising a chimeric vesicle localization moiety and a targeting moiety, which are covalently linked in a single polypeptide incorporated into a vesicle, preferably an extracellular vesicle or exosome, produced by the cell. In an embodiments, an extracellular vesicle or exosome producing cell may be considered a producer cell (for an EV or exosome). In an embodiment, more than one targeting moieties may be attached to a single chimeric vesicle localization moiety. In a separate embodiment, more than one type of chimeric vesicle localization moiety covalently linked to one or more targeting moieties may be present at or are associated with a vesicle, wherein each type of chimeric vesicle localization moiety differs by at least one amino acid. In an embodiment, the targeting moiety is coupled to the vesicle by the producing cell, during vesicle biogenesis or prior to vesicle secretion or isolation. In a different embodiment, the targeting moiety is coupled to the vesicle after the vesicles are produced and/or isolated.

Modified extracellular vesicles can be obtained from a subject, front primary cell culture cells obtained from a subject, from cell lines (e.g., immortalized cell lines), and other cell sources. One can make modified extracellular vesicles with specific markers in several ways. One such method includes engineering cells directly in culture to express targeting moieties that are then incorporated into the modified extracellular vesicles harvested as delivery vehicles from these engineered cells. Cells which are used for modified extracellular vesicle production are not necessarily related to or derived from the cell targets of interest. Once derived, vesicles may be isolated based on their size, biochemical parameters, or a combination thereof. Another method that can be used in conjunction with or independent of the direct cell engineering is physical isolation of particular subpopulations (subtypes) of modified vesicles with desired targeting moieties from the broad, general set of all vesicles produced by a subject. Another method that can be used in conjunction with the previously described two methods or independently is direct incorporation of desired targeting moieties (e.g., proteins/polypeptides) on the vesicles surface. In this method, a general population of extracellular vesicles or a specific population of extracellular vesicles are isolated from cell culture. The isolated vesicles are then treated to incorporate desired targeting moieties into the vesicles e liposomal fusion) to generate modified vesicles. It is noted that these methods can be combined in different ways.

For example, the process can be direct engineering of cells for modified vesicles production followed by isolating target modified vesicles subpopulation.

1. Example of engineering cells to produce desired modified vesicles. Vesicle producing cells can be transfected with nucleic acids such as a plasmid or virus carrying nucleic acids encoding the targeting moiety or moieties. The experimental steps can be as the following:
    a. Culture producer cell line in its optimal growth conditions.
    b. Prepare the plasmid or virus vector carrying a nucleic acid encoding the targeting moiety or moieties. The nucleic acid encoding the targeting moiety or moieties can be linked with a nucleic acid encoding a vesicle localization moiety, such as known exosomal surface protein (such as LAMP2), or a chimeric vesicle localization moiety (such as, for example, surface-and-transmembrane domains of LAMP2 and cytosolic domain of LAMP2 replaced with a cytosolic domain of a different vesicle localization moiety, such as CLSTN1) to make a fusion protein comprising a vesicle localization moiety or a chimeric vesicle localization moiety and a targeting moiety or moieties.
    c. Transfect the vesicle producing cell lines by the construct made in (b). The transfection can be performed in various ways, such as electroporation or liposome-based nucleic acid transfer. The transfection can be transient or stable transfection. For establishing a stable target protein (targeting moiety) expressing EV producing cell lines, integration of target sequence into the recipient cell genome may be needed. In a preferred embodiment, a stable fusion protein-expressing. EV-producing cell line is established wherein a nucleic acid encoding and expressing a fusion protein comprising one or more targeting moieties of interest and one or more vesicle localization moieties, preferably one or more chimeric vesicle localization moieties, is integrated into the recipient cell genome, so as to express the fusion protein(s) which are incorporated into EVs and display one or more targeting moieties of interest.
    d. The transfected cell culture is then grown in chemically defined media without FBS for further exosome collection. Alternatively, the transfected cell culture con be seeded into a bioreactor for exosome production.
    e. Collect the conditioned media after a certain period of time (e.g., 1 day, 2 days, 3 days, 4 days) from regular flask or dish culture or bioreactor culture.
    f. Isolate modified vesicles from conditioned media. Exosomes may be obtained from the appropriate biological sample using any protocol that yields exosomes useful for therapeutic use, e.g., sufficiently pure, intact exosomes with good stability. The isolation methods can include but are not limited to ultracentrifugation, ultrafiltration, polymer-based pulldown, or immunoaffinity-based pulldown. An antibody, ligand, receptor, and/or aptamer complementary to the desired EV targeting moiety(s) can be linked to immunogenetic beads or rods for binding to target EV subpopulation and subsequent isolation. Alternatively, other immune enrichment/isolation techniques can be used. Examples of immunoaffinity capture techniques that may be used to capture exosomes using a selected antibody cocktail include, but are not limited to, immunoprecipitation, column affinity chromatography, magnetic-activated cell sorting, fluorescence-activated cell sorting, adhesion-based sorting and microfluidic-based sorting. The antibodies in the antibody cocktail may be utilized together, in a single solution, or two or more solutions that are used simultaneously or consecutively.
2. Example of engineering vesicles with peptide targeting moieties (including for example an affinity peptide or any of the peptide targeting moieties describe herein) on the surface.
    a. Obtain a suitable expression vector, such as a mammalian expression vector, comprising selectable marker(s), such as puromycin resistance and/or a fluorescent protein.
    b. Clone a nucleic acid encoding a fusion protein comprising an amino terminal signal sequence, a peptide targeting moiety (such as an affinity peptide and/or any of the peptide targeting moieties described herein) and a vesicle localization moiety (preferably a chimeric vesicle localization moiety) and additionally comprising an epitope tag and linkers into the expression vector, wherein the nucleic acid is placed under the control of the promoter/enhancer of the expression vector. Examples of fusion protein could be any of the fusion proteins diagrammatically presented in FIGS. 1 and 2 with amino acid sequence provided in subsequent figures.

c. Optionally, the expression vector may be a viral vector, in which case the resulting expression vector of (b) may be used to produce viral particles, following standard protocol, d. Transfect (or infect if viral particles) a vesicle producing cell line with the expression vector now comprising the nucleic acid encoding the fusion protein of (b). The transfection can be performed in various ways, such as electroporation or liposome-based nucleic acid transfer. The transfection can be transient or stable transfection. For establishing a stable target protein (marker) expressing EV producing cell lines, integration of target sequence into the recipient cell genome may be needed.

e. The transfected cell culture is then grown on complete media with exosome-depleted FBS for further exosome collection. Alternatively, the transfected cell culture can be seeded into a bioreactor for exosome production, f. Collect the conditioned media after a certain period of time (e.g., 1 day, 2 days, 3 days, 4 days) from regular flask or dish culture or bioreactor culture.

g. Isolate modified vesicles from conditioned media using any technique known in the art or described herein.

3, Example of physical isolation of a specific EV subpopulation from a general vesicle population from a cell culture. This method can be combined with the method above or used as a stand-alone method on a non-engineered cell line. The vesicle subpopulation carrying a marker of interest can be isolated from a parental population. Preferably, the marker of interest is displayed on the surface of the vesicle, preferably an extracellular vesicle or exosome. The experimental steps can be the following:

a. Culture a vesicle producing cell line under its growth conditions with chemically defined media or in chemically defined media, free of FBS. Alternatively, the vesicle producing cell line can be seeded into a bioreactor for exosome production.

b. Collect the conditioned media after a certain period of time (e.g., 1 day, 2 days, 3 days, 4 days) from regular flask or dish culture or a bioreactor culture.

c. Isolate vesicles from the conditioned media. The isolation methods can include, but are not limited to, ultracentrifugation, ultrafiltration, polymer-based pulldown, or immunoaffinity-based pulldown.

d. Isolate modified vesicle subpopulations from parental EV populations using immunoaffinity-based pulldown. An antibody, ligand, receptor, and/or aptamer complementary to the desired EV marker(s) can be linked to immunomagnetic beads or rods for binding to target EV subpopulation and subsequent isolation. Alternatively, other immune enrichment/isolation techniques can be used, 4. Example of direct incorporation of the desired targeting moiety or moieties on the vesicle surface. A parental vesicle or vesicle subpopulation produced from regular flask/dish culture or bioreactor culture of transfected cells or non-transfected cells can be directly incorporated with the desired selective markers on the surface. In a preferred embodiment, the targeting moeity or moieties are covalently linked to a vesicle localization moiety, preferably a chimeric vesicle localization moiety of the invention. In a further embodiment, the fusion protein comprising the targeting moiety or moieties and a vesicle localization moiety, preferably a chimeric vesicle localization moiety, lacks a signal sequence. In an embodiment, the fusion protein comprising the targeting moiety or moieties and at chimeric vesicle localization moiety may be any of disclosed herein, but preferably, lacking a signal peptide. The experimental steps can be the following:

a. Purify vesicles and exchange vesicles into a suitable buffer for electroporation.

b. The binding of proteins or polypeptides on the vesicle surface can be achieved by:

i. Electroporation of the vesicle with desired selective targeting moieties. The controlled electric pulse permeabilizes areas on the vesicle surface membrane for insertion/incorporation of desired selective targeting moieties.

ii. The vesicle can also ruse with a particular liposome (or lipid/protein complex) carrying the desired selective targeting moieties on its surface. Via the fusion, the selective targeting moieties will then effectively be on the surface of the liposome-modified vesicle complex. See Sato et al., Sci. Reports 6:21933, DOI: 10.1038/srep21933 (2016), which is incorporated by reference in its entirety for all purposes. The vesicle can also be fived with an adeno-associated virus (AAV).

i. The vesicle can be incorporated with the targeting moieties directly by mixing the vesicle with the targeting moieties in a buffer of MES and NaCl in an Amicon® tube, wherein the targeting moieties can bind to proteins on the surface of the vesicle. The Amicon® tube can then be spun down to remove free-floating peptide.

The modified vesicles can be incorporated with the targeting moieties directly with or without cholesterol or other phospholipids. The modified vesicle protein mixture can be created via gentle mixing and incubation or several cycles of freezing and thawing.

The modified vesicles can be derived from eukaryotic cells that can be obtained from a subject (autologous) or from allogeneic cell lines. The subject may be any living organism. Examples of subjects include humans, dogs, cats, mice, rats, and transgenic species thereof. Vesicles can be concentrated and separated from the circulatory cells using centrifugation, filtration, or affinity chromography columns.

Payloads

The modified vesicle system described herein, for example modified vesicles such as exosomes, can be used to deliver payloads to target cells. In some instances, the payload is embedded in the vesicle, e.g., the lipid bilayer. Alternatively, or additionally, the payload can be surrounded by the vesicle or lipid bilayer.

As described above, targeting moieties on the modified vesicles traffic the modified vesicles in the body to target cells, and the targeting moieties are also involved in target cell recognition and interaction. Modified vesicles with these targeting moieties of interest can also be associated with or fused with other delivery vehicles, such as liposomes or adeno-associated viral vectors to enhance delivery to target cell. See György. Bence, et al. *Bionmaterials* 35 (2014)26:7599-7609. Modified vesicles can carry a payload that is to be delivered to the target cell.

A payload can be, for example, a small molecule, polypeptide, nucleic acid, lipid, carbohydrate, ligand, receptor, reporter, drug, or combination of the foregoing (e.g., two or more drugs, or one or more drugs combined with a lipid, etc.). Examples of payloads, include, for example therapeutic biologics (e.g., antibodies, recombinant proteins, or monoclonal antibodies), RNA (siRNA, shRNA, miRNA, antisense RNA, mRNA, noncoding RNA, tRNA, rRNA, other RNAs), reporters, lipids, carbohydrates, nucleic acid constructs (e.g., viral vectors, plasmids, lentivirus, expression constructs, other constructs), oligonucleotides, aptamers, cytotoxic agents, anti-inflammatory agents, antigenic peptides, small molecules, and nucleic acids and polypeptides for gene therapy. Payloads can also be complex molecular structures such as viral nucleic acid constructs (encoding transgenes) with accessory proteins for delivery to target cells where the nucleic acid construct can be (if needed) reverse transcribed, delivered to the nucleus, and integrated (or maintained extrachromosomally). Optionally, the construct with a desired transgene(s) can be specifically targeted to a site in the chromosome of the target cell using CRISPR/CAS and appropriate guide RNAs, Payloads may be loaded into the extracellular vesicle internal membrane space, displayed on, or partially or fully embedded in the lipid bi-layer surface of the extracellular vesicle.

Examples of pharmaceutical and biologic payloads include drugs for treating organ diseases and syndromes, cytotoxic agents, and anti-inflammatory drugs. In some cases, the payloads can be fenretinide, Doxorubicin, Mertansine (i.e. DMI) or Imatinib (i.e. Gleevec, STI-571) or any combination thereof.

Examples of RNA payloads include siRNAs, miRNAs, shRNA, antisense RNAs, small nuclear RNA (snRNA), small nucleolar RNA (snoRNA), long intergenic noncoding RNA (lincRNA), piwi interacting RNA (piRNA), ribosomal RNA (rRNA), tRNA, and rRNA. Examples of noncoding RNA payloads include microRNA (miRNA), long non-coding RNA (lncRNA), small nuclear RNA (snRNA), small nucleolar RNA (snoRNA), long intergenic non-coding RNA (lincRNA), piwi-interacting RNA (piRNA), ribosomal RNA (rRNA), yRNA and transfer RNA (tRNA). miRNAs and lncRNAs in particular are powerful regulators of homeostasis and cell signaling pathways, and delivery of such RNAs by an EV can impact the target cell.

Treatment payloads carried by the modified vesicles can include, for example nucleic acids such as miRNAs, mRNAs, siRNAs, anti-sense oligonucleotides (ASOs), DNA aptamers, CRISPR/Cas9 therapies that inhibit oncogenes, Cytotoxic transgene therapy to induce conditional toxicity, splice switching oligonucleotides or transgenes encoding toxic proteins. In some examples, the payload can be a nucleic acid payload listed in Table 4.

In some cases, a payload can be a reporter moiety. Reporters are moieties capable of being detected indirectly or directly. Reporters include, without limitation, a chromophore, a fluorophore, a fluorescent protein, a luminescent protein, a receptor, a hapten, an enzyme, and a radioisotope.

Examples of reporters include one or more of fluorescent reporter, a bioluminescent reporter, an enzyme, and an ion channel. Examples of fluorescent reporters include, for example, green fluorescent protein from *Aequorea victoria* or *Renilla reniformis*, and active variants thereof (e.g., blue fluorescent protein, yellow fluorescent protein, cyan fluorescent protein, etc.); fluorescent proteins from Hydroid jellyfishes, Copepod, Ctenophora, Anthrozoas, and Entacmaea quadricolor, and active variants thereof; and phycobiliproteins and active variants thereof, Chemiluminescent reporters include, for example, placental alkaline phosphatase (PLAP) and secreted placental alkaline phosphatase (SEAP) based on small molecule substrates such as CPSD (Disodium 3-(4-methoxyspiro {1,2-dioxetane-2'-(5'-chloro) tricyclo [3.3.1.13,7]decan}-4-yl)phenyl phosphate. β-galactosidase based on 1,2-dioxetane substrates, neuraminidase based on NA-Star® substrate, all of which are commercially available from ThermoFisher Scientific. Bioluminescent reporters include, for example, acquorin (and other Ca+2 regulated photoproteins), luciferase based on luciferin substrate, luciferase based on Coelenterazine substrate (e.g., Renilla, Gaussia, and Metridina), and luciferase from Cypridina, and active variants thereof. In some embodiments, the bioluminescent reporters include, for example, North American firefly luciferase, Japanese firefly luciferase, Italian firefly luciferase. Vast European firefly luciferase. Pennsylvania firefly luciferase, Click beetle luciferase, railroad worm luciferase. Renilla luciferase, Gaussia luciferase, Cypridina luciferase, Metrida luciferase, OLuc, and red firefly luciferase, all of which are commercially available from ThermoFisher Scientific and/or Promega. Enzyme reporters include, for example, γ-galactosidase, chloramphenicol acetyltransferase, horseradish peroxidase, alkaline phosphatase, acetylcholinesterase, and catalase. Ion channel reporters, include, for example, cAMP activated cation channels. The reporter or reporters may also include a Positron Emission Tomography (PET)-reporter, a Single Photon Emission Computed Tomography (SPECT) reporter, a photoacoustic reporter, an X-ray reporter, and an ultrasound reporter.

Nucleic acid payloads can be oligonucleotides, recombinant polynucleotides, DNA, RNA, or otherwise synthetic nucleic acids. The nucleic acids can cause splice switching of RNAs in the target cell, turn off aberrant gene expression in the target cell, replace aberrant (mutated) genes in the chromosome of the target cell with genes encoding a desired sequence. The replacement nucleic acids can be an entire transgene or can be short segments of the mutated/aberrant gene that replaces the mutated sequence with a desired sequence (e.g., a wild-type sequence). Alternatively, the nucleic acid payloads can alter a wild-type gene sequence in the target cell to a desired sequence to produce a desired result. The payload nucleic acids can also introduce a transgene into the target cell that is not normally expressed. The payload nucleic acids can also cause desired deletions of nucleic acids from the genome of the target cell.

Appropriate genome editing systems can be used with the payload nucleic acids such as CRISPR, TALEN, or Zine-Finger nucleases. The efficiency of homologous and non-homologous recombination can be facilitated by genome editing technologies that introduce targeted double-stranded breaks (DSB). Examples of DSB-generating technologies are CRISPR/Cas9, TALEN, Zinc-Finger Nuclease, or equivalent systems. See, Cong et al. Science 339.6121 (2013): 819-823, Li et al. Nucleic Acids Res. (2011); Gaj et al. Trends in Biotechnology 31.7 (2013): 397-4105, all of which are incorporated by reference in their entirety for all purposes. Payload nucleic acids can be integrated into desired sites in the genome (e.g., to repair or replace nucleic acids in the chromosome of the target cell), or transgenes can be integrated at desired sites in the genome including, for example, genomic safe harbor site, such as, (or example, the CCR5, AAVS1, human ROSA26 or PSIP1 loci.

Introducing Payloads

Payloads can be incorporated into vesicles through several methods involving physical manipulation. Physical manipulation methods include but are not limited to, electroporation, sonication, mechanical vibration, extrusion through porous membranes, electric current and combinations thereof, which cause disruption of vesicle membrane. Loading of cargo to vesicles described herein may involve passive loading processes such as mixing, co-incubation, or active loading processes such as electroporation, sonication, mechanical vibration, extrusion through porous membranes, electric current and combinations thereof. In some embodiments, said loading can be done concomitantly with vesicle assembly.

Payloads of interest can be passively loaded into vesicles by incubation with payloads to allow diffusion into the vesicles along the concentration gradient. The hydrophobicity of the drug molecules can affect the loading efficiency. Hydrophobic drugs can interact with the lipid layers of the vesicle membrane and enable stable packaging of the drug in the vesicle's lipid bilayer. In some embodiments, purified exosome solution suspended in buffer solution can be incubated with payload. In some preferred embodiments, the payload is dissolved in a solvent mixture that can include DMSO, to allow passive diffusion into exosomes. Following this, the payload-exosomes mixture is made free from unencapsulated payload. In preferred embodiments, centrifugation or size-exclusion columns are used to remove precipitates from the supernatant. LC/MS method can be used for the measurement and characterization of payload in the exosome-payload formulation, following lysis and removal of the exosome fraction.

Nucleic acids of interest can be incubated with purified exosomes to allow transfection of purified exosomes in the presence of a suitable lipid-based transfection reagent. Centrifugation can be used to purify the suspension and isolate the transfected exosome population. Transfected exosomes can then be added to target cells or used in vivo.

Payload can be diffused into cells by incubation with cells that then produce exosomes that carry the payload. For example, cells treated with a drug can secrete exosomes loaded with the drug. In a previous example, Pascucci et al., have treated SR4987 mesenchymal stroma cells with a low dose of paclitaxel for 24 h, then washed the cells and reseeded them in a new flask with fresh medium. After 48 h of culture, the cell conditioned medium was collected, and exosomes were isolated. The paclitaxel-loaded exosomes from the treated cells had significant, strong anti-proliferative activities against CFPAC-1 human pancreatic cells in vitro, as compared with the exosomes from untreated cells (Pascucci, L et al., Journal of Controlled Release, 192 (2014): 262-270.

Extracellular vesicles secreted from cells can be mixed with payloads and subsequently sonicated by using a homogenizer probe. The mechanical shear force from the sonicator probe can compromise the membrane integrity of the exosomes and subsequently allow the drug to diffuse into the exosomes during this membrane deformation, especially, a hydrophilic drug.

In another embodiment, extracellular vesicles from cells can be mixed with a payload, and the mixture can be loaded into a syringe-based lipid extruder with 100-400 nm porous membranes under a controlled temperature. The exosome membrane can be disrupted during the extrusion process can allow vigorous mixing with the drug. In some examples, the number of effective extrusions can vary from 1-10 to effectively deliver drugs into exosomes.

Payload of interest can be incubated with exosomes at room temperature for a fixed amount of time. Repeated freeze-thaw cycles are then performed to ensure drug encapsulation. The method can result in a broad distribution of size ranges for the resulting exosomes, and then, the mixture is rapidly frozen at −80° C. or in liquid nitrogen and thawed at room temperature. The number of effective freeze-thaw cycle may vary from 2-7 for effective encapsulation. In another embodiment, membrane fusion between exosomes and liposomes can be initiated through freeze-thaw cycles to create exosome-mimetic particles.

In another cases, small pores can be created in exosomes membrane through application of an electrical field to exosomes suspended in a conductive solution. The phospholipid bilayer of the exosomes can be disturbed by the electrical current. Payloads can subsequently diffuse into the interior of the exosomes via the pores. The integrity of the exosome membrane can then be recovered after the drug loading process. In some examples, nucleic acids, e.g., mRNA, siRNA or miRNA can be loaded into exosomes using this method.

In some cases, electroporation can be conducted in un optimized buffers such as trehalose disaccharide to aid in maintaining structural integrity and can inhibit the aggregation of exosomes.

Membrane permeabilization can be initiated through incubation with surfactants, such as, saponin. In some examples, hydrophilic molecules can be assisted in exosome encapsulation by this process.

Chemistry based approaches can also be used to directly attach molecules to the surfaces of exosomes via covalent bonds. In some examples, copper-catalyzed azide alkyne cycloaddition can be used for the bioconjugation of small molecules and macromolecules to the surfaces of exo-mesas shown in Wang et al., 2015 and Hood et al., 2016—the references incorporated in their entirety.

In another embodiment, fluorophores and microbeads conjugated to highly specific antibodies can bind a particular antigen on the cell surface. Specific antigen-conjugated microbeads can be used for exosome isolation and tracking in vivo.

Pharmaceutical Compositions

Pharmaceutical compositions disclosed herein may comprise modified extracellular vesicles of the invention and/or liposomes with (or without) a payload, as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants: chelating agents such as EDTA or glutathione; adjuvants (e.g., aluminum hydroxide); and preservatives. Compositions are in one aspect formulated for intravenous administration or intracranial administration or intranasal administration to the central nervous system. Compositions described herein may include lyophilized EVs (e.g., exosomes). In a preferred embodiment, composition comprises an EV or exosome and a pharmaceutically acceptable excipient.

Pharmaceutical compositions may be administered in a manner appropriate to the disease to be treated (or prevented). The quantity and frequency of administration will be determined by such factors as the condition of the patient, and the type and severity of the patient's disease, although appropriate dosages may be determined by clinical trials.

Suitable pharmaceutically acceptable excipients are well known to a person skilled in the art. Merely by way of example, excipients include, but are not limited to, surfactants, lipophilic vehicles, hydrophobic vehicles, sodium citrate, calcium carbonate, and dicalcium phosphate.

The composition can be formulated into a known form suitable for parenteral administration, for example, injection or infusion. The composition may comprise formulation additives such as a suspending agent, a preservative, a stabilizer and/or a dispersant, and a preservation agent for extending a validity term during storage.

The administration of the subject compositions may be carried out in any convenient manner, including by aerosol inhalation, injection, ingestion, transfusion, implantation or transplantation. The compositions described herein may be administered to a patient trans arterially, subcutaneously, sublingually, intradermally, intranodally, intramedullary, intramuscularly, intranasally, intraarterially, into an afferent lymph vesicle, by intravenous (i.v.) injection, or intracranially injection, or intraperitoneally. In one aspect, the compositions of the present invention are administered to a patient by intradermal or subcutaneous injection. In one aspect, the modified vesicles compositions described herein are administered by i.v. injection. Compositions can be administered in a way which allows them to cross the blood-brain harrier, vascular barrier, or other epithelial barrier, Kits of the Invention According to another aspect of the invention, kits are provided. Kits according to the invention include package(s) comprising any of the compositions of the invention (including the extracellular vesicles of the invention, chimerical vesicle localization moieties, fusion proteins, and nucleic acids).

The phrase "package" means any vessel containing compositions presented herein. In preferred embodiments, the package can be a box or wrapping. Packaging materials for use in packaging pharmaceutical products are well known to those of skill in the art. Examples of pharmaceutical packaging materials include, but are not limited to, blister packs, bottles, tubes, inhalers, pumps, bags, vials, containers, syringes (including pre-filled syringes), bottles, and any packaging material suitable for a selected formulation and intended mode of administration and treatment.

The kit can also contain items that are not contained within the package but are attached to the outside of the package, for example, pipettes.

Kits may optionally contain instructions for administering compositions of the present invention to a subject having a condition in need of treatment. Kits may also comprise instructions for approved uses of components of the composition herein by regulatory agencies, such as the United States Food and Drug Administration. Kits may optionally contain labeling or product inserts for the present compositions. The package(s) and/or any product insert(s) may themselves be approved by regulatory agencies. The kits can include compositions in the solid phase or in a liquid phase (such as buffers provided) in a package. The kits also can include buffers for preparing solutions for conducting the methods, and pipettes for transferring liquids from one container to another.

The kit may optionally also contain one or more other compositions for use in combination therapies as described herein. In certain embodiments, the package(s) is a container for any of the means for administration such as intratumoral delivery, peritumoral delivery, intraperitoneal delivery, intrathecal delivery, intramuscular injection, subcutaneous injection, intravenous delivery, intra-arterial delivery, intraventricular delivery, intrasternal delivery, intracranial delivery, or intradermal injection.

TABLE 1

Nucleic acid sequences and amino acid sequences for preferred vesicle localization moieties used to produce a chimeric vesicle localization moiety

| SEQ ID NO: | Sequence | Source |
|---|---|---|
| 1 | ATGGTGTTGCTGAGAGTGTTAATTCTGCTCCTCTCCTGGGCGGCG GGGATGGGAGGTCAGTATGGGAATCCTTTAAATAAATATATCAG ACATTATGAAGGATTATCTTACAATGTGGATTCATTACACCAAAA ACACCAGCGTGCCAAAAGAGCAGTCTCACATGAAGACCAATTTT TACGTCTAGATTTCCATGCCCATGGAAACATTTCAACCTAGCGAA TGAAGAGGGACACTTCCCTTTTCAGTGATGAATTTAAAGTAGAA ACATCAAATAAAGTACTTGATTATGATACCTCTCATATTTACACT GGACATATTTATGGTGAAGAAGGAAGTTTTAGCCATGGGTCTGT TATTGATGGAAGATTTGAAGGATTCATCCAGACTCGTGGTGGCA CATTTTATGTTGAGCCAGCAGAGAGATATATTAAAGACCGAACT CTGCCATTTCACTCTGTCATTTATCATGAAGATGATATTAACTAT CCCCATAAATACGGTCCTCAGGGGGGCTGTGCAGATCATTCAGT ATTTGAAAGAATGAGGAAATACCAGATGACTGGTGTAGAGGAA GTAACACAGATACCTCAAGAAGAACATGCTGCTAATGGTCCAGA ACTTCTGAGGAAAAAACGTACAACTTCAGCTGAAAAAAATACTT GTCAGCTTTATATTCAGACTGATCATTTGTTCTTTAAATATTACG GAACACGAGAAGCTGTGATTGCCCAGATATCCAGTCATGTTAAA GCGATTGATACAATTTACCAGACCACAGACTTCTCCGGAATCCGT AACATCAGTTTCATGGTGAAACGCATAAGAATCAATACAACTGC TGATGAGAAGGACCCTACAAATCCTTTCCGTTTCCCAAATATTGG TGTGGAGAAGTTTCTGGAATTGAATTCTGAGCAGAATCATGATG ACTACTGTTTGGCCTATGTCTTCACAGACCGAGATTTTGATGATG GCGTACTTGGTCTGGCTTGGGTTGGAGCACCTTCAGGAAGCTCTG GAGGAATATGTGAAAAAGTAAACTCTATTCAGATGGTAAGAAG AAGTCCTTAAACACTGGAATTATTACTGTTCAGAACTATGGGTCT CATGTACCTCCCAAAGTCTCTCACATTACTTTTGCTCACGAAGTT GGACATAACTTTGGATCCCCACATGATTCTGGAACAGAGTGCAC ACCAGGAGAATCTAAGAATTTGGGTCAAAAAGAAAATGGCCAATT | Transcript ID ENST00000260408; Homo Sapiens |

TABLE 1-continued

Nucleic acid sequences and amino acid sequences for preferred vesicle localization moieties used to produce a chimeric vesicle localization moiety

| SEQ ID NO: | Sequence | Source |
|---|---|---|
| | ACATCATGTATGCAAGAGCAACATCTGGGGACAAACTTAACAAC<br>AATAAATTCTCACTCTGTAGTATTAGAAATATAAGCCAAGTTCTT<br>GAGAAGAAGAGAAACAACTGTTTTGTTGAATCTGGCCAACCTAT<br>TTGTGGAAATGGAATGGTAGAACAAGGTGAAGAATGTGATTGTG<br>GCTATAGTGACCAGTGTAAAGATGAATGCTGCTTCGATGCAAAT<br>CAACCAGAGGGAAGAAAATGCAAACTGAAACCTGGGAAACAGT<br>GCAGTCCAAGTCAAGGTCCTTGTTGTACAGCACAGTGTGCATTCA<br>AGTCAAAGTCTGAGAAGTGTCGGATGATTCAGACTGTGCAAGG<br>GAAGGAATATGTAATGGCTTCACAGCTCTCTGCCCAGCATCTGA<br>CCCTAAACCAAACTTCACAGACTGTAATAGGCATACACAAGTGT<br>GCATTAATGGGCAATGTGCAGGTTCTATCTGTGAGAAATATGGC<br>TTAGAGGAGTGTACGTGTGCCAGTTCTGATGGCAAAGATGATAA<br>AGAATTATGCCATGTATGCTGTATGAAGAAAATGGACCCATCAA<br>CTTGTGCCAGTACAGGGTCTGTGCAGTGGAGTAGGCACTTCAGT<br>GGTCGAACCATCACCCTGCAACCTGGATCCCCTTGCAACGATTTT<br>AGAGGTTACTGTGATGTTTTCATGCGGTGCAGATTAGTAGATGCT<br>GATGGTCCTCTAGCTAGGCTTAAAAAAGCAATTTTTAGTCCAGA<br>GCTCTATGAAAACATTGCTGAATGGATTGTGGCTCATTGGTGGGC<br>AGTATTACTTATGGGAATTGCTCTGATCATGCTAATGGCTGGATT<br>TATTAAGATATGCAGTGTTCATACTCCAAGTAGTAATCCAAAGTT<br>GCCTCCTCCTAAACCACTTCCAGGCACTTTAAAGAGGAGGAGAC<br>CTCCACAGCCCATTCAGCAACCCCAGCGTCAGCGGCCCCGAGAG<br>AGTTATCAAATGGGACACATGAGACGCTAA | |
| 2 | MVLLRVLILLLSWAAGMGGQYGNPLNKYIRHYEGLSYNVDSLHQK<br>HQRAKRAVSHEDQFLRLDFHAHGRHFNLRMKRDTSLFSDEFKVETS<br>NKVLDYDTSHIYTGHIYGEEGSFSHGSVIDGRFEGFIQTRGGTFYVEP<br>AERYIKDRTLPFHSVIYHEDDINYPHKYGPQGGCADHSVFERMRKY<br>QMTGVEEVTQIPQEEHAANGPELLRKKRTTSAEKNTCQLYIQTDHL<br>FFKYYGTREAVIAQISSHVKAIDTIYQTTDFSGIRNISFMVKRIRINTT<br>ADEKDPTNPFRFPNIGVEKFLELNSEQNHDDYCLAYVFTDRDFDDG<br>VLGLQWVGAPSGSSGGICEKSKLYSDGKKKSLNTGIITVQNYGSHV<br>PPKVSHITFAHEGHNFGSPHDSGTECTPGESKNLGQKENGNYIMY<br>ARATSGDKLNNNKFSLCSIRNISQVLEKKRNNCFVESGQPICGNGM<br>VEQGEECDCGYSDQCKDECCFDANQPEGKCKLKPGKQCSPSQGP<br>CCTAQCAFKSKSEKCRDDSDCAREGICNGFTALCPASDKPNFTDC<br>NRHTQVCINGQCAGSICEKYGLEECTCASSDGKDDKELCHVCCMK<br>KMDPSTCASTGSVQWSRHFSGRTITLQPGSPCNDFRGYCDVFMRCR<br>LVDADGPLARLKKAIFSPELYENIAWEIVAHWWAVLLMGIALIMLM<br>AGFIKICSVHTPSSNPKLPPPKPLPGTLKRRRPPQPIQQPQRQRPRESY<br>QMGHMRR | ADAM10 protein (ENSP00000260408) encoded by Transcript ID ENSE00000260408 from Gene ID ENSG00000137845; *Homo sapiens* |
| 3 | ATGGAATCCAAGGGGGCCAGTTCCTGCCGTCTGCTCTTCTGCCTC<br>TTGATCTCCGCCACCGTCTTCAGGCCAGGCCTTGGATGGTATACT<br>GTAAATTCAGCATATGGAGATACCATTATCATACCTTGCCGACTT<br>GACGTACCTCAGAATCTCATGTTTGGCAAATGGAAATATGAAAA<br>GCCCGATGGCTCCCCAGTATTTATTGCCTTCAGATCCTCTACAAA<br>GAAAGTGTGCAGTACGACGATGTACCAGAATACAAAGACAGA<br>TTGAACCTCTCAGAAAACTACACTTTGTCTATCAGTAATGCAAGG<br>ATCAGTGATGAAAAGAGATTTGTGTGCATGCTAGTAACTGAGGA<br>CAACGTGTTTGAGGCACCTACAATAGTCAAGGTGTTCAAGCAAC<br>CATCTAACCTGAAATTGTAAGCAAAGCACTGTTTCTCGAAACA<br>GAGCAGCTAAAAAAGTTGGGTGACTGCATTTCAGAAGACAGTTA<br>TCCAGATGGCAATATCACATGGTACAGGAATGGAAAAGTGCTAC<br>ATCCCCTTGAAGGAGCGGTGGTCATAATTTTTAAAAAGGAAATG<br>GACCCAGTGACTCAGCTCTATACCATGACTTCCACCCTGGAGTAC<br>AAGACAACCAAGGCTGACATACAAATGCCATTCACCTGCTCGGT<br>GACATATTATGGACCATCTGGCCAGAAAACAATTCATTCTGAAC<br>AGGCAGTATTTGATATTTACTATCCTACAGAGCAGGTGACAATA<br>CAAGTGCTGCCACCAAAAAATGCCATCAAAGAAGGGGATAACAT<br>CACTCTTAAATGCTTAGGGAATGGCAACCCTCCCCCAGAGGAAT<br>TTTTGTTTTACTTACCAGGACAGCCCGAAGGAATAAGAAGCTCA<br>AATACTTACACACTGACGGATGTGAGGCGCAATGCAACAGGAGA<br>CTACAAGTGTTCCCTGATAGACAAAAAAAGCATGATTGCTTCAA<br>CAGCTATCACAGTTCACTATTTGGATTTGTCCTTAAACCCAAGTG<br>GAGAAGTGACTAGACAGATTGGTGATGCCCTACCCGTGTCATGC<br>ACAAATATCTGCTAGCAGGAATGCAACTGTGGTATGGATGAAAGA<br>TAACATCAGGCTTCGATCTAGCCCGTCCATTTTCTAGTCTTCATTATC<br>CAGGATGCTGGAAACTATGTCTGCGAAACTGCTCTGCAGGAGGT<br>TGAAGGACTAAAGAAAAGAGAGTCATTGACTCTCATTGTAGAAG<br>GCAAACCCTCAAATAAAAATGACAAAGAAAACTGATCCCAGTGG<br>ACTATCTAAAACAATAATCTGCCATGTGGAAGGTTTTCCAAAGC<br>CAGCCCATTCAATGGACAATTACTGGCAGTGGAAGCGTCATAAAC | Transcript ID ENST00000306107; *Homo sapiens* |

TABLE 1-continued

Nucleic acid sequences and amino acid sequences for preferred vesicle
localization moieties used to produce a chimeric vesicle localization moiety

| SEQ ID NO: | Sequence | Source |
|---|---|---|
|  | CAAACAGAGGAATCTCCTTATATTAATGGCAGGTATTATAGTAA<br>AATTATCATTTCCCCTGAAGAGAATGTTACATTAACTTGCACAGC<br>AGAAAACCAACTGGAGAGAACAGTAAACTCCTTGAATGTCTCTG<br>CTATAAGTATTCCAGAACACGATGAGGCAGACGAGATAAGTGAT<br>GAAAACAGAGAAAAGGTGAATGACCAGGCAAAACTAATTGTGG<br>GAATCGTTGTTGGTCTCCTCCTTGCTGCCCTTGTTGCTGGTGTCGT<br>CTACTGGCTGTACATGAAGAAGTCAAAGACTGCATCAAAACATG<br>TAAACAAGGACCTCGGTAATATGGAAGAAAACAAAAAGTTAGA<br>AGAAAACAATCACAAAACTGAAGCCTAA |  |
| 4 | MESKGASSCRLLFCLLISATVFRPGLGWYTVNSAYGDTIIIPCRLDVP<br>QNLMFGKWKYEKPDGSPVFIAFRSSTKKSVQYDDVPEYKDRLNLSE<br>NYTLSISNARISDEKRFVCMLVTEDNVFEAPTIVKVFKQPSKPEIVSK<br>ALFLETEQLKKLGDCISEDSYPDGNITWYRNGKVLHPLEGAVVIIFK<br>KEMDPVTQLYTMTSTLEYKTTKADIQMPFTCSVTYYGPSGQKTIHS<br>EQAVFDIYYPTEQVTIQVLPPKNAIKEGDNITLKCLGNGNPPPEEFLF<br>YLPGQPEGIRSSNTYTLTDVRRNATGDYKCSLIDKKSMIASTAITVH<br>YLDLSLNPSGEVTRQIGDALPVSCTISASRNATVVWMKDNIRLRSSP<br>SFSSLHYQDAGNYVCETALQEVEGLKKRESLTLIVEGKPQIKMTKK<br>TDPSGLSKTHCHVEGFPKPAIQWTITGSGSVINQTEESPYINGRYYSK<br>HISPEENVTLTCTAENQLERTVNSLNVSAISIPEHDEADEISDENREK<br>VNDQAKLIVGIVVGLLLAALVAGVVYWLYMKKSKTASKHVNKDL<br>GNMEENKKLEENNHKTEA | ALCAM<br>protein<br>(ENSP00000305988)<br>encoded by<br>Transcript ID<br>ENST00000306107<br>from Gene<br>ID<br>ENSG00000170017;<br>*Homo sapiens* |
| 5 | ATGGAATCCAAGGGGGCCAGTTCCTGCCGTCTGCTCTTCTGCCTC<br>TTGATCTCCGCCACCGTCTTCAGGCCAGGCCTTGGATGGTATACT<br>GTAAATTCAGCATATGGAGATACCATTATCATACCTTGCCGACTT<br>GACGTACCTCAGAATCTCATGTTTGGCAAATGGAAATATGAAA<br>GCCCGATGGCTCCCCAGTATTTATTGCCTTCAGATCCTCTACAAA<br>GAAAAGTGTGCAGTACGACGATGTACCAGAATACAAAGACAGA<br>TTGAACCTCTCAGAAAACTACACTTTGTCTATCAGTAATGCAAGG<br>ATCAGTGATGAAAAGAGATTTGTGTGCATGCTAGTAACTGAGGA<br>CAACGTGTTTGAGGCACCTACAATAGTCAAGGTGTTCAAGCAAC<br>CATCTAAACCTGAAATTGTAAGCAAAGCACTGTTTCTCGAAACA<br>GAGCAGCTAAAAAAGTTGGGTGACTGCATTTCAGAAGACAGTTA<br>TCCAGATGGCAATATCACATGGTACAGGAATGGAAAAGTGCTAC<br>ATCCCCTTGAAGGAGCGGTGGTCATAATTTTTAAAAAGGAAATG<br>GACCCAGTGACTCAGCTCTATACCATGACTTCCACCCTGGAGTAC<br>AAGACAACCAAGGCTGACATACAAATGCCATTCACCTGCTCGGT<br>GACATATTATGGACCATCTGGCCAGAAAACAATTCATTCTGAAC<br>AGGCAGTATTTGATATTTACTATCCTACAGAGCAGGTGACAATA<br>CAAGTGCTGCCACCAAAAAATGCCATCAAAGAAGGGGATAACAT<br>CACTCTTAAATGCTTAGGGAATGGCAACCCTCCCCCAGAGGAAT<br>TTTGTTTTACTTACCAGGACAGCCCGAAGGAATAAGAAGCTCA<br>AATACTTACACACTGACGGATGTGAGGCGCAATGCAACAGGAGA<br>CTACAAGTGTTCCCTGATAGACAAAAAAAGCATGATTGCTTCAA<br>CAGCTATACAGTTCACTATTTGGATTTGTCCTTAAACCCAAGTG<br>GAGAAGTGACTAGACAGATTGGTGATGCCCTACCCGTGTCATGC<br>ACAATATCTGCTAGCAGGAATGCAACTGTGGTATGGATGAAAGA<br>TAACATCAGGCTTCGATCTAGCCCGTCATTTTCTAGTCTTCATTAT<br>CAGGATGCTGGAAACTATGTCTGCGAAACTGCTCTGCAGGAGGT<br>TGAAGGACTAAAGAAAAGAGAGTCATTGACTCTCATTGTAGAAG<br>GCAAACCTCAAATAAAAATGACAAAGAAAACTGATCCCAGTGG<br>ACTATCTAAAACAATAATCTGCCATGTGGAAGGTTTTCCAAAGC<br>CAGCCATTCAATGGACAATTACTGGCAGTGGAAGCGTCATAAAC<br>CAAACAGAGGAATCTCCTTATATTAATGGCAGGTATTATAGTAA<br>AATTATCATTTCCCCTGAAGAGAATGTTACATTAACTTGCACAGC<br>AGAAAACCAACTGGAGAGAACAGTAAACTCCTTGAATGTCTCTG<br>CTAATGAAAACAGAGAAAAGGTGAATGACCAGGCAAAACTAAT<br>TGTGGGAATCGTTGTTGGTCTCCTCCTTGCTGCCCTTGTTGCTGGT<br>GTCGTCTACTGGCTGTACATGAAGAAGTCAAAGACTGCATCAAA<br>ACATGTAAACAAGGACCTCGGTAATATGGAAGAAAACAAAAAG<br>TTAGAAGAAAACAATCACAAAACTGAAGCCTAA | Transcript<br>ID<br>ENST00000472644;<br>*Homo sapiens* |

TABLE 1-continued

Nucleic acid sequences and amino acid sequences for preferred vesicle
localization moieties used to produce a chimeric vesicle localization moiety

| SEQ ID NO: | Sequence | Source |
|---|---|---|
| 6 | MESKGASSCRLLFCLLISATVFRPGLGWYTVNSAYGDTIIIPCRLDVP QNLMFGKWKYEKPDGSPVFIAFRSSTKKSVQYDDVPEYKDRLNLSE NYTLSISNARISDEKRFVCMLVTEDNVFEAPTIVKVFKQPSKPEIVSL ALFLETEQLKKLGDCISEDSYPDGNITWYRNGKVLHPLEGAVVHFK KEMDPVTQLYTMTSTLEYKTTKADIQMPFTCSVTYYGPSGQKTIHS DQAVFDIYYPTEQVTIQVLPPKNAIKEGDNITLKCLGNGNPPPEEFLF YLPGQPEGIRSSNTYTLTDVRRNATGDYKCSLIDKKSMIASTAITVH YLDLSLNPSGEVTRQIGDALPVSCTISASRNATVVWMKDNIRLRSSP SFSSLHYQDAGNYVCETALQEVEGLKKRESLTLIVEGKPQIKMTKK TDPSGLSKTIICHVEGFPKPAIQWTITGSGSVINQTEESPYINGRYYSK IIISPEENVTLTCTAENQLERTVNSLNVSANENREKVNDQAKLIVGIV VGLLLAALVAGVVYWLYMKKSKTASKHVNKDLGNMEENKKLEE NNHKTEA | ALCAM protein (ENSP00000419236) encoded by Transcript ID ENST00000472644 from Gene ID ENSG00000170017; *Homo sapiens* |
| 7 | ATGCTGCGCCGCCCCGCTCCCGCGCTGGCCCCGGCCGCCCGGCT GCTGCTGGCCGGGCTGCTGTGCGGCGGCGGGGTCTGGGCCGCGC GAGTTAACAAGCACAAGCCCTGGCTGGAGCCCACCTACCACGGC ATAGTCACAGAGAACGACAACACCGTGCTCCTCGACCCCCCACT GATCGCGCTGGATAAAGATGCGCCTCTGCGATTTGCAGGTGAGA TTTGTGGATTTAAAATTCACGGGCAGAATGTCCCCTTTGATGCAG TGGTAGTGGATAAATCCACTGGTGAGGGAGTCATTCGCTCCAAA GAGAAACTGGACTGTGAGCTGCAGAAAGACTATTCATTCACCAT CCAGGCCTATGATTGTGGGAAGGGACCTGATGGCACCAACGTGA AAAAGTCTCATAAAGCAACTGTTCATATTCAGGTGAACGACGTG AATGAGTACGCGCCCGTGTTCAAGGAGAAGTCCTACAAAGCCAC GGTCATCGAGGGGAAGCAGTACGACAGCATTTTGAGGGTGGAGG CCGTGGATGCCGACTGCTCCCCTCAGTTCAGCCAGATTTGCAGCT ACGAAATCATCACTCCAGACGTGCCCTTTACTGTTGACAAAGAT GGTTATATAAAAAACACAGAGAAATTAAACTACGGGAAAGAAC ATCAATATAAGCTGACCGTCACTGCCTATGACTGTGGGAAGAAA AGAGCCACAGAAGATGTTTTGGTGAAGATCAGCATTAAGCCCAC CTGCACCCCTGGGTGGCAAGGATGGAACAACAGGATTGAGTATG AGCCGGGCACCGGCGCGTTGGCCGTCTTTCCAAATATCCACCTG GAGACATGTGACGAGCCAGTCGCCTCAGTACAGGCCACAGTGGA GCTAGAAACCAGCCACATAGGGAAAGGCTGCGACCGAGACACC TACTCAGAGAAGTCCCTCCACCGGCTCTGTGGTGCGGCCGCGGG CACTGCCGAGCTGCTGCCATCCCCGAGTGGATCCCTCAACTGGA CCATGGGCCTGCCCACCGACAATGGCCACGACAGCGACCAGGTG TTTGAGTTCAACGGCACCCAGGCAGTGAGGATCCCGGATGGCGT CGTGTCGGTCAGCCCCAAAGAGCCGTTCACCATCTCGGTGTGGA TGAGACATGGGCCATTCGGCAGGAAGAAGGAGACAATTCTTTGC AGTTCTGATAAAACAGATATGAATCGGCACCACTACTCCCTCTAT GTCCACGGGTGCCGGCTGATCTTCCTCTTCCGTCAGGATCCTTCT GAGGAGAAGAAATACAGACCTGCAGAGTTCCACTGGAAGTTGA ATCAGGTCTGTGATGAGGAATGGCACCACTACGTCCTCAATGTA GAATTCCCGAGTGTGACTCTCTATGTGGATGGCACGTCCCACGA GCCCTTCTCTGTGACTGAGGATTACCCGCTCCATCCATCCAAGAT AGAAACTCAGCTCGTGGTGGGGCTTGCTGGCAAGAGTTTTCAG GAGTTGAAAATGACAATGAAACTGAGCCTGTGACTGTGGCCTCT GCAGGTGGCGACCTGCACATGACCCAGTTTTTCCGAGGCAATCT GGCTGGCTTAACTCTCCGTTCCGGGAAACTCGCGGATAAGAAGG TGATCGACTGTCTGTATACCTGCAAGGAGGGCTGGACCTGCAG GTCCTCGAAGACAGTGGCAGAGGCGTGCAGATCCAAGCACACCC CAGCCAGTTGGTATTGACCTTGGAGGGAGAAGACCTCGGGGAAT TGGATAAGGCCATGCAGCACATCTCGTACCTGAACTCCCGGCAG TTCCCCACGCCCGGAATTCGCAGACTCAAAATCACCAGCACAAT CAAGTGTTTTAACGAGGCACCTGCATTTCGGTCCCCCCGGTAGA TGGCTACGTGATGGTTTTACAGCCCGAGGAGCCCAAGATCAGCC TGAGTGGCGTCTCACCATTTTGCCCGAGCAGCTTCTGAATTTGAAA GCTCAGAAGGGGTGTTCCTTTTCCCTGAGCTTCGCATCATCAGCA CCATCACGAGAGAAGTGGAGCCTGAAGGGGACGGGGCTGAGGA CCCCACAGTTCAAGAATCACTGGTGTCCGAGGAGATCGTGCACG ACCTGGATACCTGTGAGGTCACCGTGGAGGGAGAGGAGCTGAAC CACGAGCAGGAGAGCCTGGAGGTGGACATGGCCCGCCTGCAGC AGAAGGGCATTGAAGTGAGCAGCTCTGAACTGGGCATGACCTTC ACAGGCGTGGACACCATGGCCAGCTACGAGGAGGTTTTGCACCT GCTGCGCTATCGGAACTGGCATGCCAGGTCCTTGCTTGACCGGA AGTTAAGCTCATCTGCTCAGAGCTGAATGGCCGCTACATCAGC AACGAATTTAAGTGGAGGTGAATGTAATCCACACGGCCAACCC CATGGAACACGCCAACCACATGGCTGCCCAGCCACAGTTCGTGC ACCCGGAACACCGCTCCTTTGTTGACCTGTCAGGCCACAACCTGG CCAACCCCCACCCGTTCGCAGTCGTCCCCAGCACTGCGACAGTTG | Transcript ID ENST00000361311; *Homo sapiens* |

TABLE 1-continued

Nucleic acid sequences and amino acid sequences for preferred vesicle localization moieties used to produce a chimeric vesicle localization moiety

| SEQ ID NO: | Sequence | Source |
|---|---|---|
| | TGATCGTGGTGTGCGTCAGCTTCCTGGTGTTCATGATTATCCTGG GGGTATTTGGGATCCGGGCCGCACATCGGCGGACCATGCGGGAT CAGGACACCGGGAAGGAGAACGAGATGGACTGGGACGACTCTG CCCTGACCATCACCGTCAACCCCATGGAGACCTATGAGGACCAG CACAGCAGTGAGGAGGAGGAGGAAGAGGAAGAGGAAGAGGAA AGCGAGGACGGCGAAGAAGAGGATGACATCACCAGCGCCGAGT CGGAGAGCAGCGAGGAGGAGGAGGGGGAGCAGGGCGACCCCCA GAACGCAACCCGGCAGCAGCAGCTGGAGTGGGATGACTCCACCC TCAGCTACTGA | |
| 8 | MLRRPAPALAPAARLLLAGLLCGGGVWAARVNKHKPWLEPTYHGI VTENDNTVLLDPPLIALDKDAPLRFAGEICGFKIHGQNVPFDAVVVD KSTGEGVIRSKEKLDCELQKDYSFTIQAYDCGKGPDGTNVKKSHKA EVHIQVNDVNEYAPVFKEKSYKATVIEGKQYDSILRVEAVDADCSP QFSQICSYEIITPDVPFTVDKDGYIKNTEKLNYGKEHQYKLTVTAYD CGKKRATEDVLVKISIKPTCTPGWQGWNNRIEYEPGTGALAVFPNI HLETCDEPVASVQATVELETSHIGKGCDRDTYSEKSLHRLCGAAAG TAELLPSPSGSLNWTMGLPTDNGHDSDQVFEFNGTQAVRIPDGVVS VSPKEPFTISVWMRHGPFGRKKETILCSSDKTDMNRIIIYSLYVHGC RLIFLFRQDPSEEKKYRPAEFHWKLNQVCDEEWHHYVLNVEFPSVT EPVTVASAGGDLHMTQFFRGNLAGLTLRSGKLADKKVIDCLYTCK EGLDLQVLEDSGRGVQIQAHPSQLVLTLEGEDLGELDKAMQHISYL NSRQFPTPGIRRLKITSTIKCFNEATCISVPPVDGYVMVLQPEEPKISL SGVHHFARAASEFESSEGVFLFPELRIISTITREVEPEGDGAEDPTVQE SLVSEEIVHDLDTCEVTVEGEELNHEQESLEVDMARLQQKGIEVSS ELGMTFTGVDTMASYEEVLHLLRYRNWHARSLLDRKFKLICSELN GRYISNEFKVEVNVIHTANPMEHANHMAAQPQFVHPEHRSFVDLSG HNLANPHPFAVVPSTATVVIVVCVSFLVFMILGVFRIRAAHRRTMR DQDTGKENEMDWDDSALTITVNPMETYEDQHSSEEEEEEEEEESE DGEEEDDITSAESESSEEEEGEQGDPQNATRQQQLEWDDSTLSY | CLSTN1 protein (ENSP00000354997) encoded by Transcript ID ENST00000361311 from Gene ID ENSG00000171603; |
| 9 | ATGCTGCGCCGCCCCGCTCCCGCGCTGGCCCCGGCCGCCCGGCT GCTGCTGGCCGGGCTGCTGTGCGGCGGCGGGGTCTGGGCCGCGC GAGTTAACAAGCACAAGCCCTGGCTGGAGCCCACCTACCACGGC ATAGTCACAGAGAACGACAACACCGTGCTCCTCGACCCCCCACT GATCGCGCTGGATAAAGATGCGCCTCTGCGATTTGCAGAGAGTT TTGAGGTGACAGTCACCAAGAAGGTGAGATTTGTGGATTTAAA ATTCACGGGCAGAATGTCCCCTTTGATGCAGTGGTAGTGGATAA ATCCACTGGTGAGGGAGTCATTCGCTCCAAAGAGAACTGGACT GTGAGCTGCAGAAAGACTATTCATTCACCATCCAGGCCTATGATT GTGGGAAGGGACCTGATGGCACCAACGTGAAAAAGTCTCATAAA GCAACTGTTCATATTCAGGTGAACGACGTGAATGAGTACGCGCC CGTGTTCAAGGAGAAGTCCTACAAAGCCACGGTCATCGAGGGGA AGCAGTACGACAGCATTTTGAGGGTGGAGGCCGTGGATGCCGAC TGCTCCCCTCAGTTCAGCCAGATTTGCAGCTACGAAATCATCACT CCAGACGTGCCCTTTACTGTTGACAAAGATGGTTATATAAAAA CACAGAGAAATTAAACTACGGGAAAGAACATCAATATAAGCTG ACCGTCACTGCCTATGACTGTGGGAAGAAAAGAGCCACAGAAGA TGTTTTGGTGAAGATCAGCATTAAGCCCACCTGCACCCCTGGGTG GCAAGGATGGAACAACAGGATTGAGTATGAGCCGGGCACCGGC GCGTTGGCCGTCTTTCCAAATATCCACCTGGAGACATGTGACGA GCCAGTCGCCTCAGTACAGGCCACAGTGGAGCTAGAAACCAGCC ACATAGGGAAAGGCTGCGACCGAGACACCTACTCAGAGAAGTCC CTCCACCGGCTCTGTGGTGCGGCCGCGGGCACTGCCGAGCTGCT GCCATCCCCGAGTGGATCCCTCAACTGGACCATGGGCCTGCCCA CCGACAATGGCCACGACAGCGACCAGGTGTTTGAGTTCAACGGC ACCCAGGCAGTGAGGATCCCGGATGGCGTCGTGTCGGTCAGCCC CAAAGAGCCGTTCACCATCTCGGTGTGGATGAGACATGGGCCAT TCGGCAGGAAGAAGGAGACAATTCTTTGCAGTTCTGATAAAACA GATATGAATCGGCACCACTACTCCCTCTATGTCCACGGGTGCCGG CTGATCTTCCTCTTCCGTCAGGATCCTTCTGAGGAGAAGAAATAC AGACCTGCAGAGTTCCACTGGAAGTTGAATCAGGTCTGTGATGA GGAATGGCACCACTACGTCCTCAATGTAGAATTCCCGAGTGTGA CTCTCTATGTGGATGGCACGTCCCACGAGCCCTTCTCTGTGACTG AGGATTACCCGCTCCATCCATCCAAGATAGAAACTCAGCTCGTG GTGGGGGCTTGCTGGCAAGAGTTTTCAGGAGTTGAAATGACAA TGAAACTGAGCCTGTGACTGTGGCCTCTGCAGGTGGCGACCTGC ACATGACCCAGTTTTTCCGAGGCAATCTGGCTGGCTTAACTCTCC GTTCCGGGAAACTCGCGGATAAGAAGGTGATCGACTGTCTGTAT ACCTGCAAGGAGGGGCTGGACCTGCAGGTCCTCGAAGACAGTGG CAGAGGCGTGCAGATCCAAGCACACCCCAGCCAGTTGGTATTGA CCTTGGAGGGAGAAGACCTCGGGGAATTGGATAAGGCCATGCAG CACATCTCGTACCTGAACTCCCGGCAGTTCCCCACGCCCGGAATT | Transcript ID ENST00000377298; *Homo sapiens* |

TABLE 1-continued

Nucleic acid sequences and amino acid sequences for preferred vesicle localization moieties used to produce a chimeric vesicle localization moiety

| SEQ ID NO: | Sequence | Source |
|---|---|---|
|  | CGCAGACTCAAAATCACCAGCACAATCAAGTGTTTTAACGAGGC<br>CACCTGCATTTCGGTCCCCCCGGTAGATGGCTACGTGATGGTTTT<br>ACAGCCCGAGGAGCCCAAGATCAGCCTGAGTGGCGTCCACCATT<br>TTGCCCGAGCAGCTTCTGAATTTGAAAGCTCAGAAGGGGTGTTC<br>CTTTTCCCTGAGCTTCGCATCATCAGCACCATCACGAGAGAAGTG<br>GAGCCTGAAGGGGACGGGGCTGAGGACCCCACAGTTCAAGAAT<br>CACTGGTGTCCGAGGAGATCGTGCACGACCTGGATACCTGTGAG<br>GTCACGGTGGAGGGAGAGGAGCTGAACCACGAGCAGGAGAGCC<br>TGGAGGTGGACATGGCCCGCCTGCAGCAGAAGGGCATTGAAGTG<br>AGCAGCTCTGAACTGGGCATGACCTTCACAGGCGTGGACACCAT<br>GGCCAGCTACGAGGAGGTTTTGCACCTGCTGCGCTATCGGAACT<br>GGCATGCCAGGTCCTTGCTTGACCGGAAGTTTAAGCTCATCTGCT<br>CAGAGCTGAATGGCCGCTACATCAGCAACGAATTTAAGGTGGAG<br>GTGAATGTAATCCACACGGCCAACCCCATGGAACACGCCAACCA<br>CATGGCTGCCCAGCCACAGTTCGTGCACCCGGAACACCGCTCCTT<br>TGTTGACCTGTCAGGCCACAACCTGGCCAACCCCCACCCGTTCGC<br>AGTCGTCCCCAGCACTGCGACAGTTGTGATCGTGGTGTGCGTCA<br>GCTTCCTGGTGTTCATGATTATCCTGGGGGTATTTCGGATCCGGG<br>CCGCACATCGGCGGACCATGCGGGATCAGGACACCGGGAAGGA<br>GAACGAGATGGACTGGGACGACTCTGCCCTGACCATCACCGTCA<br>ACCCCATGGAGACCTATGAGGACCAGCACAGCAGTGAGGAGGA<br>GGAGGAAGAGGAAGAGGAAGAGGAAAGCGAGGACGGCGAAGA<br>AGAGGATGACATCACCAGCGCCGAGTCGGAGAGCGCGAGGAG<br>GAGGAGGGGAGCAGGGCGACCCCCAGAACGCAACCCGGCAGC<br>AGCAGCTGGAGTGGGATGACTCCACCCTCAGCTACTGA |  |
| 10 | MLRRPAPALAPAARLLLAGLLCGGGVWAARVNKHKPWLEPTYHGI<br>VTENDNTVLLDPPLIALDKDAPLRFAESFEVTVTKEGEICGFKIHGQ<br>NVPFDAVVVDKSTGEGVIRSKEKLDCELQKDYSFTIQAYDCGKGPD<br>GTNVKKSHKATVHIQVNDVNEYAPVFKEKSYKATVIEGKQYDSILR<br>VEAVDADCSPQFSQICSYEIITPDVPFTVDKDGYIKNTEKLNYGKEH<br>QYKLTVTAYDCGKKRATEDVLVKISIKPTCTPGWQGWNNRIEYEPG<br>TGALAVFPNIHLETCDEPVASVQATVELETSHIGKGCDRDTYSEKSL<br>HRLCGAAAGTAELLPSPGSLNWTMGLPTDNGHDSQVFEFNGTQ<br>AVRIPDGVVSVSPKEPFTISVWMRHGPFGRKKETILCSSDKTDMNRH<br>HYSLYVHGCRLIFLFRQDPSEEKKYRPAEFHWKLNQVCDEEWHHY<br>VLNVEFPSVTLYVDGTSHEPFSVTEDYPLHPSKIETQLVVGACWQEF<br>SGVENDNETEPVTVASAGGDLHMTQFFRGNLAGLTLRSGKLADKK<br>VIDCLYTCKEGLDLQVLEDSGRGVQIQAHPSQLVLTLEGEDLGELD<br>KAMQHISYLNSRQFPTPGIRRLKITSTIKCFNEATCISVPPVDGYVMV<br>LQPEEPKISLSGVHHFARAASEFESSEGVFLFPELRIISTITREVEPEGD<br>GAEDPTVQESLVSEEIVHDLDTCEVTVEGEELNHEQESLEVDMARL<br>QQKGIEVSSSELGMTFTGVDTMASYEEVLHLLRYRNWHARSLLDR<br>KFKLICSELNGRYISNELFVEVNVIHTANPMEHANHMAAQPQFVHP<br>EHRSFVDLSGHNLANPHPFAVVPSTATVVIVVCVSFLVFMIILGVFRI<br>RAAHRRTMRDQDTGKENEMDWDDSALTITVNPMETYEDQHSSEEE<br>EEEEEEEESEDGEEEDDITSAESESSEEEEGEQGDPQNATRQQQLEW<br>DDSTLSY | CLSTN1 protein (ENSP00000366513) encoded by Transcript ID ENST00000377298 from Gene ID ENSG00000171603; *Homo sapiens* |
| 11 | ATGGGCGCCCTCAGGCCCACGCTGCTGCCGCCTTCGCTGCCGCTG<br>CTGCTGCTGCTAATGCTAGGAATGGGATGCTGGGCCCGGGAGGT<br>GCTGGTCCCCGAGGGGCCCTTGTACCGCGTGGCTGGCACAGCTG<br>TCTCCATCTCCTGCAATGTGACCGGCTATGAGGGCCCTGCCCAGC<br>AGAACTTCGAGTGGTTCCTGTATAGGCCCGAGGCCCAGATACT<br>GCACTGGGCATTGTCAGTACCAAGGATACCCAGTTCTCCTATGCT<br>GTCTTCAAGTCCCGAGTGGTGGCGGGTGAGGTGCAGGTGCAGCG<br>CCTACAAGGTGATGCCGTGGTGCTCAAGATTGCCCGCCTGCAGG<br>CCCAGGATGCCGGCATTTATGAGTGCCACACCCCCTCCACTGATA<br>CCCGCTACCTGGGCAGCTACAGCGGCAAGGTGGAGCTGAGAGTT<br>CTTCCAGATGTCCTCCAGGTGTCTGCTGCCCCCCCAGGGCCCCGG<br>GGCCGCCAGGCCCCAACCTCACCCCCACGCATGACGGTGCATGA<br>GGGGCAGGAGCTGGCACTGGGCTGCCTGGCGAGGACAAGCACA<br>CAGAAGCACACACACCTGGCAGTGTCCTTTGGGCGATCTGTGCC<br>CGAGGCACCAGTTGGGCGGTCAACTCTGCAGGAGTGGTGGGAA<br>TCCGGTCAGACTTGGCCGTGAGGCTGGAGCTCCCTATGCTGAG<br>CGATTGGCTGCAGGGGAGCTTCGTCTGGGCAAGGAAGGGACCGA<br>TCGGTACCGCATGGTAGTAGGGGGTGCCCAGGCAGGGGACGCAG<br>GCACCTACCACTGCACTGCCGCTGAGTGGATTCAGGATCCTGAT<br>GGCAGCTGGGCCCAGATTGCAGAGAAAGGGCCGTCCTGGCCCA<br>CGTGGATGTGCAGACGCTGTCCAGCCAGCTGGCAGTGACAGTGG<br>GGCCTGGTGAACGTCGGATCGGCCCAGGGGAGCCCTTGGAACTG<br>CTGTGCAATGTGTCAGGGGCACTTCCCCAGCAGGCCGTCATGCT<br>GCATACTCTGTAGGTTGGGAGATGGCACCTGCGGGGCACCTGG | Transcript ID ENST00000314485; *Homo sapiens*, Transcript ID ENST00000368086; *Homo sapiens*, Transcript ID ENST00000614243; *Homo sapiens* |

TABLE 1-continued

Nucleic acid sequences and amino acid sequences for preferred vesicle localization moieties used to produce a chimeric vesicle localization moiety

| SEQ ID NO: | Sequence | Source |
|---|---|---|
|  | GCCCGGCCGCCTGCTAGCCCAGCTGGACACAGAGGGTGTGGGCA<br>GCCTGGGCCCTGGCTATGAGGCCGACACATTGCCATGGAGAAG<br>GTGGCATCCAGAACATACCGGCTACGGCTAGAGGCTGCCAGGCC<br>TGGTGATGCGGGCACCTACCGCTGCCTCGCCAAAGCCTATGTTCG<br>AGGGTCTGGGACCCGGCTTCGTGAAGCAGCCAGTGCCCGTTCCC<br>GGCCTCTCCCTGTACATGTGCGGGAGGAAGGTGTGGTGCTGGAG<br>GCTGTGGCATGGCTAGCAGGAGGCACAGTGTACCGCGGGGAGAC<br>TGCCTCCCTGCTGTGCAACATCTCTGTGCGGGGTGGCCCCCCAGG<br>ACTGCGGCTGGCCGCCAGCTGGTGGGTGGAGCGACCAGAGGACG<br>GAGAGCTCAGCTCTGTCCCTGCCCAGCTGGTGGGTGGCGTAGGC<br>CAGGATGGTGTGGCAGAGCTGGGAGTCCGGCCTGGAGGAGGCCC<br>TGTCAGCGTAGAGCTGGTGGGGCCCCGAAGCCATCGGCTGAGAC<br>TACACAGCTTGGGGCCCGAGGATGAAGGCGTGTACCACTGTGCC<br>CCCAGCGCCTGGGTGCAGCATGCCGACTACAGCTGGTACCAGGC<br>GGGCAGTGCCCGCTCAGGGCCTGTTACAGTCTACCCCTACATGC<br>TGCCCTGGACACCCTATTTGTGCCTCTGCTGTGGGTACAGGGG<br>TGGCCCTAGTCACTGGTGCCACTGTCCTTGGTACCATCACTTGCT<br>GCTTCATGAAGAGGCTTCGAAAACGGTGA |  |
| 11 | MGALRPTLLPPSLPLLLLLMLGMGCWAREVLVPEGPLYRVAGTAV<br>SISCNVTGYEGPAQQNFEWFLYRPEAPDTALGIVSTKDTQFSYAVFK<br>SRVVAGEVQVQLQGDAVVLKIARLQAQDAGIYECHTPSTDTRYL<br>GSYSGKVELRVLPDVLQVSAAPPGPRGRQAPTSPPRMTVHEGQELA<br>LGCLARTSTQKHTHLAVSFGRSVPEAPVGRSTLQEVVGIRSDLAVE<br>AGAPYAERLAAGELRLGKEGTDRYRMVVGGAQAGDAGTYHCTAA<br>EWIQDPDGSWAQIAEKRAVLAHVDVQTLSSQLAVTVGPGERRIGPG<br>EPLELLCNVSGALPPAGRHAAYSVGWEMAPAGAPGPGRLVAQLDT<br>EGVGSLGPGYEGRHIAMEKVASRTYRLRLEAARPGDAGTYRCLAK<br>AYVRGSGTRLREAASARSRPLPVHVREEGVVLEAVAWLAGGTVYR<br>GETASLLCNISVRGGPPGLRLAASWWVERPEDGELSSVPAQLVGGV<br>GQDGVAELGVRPGGGPVSVELVGPRSHRLRLHSLGPEDEGVYHCA<br>PSAWVQHADYSWYQAGSARSGPVTVYPYMHALDTLFVPLLVGTG<br>VALVTGATVLGTITCCFMKRLRKR | IGSF8 protein (ENSP00000316664) encoded by Transcript ID ENST00000314485 from Gene ID ENSG00000162729; *Homo sapiens*, IGFS8 protein (ENSP00000357065) encoded by Transcript ID ENST00000368086 from Gene ID ENSG00000162729; *Homo sapiens*, IGFS8 protein (ENSP00000477565) encoded by Transcript ID ENST00000614243 from Gene ID ENSG00000162729; *Homo sapiens* |
| 13 | ATGGTCCTCCTTTGGCTCACGCTGCTCCTGATCGCCCTGCCCTGT<br>CTCCTGCAAACGAAGGAAGATCCAAACCCACCAATCACGAACCT<br>AAGGATGAAAGCAAAGGCTCAGCAGTTGACCTGGGACCTTAACA<br>GAAATGTGACCGATATCGAGTGTGTTAAAGACGCCGACTATTCT<br>ATGCCGGCAGTGAACAATAGCTATTGCCAGTTTGGAGCAATTTC<br>CTTATGTGAAGTGACCAACTACACCGTCCGAGTGGCCAACCCAC<br>CATTCTCCACGTGGATCCTCTTCCCTGAGAACAGTGGGAAGCCTT<br>GGGCAGGTGCGGAGAATCTGACCTGCTGGATTCATGACGTGGAT<br>TTCTTGAGCTGCAGCTGGGCGGTAGGCCCGGGGCCCCCGCGGA<br>CGTCCAGTACGACCTGTACTTGAACGTTGCCAACAGGCGTCAAC<br>AGTACGAGTGTCTTCACTACAAAACGGATGCTCAGGGAACACGT<br>ATCGGGTGTCGTTTCGATGACATCTCTCGACTCTCCAGCGGTTCT<br>CAAAGTTCCCACATCCTGGTGCGGGGCAGGAGCGCAGCCTTCGG<br>TATCCCCTGCACAGATAAGTTTGTCGTCTTTTCACAGATTGAGAT<br>ATTAACTCCACCCAACATGACTGCAAAGTGTAATAAGACACATT<br>CCTTTATGCACTGGAAATGAGAAGTCATTTCAATCGCAAATTTC<br>GCTATGAGCTTCAGATACAAAAGAGAATGCAGCCTGTAATCACA<br>GAACAGGTCAGACAGAACCTCCTTCCAGCTACTCAATCCTGG<br>AACGTACACAGTACAAATAAGAGCCCGGGAAAGAGTGTATGAA<br>TTCTTGAGCGCCTGGAGCACCCCCAGCGCTTCGAGTGCGACCA<br>GGAGGAGGCGCAAACACACGTGCCTGGCGGACGTCGCTGCTGA<br>TCGCGCTGGGGACGCTGCTGGCCCTGGTCGTGTCTTCGTGATCT<br>GCAGAAGGTATCTGGTGATGCAGAGACTCTTTCCCCGCATCCCTC | Transcript ID enst00000331035; *Homo sapiens* |

TABLE 1-continued

Nucleic acid sequences and amino acid sequences for preferred vesicle
localization moieties used to produce a chimeric vesicle localization moiety

| SEQ ID NO: | Sequence | Source |
|---|---|---|
|  | ACATGAAAGACCCCATCGGTGACAGCTTCCAAAACGACAAGCTG GTGGTCTGGGAGGCGGGCAAAGCCGGCCTGGAGGAGTGTCTGGT GACTGAAGTACAGGTCGTGCAGAAAACTTGA |  |
| 14 | MVLLWLTLLLIALPCLLQTKEDPNPPITNLRMKAKAQQLTWDLNRN VTDIECVKDADYSMPAVNNSYCQFGAISLCEVTNYTVRVANPPFST WILFPENSGKPWAGAENLTCWIHDVDFLSCSWAVGPGAPADVQYD LYLNVANRRQQYECLHYKTDAQGTRIGCRFDDISRLSSGSQSSHILV RGRSAAFGIPCTDKFVVFSQIEILTPPNMTAKCNKTHSFMHWKMRS HFNRKFRYELQIQKRMQPVITEQVRDRTSFQLLNPGTYTVQIRARER VYEFLSAWSTPQRFECDQEEGANTRAWRTSLLIALGTLLALVDVFVI CRRYLVMQRLFPRIPHMKDPIGDSFQNDKLVVWEAGKAGLEECLV TEVQVVQKT | IL3RA protein (ENSP00000327890) encoded by Transcript ID ENST00000331035 from Gene ID ENSG0000018291; *Homo sapiens* |
| 15 | ATGGTCCTCCTTTGGCTCACGCTGCTCCTGATCGCCCTGCCCTGT CTCCTGCAAACGAAGGAAGGTGGGAAGCCTTGGGCAGGTGCGG AGAATCTGACCTGCTGGATTCATGACGTGGATTTCTTGAGCTGCA GCTGGGCGGTAGGCCCGGGGCCCCCGCGGACGTCCAGTACGAC CTGTACTTGAACGTTGCCACAGGCGTCAACAGTACGAGTGTCTT CACTACAAAACGGATGCTCAGGGAACACGTATCGGGTGTCGTTT CGATGACATCTCTCGACTCTCCAGCGGTTCTCAAAGTTCCCACAT CCTGGTGCGGGGCAGGAGCGCAGCCTTCGGTATCCCCTGCACAG ATAAGTTTGTCGTCTTTTCACAGATTGAGATATTAACTCCACCCA ACATGACTGCAAAGTGTAATAAGACACATTCCTTTATGCACTGG AAAATGAGAAGTCATTTCAATCGCAAATTTCGCTATGAGCTTCA GATACAAAAGAGAATGCAGCCTGTAATCACAGAACAGGTCAGA GACAGAACCTCCTTCCAGCTACTCAATCCTGGAACGTACACAGT ACAAATAAGAGCCCGGGAAAGAGTGTATGAATTCTTGAGCGCCT GGAGCACCCCCCAGCGCTTCGAGTGCGACCAGGAGGAGGGCGC AAACACGTGCCTGGCGGACGTCGCTGCTGATCGCGCTGGGGA CGCTGCTGGCCCTGGTCTGTGTCTTCGTGATCTGCAGAAGGTATC TGGTGATGCAGAGACTCTTTCCCCGCATCCCTCACATGAAAGACC CCATCGGTGACAGCTTCCAAAACGACAAGCTGGTGGTCTGGGAG GCGGGCAAAGCCGGCCTGGAGGAGTGTCTGGTGACTGAAGTACA GGTCGTGCAGAAAACTTGA | Transcript ID enst00000381469; *Homo sapiens* |
| 16 | MVLLWLTLLLIALPCLLQTKEGGKPWAGAENLTCWIHDVDFLSCS WAVGPGAPADVQYDLYLNVANRRQQYECLHYKTDAQGTRIGCRF DDISRLSSGSQSSHILVRGRSAAFGIPCTDKFVVFSQIEILTPPNMTAK CNKTHSFMHWKMRSHFNRKFRYELQIQKRMQPVITEQVRDRTSFQ LLNPGTYTVQIRARERVYEFLSAWSTPQRFECDQEEGANTRAWRTS LLIALGTLLALVDVFVICRRYLVMQRLFPRIPHMKDPIGDSFQNDKL VVWEAKGAGLEECLVTEVQVVQKT | IL3RA protein (ENSP00000370878) encoded by Transcript ID ENST00000381469 from Gene ID ENSG00000185291; *Homo sapiens* |
| 17 | ATGGGCCCCGGCCCCAGCCGCGCGCCCCGCGCCCCACGCCTGAT GCTCTGTGCGCTCGCCTTGATGGTGGCGGCCGGCGGCTGCGTCGT CTCCGCCCTTCAACCTGGATACCCGATTCCTGGTAGTGAAGGAGG CCGGGAACCCGGGCAGCCTCTTCGGCTACTCGGTCGCCCTCCATC GGCAGACAGAGCGGCAGCAGCGCTACCTGCTCCTGGCTGGTGCC CCCCGGGAGCTCGCTGTGCCCGATGGCTACACCAACCGGACTGG TGCTGTGTACCTGTGCCCACTCACTGCCCACAAGGATGACTGTGA GCGGATGAACATCACAGTGAAAAATGACCCTGGCCATCACATTA TTGAGGACATGTGGCTTGGAGTGACTGTGGCCAGCCAGGGCCCT GCAGGCAGAGTTCTGGTCTGTGCCCACCGCTACACCCAGGTGCT GTGGTCAGGGTCAGAAGACCAGCGGCGCATGGTGGGCAAGTGCT ACGTGCGAGGCAATGACCTAGAGCTGGACTCCAGTGATGACTGC CAGACCTACCACAACGAGATGTGCAATAGCAACACAGACTACCT GGAGACGGGCATGTGCCAGCTGGGCACCAGCGGTGGCTTCACCC AGAACACTGTGTACTTCGGCGCCCCCGGTGCCTACAACTGGAAA GGAAACAGCTACATGATTCAGCGCAAGGAGTGGGACTTATCTGA GTATAGTTACAAGGACCCAGAGGACCAAGGAAACCTCTATATTG GGTACACGATGCAGGTAGGCAGCTTCATCCTGCACCCCAAAAAC ATCACCATTGTGACAGGTGCCCCACGGCACCGACATATGGGCGC GGTGTTCTTGCTGAGCCAGGAGGCAGGCGGAGACCTGCGGAGGA GGCAGGTGCTGGAGGGCTCGCAGGTGGCGCCTATTTTGGCAGC GCCATTGCCCTGGCAGACCTGAACAATGATGGGTGGCAGGACCT CCTGGTGGGCGCCCCCTACTACTTCGAGAGGAAAGAGGAAGTAG GGGGTGCCATCTATGTCTTCATGAACCAGGCGGGAACCTCCTTCC | Transcript ID ENST00000320031; *Homo sapiens* |

TABLE 1-continued

Nucleic acid sequences and amino acid sequences for preferred vesicle localization moieties used to produce a chimeric vesicle localization moiety

| SEQ ID NO: | Sequence | Source |
|---|---|---|
| | CTGCTCACCCCTCACTCCTTCTTCATGGCCCCAGTGGCTCTGCCTT<br>TGGTTTATCTGTGGCCAGCATTGGTGACATCAACCAGGATGGATT<br>TCAGGATATTGCTGTGGGAGCTCCGTTTGAAGGCTTGGGCAAAG<br>TGTACATCTATCACAGTAGCTCTAAGGGGCTCCTTAGACAGCCCC<br>AGCAGGTAATCCATGGAGAGAAGCTGGGACTGCCTGGGTTGGCC<br>ACCTTCGGCTATTCCCTCAGTGGGCAGATGGATGTGGATGAGAA<br>CTTCTACCCAGACCTTCTAGTGGGAAGCCTGTCAGACCACATTGT<br>GCTGCTGCGGGCCCGGCCCGTCATCAACATCGTCCACAAGACCT<br>TGGTGCCCAGGCCAGCTGTGCTGGACCCTGCACTTTGCACGGCC<br>ACCTCTTGTGTGCAAGTGGAGCTGTGCTTTGCTTACAACCAGAT<br>GCCGGGAACCCCAACTACAGGCGAAACATCACCCTGGCCTACAC<br>TCTGGAGGCTGACAGGGACCGCCGGCCGCCCCGGCTCCGCTTTG<br>CCGGCAGTGAGTCCGCTGTCTTCCACGGCTTCTTCTCCATGCCCG<br>AGATGCGCTGCCAGAAGCTGGAGCTGCTCCTGATGGACAACCTC<br>CGTGACAAACTCCGCCCCATCATCATCTCCATGAACTACTCTTTA<br>CCTTTGCGGATGCCCGATCGCCCCCGGCTGGGGCTGCGGTCCCTG<br>GACGCCTACCCGATCCTCAACCAGGCACAGGCTCTGGAGAACCA<br>CACTGAGGTCCAGTTCCAGAAGGAGTGCGGGCCTGACAACAAGT<br>GTGAGAGCAACTTGCAGATGCGGGCAGCCTTCGTGTCAGAGCAG<br>CAGCAGAAGCTGAGCAGGCTCCAGTACAGCAGAGACGTCCGGA<br>AATTGCTCCTGAGCATCAACGTGACGAACACCCGGACCTCGGAG<br>CGCTCCGGGGAGGACGCCCACGAGGCGCTGCTCACCCTGGTGGT<br>GCCTCCCGCCCTGCTGCTGTCCTCAGTGCGCCCCCCCGGGCCTG<br>CCAAGCTAATGAGACCATCTTTTGCGAGCTGGGGAACCCCTTCA<br>AACGGAACCAGAGGATGGAGCTGCTCATCGCCTTTGAGGTCATC<br>GGGGTGACCCTGCACACAAGGGACCTTCAGGTGCAGCTGCAGCT<br>CTCCACGTCGAGTCACCAGGACAACCTGTGGCCCATGATCCTCA<br>CTCTGCTGGTGGACTATACACTCCAGACCTCGCTTAGCATGGTAA<br>ATCACCGGCTACAAAGCTTCTTTGGGGGACAGTGATGGGTGAG<br>TCTGGCATGAAAACTGTGGAGGATGTAGGAAGCCCCCTCAAGTA<br>TGAATTCCAGGTGGGCCCAATGGGGGAGGGCTGGTGGGCCTGG<br>GGACCCTGGTCCTAGGTCTGGAGTGGCCCTACGAAGTCAGCAAT<br>GGCAAGTGGCTGCTGTATCCCACGGAGATCACCGTCCATGGCAA<br>TGGGTCCTGGCCCTGCCGACCACCTGGAGACCTTATCAACCCTCT<br>CAACCTCACTCTTTCTGACCCTGGGGACAGGCCATCATCCCCACA<br>GCGCAGGCGGCGACAGCTGGATCCAGGGGGAGGCCAGGGCCCC<br>CCACCTGTCACTCTGGCTGCTGCCAAAAAAGCCAAGTCTGAGAC<br>TGTGCTGACCTGTGCCACAGGGCGTGCCCACTGTGTGTGGCTAG<br>AGTGCCCCATCCCTGATGCCCCCGTTGTCACCAACGTGACTGTGA<br>AGGCACGAGTGTGGAACAGCACCTTCATCGAGGATTACAGAGAC<br>TTTGACCGAGTCCGGGTAAATGGCTGGGCTACCCTATTCCTCCGA<br>ACCAGCATCCCCACCATCAACATGGAGAACAAGACCACGTGGTT<br>CTCTGTGGACATTGACTCGGAGCTGGTGAGGAGCTGCCGGCCG<br>AAATCGAGCTGTGGCTGGTGCTGGTGGCCGTGGGTGCAGGGCTG<br>CTGCTGCTGGGGCTGATCATCCTCCTGCTGTGGAAGTGCGGCTTC<br>TTCAAGCGAGCCCGCACTCGCGCCCTGTATGAAGCTAAGAGGCA<br>GAAGGCGGAGATGAAGAGCCAGCCGTCAGAGACAGAGAGGCTG<br>ACCGACGACTACTGA | |
| 18 | MGPGPSRAPRAPRLMLCALALMVAAGGCVVSAFNLDTRFLVVKEA<br>GNPGSLFGYSVALHRQTERQQRYLLLAGAPRELAVPDGYTNRTGA<br>VYLCPLTAHKDDCERMNITVKNDPGHHIIEDMWLGVTVASQGPAG<br>RVLVCAHRYTQVLWSGSEDQRRMVGKCYVRNDLELDSSDDWQT<br>YHNEMCNSNTDYLETGMCQLGTSGGFTQNTVYFGAPGAYNWKGN<br>SYMIQRKEWDLSEYSYKDPEDQGNLYIGYTMQVGSFILHPKNITIVT<br>GAPRHRHMGAVFLLSQEAGGDLRRRQVLEGSQVGAYFGSAIALAD<br>LNNDGWQDLLVGAPYYFERKEEVGGAIYVFMNQAGTSFPAHPSLL<br>LHGPSGSAFGLSVASIGDINQDGPQDIAVGAPFEGLGKVYIYHSSSK<br>GLLRQPQQVIHGEKLGLPGLATFGYSLSGQMDVDENFYPDLLVGSL<br>SDHIVLLRARPVINIVHKTLVPRPAVLDPALCTATSCVQVELCFAYN<br>QSAGNPNYRRNITLAYTLEADRDRRPPRLRFAGSESAVFHGFFSMPE<br>MRCQKLELLLMDNLRDKLRPIIISMNYSLPLRMPDRPRLGLRSLDAY<br>PILNQAQALENHTEVQFQKECGPDNKCESNLQMRAAFVSEQQQKLS<br>RLQYSRDVRKLLLSINVTNTRTSERSGEDAHEALLTLVVPPALLLSS<br>VRPRGACQANETIFCELGNPFKRNQRMELLIAFEVIGVTLHTRDLQV<br>QLQLSTSSHQDNLWPMILTLLVDYTLQTLSMVNHRLQSFFGGTVM<br>GESGMKTVEDVGSPLKYEFQVGPMGEGLVGLGTLVLGLEWPYEVS<br>NGKWLLYPTEITVIIGNGSWPCRPPGDLINPLNLTLSDPGDRPSSPQR<br>RRRQLDPGGGQGPPPVTLAAAKKAKSETVLTCATGRAHCVWLECPI<br>PDAPVVTNVTVKARVWNSTFIEDYRDFDRVRVNGWATLFLRTSIPT<br>INMENKTTWFSVDIDSELVEELPAEIELWLVLVAVGAGLLLLGLIILL<br>LWKCDFFKRTRYYQIMPKYHAVRIREEERYPPPGSTLPTKKHWVTS<br>WQTRDQYY | ITGA3 protein (ENSP00000007722) encoded by Transcript ID ENST00000007722 from Gene ID ENSG00000005884; *Homo sapiens* |

TABLE 1-continued

Nucleic acid sequences and amino acid sequences for preferred vesicle
localization moieties used to produce a chimeric vesicle localization moiety

| SEQ ID NO: | Sequence | Source |
|---|---|---|
| 19 | ATGGGCCCCGGCCCCAGCCGCGCGCCCCGCGCCCCACGCCTGAT GCTCTGTGCGCTCGCCTTGATGGTGGCGGCCGGCGGCTGCGTCGT CTCCGCCTTCAACCTGGATACCCGATTCCTGGTAGTGAAGGAGG CCGGGAACCCGGGCAGCCTCTTCGGCTACTCGGTCGCCCTCCATC GGCAGACAGAGCGGCAGCAGCGCTACCTGCTCCTGGCTGGTGCC CCCCGGGAGCTCGCTGTGCCCGATGGCTACACCAACCGGACTGG TGCTGTGTACCTGTGCCCACTCACTGCCCACAAGGATGACTGTGA GCGGATGAACATCACAGTGAAAAATGACCCTGGCCATCACATTA TTGAGGACATGTGGCTTGGAGTGACTGTGGCCAGCCAGGGCCCT GCAGGCAGAGTTCTGGTCTGTGCCCACCGCTACACCCAGGTGCT GTGGTCAGGGTCAGAAGACCAGCGGCGCATGGTGGGCAAGTGCT ACGTGCGAGGCAATGACCTAGAGCTGGACTCCAGTGATGACTGG CAGACCTACCACAAGGAGATGTGCAATAGCAACACAGACTACCT GGGAGACGGGCATGTGCCAGCTGGGCACCAGCGGTGGCTTCACCC AGAACACTGTGTACTTCGGCGCCCCCGGTGCCTACAACTGGAAA GGAAACAGCTACATGATTCAGCGCAAGGAGTGGGACTTATCTGA GTATAGTTACAAGGACCCAGAGGACCAAGGAAACCTCTATATTG GGTACACGATGCAGGTAGGCAGCTTCATCCTGCACCCCAAAAAC ATCACCATTGTGACAGGTGCCCCACGGCACCGACATATGGGCGC GGTGTTCTTGCTGAGCCAGGAGGCAGGCGGAGACCTGCGGAGGA GGCAGGTGCTGGAGGGTCGCAGGTGGGCGCCTATTTTGGCAGC GCCATTGCCCTGGCAGACCTGAACAATGATGGGTGGCAGGACCT CCTGGTGGGCGCCCCCTACTACTTCGAGAGGAAAGAGGAAGTAG GGGGTGCCATCTATGTCTTCATGAACCAGGCGGGAACCTCCTTCC CTGCTCACCCCTCACTCCTTCTTCATGGCCCCAGTGGCTCTGCCTT TGGTTTATCTGTGGCCAGCATTGGTGACATCAACCAGGATGGATT TCAGGATATTGCTGTGGGAGCTCCGTTTGAAGGCTTGGGCAAAG TGTACATCTATCACAGTAGCTCTAAGGGGCTCCTTAGACAGCCCC AGCAGGTAATCCATGGAGAGAAGCTGGGACTGCCTGGGTTGGCC ACCTTCGGCTATTCCCTCAGTGGGCAGATGGATGTGGATGAGAA CTTCTACCCAGACCTTCTAGTGGGAAGCCTGTCAGACCACATTGT GCTGCTGCGGGCCCGGCCCGTCATCAACATCGTCCACAAGACCT TGGTGCCCAGGCCAGCTGTGCTGGACCCTGCACTTTGCACGGCC ACCTCTTGTGTGCAAGTGGAGCTGTGCTTTGCTTACAACCAGAGT GCCGGGAACCCCAACTACAGGCGAAACATCACCCTGGCCTACAC TCTGGAGGCTGACAGGGACCGCCGGCCGCCCCGGCTCCGCTTTG CCGGCAGTGAGTCCGCTGTCTTCCACGGCTTCTTCTCCATGCCCG AGATGCGCTGCCAGAAGCTGGAGCTGCTCCTGATGGACAACCTC CGTGACAAACTCCGCCCCATCATCATCTCCATGAACTACTCTTTA CCTTTGCGGATGCCCGATCGCCCCCCGGCTGGGGCTGCGGTCCCTG GACGCCTACCCGATCCTCAACCAGGCACAGGCTCTGGAGAACCA CACTGAGGTCCAGTTCCAGAAGGAGTGCGGGCCTGACAAGAAGT GTGAGAGCAACTTGCAGATGCGGGCAGCCTTCGTGTCAGAGCAG CAGCAGAAGCTGAGCAGGCTCCAGTACAGCAGAGACGTCCGGA AATTGCTCCTGAGCATCAACGTGACGAACACCGGACCTCGGAG CGCTCCGGGGAGGACGCCCACGAGGCGCGCTCACCCTGGTGGT GCCTCCCGCCCTGCTGCTGTCCTCAGTGCGCCCCCCGGGGCCTG CCAAGCTAATGAGACCATCTTTTGCGAGCTGGGGAACCCCTTCA AACGGAACCAGAGGATGGAGCTGCTCATCGCCTTTGAGGTCATC GGGGTGACCCTGCACACAAGGGACCTTCAGGTGCAGCTGCAGCT CTCCACGTCGAGTCACCAGGACAACCTGTGGCCCATGATCCTCA CTCTGCTGGTGGACTATACACTCCAGACCTCGCTTAGCATGGTAA ATCACCGGCTACAAAGCTTCTTTGGGGGGACAGTGATGGGTGAG TCTGGCATGAAAACTGTGGAGGATGTAGGAAGCCCCCTCAAGTA TGAATTCCAGGTGGGCCCAATGGGGAGGGGCTGGTGGGCCTGG GGACCCTGGTCCTAGGTCTGGAGTGGCCCTACGAAGTCAGCAAT GGCAAGTGCTGCTGTATCCCACGGAGATCACCGTCCATGGCAA TGGGTCCTGGCCCTGCCGACCACCTGGAGACCTTATCAACCCTCT CAACCTCACTCTTTCTGACCCTGGGGACAGGCCATCATCCCCACA GCGCAGGCGGCGACAGCTGGATCAGGGGGAGGCCAGGGCCCC CCACCTGTCACTCTGGCTGCTGCAAAAAAGCCAAGTCTGAGAC TGTGCTGACCTGTGCCACAGGGCGTGCCCACTGTGTGTGGCTAG AGTGCCCCATCCCTGATGCCCCCGTTGTCACCAACGTGACTGTGA AGGCACGAGTGTGGAACAGCACCTTCATCGAGGATTACAGAGAC TTTGACCGAGTCCGGGTAAATGGCTGGGCTACCCTATTCCTCCGA ACCAGCATCCCCACCATCAACATGGAGAACAAGACCACGTGGTT CTCTGTGGACATTGACTCGGAGCTGGTGGAGGAGCTGCCGGCCG AAATCGAGCTGTGGCTGGTGCTGGTGGCCGTGGGTGCAGGGCTG CTGCTGCTGGGCTGATCATCCTCCTGCTGTGGAAGTGCGGCTTC TTCAAGCGAGCCCGCACTCGCGCCCTGTATGAAGCTAAGAGGCA GAAGGCGGAGATGAAGAGCCAGCCGTCAGAGACAGAGAGGCTG ACCGACGACTACTGA | Transcript ID ENST00000320031; *Homo sapiens* |

TABLE 1-continued

Nucleic acid sequences and amino acid sequences for preferred vesicle
localization moieties used to produce a chimeric vesicle localization moiety

| SEQ ID NO: | Sequence | Source |
|---|---|---|
| 20 | MGPGPSRAPRAPRLMLCALALMVAAGGCCVVSAFNLDTRFLVVKEA GNPGSLFGYSVALHRQTERQQRYLLLAGAPRELAVPDGYTNRTGA VYLCPLTAHKDDCERMNITVKNDPGHHIIEDMWLGVTVASQGPAG RVLVCAHRYTQVLWSGSEDQRRMVGKCYVRGNDLLDSSDDWQT YHNEMCNSNTDYLETGMCQLGTSGGFTQNTVYFGAPGAYNWKGN SYMIQRKEWDLSEYSYKDPEDQGNLYIGYTMQVGSFILHPKNITIVT GAPRHRHMGAVFLLSQEAGGDLRRRQVLEGSQVGAYFGSAIALAD LNNDGWQDLLVGAPYYFERKEEVGGAIYVFMNQAGTSFPAHPSLL LHGPSGSAFGLSVASIGDINQDGFQDIAVGAPFEGLGKVYIYHSSSK GLLRQPQQVIHGEKLGLPGLATFGYSLSGQMDVDENFYPDLLVGSL SDHIVLLRARPVINIVHKTLVPRPAVLDPALCTATSCVQVELCFAYN QSAGNPNYRRNITLAYTLEADRDRRPPRLRFAGSESAVFHGFFSMPE MRCQKLELLLMDNLRDKLRPIIISMNYSLPLRMPDRPRLGLRSLDAY PILNQAQALENHTEVQFQKECGPDNKCESNLQMRAAFVSEQQQKLS RLQYSRDVRKLLLSINVTNTRTSERSGFDAHEALLTLVVPPALLLSS VRPPGACQANETIFCELGNPFKRNQRMELLIAFEVIGVTLHTRDLQV QLQLSTSSHQDNLWPMILTLLVDYTLQTSLSMVNHRLQSFFGGTVM GESGMKTVEDVGSPLKYEFQVGPMGEGLVLGLTLVLGLEWPYEVS NGKWLLYPTEITVHGNGSWPCRPPGDLINPLNLTLSDPGDRPSSPQR RRRQLDPGGGQGPPPVTLAAAKKAKSETVLTCATGRAHCVWLECPI PDAPVVTNVTVKARVWNSTFIEDYRDFDRVRVNGWATLFLRTSIPT INMENKTTWFSVDIDSELVEELPAEIELWLVLVAVGAGLLLLGLIILL LWKCGFFKRARTRALYEAKRQKAEMKSQPSETERLTDDY | ITGA3 protein (ENSP00000315190) encoded by Transcript ID ENST00000320031 from Gene ID ENSG00000005884; *Homo sapiens* |
| 21 | ATGAATTTACAACCAATTTTCTGGATTGGACTGATCAGTTCAGTT TGCTGTGTGTTTGCTCAAACAGATGAAAATAGATGTTTAAAAGC AAATGCCAAATCATGTGGAGAATGTATACAAGCAGGGCCAAATT GTGGGTGGTGCACAAATTCAACATTTTTACAGGAAGGAATGCCT ACTTCTGCACGATGTGATGATTTAGAAGCCTTAAAAAAGAAGGG TTGCCCTCCAGATGACATAGAAAATCCCAGAGGCTCCAAAGATA TAAAGAAAAATAAAAATGTAACCAACCGTAGCAAAGGAACAGC AGAGAAGCTCAAGCCAGAGGATATTACTCAGATCCAACCACAGC AGTTGGTTTTGCCGATTAAGATCAGGGGAGCCACAGACATTTACA TTAAAATTCAAGAGAGCTGAAGACTATCCCATTGACCTCTACTAC CTTATGGACCTGTCTTACTCAATGAAAGACGATTTGGAGAATGTA AAAAGTCTTGGAACAGATCTGATGAATGAAATGAGGAGGATTAC TTCGGACTTCAGAATTGGATTTGGCTCATTTGTGGAAAAGACTGT GATGCCTTACATTAGCACAACACCAGCTAAGCTCAGGAACCCTT GCACAAGTGAACAGAACTGCACCAGCCCATTTAGCTACAAAAATT GTGCTCAGTCTTACTAATAAAGGAGAAGTATTTAATGAACTTGTT GGAAAACAGCGCATATCTGGAAATTTGGATTCTCCAGAAGGTGG TTTCGATGCCATCATGCAAGTTGCAGTTTGTGGATCACTGATTGG CTGGAGGAATGTTACACGGCTGCTGGTGTTTTCCACAGATGCCG GGTTTCACTTTGCTGGAGATGGGAAACTTGGTGGCATTGTTTTAC CAAATGATGGACAATGTCACCTGGAAATAATATGTACACAATG AGCCATTATTATGATTATCCTTCTATTGCTCACCTTGTCCGAAA CTGAGTGAAATAATATTCAGACAATTTTTGCAGTTACTGAAGA ATTTCAGCCTGTTTACAAGGAGCTGAAAAACTTGATCCCTAAGTC AGCAGTAGGAACATTATCTGCAAATTCTAGCAATGTAATTCAGTT GATCATTGATGCATACAATTCCCTTTCCTCAGAAGTCATTTTGGA AAACGGCAAATTGTCAGAAGGCGTAACAATAAGTTACAAATCTT ACTGCAAGAACGGGTGAATGGAACAGGGGAAAATGGAAGAAA ATGTTCCAATATTTCCATTGGAGATGAGGTTCAATTTGAAATTAG CATAACTTCAAATAAGTGTCCAAAAAAGGATTCTGACAGCTTTA AAATTAGGCCTCTGGGCTTTACGGAGGAAGTAGAGGTTATTCTTC AGTACATCTGTGAATGTGAATGCCAAAGCGAAGGCATCCCTGAA AGTCCCAAGTGTCATGAAGGAAATGGGACATTTGAGTGTGGCGC GTGCAGGTGCAATGAAGGGCGTGTTGGTAGACATTGTGAATGCA GCACAGATGAAGTTAACAGTGAAGACATGGATGCTTACTGCAGG AAAGAAAACAGTTCAGAAATCTGCAGTAACAATGGAGAGTGCGT CTGCGGACAGTGTGTTTAGGAAGAGGGATAATACAAATGAAA TTTATTCTGGCAAATTCTGCGAGTGTGATAATTTCAACTGTGATA GATCCAATGGCTTAATTTGTGGAGGAAATGGTGTTTGCAAGTGTC GTGTGTGTGAGTCAACCCCAACTACACTGGCAGTGCATGTGAC TGTTCTTTGGATACTAGTACTTGTGAAGCCAGCAACGGACAGATC TGCAATGGCCGGGCATCTGCGAGTGGTGTCTGTAAGTGTAC AGATCCGAAGTTTCAAGGGCAAACGTGTGAGATGTGTCAGACCT GCCTTGGTGTCTGTGCTGAGCATAAAGAATGTGTTCAGTGCAGA GCCTTCAATAAAGGAGAAAGAAAGACACATGCACACAGGAAT GTTCCTATTTTAACATTACCAAGGTAGAAAGTCGGGACAAATTA CCCCAGCCGGTCCAACCTGATCCTGTGTCCCATTGTAAGGAGAA GGATGTTGACGACTGTTGGTTCTATTTTACGTATTCAGTGAATGG | Transcript ID ENST00000302278, *Homo sapiens* Transcript ID ENST00000396033; *Homo sapiens* |

TABLE 1-continued

Nucleic acid sequences and amino acid sequences for preferred vesicle localization moieties used to produce a chimeric vesicle localization moiety

| SEQ ID NO: | Sequence | Source |
|---|---|---|
| | GAACAACGAGGTCATGGTTCATGTTGTGGAGAATCCAGAGTGTC<br>CCACTGGTCCAGACATCATTCCAATTGTAGCTGGTGTGGTTGCTG<br>GAATTGTTCTTATTGGCCTTGCATTACTGCTGATATGGAAGCTTT<br>TAATGATAATTCATGACAGAAGGGAGTTTGCTAAATTTGAAAAG<br>GAGAAAATGAATGCCAAATGGGACACGGGTGAAAATCCTATTTA<br>TAAGAGTGCCGTAACAACTGTGGTCAATCCGAAGTATGAGGGAA<br>AATGA | |
| 22 | MNLQPIFWIGLISSVCCVFAQTDENRCLKANAKSCGECIQAGPNCG<br>WCTNSTFLQEGMPTSARCDDLEALKKKGCPPDDIENPRGSKDIKKN<br>KNVTNRSKGTAEKLKPEDITQIQPQQLVLRLRSGEPQTFTLKFKRAE<br>DYPIDLYYLMDLSYSMKDDLENVKSLGTDLMNEMRRITSDFRIGFG<br>SFVEKTVMPYISTTPAKLRNPCTSEQNCTSPFSYKNVLSLTNKGEVF<br>NELVGKQRISGNLDSPEGGFDAIMQVAVCGSLIGWRNVTRLLVFST<br>DAGFHFAGDGKLGGIVLPNDGQCHENNMYTMSHYYDYPSIAHLV<br>QKLSENNIQTIFAVTEEFQPVYKELKNLIPKSAVGTLSANSSNVIQLII<br>DAYNSLSSEVILENGKLSEGVTISYKSYCKNGVNGTGENGRKCSNIS<br>IGDEVQFEISTSNKCPKKDSDSFKIRPLGFTEEVEVILQYICECEQSE<br>GIPESPKCHEGNGTFECGACRCNEGRVGRHCCSTDEVNSEDMDAY<br>CRKENSSEICSNNGECVCGQCVCRKRDNTNEIYSGKFCECDDNFNCD<br>RSNGLICGGNGVCKCRVCECNPNYTGSACDCSLDTSTCEASNGQIC<br>NGRGICECGVCKCTDPKFQGQTCEMCQTCLGVCAEHKECVQCRAF<br>NKGEKKDTCTQECSYFNITKVESRDKLPQPVQPDPVSHCKEKDVDD<br>CWFYFTYSVNGNNEVMVHVVENPECPTGPDIIPIVAGVVAGIVLIGL<br>ALLLIWKLLMIIHDRREFAKFEKEKMNAKWDTGENPIYKSAVTTVV<br>NPKYEGK | ITGB1 protein (ENSP00000303351) encoded by Transcript ID ENST00000302278 from Gene ID ENSG00000150093; *Homo sapiens*, ITGB1 protein (ENSP00000379350) encoded by Transcript ID ENSST00000396033 from Gene ID ENSG00000150093; *Homo sapiens* |
| 23 | ATGAATTTACAACCAATTTTCTGGATTGGACTGATCAGTTCAGTT<br>TGCTGTGTGTTTGCTCAAACAGATGAAAATAGATGTTTAAAAGC<br>AAATGCCAAATCATGTGGAGAATGTATACAAGCAGGGCCAAATT<br>GTGGGTGGTGCACAAATTCAACATTTTTACAGGAAGGAATGCCT<br>ACTTCTGCACGATGTGATGATTTAGAAGCCTTAAAAAAGAAGGG<br>TTGCCCTCCAGATGACATAGAAAATCCCAGAGGCTCCAAAGATA<br>TAAAGAAAAATAAAAATGTAACCAACCGTAGCAAAGGAACAGC<br>AGAGAAGCTCAAGCCAGAGGATATTACTCAGATCCAACCACAGC<br>AGTTGGTTTTGCCGATTAAGATCAGGGGAGCCACAGACATTTACA<br>TTAAAATTCAAGAGAGCTGAAGACTATCCCATTGACCTCTACTAC<br>CTTATGGACCTGTCTTACTCAATGAAAGACGATTTGGAGAATGTA<br>AAAAGTCTTGGAACAGATCTGATGAATGAAATGAGGAGGATTAC<br>TTCGGACTTCAGAATTGGATTTGGCTCATTTGTGGAAAAGACTGT<br>GATGCCTTACATTAGCACAACACCAGCTAAGCTCAGGAACCCTT<br>GCACAAGTGAACAGAACTGCACCAGCCCATTTAGCTACAAAAATT<br>GTGCTCAGTCTTACTAATAAAGGAGAAGTATTTAATGAACTTGTT<br>GGAAAACAGCGCATATCTGGAAATTTGGATTCTCCAGAAGGTGG<br>TTTCGATGCCATCATGCAAGTTGCAGTTTGTGGATCACTGATTGG<br>CTGGAGGAATGTTACACGGCTGCTGGTGTTTTCCACAGATGCCG<br>GGTTTCACTTTGCTGGAGATGGGAAACTTGGTGGCATTGTTTTAC<br>CAAATGATGGACAATGTCACCTGGAAAATAATATGTACACAATG<br>AGCCATTATTATGATTATCCTTCTATTGCTCACCTTGTCCGAAA<br>CTGAGTGAAAATAATATTCAGACAATTTTTGCAGTTACTGAAGA<br>ATTTCAGCCTGTTTACAAGGAGCTGAAAAACTTGATCCCTAAGTC<br>AGCAGTAGGAACATTATCTGCAAATTCTAGCAATGTAATTCAGTT<br>GATCATTGATGCATACAATTCCCTTTCCTCAGAAGTCATTTTGGA<br>AAACGGCAAATTGTCAGAAGGCGTAACAATAAGTTACAATCTT<br>ACTGCAAGAACGGGTGAATGGAACAGGGGAAAATGGAAGAAA<br>ATGTTCCAATATTTCCATTGGAGATGAGGTTCAATTTGAAATTAG<br>CATAACTTCAAATAAGTGTCCAAAAAAGGATTCTGACAGCTTTA<br>AAATTAGGCCTCTGGGCTTTACGGAGGAAGTAGAGGTTATTCTTC<br>AGTACATCTGTGAATGTGAATGCCAAAGCGAAGGCATCCCTGAA<br>AGTCCCAAGTGTCATGAAGGAAATGGGACATTTGAGTGTGGCGC<br>GTGCAGGTGCAATGAAGGGCGTGTTGGTAGACATTGTAATGCA<br>GCACAGATGAAGTTAACAGTGAAGACATGGATGCTTACTGCAGG<br>AAAGAAAACAGTTCAGAAATCTGCAGTAACAATGGAGAGTGCGT<br>CTGCGGACAGTGTGTTTGTAGGAAGAGGGATAATACAAATGAAA<br>TTTATTCTGGCAAATTCTGCGAGTGTGATAATTTCAACTGTGATA<br>GATCCAATGGCTTAATTTGTGGAGGAAATGGTGTTTGCAAGTGTC<br>GTGTGTGTGAGTGCAACCCCAACTACACTGGCAGTGCATGTGAC<br>TGTTCTTTGGATACTAGTACTTGTGAAGCCAGCAACGGACAGATC<br>TGCAATGGCCGGGCATCTGCGAGTGTGGTGTCTGTAAGTGTAC<br>AGATCCGAAGTTTCAAGGCAAACGTGTGAGATGTGTCAGACCT<br>GCCTTGGTGTCTGTGCTGAGCATAAAGAATGTGTTCAGTGCAGA | Transcript ID ENST00000423113; *Homo sapiens* |

TABLE 1-continued

Nucleic acid sequences and amino acid sequences for preferred vesicle localization moieties used to produce a chimeric vesicle localization moiety

| SEQ ID NO: | Sequence | Source |
|---|---|---|
| | GCCTTCAATAAAGGAGAAAAGAAAGACACATGCACACAGGAAT GTTCCTATTTTAACATTACCAAGGTAGAAAGTCGGGACAAATTA CCCCAGCCGGTCCAACCTGATCCTGTGTCCCATTGTAAGGAGAA GGATGTTGACGACTGTTGGTTCTATTTTACGTATTCAGTGAATGG GAACAACGAGGTCATGGTTCATGTTGTGGAGAATCCAGAGTGTC CCACTGGTCCAGACATCATTCCAATTGTAGCTGGTGTGGTTGCTG GAATTGTTCTTATTGGCCTTGCATTACTGCTGATATGGAAGCTTT TAATGATAATTCATGACAGAAGGGAGTTTGCTAAATTTGAAAAG GAGAAAATGAATGCCAAATGGGACACGGGTGAAAATCCTATTT ACAAGAGTCCTATTAATAATTTCAAGAATCCAAACTACGGACGT AAAGCTGGTCTCTAA | |
| 24 | MNLQPIFWIGLISSVCCVFAQTDENRCLKANAKSCGECIQAGPNCG WCTNSTFLQEGMPTSARCDDLEALKKKGCPPDDIENPRGSKDIKKN KNVTNRSKGTAEKLKPEDITQIQPQQLVLRLRSGEPQTFTLKFKRAE DYPIDLYYLMDLSYSMKDDLENVKSLGTDLMNEMRRITSDFRIGFG SFVEKTVMPYISTTPAKLRNPCTSEQNCTSPFSYKNVLSLTNKGEVF NELVGKQRISGNLDSPEGGFDAIMQVAVCGSLIGWRNVTRLLVFST DAGFHFAGDGKLGGIVLPNDGQCHENNMYTMSHYYDYPSIAHLV QKLSENNIQTIFAVTEEFQPVYKELKNLIPKSAVGTLSANSSNVIQLII DAYNSLSSEVILENGKLSEGVTISYKSYCKNGVNGTGENGRKCSNIS IGDEVQFEISTSNKCPKKDSDSFKIRPLGFTEEVEVILQYICECEQSE GIPESPKCHEGNGTFECGACRCNEGRVGRHCCSTDEVNSEDMDAY CRKENSSEICSNNGECVCGQCVCRKRDNTNEIYSGKFCECDDNFNCD RSNGLICGGNGVCKCRVCECNPNYTGSACDCSLDTSTCEASNGQIC NGRGICECGVCKCTDPKFQGQTCEMCQTCLGVCAEHKECVQCRAF NKGEKKDTCTQECSYFNITKVESRDKLPQPVQPDPVSHCKEKDVDD CWFYFTYSVNGNNEVMVHVVENPECPTGPDIIPIVAGVVAGIVLIGL ALLLIWKLLMIIHDRREFAKFEKEKMNAKWDTQENPIYKSPINNFKN PNYGRKAGL | ITGB1 protein (ENSP00000388694) encoded by Transcript ID ENST00000423113 from Gene ID ENSG00000150093; *Homo sapiens* |
| 25 | ATGGTGTGCTTCCGCCTCTTCCCGGTTCCGGGCTCAGGGCTCGTT CTGGTCTGCCTAGTCCTGGGAGCTGTGCGGTCTTATGCATTGGAA CTTAATTTGACAGATTCAGAAAATGCCACTTGCCTTTATGCAAAA TGGCAGATGAATTTCACAGTACGCTATGAAACTACAAATAAAAC TTATAAAACTGTAACCATTTCAGACCATGGCACTGTGACATATAA TGGAAGCATTTGTGGGGATGATCAGAATGGTCCAAAATAGCAG TGCAGTTCGGACCTGGCTTTTCCTGGATTGCGAATTTTACCAAGG CAGCATCTACTTATTCAATTGACAGCGTCTCATTTTCCTACAACA CTGGTGATAACACAACATTTCCTGATGCTGAAGATAAAGGAATT CTTACGTTGATGAACTTTTGGCCATCAGAATTCCATTGAATGAC CTTTTTAGATGCAATAGTTTATCAACTTTGGAAAAGAATGATGTT GTCCAACACTACTGGGATGTTCTTGTACAAGCTTTTGTCCAAAAT GGCACAGTGAGCACAAATGAGTTCCTGTGTGATAAAGACAAAAC TTCAACAGTGGCACCCACCATACACACACCACTGTGCCATCTCCTAC TACAACACCTACTCCAAAGGAAAAACCAGAAGCTGGAACCTATT CAGTTAATAATGGCAATGATACTTGTCTGCTGGCTACCATGGGGC TGCAGCTGAACATCACTCAGGATAAGGTTGCTTCAGTTATTAACA TCAACCCCAATACAACTCACTCCACAGGCAGCTGCCGTTCTCACA CTGCTCTACTTAGACTCAATAGCAGCACCATTAAGTATCTAGACT TTGTCTTTGCTGTGAAAAATGAAAACCGATTTTATCTGAAGGAAG TGAACATCAGCATGTATTTGGTTAATGGCTCCGTTTTCAGCATTG CAAATAACAATCTCAGCTACTGGGATGCCCCCCTGGGAAGTTCTT ATATGTGCAACAAAGAGCAGACTGTTTCAGTGTCTGGAGCATTT CAGATAAATACCTTTGATCTAAGGGTTCAGCCTTTCAATGTGACA CAAGGAAAGTATTCTACAGCTCAAGACTGCAGTGCAGATGACGA CAACTTCCTTGTGCCCATAGCGGTGGGAGCTGCCTTGGCAGGAG TACTTATTCTAGTGTTGCTGGCTATTTATTGGTCTCAAGCACCA TCATGCTGGATATGAGCAATTTTAG | Transcript ID ENST00000200639; *Homo sapiens* |
| 26 | MVCFRLFPVPGSGLVLVCLVLGAVRSYALELNLTSDENATCLYAK WQMNFTVRYETTNKTYKTVTISDHGTVTYNGSICGDDQNGPKIAV QFGPGFSWIANFTKAASTYSIDSVSFSYNTGDNTTFPDAEDKGILTV DELLAIRIPLNDLFRCNSLSTLEKNDVVQHYWDVLQAFVQNGTVS TNEFLCDKDKTSTVAPTIHTTVPSPTTTPTPKEKPEAGTYSVNNGND TCLLATMGLQLNITQDKVASVININPNTTHSTGSCRSHTALLRLNSS TIKYLDFVFAVKNENRFYLKEVNISMYLVNGSVFSIANNNLSYWDA PLGSSYMCNKEQTVSVSGAFQINTFDLRVQPFNVTQGKYSTAQDCS ADDDNFLVPIAVGAALAGVLILVLLAYFIGLKHHHAGYEQF | LAMP2 protein (ENSP00000200639) encoded by Transcript ID ENST00000200639 from Gene ID ENSG00000005893; *Homo sapiens* |

TABLE 1-continued

Nucleic acid sequences and amino acid sequences for preferred vesicle
localization moieties used to produce a chimeric vesicle localization moiety

| SEQ ID NO: | Sequence | Source |
|---|---|---|
| 27 | ATGGTGTGCTTCCGCCTCTTCCCGGTTCCGGGCTCAGGGCTCGTT<br>CTGGTCTGCCTAGTCCTGGGAGCTGTGCGGTCTTATGCATTGGAA<br>CTTAATTTGACAGATTCAGAAAATGCCACTTGCCTTTATGCAAAA<br>TGGCAGATGAATTTCACAGTACGCTATGAAACTACAAATAAAAC<br>TTATAAAACTGTAACCATTTCAGACCATGGCACTGTGACATATAA<br>TGGAAGCATTTGTGGGGATGATCAGAATGGTCCCAAAATAGCAG<br>TGCAGTTCGGACCTGGCTTTTCCTGGATTGCGAATTTTACCAAGG<br>CAGCATCTACTTATTCAATTGACAGCGTCTCATTTTCCTACAACA<br>CTGGTGATAACACAACATTTCCTGATGCTGAAGATAAAGGAATT<br>CTTACGTTGATGAACTTTTGGCCATCAGAATTCCATTGAATGAC<br>CTTTTTAGATGCAATAGTTTATCAACTTTGGAAAAGAATGATGTT<br>GTCCAACACTACTGGGATGTTCTTGTACAAGCTTTTGTCCAAAAT<br>GGCACAGTGAGCACAAATGAGTTCCTGTGTGATAAAGACAAAAC<br>TTCAACAGTGGCACCCACCATACACACACCACTGTGCCATCTCCTAC<br>TACAACACCTACTCCAAAGGAAAAACCAGAAGCTGGAACCTATT<br>CAGTTAATAATGGCAATGATACTTGTCTGCTGGCTACCATGGGGC<br>TGCAGCTGAACATCACTCAGGATAAGGTTGCTTCAGTTATTAACA<br>TCAACCCCAATACAACTCACTCCACAGGCAGCTGCCGTTCTCACA<br>CTGCTCTACTTAGACTCAATAGCAGCACCATTAAGTATCTAGACT<br>TTGTCTTTGCTGTGAAAAATGAAAACCGATTTTATCTGAAGGAAG<br>TGAACATCAGCATGTATTTGGTTAATGGCTCCGTTTTCAGCATTG<br>CAAATAACAATCTCAGCTACTGGGATGCCCCCCTGGGAAGTTCTT<br>ATATGTGCAACAAAGAGCAGACTGTTTCAGTGTCTGGAGCATTT<br>CAGATAAATACCTTTGATCTAAGGGTTCAGCCTTTCAATGTGACA<br>CAAGGAAAGTATTCTACAGCCCAAGAGTGTTCGCTGGATGATGA<br>CACCATTCTAATCCCAATTATAGTTGGTGCTGGTCTTTCAGGCTT<br>GATTATCGTTATAGTGATTGCTTACGTAATTGGCAGAAGAAAAA<br>GTTATGCTGGATATCGAGACTCTGTAA | Transcript ID<br>ENST00000371335;<br>*Homo sapiens* |
| 28 | MVCFRLFPVPGSGLVLVCLVLGAVRSYALELNLTSDENATCLYAK<br>WQMNFTVRYETTNKTYKTVTISDHGTVTYNGSICGDDQNGPKIAV<br>QFGPGFSWIANFTKAASTYSIDSVSFSYNTGDNTTFPDAEDKGILTV<br>DELLAIRIPLNDLFRCNSLSTLEKNDVVQHYWDVLQAFVQNGTVS<br>TNEFLCDKDKTSTVAPTIHTTVPSPTTTPTPKEKPEAGTYSVNNGND<br>TCLLATMGLQLNITQDKVASVININPNTTHSTGSCRSHTALLRLNSS<br>TIKYLDFVFAVKNENRFYLKEVNISMYLVNGSVFSIANNNLSYWDA<br>PLGSSYMCNKEQTVSVSGAFQINTFDLRVQPFNVTQGKYSTAQDECS<br>LDDDTILIPIIVGAGLSGLIIVIVIAYVIGRRKSYAGYQTL | LAMP2 protein (ENSP00000360386) encoded by Transcript ID ENST00000371335 from Gene ID ENSG00000005893; *Homo sapiens* |
| 29 | ATGGTGTGCTTCCGCCTCTTCCCGGTTCCGGGCTCAGGGCTCGTT<br>CTGGTCTGCCTAGTCCTGGGAGCTGTGCGGTCTTATGCATTGGAA<br>CTTAATTTGACAGATTCAGAAAATGCCACTTGCCTTTATGCAAAA<br>TGGCAGATGAATTTCACAGTACGCTATGAAACTACAAATAAAAC<br>TTATAAAACTGTAACCATTTCAGACCATGGCACTGTGACATATAA<br>TGGAAGCATTTGTGGGGATGATCAGAATGGTCCCAAAATAGCAG<br>TGCAGTTCGGACCTGGCTTTTCCTGGATTGCGAATTTTACCAAGG<br>CAGCATCTACTTATTCAATTGACAGCGTCTCATTTTCCTACAACA<br>CTGGTGATAACACAACATTTCCTGATGCTGAAGATAAAGGAATT<br>CTTACGTTGATGAACTTTTGGCCATCAGAATTCCATTGAATGAC<br>CTTTTTAGATGCAATAGTTTATCAACTTTGGAAAAGAATGATGTT<br>GTCCAACACTACTGGGATGTTCTTGTACAAGCTTTTGTCCAAAAT<br>GGCACAGTGAGCACAAATGAGTTCCTGTGTGATAAAGACAAAAC<br>TTCAACAGTGGCACCCACCATACACACACCACTGTGCCATCTCCTAC<br>TACAACACCTACTCCAAAGGAAAAACCAGAAGCTGGAACCTATT<br>CAGTTAATAATGGCAATGATACTTGTCTGCTGGCTACCATGGGGC<br>TGCAGCTGAACATCACTCAGGATAAGGTTGCTTCAGTTATTAACA<br>TCAACCCCAATACAACTCACTCCACAGGCAGCTGCCGTTCTCACA<br>CTGCTCTACTTAGACTCAATAGCAGCACCATTAAGTATCTAGACT<br>TTGTCTTTGCTGTGAAAAATGAAAACCGATTTTATCTGAAGGAAG<br>TGAACATCAGCATGTATTTGGTTAATGGCTCCGTTTTCAGCATTG<br>CAAATAACAATCTCAGCTACTGGGATGCCCCCCTGGGAAGTTCTT<br>ATATGTGCAACAAAGAGCAGACTGTTTCAGTGTCTGGAGCATTT<br>CAGATAAATACCTTTGATCTAAGGGTTCAGCCTTTCAATGTGACA<br>CAAGGAAAGTATTCTACAGCCCAAGAGTGTTCGCTGGATGATGA<br>CCTCAACTTTCTTATTCCTGTTGCAGTGGGTGTGGCCTTGGGCTTC<br>CTTATAATTGTTGTCTTTATCTCTTATATGATTGGAAGAAGGAAA<br>AGTCGTACTGGTTATCAGTCTGTGTAA | Transcript ID<br>ENST00000434600;<br>*Homo sapiens* |

TABLE 1-continued

Nucleic acid sequences and amino acid sequences for preferred vesicle localization moieties used to produce a chimeric vesicle localization moiety

| SEQ ID NO: | Sequence | Source |
|---|---|---|
| 30 | MVCFRLFPVPGSGLVLVCLVLGAVRSYALELNLTSDENATCLYAK WQMNFTVRYETTNKTYKTVTISDHGTVTYNGSICGDDQNGPKIAV QFGPGFSWIANFTKAASTYSIDSVSFSYNTGDNTTFPDAEDKGILTV DELLAIRIPLNDLFRCNSLSTLEKNDVVQHYWDVLQAFVQNGTVS TNEFLCDKDKTSTVAPTIHTTVPSPTTTPTPKEKPEAGTYSVNNGND TCLLATMGLQLNITQDKVASVININPNTTHSTGSCRSHTALLRLNSS TIKYLDFVFAVKNENRFYLKEVNISMYLVNGSVFSIANNNLSYWDA PLGSSYMCNKEQTVSVSGAFQINTFDLRVQPFNVTQGKYSTAQDEECS ADSDLNFLIPVAVGVALGFLIIVVFISYMIGRRKSRTGYQSV | LAMP2 protein (ENSP00000408411) encoded by Transcript ID ENST00000434600 from Gene ID ENSG00000005893; Homo sapiens |
| 31 | ATGATCCCCACCTTCACGGCTCTGCTCTGCCTCGGGCTGAGTCTG GGCCCCAGGACCCACATGCAGGCAGGGCCCCTCCCCAAACCCAC CCTCTGGGCTGAGCCAGGCTCTGTGATCAGCTGGGGGAACTCTG TGACCATCTGGTGTCAGGGGACCCTGGAGGCTCGGGAGTACCGT CTGGATAAAGAGGAAAGCCCAGCACCCTGGGACAGACAGAACC CACTGGAGCCCAAGAACAAGGCCAGATTCTCCATCCCATCCATG ACAGAGGACTATGCAGGGAGATACCGCTGTTACTATCGCAGCCC TGTAGGCTGGTCACAGCCCAGTGACCCCCTGGAGCTGGTGATGA CAGGAGCCTACAGTAAACCCACCCTTTCAGCCCTGCCGAGTCCTC TTGTGACCTCAGGAAAGAGCGTGACCCTGCTGTGTCAGTCACGG AGCCCAATGGACACTTTCCTTCTGATCAAGGAGCGGGCAGCCCA TCCCCTACTGCATCTGAGATCAGAGCACGGAGCTCAGCAGCACC AGGCTGAATTCCCCATGAGTCCTGTGACCTCAGTGCACGGGGGG ACCTACAGGTGCTTCAGCTCACACGGCTTCTCCCACTACCTGCTG TCACACCCCAGTGACCCCCTGGAGCTCATAGTCTCAGGATCCTTG GAGGATCCCAGGCCCTCACCCACAAGGTCCGTCTCAACAGCTGC AGGCCCTGAGGACCAGCCCCTCATGCCTACAGGGTCAGTCCCCC ACAGTGGTCTGAGAAGGCACTGGAGGTACTGATCGGGGTCTTG GTGGTCTCCATCCTGCTTCTCTCCCTCCTCCTCTTCCTCCTCCTCC AACACTGGCGTCAGGGAAAACACAGGACATTGGCCCAGAGACA GGCTGATTTCCAACGTCCTCCAGGGGCTGCCGAGCCAGAGCCCA AGGACGGGGCCTACAGAGGAGGTCCAGCCCAGCTGCTGACGTC CAGGGAGAAAACTTCTGTGCTGCCGTGAAGAACACACAGCCTGA GGACGGGGTGGAAATGGACACTCGGCAGAGCCCACACGATGAA GACCCCCAGGCAGTGACGTATGCCAAGGTGAAACACTCCAGACC TAGGAGAGAAATGGCCTCTCCTCCCTCCCCACTGTCTGGGGAATT CCTGGACACAAAGGACAGACAGGCAGAAGAGGACAGACAGATG GACACTGAGGCTGCTGCATCTGAAGCCCCCCAGGATGTGACCTA CGCCCAGCTGCACAGCTTTACCCTCAGACAGAAGGCAACTGAGC CTCCTCCATCCCAGGAAGGGGCCTCTCCAGCTGAGCCCAGTGTCT ATGCCACTCTGGCCATCCACTAA | Transcript ID ENST00000391736; Homo sapiens |
| 34 | MIPTFTALLCLGLSLGPRTHMQAGPLPKPTLWAEPGSVISWGNSVTI WCQGTLEAREYRLDKEESPAPWDRQNPLEPKNKARFSIPSMTEDYA GRYRCYYRSPVGWSQPSDPLELVMTGAYSKPTLSALPSPLVTSGKS VTLLCQSRSPMDTFLLIKERAAHPLLHLRSEHGAQQHQAEPPMSPVT SVHGGTYRCFSSHGFSHYLLSHPSDPLELIVSGSLEDPRPSPTRSVST AAGPEDQPLMPTGSVPHSGLRRHWEVLIGVLVVSILLLSLLLFLLLQ HWRQGKHRTLAQRQADFQRPPGAAEPEPKDGGLQRRSSPAADVQG ENFCAAVKNTQPEDGVEMDTRQSPHDEDPQAVTYAKVKHSRPRRE MASPPSPLSGEFLDTKDRQAEEDRQMDTEAAASEAPQDVTYAQLHS FTLRQKATEPPPSQEGASPAEPSVYATLAIH | LILRB4 protein (ENSP00000479829) encoded by Transcript ID ENST00000612454 from Gene ID ENSG00000275730; Homo sapiens |
| 35 | ATGATCCCCACCTTCACGGCTCTGCTCTGCCTCGGGCTGAGTCTG GGCCCCAGGACCCACATGCAGGCAGGGCCCCTCCCCAAACCCAC CCTCTGGGCTGAGCCAGGCTCTGTGATCAGCTGGGGGAACTCTG TGACCATCTGGTGTCAGGGGACCCTGGAGGCTCGGGAGTACCGT CTGGATAAAGAGGAAAGCCCAGCACCCTGGGACAGACAGAACC CACTGGAGCCCAAGAACAAGGCCAGATTCTCCATCCCATCCATG ACAGAGGACTATGCAGGGAGATACCGCTGTTACTATCGCAGCCC TGTAGGCTGGTCACAGCCCAGTGACCCCCTGGAGCTGGTGATGA CAGGAGCCTACAGTAAACCCACCCTTTCAGCCCTGCCGAGTCCTC TTGTGACCTCAGGAAAGAGCGTGACCCTGCTGTGTCAGTCACGG AGCCCAATGGACACTTTCCTTCTGATCAAGGAGCGGGCAGCCCA TCCCCTACTGCATCTGAGATCAGAGCACGGAGCTCAGCAGCACC AGGCTGAATTCCCCATGAGTCCTGTGACCTCAGTGCACGGGGGG ACCTACAGGTGCTTCAGCTCACACGGCTTCTCCCACTACCTGCTG TCACACCCCAGTGACCCCCTGGAGCTCATAGTCTCAGGATCCTTG GAGGATCCCAGGCCCTCACCCACAAGGTCCGTCTCAACAGCTGC AGGCCCTGAGGACCAGCCCCTCATGCCTACAGGGTCAGTCCCCC ACAGTGGTCTGAGAAGGCACTGGAGGTACTGATCGGGGTCTTG GTGGTCTCCATCCTGCTTCTCTCCCTCCTCCTCTTCCTCCTCCTCC | Transcript ID ENST00000614699; Homo sapiens |

TABLE 1-continued

Nucleic acid sequences and amino acid sequences for preferred vesicle localization moieties used to produce a chimeric vesicle localization moiety

| SEQ ID NO: | Sequence | Source |
|---|---|---|
| | AACACTGGCGTCAGGGAAAACACAGGACATTGGCCCAGAGACA<br>GGCTGATTTCCAACGTCCTCCAGGGGCTGCCGAGCCAGAGCCCA<br>AGGACGGGGGCCTACAGAGGAGGTCCAGCCCAGCTGCTGACGTC<br>CAGGGAGAAAACTTCTCAGGTGCTGCCGTGAAGAACACACAGCC<br>TGAGGACGGGGTGGAAATGGACACTCGGCAGAGCCCACACGAT<br>GAAGACCCCCAGGCAGTGACGTATGCCAAGGTGAAACACTCCAG<br>ACCTAGGAGAGAAATGGCCTCTCCTCCCTCCCCACTGTCTGGGG<br>AATTCCTGGACACAAAGGACAGACAGGCAGAAGAGGACAGACA<br>GATGGACACTGAGGCTGCTGCATCTGAAGCCCCCCAGGATGTGA<br>CCTACGCCCAGCTGCACAGCTTTACCCTCAGACAGAAGGCAACT<br>GAGCCTCCTCCATCCCAGGAAGGGGCCTCTCCAGCTGAGCCCAG<br>TGTCTATGCCACTCTGGCCATCCACTAA | |
| 36 | MIPTFTALLCLGLSLGPRTHMQAGPLPKPTLWAEPGSVISWGNSVTI<br>WCQGTLEAREYRLDKEESPAPWDRQNPLEPKNKARFSIPSMTEDYA<br>GRYRCYYRSPVGWSQPSDPLELVMTGAYSKPTLSALPSPLVTSGKS<br>VTLLCQSRSPMDTFLLIKERAAHPLLHLRSEHGAQQHQAEPPMSPVT<br>SVHGGTYRCFSSHGFSHYLLSHPSDPLELIVSGSLEDPRPSPTRSVST<br>AAGPEDQPLMPTGSVPHSGLRRHWEVLIGVLVVSILLLSLLLFLLLQ<br>HWRQGKHRTLAQRQADFQRPPGAAEPEPKDGGLQRRSSPAADVQG<br>ENFSGAAVKNTQPEDGVEMDTRQSPHDEDPQAVTYAKVKHSRPRR<br>EMASPPSPLSGEFLDTKDRQAEEDRQMDTEAAASEAPQDVTYAQL<br>HSFTLRQKATEPPPSQEGASPAEPSVYATLAIH | LILRB4 protein (ENSP00000478543) encoded by Transcript ID ENST00000614699 from Gene ID ENSG00000275730; *Homo sapiens* |
| 37 | ATGATCCCCACCTTCACGGCTCTGCTCTGCCTCGGGCTGAGTCTG<br>GGCCCCAGGACCCACATGCAGGCAGGGCCCCTCCCCAAACCCAC<br>CCTCTGGGCTGAGCCAGGCTCTGTGATCAGCTGGGGGAACTCTG<br>TGACCATCTGGTGTCAGGGGACCCTGGAGGCTCGGGAGTACCGT<br>CTGGATAAAGAGGAAAGCCCAGCACCCTGGGACAGACAGAACC<br>CACTGGAGCCCAAGAACAAGGCCAGATTCTCCATCCCATCCATG<br>ACAGAGGACTATGCAGGGAGATACCGCTGTTACTATCGCAGCCC<br>TGTAGGCTGGTCACAGCCCAGTGACCCCCTGGAGCTGGTGATGA<br>CAGGAGCCTACAGTAAACCCACCCTTTCAGCCCTGCCGAGTCCTC<br>TTGTGACCTCAGGAAAGAGCGTGACCCTGCTGTGTCAGTCACGG<br>AGCCCAATGGACACTTTCCTTCTGATCAAGGAGCGGGCAGCCCA<br>TCCCCTACTGCATCTGAGATCAGAGCACGGAGCTCAGCAGCACC<br>AGGCTGAATTCCCATGAGTCCTGTGACCTCAGTGCACGGGGG<br>ACCTACAGGTGCTTCAGCTCACACGCGTTCTCCCACTACCTGCTG<br>TCACACCCCAGTGACCCCCTGGAGCTCATAGTCTCAGGATCCTTG<br>GAGGATCCCAGGCCCTCACCCACAAGGTCCGTCTCAACAGCTGC<br>AGGCCCTGAGGACCAGCCCCTCATGCCTACAGGGTCAGTCCCCC<br>ACAGTGGTCTGAGAAGGCACTGGGAGGTACTGATCGGGGTCTTG<br>GTGGTCTCCATCCTGCTTCTCTCCCTCCTCCTCTTCCTCCTCCTCC<br>AACACTGGCGTCAGGGAAAACACAGGACATTGGCCCAGAGACA<br>GGCTGATTTCCAACGTCCTCCAGGGGCTGCCGAGCCAGAGCCCA<br>AGGACGGGGGCCTACAGAGGAGGTCCAGCCCAGCTGCTGACGTC<br>CAGGGAGAAAACTTCTGTGCTGCCGTGAAGAACACACAGCCTGA<br>GGACGGGGTGGAAATGGACACTCGGAGCCCACACGATGAAGAC<br>CCCCAGGCAGTGACGTATGCCAAGGTGAAACACTCCAGACCTAG<br>GAGAGAAATGGCCTCTCCTCCCTCCCCACTGTCTGGGGAATTCCT<br>GGACACAAAGGACAGACAGGCAGAAGAGGACAGACAGATGGAC<br>ACTGAGGCTGCTGCATCTGAAGCCCCCAGGATGTGACCTACGC<br>CCAGCTGCACAGCTTTACCCTCAGACAGAAGGCAACTGAGCCTC<br>CTCCATCCCAGGAAGGGGCCTCTCCAGCTGAGCCCAGTGTCTAT<br>GCCACTCTGGCCATCCACTAA | Transcript ID ENST00000621693; *Homo sapiens* |
| 38 | MIPTFTALLCLGLSLGPRTHMQAGPLPKPTLWAEPGSVISWGNSVTI<br>WCQGTLEAREYRLDKEESPAPWDRQNPLEPKNKARFSIPSMTEDYA<br>GRYRCYYRSPVGWSQPSDPLELVMTGAYSKPTLSALPSPLVTSGKS<br>VTLLCQSRSPMDTFLLIKERAAHPLLHLRSEHGAQQHQAEPPMSPVT<br>SVHGGTYRCFSSHGFSHYLLSHPSDPLELIVSGSLEDPRPSPTRSVST<br>AAGPEDQPLMPTGSVPHSGLRRHWEVLIGVLVVSILLLSLLLFLLLQ<br>HWRQGKHRTLAQRQADFQRPPGAAEPEPKDGGLQRRSSPAADVQG<br>ENFCAAVKNTQPEDGVEMDTRSPHDEDPQAVTYAKVKHSRPRREM<br>ASPPSPLSGEFLDTKDRQAEEDRQMDTEAAASEAPQDVTYAQLHSF<br>TLRQKATEPPPSQEGASPAEPSVYATLAIH | LILRB4 protein (ENSP00000482234) encoded by Transcript ID ENST00000621693 from Gene ID ENSG00000275730; *Homo sapiens* |
| 39 | ATGGGGCGCCTGGCCTCGAGGCCGCTGCTGCTGGCGCTCCTGTC<br>GTTGGCTCTTTGCCGAGGGCGTGTGGTGAGAGTCCCCACAGCGA<br>CCCTGGTTCGAGTGGTGGGCACTGAGCTGGTCATCCCCTGCAAC<br>GTCAGTGACTATGATGGCCCCAGCGAGCAAAACTTTGACTGGAG<br>CTTCTCATCTTTGGGGAGCAGCTTTGTGGAGCTTGCAAGCACCTG<br>GGAGGTGGGGTTCCCAGCCCAGCTGTACCAGGAGCGGCTGCAGA | Transcript ID ENST00000393203; *Homo sapiens* |

TABLE 1-continued

Nucleic acid sequences and amino acid sequences for preferred vesicle localization moieties used to produce a chimeric vesicle localization moiety

| SEQ ID NO: | Sequence | Source |
|---|---|---|
|  | GGGGCGAGATCCTGTTAAGGCGGACTGCCAACGACGCCGTGGAG<br>CTCCACATAAAGAACGTCCAGCCTTCAGACCAAGGCCACTACAA<br>ATGTTCAACCCCAGCACAGATGCCACTGTCCAGGGAAACTATG<br>AGGACACAGTGCAGGTTAAAGTGCTGGCCGACTCCCTGCACGTG<br>GGAGCCCTTCGAGCTGCGCTGCACCGCCGCCTCCGCCTCGCCGCT<br>GCACACGCACCTGGCGCTCTGTGGGAGGTGCACCGCGGCCCGG<br>CCAGGCGGAGCGTCCTCGCCCTGACCCACGAGGGCAGGTTCCAC<br>CCGGGCCTGGGGTACGAGCAGCGCTACCACAGTGGGGACGTGCG<br>CCTCGACACCGTGGGCAGCGACGCCTACCGCCTCTCAGTGTCCC<br>GGGCTCTGTCTGCCGACCAGGGCTCCTACAGGTGTATCGTCAGC<br>GAGTGGATCGCCGAGCAGGGCAACTGGCAGGAAATCCAAGAAA<br>AGGCCGTGGAAGTTGCCACCGTGGTGATCCAGCCATCAGTTCTG<br>CGAGCAGCTGTGCCCAAGAATGTGTCTGTGGCTGAAGGAAAGGA<br>ACTGGACCTGACCTGTAACATCACAACAGACCGAGCCGATGACG<br>TCCGGCCCGAGGTGACGTGGTCCTTCAGCGGATGCCTGACAGC<br>ACCCTACCTGGCTCCCGCGTGTTGGCGCCGCTTGACCGTGATTCC<br>CTGGTGCACAGCTCGCCTCATGTTGCTTTGAGTCATGTGGATCA<br>CGCTCCTACCATTTACTGGTTCGGGATGTTAGCAAAGAAAACTCT<br>GGCTACTATTACTGCCACGTGTCCCTGTGGGCACCCGGACACAA<br>CAGGAGCTGGCACAAAGTGGCAGAGGCCGTGTCTTCCCCAGCTG<br>GTGTGGGTGTGACCTGGCTAGAACCAGACTACCAGGTGTACCTG<br>AATGCTTCCAAGGTCCCCGGGTTTGCGGATGACCCCCAGAGCT<br>GGCATGCCGGGTGGTGGACACGAAGAGTGGGGAGGCGAATGTC<br>CGATTCACGGTTTCGTGGTACTACAGGATGAACCGGCGCAGCGA<br>CAATGTGGTGACCAGCGAGCTGCTTGCAGTCATGGACGGGGACT<br>GGACGCTAAAATATGGAGAGAGGAGCAAGCAGCGGCCCAGGA<br>TGGAGACTTTATTTTTCTAAGGAACATACAGACACGTTCAATTT<br>CCGGATCCAAAGGACTACAGAGGAAGACAGAGGCAATTATTACT<br>GTGTTGTGTCTGCCTGGACCAAACAGCGGAACAACAGCTGGGTG<br>AAAAGCAAGGATGTCTTCTCCAAGCCTGTTAACATATTTTGGGCA<br>TTAGAAGATTCCGTGCTTGTGGTGAAGGCGAGGCAGCCAAAGCC<br>TTTCTTTGCTGCCGGAAATACATTTGAGATGACTTGCAAAGTATC<br>TTCCAAGAATATTAAGTCGCCACGCTACTCTGTTCTCATCATGGC<br>TGAGAAGCCTGTCGGCGACCTCTCCAGTCCCAATGAAACGAAGT<br>ACATCATCTCTCTGGACCAGGATTCTGTGGTGAAGCTGGAGAATT<br>GGACAGATGCATCACGGGTGGATGGCGTTGTTTTAGAAAAAGTG<br>CAGGAGGATGAGTTCCGCTATCGAATGTACCAGACTCAGGTCTC<br>AGACGCAGGGCTGTACCGCTGCATGGTGACAGCCTGGTCTCCTG<br>TCAGGGGCAGCCTTTGGCGAGAAGCAGCAACCAGTCTCTCCAAT<br>CCTATTGAGATAGACTTCCAAACCTCAGGTCCTATATTTAATGCT<br>TCTGTGCATTCAGACACACCATCAGTAATTCGGGGAGATCTGATC<br>AAATTGTTCTGTATCATCACTGTCGAGGGAGCAGCACTGGATCC<br>AGATGACATGGCCTTTGATGTGTCCTGGTTTGCGGTGCACTCTTT<br>TGGCCTGGACAAGGCTCCTGTGCTCCTGTCTTCCCTGGATCGGAA<br>GGGCATCGTGACCACCTCCCGGAGGGACTGGAAGAGCGACCTCA<br>GCCTGGAGCGCGTGAGTGTGCTGGAATTCTTGCTGCAAGTGCAT<br>GGCTCCGAGGACCAGGACTTTGGCAACTACTACTGTTCCGTGACT<br>CCATGGGTGAAGTCACCAACAGGTTCCTGGCAGAAGGAGGCAGA<br>GATCCACTCCAAGCCCGTTTTTATAACTGTGAAGATGGATGTGCT<br>GAACGCCTTCAAGTATCCCTTGCTGATCGGCGTCGGTCTGTCCAC<br>GGTCATCGGGCTCCTGTCCTGTCTCATCGGGTACTGCAGCTCCCA<br>CTGGTGTTGTAAGAAGGAGGTTCAGGAGACACGGCGCCGAGCGCC<br>GCAGGCTCATGTCGATGGAGATGGACTAG |  |
| 40 | MGRLASRPLLLALLSLALCRGRVVRVPTATLVRVVGTELVIPCNVS<br>DYDGPSEQNFDWSFSSLGSSFVELASTWEVGFPAQLYQERLQRGEIL<br>LRRTANDAVELHIKNVQPSDQGHYKCSTPSTDATVQGNYEDTVQV<br>KVLADSLHVGPSARPPPSLSLREGEPFELRCTAASASPLHTHLALLW<br>EVHRGPARRSVLALTHEGRFHPGLGYEQRYHSGDVRLDTVGSDAY<br>RLSVSRALSADQGSYRCIVSEWIAEQGNWQEIQEKAVEVATVVIQPS<br>VLRAAVPKNVSVAEGKELDLTCNITTDRADDVRPEVTWSFSRMPDS<br>TLPGSRVLARLDRDSLVHSSPHVALSHVDARSYHLLVRDVSKENSG<br>YYYCHVSLWAPGHNRSWHKVAEAVSSPAGVGVTWLEPDYQVYLN<br>ASKVPGFADDPTELACRVVDTKSGEANVRFTVSWYYRMNRRSDNV<br>VTSELLAVMDGDWTLKYGERSKQRAQDGDFIFSKEHTDTFNFRIQR<br>TTEEDRGNYYCVVSAWTKQRNNSWVKSKDVFSKPVNIFWALEDSV<br>LVVKARQPKPFFAAGNTFEMTCKVSSKNIKSPRYSVLIMAEKPVGD<br>LSSPNETKYIISLDQDSVVKLENWTDASRVDGVVLEKVQEDEFRYR<br>MYQTQVSDAGLYRCMVTAWSPVRGSLWREAATSLSNPIIEIDFQTSG<br>PIFNASVHSDTPSVIRGDLIKLFCIITVEGAALDPDDMAFDVSWFAVH | PTGFRN protein (ENSP00000396899) encoded by Transcript ID ENST00000393203 from Gene ID ENSG00000134247 *Homo sapiens* |

TABLE 1-continued

Nucleic acid sequences and amino acid sequences for preferred vesicle
localization moieties used to produce a chimeric vesicle localization moiety

| SEQ ID NO: | Sequence | Source |
|---|---|---|
|  | SFGLDKAPVLLSSLDRKGIVTTSRRDWKSDLSLERVSVLEFLLQVHG SEDQDFGNYYCSVTPWVKSPTGSWQKEAEIHSKPVFITVKMDVLNA FKYPLLIGVGLSTVIGLLSCLIGYCSSHWCCKKEVQETRRERRLMS MEMD |  |
| 41 | ATGGCAGTGGGGGCCAGTGGTCTAGAAGGAGATAAGATGGCTG GTGCCATGCCTCTGCAACTCCTCCTGTTGCTGATCCTACTGGGCC CTGGCAACAGCTTGCAGCTGTGGACACCTGGGCAGATGAAGCC GAGAAAGCCTTGGGTCCCCTGCTTGCCCGGGACCGGAGACAGGC CACCGAATATGAGTACCTAGATTATGATTTCCTGCCAGAAACGG AGCCTCCAGAAATGCTGAGGAACAGCACTGACACCACTCCTCTG ACTGGGCCTGGAACCCCTGAGTCTACCACTGTGGAGCCTGCTGC AAGGCGTTCTACTGGCCTGGATGCAGGAGGGGCAGTCACAGAGC TGACCACGGAGCTGGCCAACATGGGGAACCTGTCCACGGATTCA GCAGCTATGGAGATACAGACCACTCAACCAGCAGCCACGGAGGC ACAGACCACTCAACCAGTGCCCACGGAGGCACAGACCACTCCAC TGGCAGCCACAGAGGCACAGACCAACTCGACTGACGGCCACGGA GGCACAGACCACTCCACTGGCAGCCACAGAGGCACAGACCACTC CACCAGCAGCCACGGAAGCACAGACCACTCAACCCACAGGCCTG GAGGCACAGACCACTGCACCAGCAGCCATGGAGGCACAGACCA CTGCACCAGCAGCCATGGAAGCACAGACCACTCCACCAGCAGCC ATGGAGGCACAGACCACTCAAACCACAGCCATGGAGGCACAGA CCACTGCACCAGAAGCCACGGAGGCACAGACCACTCAACCCACA GCCACGGAGGCACAGACCACTCCACTGGCAGCCATGGAGGCCCT GTCCACAGAACCCAGTGCCACAGAGGCCCTGTCCATGGAACCTA CTACCAAAAGAGGTCTGTTCATACCCTTTTCTGTGTCCTCTGTTA CTCACAAGGGCATTCCCATGGCAGCCAGCAATTTGTCCGTCAACT ACCCAGTGGGGCCCCAGACCACATCTCTGTGAAGCAGTGCCTG CTGGCCATCCTAATCTTGGCGCTGGTGGCCACTATCTTCTTCGTG TGCACTGTGGTGCTGGCGGTCCGCCTCTCCCGCAAGGGCCACAT GTACCCCGTGCGTAATTACTCCCCCACCGAGATGGTCTGCATCTC ATCCCTGTTGCCTGATGGGGTGAGGGGCCCTCTGCCCAGCCA ATGGGGGCCTGTCCAAGGCCAAGAGCCCGGGCCTGACGCCAGAG CCCAGGGAGGACCGTGAGGGGGATGACCTCACCCTGCACAGCTT CCTCCCTTAG | Transcript ID ENST00000228463; *Homo sapiens* |
| 42 | MAVGASGLEGDKMAGAMPLQLLLLLILLGPGNSLQLWDTWADEA EKALGPLLARDRRQATEYEYLDYDFLPETEPPEMLRNSTDTTPLTGP GTPESTTVEPAARRSTGLDAGGAVTELTTELANMGNLSTDSAAMEI QTTQPAATEAQTTQPVPTEAQTTPLAATEAQTTRLTATEAQTTPLA QTEAQTTPPAATEAQTTQPTGLEAQTTAPAAMEAQTTAPAAMEAQ TTPPAAMEAQTTQTTAMEAQTTAPEATEAQTTQPTATEAQTTPLAA MEALSTEPSATEALSMEPTTKRGLFIPFSVSSVTHKGIPMAASNLSVN YPVGAPDHISVKQCLLAILILALVATIFFVCTVYLAVRLSRKGHMYP VRNYSPTEMVCISSLLPDGGEGPSATANGGLSKAKSPGLTPEPREDR EGDDLTLHSFLP | SELPLG protein (ENSP00000228463) encoded by Transcript ID ENST00000228463 from Gene ID ENSG00000110876; *Homo sapiens* |
| 43 | ATGCCTCTGCAACTCCTCCTGTTGCTGATCCTACTGGGCCCTGGC AACAGCTTGCAGCTGTGGACACCTGGGCAGATGAAGCCGAGAA AGCCTTGGGTCCCCTGCTTGCCCGGGACCGGAGACAGGCCACCG AATATGAGTACCTAGATTATGATTTCCTGCCAGAAACGGAGCCT CCAGAAATGCTGAGGAACAGCACTGACACCACTCCTCTGACTGG GCCTGGAACCCCTGAGTCTACCACTGTGGAGCCTGCTGCAAGGC GTTCTACTGGCCTGGATGCAGGAGGGCAGTCACAGAGCTGACC ACGGAGCTGGCCAACATGGGGAACCTGTCCACGGATTCAGCAGC TATGGAGATACAGACCACTCAACCAGCAGCCACGGAGGCACAG ACCACTCAACCAGTGCCCACGGAGGCACAGACCACTCCACTGGC AGCCACAGAGGCACAGACAACTCGACTGACGGCCACGGAGGCA CAGACCACTCCACTGGCAGCCACAGAGGCACAGACCACTCCACC AGCAGCCACGGAAGCACAGACCACTCAACCCACAGGCCTGGAG GCACAGACCACTGCACCAGCAGCCATGGAGGCACAGACCACTGC ACCAGCAGCCATGGAAGCACAGACCACTCCACCAGCAGCCATGG AGGCACAGACCACTCAAACCACAGCCATGGAGGCACAGACCACT GCACCAGAAGCCACGGAGGCACAGACCACTCAACCCACAGCCA CGGAGGCACAGACCACTCCACTGGCAGCCATGGAGGCCCTGTCC ACAGAACCCAGTGCCACAGAGGCCCTGTCCATGGAACCTACTAC CAAAAGAGGTCTGTTCATACCCTTTTCTGTGTCCTCTGTTACTCA CAAGGGCATTCCCATGGCAGCCAGCAATTTGTCCGTCAACTACC CAGTGGGGCCCCAGACCACATCTCTGTGAAGCAGTGCCTGCTG GCATCCTAATCTTGGCGCTGGTGGCCACTATCTTCTTCGTGTGC ACTGTGGTGCTGGCGGTCCGCCTCTCCCGCAAGGGCCACATGTA CCCCGTGCGTAATTACTCCCCCACCGAGTGGTCTGCATCTCATC CCTGTTGCCTGATGGGGTGAGGGGCCCTCTGCCACAGCCAATG | Transcript ID ENST00000550948; *Homo sapiens* |

TABLE 1-continued

Nucleic acid sequences and amino acid sequences for preferred vesicle
localization moieties used to produce a chimeric vesicle localization moiety

| SEQ ID NO: | Sequence | Source |
|---|---|---|
|  | GGGGCCTGTCCAAGGCCAAGAGCCCGGGCCTGACGCCAGAGCCC AGGGAGGACCGTGAGGGGATGACCTCACCCTGCACAGCTTCCT CCCTTAG |  |
| 44 | MPLQLLLLLILLGPGNSLQLWDTWADEAEKALGPLLARDRRQATE YEYLDYDFLPETEPPEMLRNSTDTTPLTGPGTPESTTVEPAARRSTG LDAGGAVTELTTELANMGNLSTDSAAMEIQTTQPAATEAQTTQPVP TEAQTTPLAATEAQTTRLTATEAQTTPLAATEAQTTPPAATEAQTTQ PTGLEAQTTAPAAMEAQTTAPAAMEAQTTPPAAMEAQTTQTTAME AQTTAPEATEAQTTQPTATEAQTTPLAAMEALSTEPSATEALSMEPT TKRGLFIPFSVSSVTHKGIPMAASNLSVNYPVGAPDHISVKQCLLAIL ILALVATIFFVCTVVLAVRLSRKGHMYPVRNYSPTEMVCISSLLPDG GEGPSATANGGLSKAKSPGLTPEPREDREGDDLTLHSFLP | SELPLG protein (ENSP00000447752) encoded by Transcript ID ENST00000550948 from Gene ID ENSG00000110876; *Homo sapiens* |

*based on assembled sequence in Genome Reference Consortium Human Build 38 patch release 1 (GRCh38.p13; GenBank assembly accession GCA_000001405.28 and RefSeq assembly accession GCF_000001405.39) note multiple listings for the same vesicle localization moiety reflect different transcripts (different ENST numbers) resulting potentially in multiple isoforms of a vesicle localization moiety when transcripts differ outside the 5' and 3' untranslated region (UTR) (i.e., differ in the coding sequences).

TABLE 2

Additional vesicle localization moieties which may be
used to produce a chimeric vesicle localization moiety

| PROT ID NO: | Gene Symbol | Protein | Sequence Identifiers |
|---|---|---|---|
| 1 | ACE | P12821 | ENST00000290866, ENST00000290863, ENST00000413513 |
| 2 | ADAM15 | Q13444 | ENST00000529473, ENST00000526491, ENST00000356955, ENST00000449910, ENST00000359280, ENST00000360674, ENST00000368412, ENST00000355956, ENST00000271836, ENST00000368413, BNST00000531455, ENST00000447332 |
| 3 | ADAM9 | Q13443 | ENST00000487273, ENST00000379917 |
| 4 | AGRN | O00468 | ENST00000379370 |
| 5 | ANPEP | P15144 | ENST00000300060 |
| 6 | ANTXR2 | P58335 | ENST00000403729, ENST00000346652, ENST00000307333 |
| 7 | ATP1A1 | P05023 | ENST00000295598, ENST00000369496, ENST00000537345, |
| 8 | ATP1B3 | P54709 | ENST00000286371 |
| 9 | BSG | P35613 | ENST00000545507, ENST00000346916, ENST00000333511, ENST00000353555 |
| 10 | BTN2A1 | Q7KYR7 | ENST00000312541, ENST00000429381, ENST00000469185, ENST00000541522 |
| 11 | CALM1 | P0DP23 | ENST00000356978 |
| 12 | CANX | P27824 | ENST00000504734, ENST00000247461, ENST00000452673, ENST00000638425, ENST00000639938, ENST00000638706 |
| 13 | CD151 | P48509 | ENST00000322008, ENST00000397420, ENST00000530726, ENST00000397421 |
| 14 | CD19 | P15391 | ENST00000538922, ENST00000324662 |
| 15 | CD1A | P06126 | ENST00000289429 |
| 16 | CD1B | P29016 | ENST00000368168 |
| 17 | CD1C | P29017 | ENST00000368170 |
| 18 | CD2 | P06729 | ENST00000369478 |
| 19 | CD200 | P41217 | ENST00000473539, ENST00000315711 |
| 20 | CD200R1 | Q8TD46 | ENST00000471858, ENST00000308611, ENST00000440122, ENST00000490004 |
| 21 | CD226 | Q15762 | ENST00000280200, ENST00000582621 |
| 22 | CD247 | F20963 | ENST00000362089, ENST00000392122 |
| 23 | CD274 | Q9NZQ7 | ENST00000381577, ENST00000381573 |
| 24 | CD276 | Q5ZPR3 | ENST00000318443, ENST00000561213, ENST00000564751, ENST00000318424 |
| 25 | CD33 | P20138 | ENST00000421133, ENST00000391796, ENST00000262262 |

TABLE 2-continued

Additional vesicle localization moieties which may be used to produce a chimeric vesicle localization moiety

| PROT ID NO: | Gene Symbol | Protein | Sequence Identifiers |
|---|---|---|---|
| 26 | CD34 | P28906 | ENST00000310833, ENST00000356522 |
| 27 | CD36 | P16671 | ENST00000435819, ENST00000309881, ENST00000394788, ENST00000447544, ENST00000433696, ENST00000432207, ENST00000538969, ENST00000544133 |
| 28 | CD37 | P11049 | ENST00000598095, ENST00000426897, ENST00000323906 |
| 29 | CD3E | P07766 | ENST00000361763 |
| 30 | CD40 | P25942 | ENST00000372285, ENST00000372276 |
| 31 | CD40LG | P29965 | ENST00000370629 |
| 32 | CD44 | P16070 | ENST00000263398, ENST00000428726, ENST00000415148, ENST00000433892, ENST00000278386, ENST00000434472, ENST00000352818 |
| 33 | CD47 | Q08722 | ENST00000355354, ENST00000361309 |
| 34 | CD53 | P19397 | ENST00000648608, ENST00000271324 |
| 35 | CD58 | P19256 | ENST00000369489, ENST00000464088, ENST00000457047 |
| 36 | CD63 | P08962 | ENST00000546939, ENST00000552692, ENST00000549117, ENST00000257857, ENST00000552754, ENST00000550776, ENST00000420846 |
| 37 | CD81 | P60033 | ENST00000263645 |
| 38 | CD82 | P27701 | ENST00000227155, ENST00000342935 |
| 39 | CD84 | Q9U1B8 | ENST00000368054, ENST00000368048, ENST00000311224, ENST00000368051, ENST00000534968 |
| 40 | CD86 | P42081 | ENST00000469710, ENST00000493101, ENST00000330540, ENST00000393627, ENST00000264468 |
| 41 | CD9 | P21926 | ENST00000382518, ENST00000538834, ENST00000009180 |
| 42 | CHMP1A | Q9HD42 | ENST00000397901 |
| 43 | CHMP1B | Q7LBR1 | ENST00000526991 |
| 44 | CHMP2A | O43633 | ENST00000600118, ENST00000601220, ENST00000312547 |
| 45 | CHMP3 | Q9Y3E7 | ENST00000263856, ENST00000409727, ENST00000409225 |
| 46 | CHMP4A | Q9BY43 | ENST00000347519, ENST00000609024, ENST00000645308, ENST00000645179 |
| 47 | CHMP4B | Q9H444 | ENST00000217402 |
| 48 | CHMP5 | Q9NZZ3 | ENST00000223500, ENST00000419016 |
| 49 | CHMP6 | Q96FZ7 | ENST00000325167 |
| 50 | COL6A1 | P12109 | ENST00000361866 |
| 51 | CR1 | P17927 | ENST00000400960, ENST00000367051, ENST00000367053 |
| 52 | CSF1R | P07333 | BNST00000286301, ENST00000543093 |
| 53 | CXCR4 | P61073 | ENST00000409817, ENST00000241393 |
| 54 | DDOST | P39656 | ENST00000375048, ENST00000415136 |
| 55 | DLL1 | O00548 | ENST00000616526, ENST00000366756 |
| 56 | DLL4 | Q9NR61 | ENST00000249749 |
| 57 | DSG1 | Q02413 | ENST00000257192 |
| 58 | EMB | Q6PCB8 | ENST00000303221, ENST00000514111 |
| 59 | ENG | P17813 | ENST00000373203, ENST00000344849 |
| 60 | EVI2B | P34910 | ENST00000330927, ENST00000577894 |
| 61 | F11R | Q9Y623 | ENST00000368026, ENST00000537746 |
| 62 | FASN | P49327 | ENST00000306749 |
| 63 | FCER1G | P30273 | ENST00000289902 |
| 64 | FCGR2C | P31995 | * P31995-1, P31995-2, P31995-3, P31995-4 |
| 65 | FLOT1 | O75955 | ENST00000436822, ENST00000383562, ENST00000376389, ENST00000444632, ENST00000383382 |
| 66 | FLOT2 | Q14254 | ENST00000394908 |
| 67 | FLT3 | P36888 | ENST00000241453 |
| 68 | FN1 | P02751 | ENST00000421182, ENST00000323926, ENST00000336916, ENST00000357867, ENST00000354785, ENST00000446046, ENST00000443816, ENST00000432072, ENST00000356005, ENST00000426059, ENST00000359671 |
| 69 | GAPDH | P04406 | ENST00000229239, ENST00000396861, ENST00000396859, ENST00000396858, ENST00000619601 |

TABLE 2-continued

Additional vesicle localization moieties which may be
used to produce a chimeric vesicle localization moiety

| PROT ID NO: | Gene Symbol | Protein | Sequence Identifiers |
|---|---|---|---|
| 70 | GLG1 | Q92896 | ENST00000205061, ENST00000422840, ENST00000447066 |
| 71 | GRIA2 | P42262 | ENST00000507898, ENST00000393815, ENST00000645636, ENST00000296526, ENST00000264426 |
| 72 | GRIA3 | P42263 | ENST00000541091, ENST00000620443, ENST00000622768 |
| 73 | GYPA | P02724 | ENST00000324022, ENST00000646447, ENST00000642713 |
| 74 | HSPG2 | P98160 | ENST00000374695 |
| 75 | ICAM1 | P05362 | ENST00000264832 |
| 76 | ICAM2 | P13598 | ENST00000449662, ENST00000579788, ENST00000579687, ENST00000412356, ENST00000418105 |
| 77 | ICAM3 | P32942 | BNST00000160262 |
| 78 | IL1RAP | Q9NPH3 | BNST00000072516, ENST00000439062, ENST00000447382, ENST00000422485, ENST00000422940, ENST00000413869, ENST00000342550, ENST00000317757, ENST00000443369, ENST00000412504 |
| 79 | IL5RA | Q01344 | ENST00000446632, ENST00000438560, ENST00000256452, ENST00000383846, ENST00000311981, ENST00000430514, ENST00000456302 |
| 80 | IST1 | P53990 | ENST00000544564, ENST00000541571, ENST00000378799, ENST00000329908, ENST00000538850, ENST00000378798, ENST00000606369, ENST00000535424 |
| 81 | ITGA2 | P17301 | ENST00000296585 |
| 82 | ITGA2B | P08514 | ENST00000262407 |
| 83 | ITGA4 | P13612 | ENST00000339307, ENST00000397033 |
| 84 | ITGA5 | P08648 | ENST00000293370 |
| 85 | ITGA6 | P23220 | ENST00000409532, ENST00000264107, ENST00000409080, ENST00000442250, ENST00000458358 |
| 86 | ITGAL | P20701 | BNST00000356798, ENST00000358164 |
| 87 | ITGAM | P11215 | ENST00000648685, ENST00000544665 |
| 88 | ITGAV | P06756 | ENST00000261023, ENST00000374907, ENST00000433736 |
| 89 | ITGAX | P20702 | ENST00000268296 |
| 90 | ITGB2 | P05107 | ENST00000397852, ENST00000397857, ENST00000355153, ENST00000397850, ENST00000302347 |
| 91 | ITGB3 | P05106 | ENST00000559488 |
| 92 | ITGB4 | P16144 | ENST00000579662, ENST00000200181, ENST00000450894, ENST00000449880 |
| 93 | ITGB5 | P18084 | ENST00000296181 |
| 94 | ITGB6 | P18564 | ENST00000283249, ENST00000409967, ENST00000409872 |
| 95 | ITGB7 | P26010 | ENST00000267082, ENST00000422257, ENST00000550743 |
| 96 | JAG1 | P78504 | ENST00000254958 |
| 97 | JAG2 | Q9Y219 | ENST00000331782, ENST00000347004 |
| 98 | KIT | P10721 | ENST00000412167, ENST00000288135 |
| 99 | LGALS3BP | Q08380 | ENST00000262770 |
| 100 | LILRA6 | Q6PI73 | ENST00000613333, ENST00000621570, ENST00000616720, ENST00000430421, ENST00000396365, ENST00000614434 |
| 101 | LILRB1 | Q8NI1L6 | ENST00000616408, ENST00000618055, ENST00000618681, ENST00000617686, ENST00000612636 |
| 102 | LILRB2 | Q8N423 | ENST00000619122, ENST00000621020, ENST00000614225, ENST00000618705, ENST00000391748, ENST00000314446, ENST00000391746, ENST00000391749, ENST00000434421, ENST00000617886, ENST00000617341, ENST00000610886, ENST00000618392 |
| 103 | LILRB3 | O75022 | ENST00000611086, ENST00000391750, ENST00000245620, ENST00000613698 |
| 104 | LMAN2 | Q12907 | ENST00000303127 |
| 105 | LRRC25 | Q8N386 | ENST00000339007, ENST00000595840 |
| 106 | LY75 | O60449 | ENST00000263636 |
| 107 | M6PR | P20645 | ANST00000000412 |

TABLE 2-continued

Additional vesicle localization moieties which may be
used to produce a chimeric vesicle localization moiety

| PROT ID NO: | Gene Symbol | Protein | Sequence Identifiers |
|---|---|---|---|
| 108 | MFGE8 | Q08431 | ENST00000268151, ENST00000268150, ENST00000566497, ENST00000542878 |
| 109 | MMP14 | P50281 | ENST00000311852 |
| 110 | MPL | P40238 | ENST00000372470 |
| 111 | MRC1 | P22897 | ENST00000569591 |
| 112 | MVB12B | Q9H7P6 | ENST00000361171, ENST00000489637 |
| 113 | NECTIN1 | Q15223 | ENST00000341398, ENST00000264025, ENST00000340882 |
| 114 | NOMO1 | Q15155 | ENST00000619292, ENST00000287667 |
| 115 | NOTCH1 | P46531 | ENST00000651671 |
| 116 | NOTCH2 | Q04721 | ENST00000256646 |
| 117 | NOTCH3 | Q9UM47 | ENST00000263388 |
| 118 | NOTCH4 | Q99466 | ENST00000457094, ENST00000375023, ENST00000425600, ENST00000439349 |
| 119 | NPTN | Q9Y639 | ENST00000345330, ENST00000351217, ENST00000562924, ENST00000563691 |
| 120 | NRP1 | O14786 | ENST00000265371, ENST00000374821, ENST00000374822, ENST00000374867 |
| 121 | PDCD1 | O15116 | ENST00000618185, ENST00000334409 |
| 122 | PDCD1LG2 | Q9BQ51 | ENST00000397747 |
| 123 | PDCD6IP | Q8WUM4 | ENST00000307296, ENST00000457054 |
| 124 | PDGFRB | P09619 | ENST00000261799 |
| 125 | PECAM1 | P16284 | ENST00000563924 |
| 126 | PLXNB2 | O15031 | ENST00000449103, ENST00000359337 |
| 127 | PLXND1 | Q9Y4D7 | ENST00000324093 |
| 128 | PROM1 | O43490 | ENST00000505450, ENST00000508167, ENST00000510224. ENST00000447510, ENST00000540805, ENST00000539194 |
| 129 | PTGES2 | Q917Z7 | ENST00000338961 |
| 130 | PTPRA | P18433 | ENST00000380393, ENST00000216877, ENST00000318266, ENST00000356147, ENST00000399903 |
| 131 | PTPRC | P08575 | ENST00000573679, ENST00000573477, ENST00000348564, ENST00000442510 |
| 132 | PTPRJ | Q12913 | ENST00000418331, ENST00000440289 |
| 133 | PTPRO | Q16827 | ENST00000281171, ENST00000543886, ENST00000348962, ENST00000442921, ENST00000542557, ENST00000445537, ENST00000544244 |
| 134 | RPN1 | P04843 | ENST00000296255 |
| 135 | SDC1 | P18827 | ENST00000254351, ENST00000381150 |
| 136 | SDC2 | P34741 | ENST00000302190 |
| 137 | SDC3 | O75056 | ENST00000339394 |
| 138 | SDC4 | P31431 | ENST00000372733 |
| 139 | SDCBP | O00560 | ENST00000260130, ENST00000447182, ENST00000413219, ENST00000424270 |
| 140 | SDCBP2 | Q9H190 | ENST00000381812, ENST00000381808, ENST00000339987, ENST00000360779 |
| 141 | SIGLEC7 | Q9Y286 | ENST00000317643, ENST00000305628, ENST00000536156, ENST00000600577 |
| 142 | SIGLEC9 | Q9Y336 | ENST00000250360, ENST00000440804 |
| 143 | SIRPA | P78324 | ENST00000622179, ENST00000356025, ENST00000358771, ENST00000400068 |
| 144 | SLIT2 | O94813 | ENST00000504154 |
| 145 | SNF8 | Q96H20 | ENST00000502492, ENST00000290330 |
| 146 | SPN | P16150 | ENST00000395389, ENST00000563039, ENST00000652691, ENST00000360121 |
| 147 | STX3 | Q13277 | ENST00000337979, ENST00000529177 |
| 148 | TACSTD2 | P09758 | ENST00000371225 |
| 149 | TFRC | P02786 | ENST00000360110, ENST00000392396 |
| 150 | TLR2 | O60603 | ENST00000642580, ENST00000642700, ENST00000260010 |
| 151 | TMED10 | P49755 | ENST00000303575 |
| 152 | TNFRSF8 | P28908 | ENST00000263932, ENST00000413146, ENST00000417814 |
| 153 | TRAC | P01848 | * P01848-1 |
| 154 | TSG101 | Q99816 | ENST00000251968 |
| 155 | TSPAN14 | Q8NG11 | ENST00000429989, ENST00000481124, ENST00000372164, ENST00000372158, ENST00000372156, ENST00000616406 |
| 156 | TSPAN7 | P41732 | ENST00000378482 |
| 157 | TSPAN8 | P19075 | ENST00000393330, ENST00000247829, ENST00000546561 |

TABLE 2-continued

Additional vesicle localization moieties which may be used to produce a chimeric vesicle localization moiety

| PROT ID NO: | Gene Symbol | Protein | Sequence Identifiers |
|---|---|---|---|
| 158 | TYROBP | O43914 | ENST00000544690, ENST00000262629, ENST00000589517 |
| 159 | VPS25 | Q9BRG1 | ENST00000253794 |
| 160 | VPS28 | Q9UK41 | ENST00000529182, ENST00000526054, ENST00000292510, ENST00000377348, ENST00000646588, ENST00000642202, ENST00000642867, ENST00000643186 |
| 161 | VPS36 | Q86VN1 | ENST00000378060, ENST00000611132 |
| 162 | VPS37A | Q8NEZ2 | ENST00000324849, ENST00000425020, ENST00000521829 |
| 163 | VPS37B | Q9H9H4 | ENST00000267202 |
| 164 | VPS37C | A5D8V6 | ENST00000301765 |
| 165 | VPS37D | Q86XT2 | ENST00000324941 |
| 166 | VPS4A | Q9UN37 | ENST00000254950 |
| 167 | VPS4B | O75351 | ENST00000238497 |
| 168 | VTI1A | Q96AJ9 | ENST00000393077 |
| 169 | VTI1B | Q9UEU0 | ENST00000554659 | and* UniProt Release 2019_11 (11 Dec. 2019); note amino acid sequence as well as functional and domain structure of vesicle localization moieties may be found under each accession number.
@ based on assembled sequence in Genome Reference Consortium Human Build 38 patch release 13 (GRCh38.p13; GenBank assembly accession GCA_000001405.28 and RefSeq assembly accession GCF_000001405.39); nucleic acid sequence coding a vesicle localization moiety may be found within sequence associated with an ENST number; note multiple ENST numbers associated with each vesicle localization moiety referred through its Gene Symbol or UniProtKB accession number potentially indicate multiple isoforms of a vesicle localization moiety.

TABLE 3

Nucleic acid sequences and amino acid sequences for fusion proteins of FIGS. 1 and 2 comprising a chimeric vesicle localization moiety (or a vesicle localization moiety) and an epitope tag and optionally an affinity peptide as a targeting moiety

| SEQ ID NO: | Sequence | Source |
|---|---|---|
| 45 | ATGTGGTGGCGTCTTTGGTGGTTGTTGCTTCTTCTTCTTCTCCTGTG GCCCATGGTGTGGGCCGACTACAAAGACCATGACGGAGATTATAA AGATCATGACATCGATTACAAGGATGACGATGACAAGGGAGGAG GGTCTGGAAACTCTACCATGGGCTCTGGTGGCGGCGGCGGCTCCG GCGGCGGCGGATCTCTCGAACTTAATTTGACCGATTCAGAGAATG CCACATGCCTTTATGCGAAATGGCAGATGAATTTCACTGTTCGGTA TGAAACCACAAATAAAACTTATAAAACCGTTACCATAAGCGACCA TGGAACTGTGACCTATAATGGAAGCATATGTGGAGATGATCAGAA TGGTCCCAAAATTGCTGTTCAGTTCGGACCTGGTTTCTCCTGGATT GCTAATTTTACTAAGGCAGCCTCTACCTATTCCATAGACTCAGTTT CTTTTAGTTACAACACAGGGGATAACACAACGTTTCCTGATGCCGA AGATAAAGGCATACTCACCGTTGATGAACTCTTGGCCATCAGAAT ACCTCTTAATGACCTGTTTAGATGCAATAGCCTCTCCACCCTGGAG AAGAATGATGTGGTACAACACTACTGGGATGTGTTGGTTCAAGCTT TTGTACAAAATGGGACCGTCTCTACAAATGAGTTCCTCTGTGATAA AGACAAAACCAGTACTGTGGCACCAACCATACACACAACAGTGCC ATCTCCAACGACCACCCCTACACCCAAGGAGAAACCTGAAGCCGG TACATATTCAGTGAATAATGGAAATGATACATGCCTTCTGGCCACC ATGGGCCTTCAGCTCAACATCACTCAGGATAAGGTCGCTTCAGTCA TTAACATTAACCCCAATACTACTCACTCTACAGGCTCTTGCAGGAG TCACACGGCGCTCCTGCGGTTGAATAGCAGCACCATTAAGTATCTT GACTTTGTCTTTGCTGTCAAGAATGAGAACAGATTTTATCTGAAAG AGGTCAACATCTCTATGTATTTGGTCAATGGGAGTGTGTTCTCCAT TGCTAATAACAATCTCAGCTACTGGGATGCCCCTCTGGGTTCTTCC TATATGTGCAACAAAGAGCAGACTGTTTCAGTGTCCGGCGCATTTC AGATTAATACTTTTGATCTTCGGGTGCAGCCTTTCAATGTGACACA AGGAAAGTATTCCACCGCCCAAGAGTGTTCTTTGGATGATGACAC CATACTGATCCCCATCATTGTAGGTGCCGGCCTGAGCGGCCTTATT ATCGTTATCGTCATTGCATACGTGATTGGACGGCGGAAATCTTATG CCGGTTATCAGACGCTT | cDNA of fusion protein produced from vector 91; Artificial Sequence |
| 46 | MWWRLWWLLLLLLLLWPMVWADYKDHDGDYKDHDIDYKDDDDK GGGSgnstmGSGGGGGSGGGGSLELNLTDSENATCLYAKWQMNFTVR YETTNKTYKTVTISDHGTVTYNGSICGDDQNGPKIAVQFGPGFSWIAN FTKAASTYSIDSVSFSYNTGDNTTFPDAEDKGILTVDEALLAIRIPLNDLF RCNSLSTLEKNDVVQHYWDVLVQAFVQNGTVSTNEFLCDKDKTSTV | Fusion protein produced from vector |

TABLE 3-continued

Nueleic acid sequences and amino acid sequences for fusion proteins of FIGS. 1 and 2 comprising a chimeric vesicle localization moiety (or a vesicle localization moiety) and an epitope tag and optionally an affinity peptide as a targeting moiety

| SEQ ID NO: | Sequence | Source |
|---|---|---|
| | APTIHTTVPSPTTTPTPKEKPEAGTYSVNNGNDTCLLATMGLQLNITQ DKVASVININPNTTHSTGSCRSHTALLRLNSSTIKYLDFVFAVKNENRF YLKEVNISMYLVNGSVFSIANNNLSYWDAPLGSSYMCNKEQTVSVSG AFQINTFDLRVQPFNVTQGKYSTAQECSLDDDTILIPIIVGAGLSGLIIVI VIAYVIGRRKSYAGYQTL | 91; Artificial Sequence |
| 47 | ATGTGGTGGAGATTGTGGTGGTTGCTCCTTCTCTTGTTGTTGCTTTG GCCAATGGTATGGGCGACCCACCGGCCGCCCATGTGGAGCCCTGT GTGGCCCGGCGGTGGGTCCGACTACAAAGACCATGACGGAGATTA TAAAGATCATGACATCGATTACAAGGATGACGATGACAAGGGAAA CAGTACCATGGGCTCAGGCGGTGGAGGAGGCTCCGGAGGAGGTGG CAGCGCACGCGTGAATAAACATAAACCGTGGTTGGAACCAACATA TCATGGGATCGTTACCGAAAATGATAATACAGTACTTCTGGATCCA CCTCTCATTGCTTTGGACAAGGACGCACCCCTCAGGTTCGCTGAAT CATTCGAAGTTACCGTTACGAAGGAAGGGGAAATATGCGGTTTCA AGATCCATGGTCAAAACGTTCCTTTCGACGCCGTCGTGGTTGACAA GAGCACCGGCGAAGGGGTTATAAGATCTAAGGAAAAGCTCGATTG CGAACTTCAAAAGGATTACAGCTTTACTATACAAGCGTACGACTG CGGCAAAGGGCCCGACGGGACAAATGTTAAGAAATCCCACAAGG CCACGGTCCACATCCAAGTCAATGATGTTAACGAATATGCACCTGT TTTCAAAGAGAAAAGCTATAAGGCTACTGTGATAGAAGGAAAACA ATATGATAGTATCCTGAGAGTCGAAGCTGTCGACGCAGATTGTAG CCCACAATTTTCCCAAATATGTTCCTATGAGATTATAACACCTGAT GTCCCTTTCACCGTAGATAAGGACGGATACATCAAGAATACTGAA AAGCTGAATTATGGTAAAGAGCACCAGTACAAACTCACGGTGACG GCGTACGATTGCGGAAAGAAGCGTGCAACTGAGGACGTACTTGTT AAAATTAGTATCAAACCGACGTGTACACCAGGCTGGCAGGGCTGG AATAATCGGATCGAATACGAACCCGGAACAGGAGCACTGGCTGTG TTCCCTAACATTCATCTCGAAACTTGCGATGAACCTGTGGCAAGCG TCCAAGCTACGGTAGAACTGGAGACATCTCATATTGGTAAGGGAT GTGATAGAGATACTTATAGCGAGAAAAGCCTTCATCGCTTGTGCG GCGCCGCAGCCGGAACAGCAGAACTCTTGCCTTCTCCCTCTGGCAG CCTTAATTGGACTATGGGATTGCCTACTGATAACGGTCATGATTCC GATCAAGTCTTCGAATTTAATGGAACACAAGCTGTACGCATTCCTG ACGGAGTGGTAAGTGTTTCTCCGAAGGAACCCTTTACAATTAGCGT ATGGATGCGCCACGGCCCCTTTGGACGGAAGAAAGAAACTATCCT GTGTAGCTCAGACAAGACTGACATGAACCGCCATCATTATTCTTTG TACGTACATGGTTGTCGTCTTATTTTCCTGTTTCGCCAAGACCCATC CGAAGAAAAGAAGTATAGGCCCGCCGAATTTCATTGGAAACTCAA CCAAGTGTGCGACGAAGAGTGGCATCATTATGTTCTGAACGTTGA GTTTCCATCCGTCACACTGTACGTCGACGGTACCAGCCATGAACCA TTTAGTGTCACAGAAGACTATCCCCTGCACCCGAGTAAAATCGAG ACGCAACTGGTTGTCGGCGCATGTTGGCAGGAATTTAGTGGCGTC GAGAACGATAACGAGACCGAACCCGTCACCGTAGCGTCCGCCGGC GGGGATCTCCATATGACGCAATTCTTTCGGGGTAACTTGGCCGGGC TGACACTGCGCTCTGGCAAGCTGGCTGACAAGAAAGTTATTGATT GCTTGTACACGTGTAAAGAAGGCCTTGATCTCCAAGTTCTGGAAG ATTCAGGACGAGGGGTCCAAATTCAGGCTCATCCATCCCAACTGG TGCTTACACTGGAAGGCGAGGATCTGGGAGAGCTGGACAAAGCTA TGCAACATATTTCCTATCTCAATAGTCGCCAATTTCCAACACCTGG CATCCGACGACTGAAGATTACGTCAACCATTAAATGCTTCAATGA AGCAACATGTATCAGCGTGCCACCTGTGGACGGATATGTTATGGT ACTGCAACCTGAAGAACCAAAGATTTCCCTCTCTGGGGTTCATCAC TTCGCAAGGGCCGCAAGTGAGTTCGAGTCCTCTGAGGGAGTCTTTC TCTTTCCCGAACTGCGGATAATAAGTACTATTACAAGGGAAGTCG AACCAGAGGGAGATGGAGCCGAAGATCCAACCGTGCAGGAGTCTC TCGTATCAGAAGAAATTGTCCATGATCTTGACACGTGCGAAGTGA CAGTAGAAGGGGAAGAACTCAATCATGAACAAGAATCATTGGAA GTAGATATGGCACGATTGCAACAAAAGGGAATCGAGGTCTCCTCA TCCGAGCTTGGTATGACTTTTACTGGAGTAGATACGATGGCTTCCT ATGAAGAAGTGCTGCATCTTCTCAGATACCGCAATTGGCACGCGC GTTCTCTGCTGGACAGAAAATTCAAACTGATTTGTAGCGAACTTAA CGGACGGTACATATCTAATGAGTTCAAAGTAGAAGTTAACGTGAT TCATACTGCAAATCCTATGGAGCATGCGGCCGCTGCCGCCGCTCAA CCTCAATTTGTCCATCCCGAGCATAGGTCATTCGTGGATCTCTCTG GTCATAATTTGGCAAATCCACATCCCTTTGCTGTGGTTCCATCTAC AGCAACTGTAGTTATTGTAGTATGTGTGTCCTTTCTCGTCTTTATGA TCATATTGGGCGTCTTCCGCATAAGAGCGGCCCACAGGAGAACAA TGAGGGACCAAGATACAGGAAAAGAAATGAAATGGATTGGGAT GATAGCGCACTCACAATAACGGTGAATCCAATGGAAACGTACGAA GATCAACATTCTAGCGAAGAAGAAGAAGAGGAAGAGGAAGAGGA | cDNA of fusion protein produced from vector 112; Artificial Sequence |

TABLE 3-continued

Nucleic acid sequences and amino acid sequences for fusion proteins
of FIGS. 1 and 2 comprising a chimeric vesicle localization moiety
(or a vesicle localization moiety) and an epitope tag and
optionally an affinity peptide as a targeting moiety

| SEQ ID NO: | Sequence | Source |
|---|---|---|
| | AGAGTCAGAAGATGGAGAAGAGGAAGACGATATTACATCAGCTG<br>AAAGCGAATCTTCAGAAGAAGAAGAAGGTGAACAAGGTGATCCTC<br>AAAATGCCACACGCCAACAACAACTCGAATGGGACGATTCTACAT<br>TGTCCTAT | |
| 48 | MWWRLWWLLLLLLLLWPMVWATHRPPMWSPVWPGGGSDYKDHD<br>GDYKDHDIDYKDDDDKgnstmGSGGGGGSGGGGSARVNKHKPWLEP<br>TYHGIVTENDNTVLLDPPLIALDKDAPLRFAESFEVTVTKEGEICGFKI<br>HGQNVPFDAVVVDKSTGEGVIRSKEKLDCELQKDYSFTIQAYDCGKG<br>PDGTNVKKSHKATVHIQVNDVNEYAPVFKEKSYKATVIEGKQYDSIL<br>RVEAVDADCSPQFSQICSYEIITPDVPFTVDKDGYIKNTEKLNYGKEH<br>QYKLTVTAYDCGKKRATEDVLVKISIKPTCTPGWQGWNNRIEYEPGT<br>GALAVFPNIHLETCDEPVASVQATVELETSHIGKGCDRDTYSEKSLHR<br>LCGAAAGTAELLPSPSGSLNWTMGLPTDNGHDSDQVFEFNGTQAVRI<br>PDGVVSVSPKEPFTISVWMRHGPFGRKKETILCSSDKTDMNRHHYSL<br>YVHGCRLIFLFRQDPSEEKKYRPAEFHWKLNQVCDEEWHHYVLNVE<br>FPSVTLYVDGTSHEPFSVTEDYPLHPSKIETQLVVGACWQEFSGVEND<br>NETEPVTVASAGGDLHMTQFFRGNLAGLTLRSGKLADKKVIDCLYTC<br>KEGLDLQVLEDSGRGVQIQAHPSQLVLTLEGEDLGELDKAMQHISYL<br>NSRQFPTPGIRRLKITSTIKCFNEATCISVPPVDGYVMVLQPEEPKISLS<br>GVHHFARAASEFESSEGVFLFPELRIISTITREVEPEGDGAEDPTVQESL<br>VSEEIVHDLDTCEVTVEGEELNHEQESLEVDMARLQQKGIEVSSSELG<br>MTFTGVDTMASYEEVLHLLRYRNWHARSLLDRKFKLICSELNGRYIS<br>NEFKVEVNVIHTANPMEHAAAAAAQPQFVHPEHRSFVDLSGHNLAN<br>PHPFAVVPSTATVVIVVCVSFLVFMIILGVFRIRAAHRRTMRDQDTGK<br>ENEMDWDDSALTITVNPMETYEDQHSSEEEEEEEEEEESEDGEEEDDI<br>TSAESESSEEEEGEQGDPQNATRQQQLEWDDSTLSY | Fusion protein produced from vector 112; Artificial Sequence |
| 49 | ATGTGGTGGCGATTGTGGTGGCTCCTTCTTCTTCTGCTCCTGCTTTG<br>GCCAATGGTGTGGGCCGACTACAAAGACCACGACGGGGATTATAA<br>AGATCATGACATCGATTACAAGGATGACGATGATAAGACCCACGT<br>CAGCCCAAACCAGGGCGGCCTGCCTTCAGGTGGCGGTAGTGGAAA<br>CTCCACCATGGGCTCTGGCGGCGGTGGCGGCTCTGGCGGAGGAGG<br>CTCATTGGAACTTAATTTGACAGATTCAGAAAATGCCACTTGCCTT<br>TATGCAAAATGGCAGATGAATTTCACAGTACGCTATGAAACTACA<br>AATAAAACTTATAAAACTGTAACCATTTCAGACCATGGCACTGTG<br>ACATATAATGGAAGCATTTGTGGGGATGATCAGAATGGTCCCAAA<br>ATAGCAGTTGCAGTTCGGACCTGGCTTTTCCTGGATTGCGAATTTTA<br>CCAAGGCAGCATCTACTTATTCAATTGACAGCGTCTCATTTTCCTA<br>CAACACTGGTGATAACACAACATTTCCTGATGCTGAAGATAAAGG<br>AATTCTTACTGTTGATGAACTTTTGGCCATCAGAATTCCATTGAAT<br>GACCTTTTTAGATGCAATAGTTTATCAACTTTGGAAAAGAATGATG<br>TTGTCCAACACTACTGGGATGTTCTTGTACAAGCTTTTGTCCAAAA<br>TGGCACAGTGAGCACAAATGAGTTCCTGTGTGATAAAGACAAAAC<br>TTCAACAGTGGCACCCACCATACACACCACTGTGCCATCTCCTACT<br>ACAACACCTACTCCAAAGGAAAAACCAGAAGCTGGAACCTATTCA<br>GTTAATAATGGCAATGATACTTGTCTGCTGGCTACCATGGGGCTGC<br>AGCTGAACATCACTCAGGATAAGGTTGCTTCAGTTATTAACATCAA<br>CCCCAATACAACTCACTCCACAGGCAGCTGCCGTTCTCACACTGCT<br>CTACTTAGACTCAATAGCAGCACCATTAAGTATCTAGACTTTGTCT<br>TTGCTGTGAAAAATGAAAACCGATTTTATCTGAAGGAAGTGAACA<br>TCAGCATGTATTTGGTTAATGGCTCCGTTTTCAGCATTGCAAATAA<br>CAATCTCAGCTACTGGGATGCCCCCCTGGGAAGTTCTTATATGTGC<br>AACAAAGAGCAGACTGTTTCAGTGTCTGGAGCATTTCAGATAAAT<br>ACCTTTGATCTAAGGGTTCAGCCTTTCAATGTGACACAAGGAAAGT<br>ATTCTACAGCCCAAGAGTGTTCGCTGGATGATGACACCATTCTAAT<br>CCCAATTATAGTTGGTGCTGGTCTTTCAGGCTTGATTATCGTTATA<br>GTGATTGCTAGCTCCCACTGGTGTTGTAAGAAGGAGGTTCAGGAG<br>ACACGGCGCGAGCGCCGCAGGCTCATGTCGATGGAGATGGAC | cDNA of fusion protein produced from vector 135; Artificial Sequence |
| 50 | MWWRLWWLLLLLLLLWPMVWADYKDHDGDYKDHDIDYKDDDDK<br>THVSPNQGGLPSGGGSgnstmGSGGGGGSGGGGSLELNLTDSENATCL<br>YAKWQMNFTVRYETTNKTYKTVTISDHGTVTYNGSICGDDQNGPKI<br>AVQFGPGFSWIANFTKAASTYSIDSVSFSYNTGDNTTFPDAEDKGILT<br>VDELLAIRIPLNDLFRCNSLSTLEKNDVVQHYWDVLVQAFVQNGTVS<br>TNEFLCDKDKTSTVAPTIHTTVPSPTTTPTPKEKPEAGTYSVNNGNDT<br>CLLATMGLQLNITQDKVASVININPNTTHSTGSCRSHTALLRLNSSTIK<br>YLDFVFAVKNENRFYLKEVNISMYLVNGSVFSIANNNLSYWDAPLGS<br>SYMCNKEQTVSVSGAFQINTFDLRVQPFNVTQGKYSTAQECSLDDDT<br>ILIPIIVGAGLSGLIIVIVIASSHWCCKKEVQETRRERRRLMSMEMD | Fusion protein produced from vector 135; Artificial Sequence |

TABLE 3-continued

Nucleic acid sequences and amino acid sequences for fusion proteins of FIGS. 1 and 2 comprising a chimeric vesicle localization moiety (or a vesicle localization moiety) and an epitope tag and optionally an affinity peptide as a targeting moiety

| SEQ ID NO: | Sequence | Source |
| --- | --- | --- |
| 51 | ATGTGGTGGCGATTGTGGTGGCTCCTTCTTCTTCTGCTCCTGCTTTG GCCAATGGTGTGGGCCGACTACAAAGACCACGACGGGGATTATAA AGATCATGACATCGATTACAAGGATGACGATGATAAGACCCACGT CAGCCCAAACCAGGGCGGCCTGCCTTCAGGTGGCGGTAGTGGAAA CTCCACCATGGGCTCTGGCGGCGGTGGCGGCTCTGGCGGAGGAGG CTCATTGGAACTTAATTTGACAGATTCAGAAAATGCCACTTGCCTT TATGCAAAATGGCAGATGAATTTCACAGTACGCTATGAAACTACA AATAAAACTTATAAAACTGTAACCATTTCAGACCATGGCACTGTG ACATATAATGGAAGCATTTGTGGGGATGATCAGAATGGTCCCAAA ATAGCAGTGCAGTTCGGACCTGGCTTTTCCTGGATTGCGAATTTTA CCAAGGCAGCATCTACTTATTCAATTGACAGCGTCTCATTTTCCTA CAACACTGGTGATAACACAACATTTCCTGATGCTGAAGATAAAGG AATTCTTACTGTTGATGAACTTTTGGCCATCAGAATTCCATTGAAT GACCTTTTTAGATGCAATAGTTTATCAACTTTGGAAAAGAATGATG TTGTCCAACACTACTGGGATGTTCTTGTACAAGCTTTTGTCCAAAA TGGCACAGTGAGCACAAATGAGTTCCTGTGTGATAAAGACAAAAC TTCAACAGTGGCACCCACCATACACACCACTGTGCCATCTCCTACT ACAACACCTACTCCAAAGGAAAAACCAGAAGCTGGAACCTATTCA GTTAATAATGGCAATGATACTTGTCTGCTGGCTACCATGGGGCTGC AGCTGAACATCACTCAGGATAAGGTTGCTTCAGTTATTAACATCAA CCCCAATACAACTCACTCCACAGGCAGCTGCCGTTCTCACACTGCT CTACTTAGACTCAATAGCAGCACCATTAAGTATCTAGACTTTGTCT TTGCTGTGAAAAATGAAAACCGATTTATCTGAAGGAAGTGAACA TCAGCATGTATTTGGTTAATGGCTCCGTTTTCAGCATTGCAAATAA CAATCTCAGCTACTGGGATGCCCCCTGGGAAGTTCTTATATGTGC AACAAAGAGCAGACTGTTTCAGTGTCTGGAGCATTTCAGATAAAT ACCTTTGATCTAAGGGTTCAGCCTTTCAATGTGACACAAGGAAAGT ATTCTACAGCCCAAGAGTGTTCGCTGGATGATGACACCATTCTAAT CCCAATTATAGTTGGTGCTGGTCTTTCAGGCTTGATTATCGTTATA GTGATTGCTAAGTGCGGCTTCTTCAAGCGAGCCCGCACTCGCGCCC TGTATGAAGCTAAGAGGCAGAAGGCGGAGATGAAGAGCCAGCCG TCAGAGACAGAGAGGCTGACCGACGACTAC | cDNA of fusion protein produced from vector 140; Artificial Sequence |
| 52 | MWWRLWWLLLLLLLLWPMVWADYKDHDGDYKDHDIDYKDDDDK THVSPNQGGLPSGGGSgnstmGSGGGGGSGGGGSLELNLTDSENATCL YAKWQMNFTVRYETTNKTYKTVTISDHGTVTYNGSICGDDQNGPKI AVQFGPGFSWIANFTKAASTYSIDSVSFSYNTGDNTTFPDAEDKGILT VDELLAIRIPLNDLFRCNSLSTLEKNDVVQHYWDVLVQAFVQNGTVS TNEFLCDKDKTSTVAPTIHTTVPSPTTTPTPKEKPEAGTYSVNNGNDT CLLATMGLQLNITQDKVASVININPNTTHSTGSCRSHTALLRLNSSTIK YLDFVFAVKNENRFYLKEVNISMYLVNGSVFSIANNNLSYWDAPLGS SYMCNKEQTVSVSGAFQINTFDLRVQPFNVTQGKYSTAQECSLDDDT ILIPIIVGAGLSGLIIVIVIAKCGFFKRARTRALYEAKRQKAEMKSQPSE TERLTDDY | Fusion protein produced from vector 140; Artificial Sequence |
| 53 | ATGTGGTGGCGATTGTGGTGGCTCCTTCTTCTTCTGCTCCTGCTTTG GCCAATGGTGTGGGCCGACTACAAAGACCACGACGGGGATTATAA AGATCATGACATCGATTACAAGGATGACGATGATAAGACCCACGT CAGCCCAAACCAGGGCGGCCTGCCTTCAGGTGGCGGTAGTGGAAA CTCCACCATGGGCTCTGGCGGCGGTGGCGGCTCTGGCGGAGGAGG CTCATTGGAACTTAATTTGACAGATTCAGAAAATGCCACTTGCCTT TATGCAAAATGGCAGATGAATTTCACAGTACGCTATGAAACTACA AATAAAACTTATAAAACTGTAACCATTTCAGACCATGGCACTGTG ACATATAATGGAAGCATTTGTGGGGATGATCAGAATGGTCCCAAA ATAGCAGTGCAGTTCGGACCTGGCTTTTCCTGGATTGCGAATTTTA CCAAGGCAGCATCTACTTATTCAATTGACAGCGTCTCATTTTCCTA CAACACTGGTGATAACACAACATTTCCTGATGCTGAAGATAAAGG AATTCTTACTGTTGATGAACTTTTGGCCATCAGAATTCCATTGAAT GACCTTTTTAGATGCAATAGTTTATCAACTTTGGAAAAGAATGATG TTGTCCAACACTACTGGGATGTTCTTGTACAAGCTTTTGTCCAAAA TGGCACAGTGGCACCCACCATACACACCACTGTGCCATCTCCTACT ACAACACCTACTCCAAAGGAAAAACCAGAAGCTGGAACCTATTCA GTTAATAATGGCAATGATACTTGTCTGCTGGCTACCATGGGGCTGC AGCTGAACATCACTCAGGATAAGGTTGCTTCAGTTATTAACATCAA CCCCAATACAACTCACTCCACAGGCAGCTGCCGTTCTCACACTGCT CTACTTAGACTCAATAGCAGCACCATTAAGTATCTAGACTTTGTCT TTGCTGTGAAAAATGAAAACCGATTTATCTGAAGGAAGTGAACA TCAGCATGTATTTGGTTAATGGCTCCGTTTTCAGCATTGCAAATAA CAATCTCAGCTACTGGGATGCCCCCCTGGGAAGTTCTTATATGTGC AACAAAGAGCAGACTGTTTCAGTGTCTGGAGCATTTCAGATAAAT | cDNA of fusion protein produced from vector 141; Artificial Sequence |

TABLE 3-continued

Nucleic acid sequences and amino acid sequences for fusion proteins of FIGS. 1 and 2 comprising a chimeric vesicle localization moiety (or a vesicle localization moiety) and an epitope tag and optionally an affinity peptide as a targeting moiety

| SEQ ID NO: | Sequence | Source |
|---|---|---|
| | ACCTTTGATCTAAGGGTTCAGCCTTTCAATGTGACACAAGGAAAGT<br>ATTCTACAGCCCAAGAGTGTTCGCTGGATGATGACACCATTCTAAT<br>CCCAATTATAGTTGGTGCTGGTCTTTTCAGGCTTGATTATCGTTATA<br>GTGATTGCTGTGATGCAGAGACTCTTTCCCCGCATCCCTCACATGA<br>AAGACCCCATCGGTGACAGCTTCCAAAACGACAAGCTGGTGGTCT<br>GGGAGGCGGGCAAAGCCGGCCTGGAGGAGTGTCTGGTGACTGAA<br>GTACAGGTCGTGCAGAAAACT | |
| 54 | MWWRLWWLLLLLLLLWPMVWADYKDHDGDYKDHDIDYKDDDDK<br>THVSPNQGGLPSGGGSgnstmGSGGGGGSGGGGSLELNLTDSENATCL<br>YAKWQMNFTVRYETTNKTYKTVTISDHGTVTYNGSICGDDQNGPKI<br>AVQFGPGFSWIANFTKAASTYSIDSVSFSYNTGDNTTFPDAEDKGILT<br>VDELLAIRIPLNDLFRCNSLSTLEKNDVVQHYWDVLVQAFVQNGTVS<br>TNEFLCDKDKTSTVAPTIHTTVPSPTTTPTPKEKPEAGTYSVNNGNDT<br>CLLATMGLQLNITQDKVASVININPNTTHSTGSCRSHTALLRLNSSTIK<br>YLDFVFAVKNENRFYLKEVNISMYLVNGSVFSIANNNLSYWDAPLGS<br>SYMCNKEQTVSVSGAFQINTFDLRVQPFNVTQGKYSTAQECSLDDDT<br>ILIPIIVGAGLSGLIIVIVIAVMQRLFPRIPHMKDPIGDSFQNDKLVVWE<br>AGKAGLEECLVTEVQVVQKT | Fusion protein produced from vector 141; Artificial Sequence |
| 55 | ATGTGGTGGCGATTGTGGTGGCTCCTTCTTCTTCTGCTCCTGCTTTG<br>GCCAATGGTGTGGGCCGACTACAAAGACCACGACGGGGATTATAA<br>AGATCATGACATCGATTACAAGGATGACGATGATAAGACCCACGT<br>CAGCCCAAACCAGGGCGGCCTGCCTTCAGGTGGCGGTAGTGGAAA<br>CTCCACCATGGGCTCTGGCGGCGGTGGCGGCTCTGGCGGAGGAGG<br>CTCATTGGAACTTAATTTGACAGATTCAGAAAATGCCACTTGCCTT<br>TATGCAAAATGGCAGATGAATTTCACAGTACGCTATGAAACTACA<br>AATAAAACTTATAAAACTGTAACCATTTCAGACCATGGCACTGTG<br>ACATATAATGGAAGCATTTGTGGGGATGATCAGAATGGTCCCAAA<br>ATAGCAGTGCAGTTCGGACCTGGCTTTTCCTGGATTGCGAATTTTA<br>CCAAGGCAGCATCTACTTATTCAATTGACAGCGTCTCATTTTCCTA<br>CAACACTGGTGATAACACAACATTTCCTGATGCTGAAGATAAAGG<br>AATTCTTACTGTTGATGAACTTTTGGCCATCAGAATTCCATTGAAT<br>GACCTTTTTAGATGCAATAGTTTATCAACTTTGGAAAAGAATGATG<br>TTGTCCAACACTACTGGGATGTTCTTGTACAAGCTTTTGTCCAAAA<br>TGGCACAGTGAGCACAAATGAGTTCCTGTGTGATAAAGACAAAAC<br>TTCAACAGTGGCACCCACCATACACACCACTGTGCCATCTCCTACT<br>ACAACACCTACTCCAAAGGAAAAACCAGAAGCTGGAACCTATTCA<br>GTTAATAATGGCAATGATACTTGTCTGCTGGCTACCATGGGGCTGC<br>AGCTGAACATCACTCAGGATAAGGTTGCTTCAGTTATTAACATCAA<br>CCCCAATACAACTCACTCCACAGGCAGCTGCCGTTCTCACACTGCT<br>CTACTTAGACTCAATAGCAGCACCATTAAGTATCTAGACTTTGTCT<br>TTGCTGTGAAAAATGAAAACCGATTTTATCTGAAGGAAGTGAACA<br>TCAGCATGTATTTGGTTAATGGCTCCGTTTTCAGCATTGCAAATAA<br>CAATCTCAGCTACTGGGATGCCCCCCTGGGAAGTTCTTATATGTGC<br>AACAAAGAGCAGACTGTTTCAGTGTCTGGAGCATTTCAGATAAAT<br>ACCTTTGATCTAAGGGTTCAGCCTTTCAATGTGACACAAGGAAAGT<br>ATTCTACAGCCCAAGAGTGTTCGCTGGATGATGACACCATTCTAAT<br>CCCAATTATAGTTGGTGCTGGTCTTTTCAGGCTTGATTATCGTTATA<br>GTGATTGCTCGCCTCTCCCGCAAGGGCCACATGTACCCCGTGCGTA<br>ATTACTCCCCCACCGAGATGGTCTGCATCTCATCCCTGTTGCCTGA<br>TGGGGGTGAGGGGCCCTCTGCCACAGCCAATGGGGGCCTGTCCAA<br>GGCCAAGAGCCCGGGCTGACGCCAGAGCCCAGGGAGGACCGTG<br>AGGGGGATGACCTCACCCTGCACAGCTTCCTCCCT | cDNA of fusion protein produced from vector 142; Artificial Sequence |
| 56 | MWWRLWWLLLLLLLLWPMVWADYKDHDGDYKDHDIDYKDDDDK<br>THVSPNQGGLPSGGGSgnstmGSGGGGGSGGGGSLELNLTDSENATCL<br>YAKWQMNFTVRYETTNKTYKTVTISDHGTVTYNGSICGDDQNGPKI<br>AVQFGPGFSWIANFTKAASTYSIDSVSFSYNTGDNTTFPDAEDKGILT<br>VDELLAIRIPLNDLFRCNSLSTLEKNDVVQHYWDVLVQAFVQNGTVS<br>TNEFLCDKDKTSTVAPTIHTTVPSPTTTPTPKEKPEAGTYSVNNGNDT<br>CLLATMGLQLNITQDKVASVININPNTTHSTGSCRSHTALLRLNSSTIK<br>YLDFVFAVKNENRFYLKEVNISMYLVNGSVFSIANNNLSYWDAPLGS<br>SYMCNKEQTVSVSGAFQINTFDLRVQPFNVTQGKYSTAQECSLDDDT<br>ILIPIIVGAGLSGLIIVIVIARLSRKGHMYPVRNYSPTEMVCISSLLPDGG<br>EGPSATANGGLSKAKSPGLTPEPREDREGDDLTLHSFLP | Fusion protein produced from vector 142; Artificial Sequence |
| 57 | ATGTGGTGGCGATTGTGGTGGCTCCTTCTTCTTCTGCTCCTGCTTTG<br>GCCAATGGTGTGGGCCGACTACAAAGACCACGACGGGGATTATAA<br>AGATCATGACATCGATTACAAGGATGACGATGATAAGACCCACGT<br>CAGCCCAAACCAGGGCGGCCTGCCTTCAGGTGGCGGTAGTGGAAA | cDNA of fusion protein produced |

TABLE 3-continued

Nucleic acid sequences and amino acid sequences for fusion proteins
of FIGS. 1 and 2 comprising a chimeric vesicle localization moiety
(or a vesicle localization moiety) and an epitope tag and
optionally an affinity peptide as a targeting moiety

| SEQ ID NO: | Sequence | Source |
|---|---|---|
|  | CTCCACCATGGGCTCTGGCGGCGGTGGCGGCTCTGGCGGAGGAGG<br>CTCATTGGAACTTAATTTGACAGATTCAGAAAATGCCACTTGCCTT<br>TATGCAAAATGGCAGATGAATTTCACAGTACGCTATGAAACTACA<br>AATAAAACTTATAAAACTGTAACCATTTCAGACCATGGCACTGTG<br>ACATATAATGGAAGCATTTGTGGGGATGATCAGAATGGTCCCAAA<br>ATAGCAGTGCAGTTCGGACCTGGCTTTTCCTGGATTGCGAATTTTA<br>CCAAGGCAGCATCTACTTATTCAATTGACAGCGTCTCATTTTCCTA<br>CAACACTGGTGATAACACAACATTTCCTGATGCTGAAGATAAAGG<br>AATTCTTACTGTTGATGAACTTTTGGCCATCAGAATTCCATTGAAT<br>GACCTTTTTAGATGCAATAGTTTATCAACTTTGGAAAAGAATGATG<br>TTGTCCAACACTACTGGGATGTTCTTGTACAAGCTTTTGTCCAAAA<br>TGGCACAGTGAGCACAAATGAGTTCCTGTGTGATAAAGACAAAAC<br>TTCAACAGTGGCACCCACCATACACACCACTGTGCCATCTCCTACT<br>ACAACACCTACTCCAAAGGAAAAACCAGAAGCTGGAACCTATTCA<br>GTTAATAATGGCAATGATACTTGTCTGCTGGCTACCATGGGCTGC<br>AGCTGAACATCACTCAGGATAAGGTTGCTTCAGTTATTAACATCAA<br>CCCCAATACAACTCACTCCACAGGCAGCTGCCGTTCTCACACTGCT<br>CTACTTAGACTCAATAGCAGCACCATTAAGTATCTAGACTTTGTCT<br>TTGCTGTGAAAAATGAAAACCGATTTTATCTGAAGGAAGTGAACA<br>TCAGCATGTATTTGGTTAATGGCTCCGTTTTCAGCATTGCAAATAA<br>CAATCTCAGCTACTGGGATGCCCCCCTGGGAAGTTCTTATATGTGC<br>AACAAAGAGCAGACTGTTTCAGTGTCTGGAGCATTTCAGATAAAT<br>ACCTTTGATCTAAGGGTTCAGCCTTTCAATGTGACACAAGGAAAGT<br>ATTCTACAGCCCAAGAGTGTTCGCTGGATGATGACACCATTCTAAT<br>CCCAATTATAGTTGGTGCTGGTCTTTCAGGCTTGATTATCGTTATA<br>GTGATTGCTCTTTTAATGATAATTCATGCAGAAGGGAGTTTGCTA<br>AATTTGAAAAGGAGAAAATGAATGCCAAATGGGACACGGGTGAA<br>AATCCTATTTATAAGAGTGCCGTAACAACTGTGGTCAATCCGAAGT<br>ATGAGGGAAAA |  |
| 58 | MWWRLWWLLLLLLLLWPMVWADYKDHDGDYKDHDIDYKDDDDK<br>THVSPNQGGLPSGGGSgnstmGSGGGGGSGGGGSLELNLTDSENATCL<br>YAKWQMNFTVRYETTNKTYKTVTISDHGTVTYNGSICGDDQNGPKI<br>AVQFGPGFSWIANFTKAASTYSIDSVSFSYNTGDNTTFPDAEDKGILT<br>VDELLAIRIPLNDLFRCNSLSTLEKNDVVQHYWDVLVQAFVQNGTVS<br>TNEFLCDKDKTSTVAPTIHTTVPSPTTTPTPKEKPEAGTYSVNNGNDT<br>CLLATMGLQLNITQDKVASVININPNTTHSTGSCRSHTALLRLNSSTIK<br>YLDFVFAVKNENRFYLKEVNISMYLVNGSVFSIANNNLSYWDAPLGS<br>SYMCNKEQTVSVSGAFQINTFDLRVQPFNVTQGKYSTAQECSLDDDT<br>ILIPIIVGAGLSGLIIVIVIALLMIIHDRREFAKFEKEKMNAKWDTGENPI<br>YKSAVTTVVNKPKYEGK | Fusion protein produced from vector 143; Artificial Sequence |
| 59 | ATGTGGTGGCGATTGTGGTGGCTCCTTCTTCTTCTGCTCCTGCTTTG<br>GCCAATGGTGTGGGCCGACTACAAAGACCACGACGGGGATTATAA<br>AGATCATGACATCGATTACAAGGATGACGATGATAAGACCCACGT<br>CAGCCCAAACCAGGGCGGCCTGCCTTCAGGTGGCGGTAGTGGAAA<br>CTCCACCATGGGCTCTGGCGGCGGTGGCGGCTCTGGCGGAGGAGG<br>CTCATTGGAACTTAATTTGACAGATTCAGAAAATGCCACTTGCCTT<br>TATGCAAAATGGCAGATGAATTTCACAGTACGCTATGAAACTACA<br>AATAAAACTTATAAAACTGTAACCATTTCAGACCATGGCACTGTG<br>ACATATAATGGAAGCATTTGTGGGGATGATCAGAATGGTCCCAAA<br>ATAGCAGTGCAGTTCGGACCTGGCTTTTCCTGGATTGCGAATTTTA<br>CCAAGGCAGCATCTACTTATTCAATTGACAGCGTCTCATTTTCCTA<br>CAACACTGGTGATAACACAACATTTCCTGATGCTGAAGATAAAGG<br>AATTCTTACTGTTGATGAACTTTTGGCCATCAGAATTCCATTGAAT<br>GACCTTTTTAGATGCAATAGTTTATCAACTTTGGAAAAGAATGATG<br>TTGTCCAACACTACTGGGATGTTCTTGTACAAGCTTTTGTCCAAAA<br>TGGCACAGTGAGCACAAATGAGTTCCTGTGTGATAAAGACAAAAC<br>TTCAACAGTGGCACCCACCATACACACCACTGTGCCATCTCCTACT<br>ACAACACCTACTCCAAAGGAAAAACCAGAAGCTGGAACCTATTCA<br>GTTAATAATGGCAATGATACTTGTCTGCTGGCTACCATGGGCTGC<br>AGCTGAACATCACTCAGGATAAGGTTGCTTCAGTTATTAACATCAA<br>CCCCAATACAACTCACTCCACAGGCAGCTGCCGTTCTCACACTGCT<br>CTACTTAGACTCAATAGCAGCACCATTAAGTATCTAGACTTTGTCT<br>TTGCTGTGAAAAATGAAAACCGATTTTATCTGAAGGAAGTGAACA<br>TCAGCATGTATTTGGTTAATGGCTCCGTTTTCAGCATTGCAAATAA<br>CAATCTCAGCTACTGGGATGCCCCCCTGGGAAGTTCTTATATGTGC<br>AACAAAGAGCAGACTGTTTCAGTGTCTGGAGCATTTCAGATAAAT<br>ACCTTTGATCTAAGGGTTCAGCCTTTCAATGTGACACAAGGAAAGT<br>ATTCTACAGCCCAAGAGTGTTCGCTGGATGATGACACCATTCTAAT<br>CCCAATTATAGTTGGTGCTGGTCTTTCAGGCTTGATTATCGTTATA | cDNA of fusion protein produced from vector 144; Artificial Sequence |

TABLE 3-continued

Nucleic acid sequences and amino acid sequences for fusion proteins of FIGS. 1 and 2 comprising a chimeric vesicle localization moiety (or a vesicle localization moiety) and an epitope tag and optionally an affinity peptide as a targeting moiety

| SEQ ID NO: | Sequence | Source |
|---|---|---|
| | GTGATTGCTCGGATCCGGGCCGCACATCGGCGGACCATGCGGGAT<br>CAGGACACCGGGAAGGAGAACGAGATGGACTGGGACGACTCTGC<br>CCTGACCATCACCGTCAACCCCATGGAGACCTATGAGGACCAGCA<br>CAGCAGTGAGGAGGAGGAAGAGGAAGAGGAAGAGGAAAGC<br>GAGGACGGCGAAGAAGAGGATGACATCACCAGCGCCGAGTCGGA<br>GAGCAGCGAGGAGGAGGAGGGGGAGCAGGGCGACCCCCAGAACG<br>CAACCCGGCAGCAGCAGCTGGAGTGGGATGACTCCACCCTCAGCT<br>AC | |
| 60 | MWWRLWWLLLLLLLLWPMVWADYKDHDGDYKDHDIDYKDDDDK<br>THVSPNQGGLPSGGGSgnstmGSGGGGGSGGGGSLELNLTDSENATCL<br>YAKWQMNFTVRYETTNKTYKTVTISDHGTVTYNGSICGDDQNGPKI<br>AVQFGPGFSWIANFTKAASTYSIDSVSFSYNTGDNTTFPDAEDKGILT<br>VDELLAIRIPLNDLFRCNSLSTLEKNDVVQHYWDVLVQAFVQNGTVS<br>TNEFLCDKDKTSTVAPTIHTTVPSPTTTPTPKEKPEAGTYSVNNGNDT<br>CLLATMGLQLNITQDKVASVININPNTTHSTGSCRSHTALLRLNSSTIK<br>YLDFVFAVKNENRFYLKEVNISMYLVNGSVFSIANNNLSYWDAPLGS<br>SYMCNKEQTVSVSGAFQINTFDLRVQPFNVTQGKYSTAQECSLDDDT<br>ILIPIIVGAGLSGLIIVIVIARIRAAHRRTMRDQDTGKENEMDWDDSAL<br>TITVNPMETYEDQHSSEEEEEEEEEEEESEDGEEEDDITSAESESSEEEG<br>EQGDPQNATRQQQLEWDDSTLSY | Fusion protein produced from vector 144; Artificial Sequence |
| 61 | ATGTGGTGGCGATTGTGGTGGCTCCTTCTTCTTCTGCTCCTGCTTTG<br>GCCAATGGTGTGGGCCGACTACAAAGACCACGACGGGGATTATAA<br>AGATCATGACATCGATTACAAGGATGACGATGATAAGACCCACGT<br>CAGCCCAAACCAGGGCGGCCTGCCTTCAGGTGGCGGTAGTGGAAA<br>CTCCACCATGGGCTCTGGCGGCGGTGGCGGCTCTGGCGGAGGAGG<br>CTCATTGGAACTTAATTTGACAGATTCAGAAAATGCCACTTGCCTT<br>TATGCAAAATGGCAGATGAATTTCACAGTACGCTATGAAACTACA<br>AATAAAACTTATAAAACTGTAACCATTTCAGACCATGGCACTGTG<br>ACATATAATGGAAGCATTTGTGGGGATGATCAGAATGGTCCCAAA<br>ATAGCAGTGCAGTTCGGACCTGGCTTTTCCTGGATTGCGAATTTTA<br>CCAAGGCAGCATCTACTTATTCAATTGACAGCGTCTCATTTTCCTA<br>CAACACTGGTGATAACACAACATTTCCTGATGCTGAAGATAAAGG<br>AATTCTTACTGTTGATGAACTTTTGGCCATCAGAATTCCATTGAAT<br>GACCTTTTTAGATGCAATAGTTTATCAACTTTGGAAAAGAATGATG<br>TTGTCCAACACTACTGGGATGTTCTTGTACAAGCTTTTGTCCAAAA<br>TGGCACAGTGAGCACAAATGAGTTCCTGTGTGATAAAGACAAAAC<br>TTCAACAGTGGCACCCACCATACACACCACTGTGCCATCTCCTACT<br>ACAACACCTACTCCAAAGGAAAAACCAGAAGCTGGAACCTATTCA<br>GTTAATAATGGCAATGATACTTGTCTGCTGGCTACCATGGGGCTGC<br>AGCTGAACATCACTCAGGATAAGGTTGCTTCAGTTATTAACATCAA<br>CCCCAATACAACTCACTCCACAGGCAGCTGCCGTTCTCACACTGCT<br>CTACTTAGACTCAATAGCAGCACCATTAAGTATCTAGACTTTGTCT<br>TTGCTGTGAAAAATGAAAACCGATTTTATCTGAAGGAAGTGAACA<br>TCAGCATGTATTTGGTTAATGGCTCCGTTTTCAGCATTGCAAATAA<br>CAATCTCAGCTACTGGGATGCCCCCCTGGGAAGTTCTTATATGTGC<br>AACAAAGAGCAGACTGTTTCAGTGTCTGGAGCATTTCAGATAAAT<br>ACCTTTGATCTAAGGGTTCAGCCTTTCAATGTGACACAAGGAAAGT<br>ATTCTACAGCCCAAGAGTGTTCGCTGGATGATGACACCATTCTAAT<br>CCCAATTATAGTTGGTGCTGGTCTTTCAGGCTTGATTATCGTTATA<br>GTGATTGCTaagaagccacgt | cDNA of fusion protein produced from vector 145; Artificial Sequence |
| 62 | MWWRLWWLLLLLLLLWPMVWADYKDHDGDYKDHDIDYKDDDDK<br>THVSPNQGGLPSGGGSgnstmGSGGGGGSGGGGSLELNLTDSENATCL<br>YAKWQMNFTVRYETTNKTYKTVTISDHGTVTYNGSICGDDQNGPKI<br>AVQFGPGFSWIANFTKAASTYSIDSVSFSYNTGDNTTFPDAEDKGILT<br>VDELLAIRIPLNDLFRCNSLSTLEKNDVVQHYWDVLVQAFVQNGTVS<br>TNEFLCDKDKTSTVAPTIHTTVPSPTTTPTPKEKPEAGTYSVNNGNDT<br>CLLATMGLQLNITQDKVASVININPNTTHSTGSCRSHTALLRLNSSTIK<br>YLDFVFAVKNENRFYLKEVNISMYLVNGSVFSIANNNLSYWDAPLGS<br>SYMCNKEQTVSVSGAFQINTFDLRVQPFNVTQGKYSTAQECSLDDDT<br>ILIPIIVGAGLSGLIIVIVIAKKPR | Fusion protein produced from vector 145; Artificial Sequence |
| 63 | ACCCACCGGCCGCCCATGTGGAGCCCTGTGTGGCCC | cDNA of affinity peptide; Artificial Sequence |

TABLE 3-continued

Nucleic acid sequences and amino acid sequences for fusion proteins of FIGS. 1 and 2 comprising a chimeric vesicle localization moiety (or a vesicle localization moiety) and an epitope tag and optionally an affinity peptide as a targeting moiety

| SEQ ID NO: | Sequence | Source |
| --- | --- | --- |
| 64 | THRPPMWSPVWP | Affinity Peptide; Artificial Sequence |
| 65 | ACCCACGTCAGCCCAAACCAGGGCGGCCTGCCTTCA | cDNA of affinity peptide: Artificial Sequence |
| 66 | THVSPNQGGLPS | Affinity Peptide: Artificial Sequence |

TABLE 4

Nucleic acid payloads

| Class of payload | Payload details | Target |
| --- | --- | --- |
| anti-miRNA | antimiR-494 | Targets the "oncomiR", miR-494 miRNA |
| anti-miRNA | antimiR-221/222 | Targets the "oncomiR", miR 221/222 miRNA |
| anti-miRNA | antimiR-132 | Targets the "oncomiR", miR-132 miRNA |
| anti-miRNA | antimiR-155 | Targets the "oncomiR", miR-155 miRNA |
| Antisense Oligonucleotide (ASO) | ASO, OGX-011 | Clusterin |
| Antisense Oligonucleotide (ASO) | EGFR antisense DNA | EGFR |
| Antisense Oligonucleotide (ASO) | ASO, OGX-427 | Hsp27 |
| Antisense Oligonucleotide (ASO) | ASO, ISIS-STAT3Rx | STAT3 |
| Antisense Oligonucleotide (ASO) | ASO, AP 12009 | TGFB2 |
| Antisense Oligonucleotide (ASO) | ASO, EZN-2968 | H1F-1a |
| Antisense Oligonucleotide (ASO) | ASO, LErafAON-ETU | c-raf |
| Antisense Oligonucleotide (ASO) | ASO, K-Ras mutation matched | Mutated K-Ras |
| Antisense Oligonucleotide (ASO) | ASO, Wnt/beta-catenin | WNT/beta-catenin signaling |
| Antisense Oligonucleotide (ASO) | ASO, myc | Estrogen induced c-myc expression |
| Antisense Oligonucleotide (ASO) | ASO, Raf1 | Raf-1 |
| Aptamer | DNA Aptamer, AS1411 | Nucleolin |
| Aptamer | RNA Aptamer, NOX-A12 | CXCL12/SDF-1 (CXC chemokine ligand 12/stromal cell derived factor-1) |
| CRISPR/Cas9 | CRISPR/Cas9 | E6, E7 HPV oncogenes |
| CRISPR/Cas9 | CRISPR/Cas9 | EBV genome, EBNA1 |
| CRISPR/Cas9 | CRISPR/Cas9 under an AND logic gate | sgRNA to Lac1 gene, only in the presence of the cancer-specific human telomerase reverse transcriptase promoter and urothelium-specific human uroplakin II promoter (AND logic gate, both promotors only present in bladder cancer cells). |

TABLE 4-continued

Nucleic acid payloads

| Class of payload | Payload details | Target |
| --- | --- | --- |
| Cytotoxic trans-genes | Herpes Simplex Type 1 thymidine kinase (TK) | Converts this prodrug ganciclovir (or valacyclovir) into the highly toxic deoxyguanosine triphosphate causing early chain termination of nascent DNA strands |
| miRNA | miRNA-34a | Poorly understood tumor suppressor gene. Targets include SIRT1, BCL2, YY1, MYC, CDK6, CCND1, FOXP1, HNF4a, CDKN2C, ACSL4, LEF1, ACSL1, MTA2, AXL, LDHA, HDAC1, CD44, BCL2, E2F3 |
| miRNA | miR-200 | Poorly understood tumor suppressor gene. Targets include ZEB1, CTNNB1, BAP1, GEMIN2, PTPRD, WDR37, KLF11, SEPT9, HOXB5, ERBB2IP, KLHL20, FOG2, RIN2, RASSF2, ELMO2, TCF7L1, VAC14, SHC1, SEPT7, FOG2 |
| miRNA | miR-15/16 | Poorly understood tumor suppressor gene. Targets include BACE1, DMTF1, C22orf5, BCL2, ARL2, CCNT2, TPPP3, VEGFA, RARS, FGF2, ZNF622, DNAJB4, PURA, SHOC2, LUZP1, FNDC3B, ITGA2, ATG9A, CA12, TMEM43, YIF1B, TMEM189, VTI1B, RTN4, TOMM34, NAA15, PNP, SRPR, IPO4, NAPg, PFAH1B2, SLC12A2, SEC24A, NOTCH2, PPP2R5C, KCNN4, UBE4A, KPNA3, RAB30, ACP2, SRPRB, EIF4E, ABCF2, TPM3, ARHGDIA, GALNT7, LYPLA2, CHORDC1, TMEM109, LAMC1, EGFR, GPAM, ADSS, PPIF, RFT1, TNFSF9, IGF2R, TXN2, GPPT1, SLC7A1, SQSTM1, PANX1, UTP15, NPR3, SLC16A3, PTGS2, HARS, LAMTOR3, HSPA1B |
| miRNA | let-7 | Poorly understood tumor suppressor gene. Targets include NIRF, NF2, CASP3, TRIM71 |
| miRNA | miR-26a | Induces cell-cycle arrest associated with direct targeting of cyclins D2 and E2 |
| miRNA | miR-143 | MACC1 |
| miRNA | miR-145, miR-33a | ERK5, c-Myc |
| mRNA | mRNAs encoding OX46L, IL-36γ, and IL-23 | OX40L, IL-36γ, and IL-23 |
| siRNA | siRNA against targets | Knockdown c-Myc/MDM2/VEGF |
| siRNA | siRNA against targets | EphA2 oncoprotein |
| siRNA | siRNA against targets | Oncogenic KRAS(G12D) |
| siRNA | siRNA against targets | PLK1 (polo-like kinase-1) |
| siRNA | siRNA against targets | protein kinase N3 (PKN3) gene expression in vascular endothelial cells |
| siRNA | siRNA against targets | VEGF gene, kinesin spindle (KSP) protein gene |
| Splice-switching oligonucleotides (SSOs) | SSO to Bcl-x | Apoptotic regulator Bcl-x is alternatively spliced to express anti-apoptotic Bcl-xL and pro-apoptotic Bcl-xS |
| Splice-switching oligonucleotides (SSOs) | SSO, SSO111 | HER2 Exon 15, transmembrane domain |
| Transgene encoding toxic proteins | Pseudomonas exotoxin encoded transgene connected to human IL-13. 50-80% of human GBM cells overexpress a variant of the IL-13 receptor not found in normal tissue. | IL12 variant, IL13Rα2, common in GBM |

TABLE 5

Nucleic acid sequences and amino acid sequences for chimeric vesicle localizations moieties*

| SEQ ID NO: | Sequence | Source |
| --- | --- | --- |
| 67 | CTCGAACTTAATTTGACCGATTCAGAGAATGCCACATGCCTTTA TGCGAAATGGCAGATGAATTTCACTGTTCGGTATGAAACCACA AATAAAACTTATAAAACCGTTACCATAAGCGACCATGGAACTG TGACCTATAATGGAAGCATATGTGGAGATGATCAGAATGGTCC CAAAATTGCTGTTCAGTTCGGACCTGGTTTCTCCTGGATTGCTA ATTTTACTAAGGCAGCCTCTACCTATTCCATAGACTCAGTTTCG TTTAGTTACAACACAGGGGATAACACAACGTTTCCTGATGCCG AAGATAAAGGCATACTCACCGTTGATGAACTCTTGGCCATCAG | Coding sequence for LAMP2 (mature form) from vector 91; Artificial Sequence |

TABLE 5-continued

Nucleic acid sequences and amino acid sequences for chimeric vesicle localizations moieties*

| SEQ ID NO: | Sequence | Source |
|---|---|---|
| | AATACCTCTTAATGACCTGTTTAGATGCAATAGCCTCTCCACCC<br>TGGAGAAGAATGATGTGGTACAACACTACTGGGATGTGTTGGT<br>TCAAGCTTTTGTACAAAATGGGACCGTCTCTACAAATGAGTTCC<br>TCTGTGATAAAGACAAAACCAGTACTGTGGCACCAACCATACA<br>CACAACAGTGCCATCTCCAACGACCACCCCTACACCCAAGGAG<br>AAACCTGAAGCCGGTACATATTCAGTGAATAATGGAAATGATA<br>CATGCCTTCTGGCCACCATGGGCCTTCAGCTCAACATCACTCAG<br>GATAAGGTCGCTTCAGTCATTAACATTAACCCCAATACTACTCA<br>CTCTACAGGCTCTTGCAGGAGTCACACGGCGCTCCTGCGGTTG<br>AATAGCAGCACCATTAAGTATCTTGACTTTGTCTTTGCTGTCAA<br>GAATGAGAACAGATTTTATCTGAAAGAGGTCAACATCTCTATG<br>TATTTGGTCAATGGGAGTGTGTTCTCCATTGCTAATAACAATCT<br>CAGCTACTGGGATGCCCCTCTGGGTTCTTCCTATATGTGCAACA<br>AAGAGCAGACTGTTTCAGTGTCCGGCGCATTTCAGATTAATACT<br>TTTGATCTTCGGGTGCAGCCTTTCAATGTGACACAAGGAAAGT<br>ATTCCACCGCCCAAGAGTGTTCTTTGGATGATGACACCATACTG<br>ATCCCCATCATTGTAGGTGCCGGCCTGAGCGGCCTTATTATCGT<br>TATCGTCATTGCATACGTGATTGGACGGCGGAAATCTTATGCCG<br>GTTATCAGACGCTT | |
| 68 | LELNLTDSENATCLYAKWQMNFTVRYETTNKTYKTVTISDHGTV<br>TYNGISCGDDQNGPKIAVQFGPGFSWIANFTKAASTYSIDSVSFSY<br>NTGDNTTFPDAEDKGILTVDELLAIRIPLNDLFRCNSLSTLEKNDV<br>VQHYWDVLVQAFVQNGTVSTNEFLCDKDKTSTVAPTIHTTVPSPT<br>TTPTPKEKPEAGTYSVNNGNDTCLLATMGLQLNITQDKVASVINI<br>NPNTTHSTGSCRSHTALLRLNSSTIKYLDFVFAVKNENRFYLKEVN<br>ISMYLVNGSVFSIANNNLSYWDAPLGSSYMCNKEQTVSVSGAFQI<br>NTFDLRVQPFNVTQGKYSTAQECSLDDDT,<br>ILIPIIVGAGLSGLIIVIVIA, YVIGRRKSYAGYQTL | LAMP2 amino acid sequence (mature form) from vector 91; Artificial Sequence |
| 69 | GCACGCGTGAATAAACATAAACCGTGGTTGGAACCAACATATC<br>ATGGGATCGTTACCGAAAATGATAATACAGTACTTCTGGATCC<br>ACCTCTCATTGCTTTGGACAAGGACGCACCCCTCAGGTTCGCTG<br>AATCATTCGAAGTTACCGTTACGAAGGAAGGGGAAATATGCGG<br>TTTCAAGATCCATGGTCAAAACGTTCCTTTCGACGCCGTCGTGG<br>TTGACAAGAGCACCGGCGAAGGGGTTATAAGATCTAAGGAAA<br>AGCTCGATTGCGAACTTCAAAAGGATTACAGCTTTACTATACA<br>GAAATCCCACAAGGCCACGGTCCACATCCAAGTCAATGATGTT<br>AACGAATATGCACCTGTTTTCAAAGAGAAAAGCTATAAGGCTA<br>CTGTGATAGAAGGAAAACAATATGATAGTATCCTGAGAGTCGA<br>AGCTGTCGACGCAGATTGTAGCCCACAATTTTCCCAAATATGTT<br>CCTATGAGATTATAACACCTGATGTCCCTTTCACCGTAGATAAG<br>GACGGATACATCAAGAATACTGAAAAGCTGAATTATGGTAAAG<br>AGCACCAGTACAAACTCACGGTGACGGCGTACGATTGCGGAAA<br>GAAGCGTGCAACTGAGGACGTACTTGTTAAAATTAGTATCAAA<br>CCGACGTGTACACCAGGCTGGCAGGGCTGGAATAATCGGATCG<br>AATACGAACCCGGAACAGGAGCACTGGCTGTGTTCCCTAACAT<br>TCATCTCGAAACTTGCGATGAACCTGTGGCAAGCGTCCAAGCT<br>ACGGTAGAACTGGAGACATCTCATATTGGTAAGGGATGTGATA<br>GAGATACTTATAGCGAGAAAAGCCTTCATCGCTTGTGCGGCGC<br>CGCAGCCGGAACAGCAGAACTCTTGCCTTCTCCCTCTGGCAGC<br>CTTAATTGGACTATGGGATTGCCTACTGATAACGGTCATCATTC<br>CGATCAAGTCTTCGAATTTAATGGAACACAAGCTGTACGCATT<br>CCTGACGGAGTGGTAAGTGTTTCTCCGAAGGAACCCTTTACAA<br>TTAGCGTATGGATGCGCCACGCCCCTTTGGACGGAAGAAAGA<br>AACTATCCTGTGTAGCTCAGACAAGACTGACATGAACCGCCAT<br>CATTATTCTTTCTACGTACATGGTTGTCGTCTTATTTTCCTGTTT<br>CGCCAAGACCCATCCGAAGAAAAGAAGTATAGGCCCGCCGAA<br>TTTCATTGGAAACTCAACCAAGTGTGCGACGAAGAGTGGCATC<br>ATTATGTTCTGAACGTTGAGTTTCCATCCGTCACACTGTACGTC<br>GACGGTACCAGCCATGAACCATTTAGTGTCACAGAAGACTATC<br>CCCTGCACCCGAGTAAAATCGAGACGCAACTGGTTGTCGGCGG<br>ATGTTGGCAGGAATTTAGTGGCGTCGAGAACGATAACGAGACC<br>GAACCCGTCACCGTAGCGTCCGCCGGCGGGGATCTCCATATGA<br>CGCAATTCTTTCGGGGTAACTTGGCCGGGCTGACACTGCGCTCT<br>GGCAAGCTGGCTGACAAGGGGCTTATTGATTGCTTGTACACGT<br>GTAAAGAAGGCCTTGATCTCCAAGTTCTGGAAGATTCAGGACG<br>AGGGGTCCAAATTCAGGCTCATCCATCCCAACTGGTGCTTACA<br>CTGGAAGGCGAGGATCTGGAGAGCTGGACAAAGCTATGCAA<br>CATATTTCCTATCTCAATAGTCGCCAATTTCCAACACCTGGCAT<br>CCGACGACTGAAGATTACGTCAACCATTAAATGCTTCAATGAA<br>GCAACATGTATCAGCGTGCCACCTGTGGACGGATATGTTATGG<br>TACTGCAACCTGAAGAACCAAAGATTTCCCTCTCTGGGGTTCAT | Coding sequence for CLSTN1 (mature form) from vector 112; Artificial Sequence |

TABLE 5-continued

Nucleic acid sequences and amino acid sequences for chimeric vesicle localizations moieties*

| SEQ ID NO: | Sequence | Source |
|---|---|---|
| | CACTTCGCAAGGGCCGCAAGTGAGTTCGAGTCCTCTGAGGGAG<br>TCTTTCTCTTTCCCGAACTGCGGATAATAAGTACTATTACAAGG<br>GAAGTCGAACCAGAGGGAGATGGAGCCGAAGATCCAACCGTG<br>CAGGAGTCTCTCGTATCAGAAGAAATTGTCCATGATCTTGACA<br>CGTGCGAAGTGACAGTAGAAGGGGAAGAACTCAATCATGAAC<br>AAGAATCATTGGAAGTAGATATGGCACGATTGCAACAAAAGG<br>GAATCGAGGTCTCCTCATCCGAGCTTGGTATGACTTTTACTGGA<br>GTAGATACGATGGCTTCCTATGAAGAAGTGCTGCATCTTCTCAG<br>ATACCGCAATTGGCACGCGCGTTCTCTGCTGGACAGAAAATTC<br>AAACTGATTTGTAGCGAACTTAACGGACGGTACATATCTAATG<br>AGTTCAAAGTAGAAGTTAACGTGATTCATACTGCAAATCCTAT<br>GGAGCATGCGGCCGCTGCCGCCGCTCAACCTCAATTTGTCCATC<br>CCGAGCATAGGTCATTCGTGGATCTCTCTGGTCATAATTTGGCA<br>AATCCACATCCCTTTGCTGTGGTTCCATCTACAGCAACTGTAGT<br>TATTGTAGTATGTGTGTCCTTTCTCGTCTTTATGATCATATTGGG<br>CGTCTTCCGCATAAGAGCGGCCCACAGGAGAACAATGAGGGAC<br>CAAGATACAGGAAAAGAAAATGAAATGGATTGGGATGATAGC<br>GCACTCACAATAACGGTGAATCCAATGGAAACGTACGAAGATC<br>AACATTCTAGCGAAGAAGAAGAAGAGGAAGAGGAAGAGGAAG<br>AGTCAGAAGATGGAGAAGAGGAAGACGATATTACATCAGCTG<br>AAAGCGAATCTTCAGAAGAAGAAGAAGGTGAACAAGGTGATC<br>CTCAAAATGCCACACGCCAACAACAACTCGAATGGGACGATTC<br>TACATTGTCCTAT | |
| 70 | ARVNKHKPWLEPTYHGIVTENDNTVLLDPPLIALDKDAPLRFAES<br>FEVTVTKEGEICGFKIHGQNVPFDAVVVDKSTGEGVIRSKEKLDCE<br>LQKDYSFTIQAYDCGKGPDGTNVKKSHKATVHIQVNDVNEYAPV<br>FKEKSYKATVIEGKQYDSILRVEAVDADCSPQFSQICSYEIITPDVP<br>FTVDKDGYIKNTEKLNYGKEHQYKLTVTAYDCGKKRATEDVLV<br>KISIKPTCTPGWQGWNNRIEYEPGTGALAVFPNIHLETCDEPVASV<br>QATVELETSHIGKGCDRDTYSEKSLHRLCGAAAGTAELLPSPSGSL<br>NWTMGLPTDNGHDSDQVFEFNGTQAVRIPDGVVSVSPKEPFTISV<br>WMRHGPFGRKKETILCSSDKTDMNRHHYSLYVHGCRLIFLFRQDP<br>SEEKKYRPAEFHWKLNQVCDEEWHHYVLNVEFPSVTLYVDGTSH<br>EPFSVTEDYPLHPSKIETQLVVGACWQEFSGVENDNETEPVTVAS<br>AGGDLHMTQFFRGNLAGLTLRSGKLADKKVIDCLYTCKEGLDLQ<br>VLEDSGRGVQIQAHPSQLVLTLEGEDLGELDKAMQHISYLNSRQF<br>PTPGIRRLKITSTIKCFNEATCISVPPVDGYVMVLQPEEPKISLSGVH<br>HFARAASEFESSEGVFLFPELRIISTITREVEPEGDGAEDPTVQESLV<br>SEEIVHDLDTCEVTVEGEELNHEQESLEVDMARLQQKGIEVSSSELG<br>MTFTGVDTMASYEEVLHLLRYRNWHARSLLDRKFKLICSELNG<br>RYISNEFKVEVNVIHTANPMEHAAAAAAQPQFVHPEHRSFVDLSG<br>HNLANPHPFAVVPSTATVVIVVCVSFLVFMIILGVF,<br>RIRAAHRRTMRDQDTGKENEMDWDDSALTITVNPMETYEDQHSS<br>EEEEEEEEEESEDGEEEDDITSAESESSEEEEGEQGDPQNATRQQQ<br>LEWDDSTLSY | CLSTN1 amino acid sequence (mature form) from vector 112; Artificial Sequence |
| 71 | TTGGAACTTAATTTGACAGATTCAGAAAATGCCACTTGCCTTTA<br>TGCAAAATGGCAGATGAATTTCACAGTACGCTATGAAACTACA<br>AATAAAACTTATAAAACTGTAACCATTTCAGACCATGGCACTG<br>TGACATATAATGGAAGCATTTGTGGGGATGATCAGAATGGTCC<br>CAAAATAGCAGTGCAGTTCGGACCTGGCTTTTCCTGGATTGCG<br>AATTTTACCAAGGCAGCATCTACTTATTCAATTGACAGCGTCTC<br>ATTTTCCTACAACACTGGTGATAACACAACATTTCCTGATGCTG<br>AAGATAAAGGAATTCTTACTGTTGATGAACTTTTGGCCATCAG<br>AATTCCATTGAATGACCTTTTTAGATGCAATAGTTTATCAACTT<br>TGGAAAAGAATGATGTTGTCCAACACTACTGGGATGTTCTTGT<br>ACAAGCTTTTGTCCAAAATGGCACAGTGAGCACAAATGAGTTC<br>CTGTGTGATAAAGACAAAACTTCAACAGTGGCACCCACCATAC<br>ACACCACTGTGCCATCTCCTACTACAACACCTACTCCAAAGGA<br>AAAACCAGAAGCTGGAACCTATTCAGTTAATAATGGCAATGAT<br>ACTTGTCTGCTGGCTACCATGGGGCTGCAGCTGAACATCACTCA<br>GGATAAGGTTGCTTCAGTTATTAACATCAACCCCAATACAACTC<br>ACTCCACAGGCAGCTGCCGTTCTCACACTGCTCTACTTAGACTC<br>AATAGCAGCACCATTAAGTATCTAGACTTTGTCTTTGCTGTGAA<br>AAATGAAAACCGATTTATCTGAAGGAAGTGAACATCAGCATG<br>TATTTGGTTAATGGCTCCGTTTTCAGCATTGCAAATAACAATCT<br>CAGCTACTGGGATGCCCCCTGGGAAGTTCTTATATGTGCAAC<br>AAAGAGCAGACTGTTTCAGTGTCTGGAGCATTTCAGATAAATA<br>CCTTTGATCTAAGGGTTCAGCCTTTCAATGTGACACAAGGAAA | Coding sequence for LAMP2 surface-and-transmembrane domain and PTGFRN cytosolic domain from vecto 135; Artificial Sequence |

TABLE 5-continued

Nucleic acid sequences and amino acid sequences for chimeric vesicle localizations moieties*

| SEQ ID NO: | Sequence | Source |
|---|---|---|
| | GTATTCTACAGCCCAAGAGTGTTCGCTGGATGATGACACCATTC<br>TAATCCCAATTATAGTTGGTGCTGGTCTTTCAGGCTTGATTATC<br>GTTATAGTGATTGCTAGCTCCCACTGGTGTTGTAAGAAGGAGG<br>TTCAGGAGACACGGCGCGAGCGCCGCAGGCTCATGTCGATGGA<br>GATGGAC | |
| 72 | LELNLTDSENATCLYAKWQMNFTVRYETTNKTYKTVTISDHGTV<br>TYNGISCGDDQNGPKIAVQFGPGFSWIANFTKAASTYSIDSVSFSY<br>NTGDNTTFPDAEDKGILTVDELLAIRIPLNDLFRCNSLSTLEKNDV<br>VQHYWDVLVQAFVQNGTVSTNEFLCDKDKTSTVAPTIHTTVPSPT<br>TTPTPKEKPEAGTYSVNNGNDTCLLATMGLQLNITQDKVASVINI<br>NPNTTHSTGSCRSHTALLRLNSSTIKYLDFVFAVKNENRFYLKEVN<br>ISMYLVNGSVFSIANNNLSYWDAPLGSSYMCNKEQTVSVSGAFQI<br>NTFDLRVQPFNVTQGKYSTAQECSLDDDT,<br>ILIPIIVGAGLSGLIIVIVIA,<br>SSHWCCKKEVQETRRERRRLMSMEMD | LAMP2 surface-and-transmembrane domain and PTGFRN cytosolic domain amino acid sequence from vecto 135; Artificial Sequence |
| 73 | TTGGAACTTAATTTGACAGATTCAGAAAATGCCACTTGCCTTTA<br>TGCAAAATGGCAGATGAATTTCACAGTACGCTATGAAACTACA<br>AATAAAACTTATAAAACTGTAACCATTTCAGACCATGGCACTG<br>TGACATATAATGGAAGCATTTGTGGGGATGATCAGAATGGTCC<br>GAAAATAGCAGTGCAGTTCGGACCTGGCTTTTCCTGGATTGCG<br>AATTTTACCAAGGCAGCATCTACTTATTCAATTGACAGCGTCTC<br>ATTTTCCTACAACACTGGTGATAACACAACATTTCCTGATGCTG<br>AAGATAAAGGAATTCTTACTGTTGATGAACTTTTGGCCATCAG<br>AAGATAAAGGAATTCTTACTGTTGATGAACTTTTGGCCATCAG<br>AATTCCATTGAATGACCTTTTTAGATGCAATAGTTTATCAACTT<br>ATTTTCCTACAACACTGGTGATAACACAACATTTCCTGATGCTG<br>AAGATAAAGGAATTCTTACTGTTGATGAACTTTTGGCCATCAG<br>AATTCCATTGAATGACCTTTTTAGATGCAATAGTTTATCAACTT<br>TGGAAAAGAATGATGTTGTCCAACACTACTGGGATGTTCTTGT<br>ACAAGCTTTTGTCCAAAATGGCACAGTGAGCACAAATGAGTTC<br>CTGTGTGATAAAGACAAAACTTCAACAGTGGCACCCACCATAC<br>ACACCACTGTGCCATCTCCTACTACAACACCTACTCCAAAGGA<br>AAAACCAGAAGCTGGAACCTATTCAGTTAATAATGGCAATGAT<br>ACTTGTCTGCTGGCTACCATGGGCTGCAGCTGAACATCACTCA<br>GGATAAGGTTGCTTCAGTTATTAACATCAACCCCAATACAACTC<br>ACTCCACAGGCAGCTGCCGTTCTCACACTGCTCTACTTAGACTC<br>AATAGCAGCACCATTAAGTATCTAGACTTTGTCTTTGCTGTGAA<br>AAATGAAAACCGATTTTATCTGAAGGAAGTGAACATCAGCATG<br>TATTTGGTTAATGGCTCCGTTTTCAGCATTGCAAATAACAATCT<br>CAGCTACTGGGATGCCCCCCTGGGAAGTTCTTATATGTGCAAC<br>AAAGAGCAGACTGTTTCAGTGTCTGGAGCATTTCAGATAAATA<br>CCTTTGATCTAAGGGTTCAGCCTTTCAATGTGACACAAGGAAA<br>GTATTCTACAGCCCAAGAGTGTTCGCTGGATGATGACACCATTC<br>TAATCCCAATTATAGTTGGTGCTGGTCTTTCAGGCTTGATTATC<br>GTTATAGTGATTGCTAAGTGCGGCTTCTTCAAGCGAGCCCGCAC<br>TCGCGCCCTGTATGAAGCTAAGAGGCAGAAGGCGGAGATGAA<br>GAGCCAGCCGTCAGAGCAGAGAGGCTGACCGACGACTAC | Coding sequence for LAMP2 surface-and-transmembrane domain and ITGA3 cytosolic domain from vecto 140; Artificial Sequence |
| 74 | LELNLTDSENATCLYAKWQMNFTVRYETTNKTYKTVTISDHGTV<br>TYNGISCGDDQNGPKIAVQFGPGFSWIANFTKAASTYSIDSVSFSY<br>NTGDNTTFPDAEDKGILTVDELLAIRIPLNDLFRCNSLSTLEKNDV<br>VQHYWDVLVQAFVQNGTVSTNEFLCDKDKTSTVAPTIHTTVPSPT<br>TTPTPKEKPEAGTYSVNNGNDTCLLATMGLQLNITQDKVASVINI<br>NPNTTHSTGSCRSHTALLRLNSSTIKYLDFVFAVKNENRFYLKEVN<br>ISMYLVNGSVFSIANNNLSYWDAPLGSSYMCNKEQTVSVSGAFQI<br>NTFDLRVQPFNVTQGKYSTAQECSLDDDT,<br>ILIPIIVGAGLSGLIIVIVIA,<br>KCGFFKRARTRALYEAKRQKAEMKSQPSERERLTDDY | LAMP2 surface-and-transmembrane domain and ITGA3 cytosolic domain amino acid sequence from vecto 140; Artificial Sequence |
| 75 | TTGGAACTTAATTTGACAGATTCAGAAAATGCCACTTGCCTTTA<br>TGCAAAATGGCAGATGAATTTCACAGTACGCTATGAAACTACA<br>AATAAAACTTATAAAACTGTAACCATTTCAGACCATGGCACTG<br>TGACATATAATGGAAGCATTTGTGGGGATGATCAGAATGGTCC<br>CAAAATAGCAGTGCAGTTCGGACCTGGCTTTTCCTGGATTGCG<br>AATTTTACCAAGGCAGCATCTACTTATTCAATTGACAGCGTCTC | Coding sequence for LAMP2 surface-and-transmembrane domain and |

TABLE 5-continued

Nucleic acid sequences and amino acid sequences for chimeric vesicle localizations moieties*

| SEQ ID NO: | Sequence | Source |
|---|---|---|
|  | ATTTTCCTACAACACTGGTGATAACACAACATTTCCTGATGCTG<br>AAGATAAAGGAATTCTTACTGTTGATGAACTTTTGGCCATCAG<br>AATTCCATTGAATGACCTTTTTAGATGCAATAGTTTATCAACTT<br>TGGAAAAGAATGATGTTGTCCAACACTACTGGGATGTTCTTGT<br>ACAAGCTTTTGTCCAAAATGGCACAGTGAGCACAAATGAGTTC<br>CTGTGTGATAAAGACAAAACTTCAACAGTGGCACCCACCATAC<br>ACACCACTGTGCCATCTCCTACTACAACACCTACTCCAAAGGA<br>AAAACCAGAAGCTGGAACCTATTCAGTTAATAATGGCAATGAT<br>ACTTGTCTGCTGGCTACCATGGGGCTGCAGCTGAACATCACTCA<br>GGATAAGGTTGCTTCAGTTATTAACATCAACCCCAATACAACTC<br>ACTCCACAGGCAGCTGCCGTTCTCACACTGCTCTACTTAGACTC<br>AATAGCAGCACCATTAAGTATCTAGACTTTGTCTTTGCTGTGAA<br>AAATGAAAACCGATTTTATCTGAAGGAAGTGAACATCAGCATG<br>TATTTGGTTAATGGCTCCGTTTTCAGCATTGCAAATAACAATTC<br>CAGCTACTGGGATGCCCCCTGGGAAGTTCTTATATGTGCAAC<br>AAAGAGCAGACTGTTTCAGTGTCTGGAGCATTTCAGATAAATA<br>CCTTTGATCTAAGGGTTCAGCCTTTCAATGTGACACAAGGAAA<br>GTATTCTACAGCCCAAGAGTGTTCGCTGGATGATGACACCATTC<br>TAATCCCAATTATAGTTGGTGCTGGTCTTTTCAGGCTTGATTATC<br>GTTATAGTGATTGCTGTGATGCAGAGACTCTTTCCCCGCATCCC<br>TCACATGAAAGACCCCATCGGTGACAGCTTCCAAAACGACAAG<br>CTGGTGGTCTGGGAGGCGGGCAAAGCCGGCCTGGAGGAGTGTC<br>TGGTGACTGAAGTACAGGTCGTGCAGAAAACT | IL3RA cytosolic domain from vecto 141; Artificial Sequence |
| 76 | LELNLTDSENATCLYAKWQMNFTVRYETTNKTYKTVTISDHGTV<br>TYNGISCGDDQNGPKIAVQFGPGFSWIANFTKAASTYSIDSVSFSY<br>NTGDNTTFPDAEDKGILTVDELLAIRIPLNDLFRCNSLSTLEKNDV<br>VQHYWDVLVQAFVQNGTVSTNEFLCDKDKTSTVAPTIHTTVPSPT<br>TTPTPKEKPEAGTYSVNNGNDTCLLATMGLQLNITQDKVASVINI<br>NPNTTHSTGSCRSHTALLRLNSSTIKYLDFVFAVKNENRFYLKEVN<br>ISMYLVNGSVFSIANNNLSYWDAPLGSSYMCNKEQTVSVSGAFQI<br>NTFDLRVQPFNVTQGKYSTAQECSLDDDT,<br>ILIPIIVGAGLSGLIIVIVIA,<br>VMQRLFPRIPHMKDPIGDSFQNDKLVVWEAGKAGLEECLVTEVQ<br>VVQKT | LAMP2 surface-and-transmembrane domain and IL3RA cytosolic domain amino acid sequence from vecto 141; Artificial Sequence |
| 77 | TTGGAACTTAATTTGACAGATTCAGAAAATGCCACTTGCCTTTA<br>TGCAAAATGGCAGATGAATTTCACAGTACGCTATGAAACTACA<br>AATAAAACTTATAAAACTGTAACCATTTCAGACCATGGCACTG<br>TGACATATAATGGAAGCATTTGTGGGGATGATCAGAATGGTCC<br>CAAAATAGCAGTGCAGTTCGGACCTGGCTTTTCCTGGATTGCG<br>AATTTTACCAAGGCAGCATCTACTTATTCAATTGACAGCGTCTC<br>ATTTTCCTACAACACTGGTGATAACACAACATTTCCTGATGCTG<br>AAGATAAAGGAATTCTTACTGTTGATGAACTTTTGGCCATCAG<br>AATTCCATTGAATGACCTTTTTAGATGCAATAGTTTATCAACTT<br>TGGAAAAGAATGATGTTGTCCAACACTACTGGGATGTTCTTGT<br>ACAAGCTTTTGTCCAAAATGGCACAGTGAGCACAAATGAGTTC<br>CTGTGTGATAAAGACAAAACTTCAACAGTGGCACCCACCATAC<br>ACACCACTGTGCCATCTCCTACTACAACACCTACTCCAAAGGA<br>AAAACCAGAAGCTGGAACCTATTCAGTTAATAATGGCAATGAT<br>ACTTGTCTGCTGGCTACCATGGGGCTGCAGCTGAACATCACTCA<br>GGATAAGGTTGCTTCAGTTATTAACATCAACCCCAATACAACTC<br>ACTCCACAGGCAGCTGCCGTTCTCACACTGCTCTACTTAGACTC<br>AATAGCAGCACCATTAAGTATCTAGACTTTGTCTTTGCTGTGAA<br>AAATGAAAACCGATTTTATCTGAAGGAAGTGAACATCAGCATG<br>TATTTGGTTAATGGCTCCGTTTTCAGCATTGCAAATAACAATCT<br>CAGCTACTGGGATGCCCCCTGGGAAGTTCTTATATGTGCAAC<br>AAAGAGCAGACTGTTTCAGTGTCTGGAGCATTTCAGATAAATA<br>CCTTTGATCTAAGGGTTCAGCCTTTCAATGTGACACAAGGAAA<br>GTATTCTACAGCCCAAGAGTGTTCGCTGGATGATGACACCATTC<br>TAATCCCAATTATAGTTGGTGCTGGTCTTTTCAGGCTTGATTATC<br>GTTATAGTGATTGCTCGCCTCTCCCGCAAGGGCCACATGTACCC<br>CGTGCGTAATTACTCCCCACCGAGATGGTCTGCATCTCATCCC<br>TGTTGCCTGATGGGGGTGAGGGGCCCTCTGCCACAGCCAATGG<br>GGGCCTGTCCAAGGCCAAGAGCCCGGGCCTGACGCCAGAGCCC<br>AGGGAGGACCGTGAGGGGGATGACCTCACCCTGCACAGCTTCC<br>TCCCT | Coding sequence for LAMP2 surface-and-transmembrane domain and SELPLG cytosolic domain from vecto 142; Artificial Sequence |
| 78 | LELNLTDSENATCLYAKWQMNFTVRYETTNKTYKTVTISDHGTV<br>TYNGISCGDDQNGPKIAVQFGPGFSWIANFTKAASTYSIDSVSFSY<br>NTGDNTTFPDAEDKGILTVDELLAIRIPLNDLFRCNSLSTLEKNDV<br>VQHYWDVLVQAFVQNGTVSTNEFLCDKDKTSTVAPTIHTTVPSPT<br>TTPTPKEKPEAGTYSVNNGNDTCLLATMGLQLNITQDKVASVINI | LAMP2 surface-and-transmembrane domain and SELPLG |

TABLE 5-continued

Nucleic acid sequences and amino acid sequences for chimeric vesicle localizations moieties*

| SEQ ID NO: | Sequence | Source |
|---|---|---|
| | NPNTTHSTGSCRSHTALLRLNSSTIKYLDFVFAVKNENRFYLKEVN ISMYLVNGSVFSIANNNLSYWDAPLGSSYMCNKEQTVSVSGAFQI NTFDLRVQPFNVTQGKYSTAQECSLDDDT, ILIPIIVGAGLSGLIIVIVIA, RLSRKGHMYPVRNYSPTEMVCISSLLPDGGEGPSATANGGLSKAK SPGLTPEPREDREQDDTLHSFLP | cytosolic domain amino acid sequence from vecto 142; Artificial Sequence |
| 79 | TTGGAACTTAATTTGACAGATTCAGAAAATGCCACTTGCCTTTA TGCAAAATGGCAGATGAATTTCACAGTACGCTATGAAACTACA AATAAAACTTATAAAACTGTAACCATTTCAGACCATGGCACTG TGACATATAATGGAAGCATTTGTGGGGATGATCAGAATGGTCC CAAAATAGCAGTGCAGTTCGGACCTGGCTTTTCCTGGATTGCG AATTTTACCAAGGCAGCATCTACTTATTCAATTGACAGCGTCTC ATTTTCCTACAACACTGGTGATAACACAACATTTCCTGATGCTG AAGATAAAGGAATTCTTACTGTTGATGAACTTTTGGCCATCAG AATTCCATTGAATGACCTTTTTAGATGCAATAGTTTATCAACTT TGGAAAAGAATGATGTTGTCCAACACTACTGGGATGTTCTTGT ACAAGCTTTTGTCCAAAATGGCACAGTGAGCACAAATGAGTTC CTGTGTGATAAAGACAAAACTTCAACAGTGGCACCCACCATAC ACACCACTGTGCCATCTCCTACTACAACACCTACTCCAAAGGA AAAACCAGAAGCTGGAACCTATTCAGTTAATAATGGCAATGAT ACTTGTCTGCTGGCTACCATGGGGCTGCAGCTGAACATCACTCA GGATAAGGTTGCTTCAGTTATTAACATCAACCCCAATACAACTC ACTCCACAGGCAGCTGCCGTTCTCACACTGCTCTACTTAGACTC AATAGCAGCACCATTAAGTATCTAGACTTTGTCTTTGCTGTGAA AAATGAAAACCGATTTTATCTGAAGGAAGTGAACATCAGCATG TATTTGGTTAATGGCTCCGTTTTCAGCATTGCAAATAACAATCT CAGCTACTGGGATGCCCCCCTGGGAAGTTCTTATATGTGCAAC AAAGAGCAGACTGTTTCAGTGTCTGGAGCATTTCAGATAAATA CCTTTGATCTAAGGGTTCAGCCTTTCAATGTGACACAAGGAAA GTATTCTACAGCCCAAGAGTGTTCGCTGGATGATGACACCATTC TAATCCCAATTATAGTTGGTGCTGGTCTTTCAGGCTTGATTATC GTTATAGTGATTGCTCTTTTAATGATAATTCATGACAGAAGGGA GTTTGCTAAATTTGAAAAGGAGAAAATGAATGCCAAATGGGAC ACGGGTGAAAATCCTATTTATAAGAGTGCCGTAACAACTGTGG TCAATCCGAAGTATGAGGGAAAA | Coding sequence for LAMP2 surface-and-transmembrane domain and ITGB1 cytosolic domain from vecto 143; Artificial Sequence |
| 80 | LELNLTDSENATCLYAKWQMNFTVRYETTNKTYKTVTISDHGTV TYNGISCGDDQNGPKIAVQFGPGFSWIANFTKAASTYSIDSVSFSY NTGDNTTFPDAEDKGILTVDELLAIRIPLNDLFRCNSLSTLEKNDV VQHYWDVLVQAFVQNGTVSTNEFLCDKDKTSTVAPTIHTTVPSPT TTPTPKEKPEAGTYSVNNGNDTCLLATMGLQLNITQDKVASVINI NPNTTHSTGSCRSHTALLRLNSSTIKYLDFVFAVKNENRFYLKEVN ISMYLVNGSVFSIANNNLSYWDAPLGSSYMCNKEQTVSVSGAFQI NTFDLRVQPFNVTQGKYSTAQECSLDDDT, ILIPIIVGAGLSGLIIVIVIA, LLMIIHDRREFAKFEKEKMNAKWDTGENPIYLSAVTTVVNKPYES K | LAMP2 surface-and-transmembrane domain and ITGB1 cytosolic domain amino acid sequence from vecto 143; Artificial Sequence |
| 81 | TTGGAACTTAATTTGACAGATTCAGAAAATGCCACTTGCCTTTA TGCAAAATGGCAGATGAATTTCACAGTACGCTATGAAACTACA AATAAAACTTATAAAACTGTAACCATTTCAGACCATGGCACTG TGACATATAATGGAAGCATTTGTGGGGATGATCAGAATGGTCC CAAAATAGCAGTGCAGTTCGGACCTGGCTTTTCCTGGATTGCG AATTTTACCAAGGCAGCATCTACTTATTCAATTGACAGCGTCTC ATTTTCCTACAACACTGGTGATAACACAACATTTCCTGATGCTG AAGATAAAGGAATTCTTACTGTTGATGAACTTTTGGCCATCAG AATTCCATTGAATGACCTTTTTAGATGCAATAGTTTATCAACTT TGGAAAAGAATGATGTTGTCCAACACTACTGGGATGTTCTTGT ACAAGCTTTTGTCCAAAATGGCACAGTGAGCACAAATGAGTTC CTGTGTGATAAAGACAAAACTTCAACAGTGGCACCCACCATAC ACACCACTGTGCCATCTCCTACTACAACACCTACTCCAAAGGA AAAACCAGAAGCTGGAACCTATTCAGTTAATAATGGCAATGAT ACTTGTCTGCTGGCTACCATGGGGCTGCAGCTGAACATCACTCA GGATAAGGTTGCTTCAGTTATTAACATCAACCCCAATACAACTC ACTCCACAGGCAGCTGCCGTTCTCACACTGCTCTACTTAGACTC AATAGCAGCACCATTAAGTATCTAGACTTTGTCTTTGCTGTGAA AAATGAAAACCGATTTTATCTGAAGGAAGTGAACATCAGCATG TATTTGGTTAATGGCTCCGTTTTCAGCATTGCAAATAACAATCT CAGCTACTGGGATGCCCCCCTGGGAAGTTCTTATATGTGCAAC AAAGAGCAGACTGTTTCAGTGTCTGGAGCATTTCAGATAAATA CCTTTGATCTAAGGGTTCAGCCTTTCAATGTGACACAAGGAAA GTATTCTACAGCCCAAGAGTGTTCGCTGGATGATGACACCATTC | Coding sequence for LAMP2 surface-and-transmembrane domain and CLSTN1 cytosolic domain from vecto 144; Artificial Sequence |

TABLE 5-continued

Nucleic acid sequences and amino acid sequences for chimeric vesicle localizations moieties*

| SEQ ID NO: | Sequence | Source |
|---|---|---|
| | TAATCCCAATTATAGTTGGTGCTGGTCTTTCAGGCTTGATTATC<br>GTTATAGTGATTTGCTCGGATCCGGGCCGCACATCGGCGGACCA<br>CCTTTGATCTAAGGGTTCAGCCTTTCAATGTGACACAAGGAAA<br>GTATTCTACAGCCCAAGAGTGTTCGCTGGATGATGACACCATTC<br>TAATCCCAATTATAGTTGGTGCTGGTCTTTCAGGCTTGATTATC<br>GTTATAGTGATTGCTCGGATCCGGGCCGCACATCGGCGGACCA<br>TGCGGGATCAGGACACCGGGAAGGAGAACGAGATGGACTGGG<br>ACGACTCTGCCCTGACCATCACCGTCAACCCCATGGAGACCTA<br>TGAGGACCAGCACAGCAGTGAGGAGGAGGAGGAAGAGGAAGA<br>GGAAGAGGAAAGCGAGGACGGCGAAGAAGAGGATGACATCAC<br>CAGCGCCGAGTCGGAGAGCAGCGAGGAGGAGGAGGGGGAGCA<br>GGGCGACCCCCAGAACGCAACCCGGCAGCAGCAGCTGGAGTG<br>GGATGACTCCACCCTCAGCTAC | |
| 82 | LELNLTDSENATCLYAKWQMNFTVRYETTNKTYKTVTISDHGTV<br>TYNGISCGDDQNGPKIAVQFGPGFSWIANFTKAASTYSIDSVSFSY<br>NTGDNTTFPDAEDKGILTVDELLAIRIPLNDLFRCNSLSTLEKNDV<br>VQHYWDVLVQAFVQNGTVSTNEFLCDKDKTSTVAPTIHTTVPSPT<br>TTPTPKEKPEAGTYSVNNGNDTCLLATMGLQLNITQDKVASVINI<br>NPNTTHSTGSCRSHTALLRLNSSTIKYLDFVFAVKNENRFYLKEVN<br>ISMYLVNGSVFSIANNNLSYWDAPLGSSYMCNKEQTVSVSGAFQI<br>NTFDLRVQPFNVTQGKYSTAQECSLDDDT,<br>ILIPIIVGAGLSGLIIVIVIA,<br>EEEEEEEEEESEDGEEEDDITSAEDEDDEEEEGEQGDPQNATRQQQ<br>LEWDDSTLSY | LAMP2 surface-and-transmembrane domain and CLSTN1 cytosolic domain amino acid sequence from vecto 144; Artificial Sequence |
| 83 | TTGGAACTTAATTTGACAGATTCAGAAAATGCCACTTGCCTTTA<br>TGCAAAATGGCAGATGAATTTCACAGTACGCTATGAAACTACA<br>AATAAAACTTATAAAACTGTAACCATTTCAGACCATGGCACTG<br>TGACATATAATGGAAGCATTTGTGGGGATCATCAGAATGGTCC<br>CAAAATAGCAGTGCAGTTCGGACCTGGCTTTTCCTGGATTGCG<br>AATTTTACCAAGGCAGCATCTACTTATTCAATTGACAGCGTCTC<br>ATTTTCCTACAACACTGGTGATAACACAACATTTCCTGATGCTG<br>AAGATAAAGGAATTCTTACTGTTGATGAACTTTTGGCCATCAG<br>AATTCCATTGAATGACCTTTTTAGATGCAATAGTTTATCAACTT<br>TGGAAAAGAATGATGTTGTCCAACACTACTGGGATGTTCTTGT<br>ACAAGCTTTTGTCCAAAATGGCACAGTGAGCACAAATGAGTTC<br>CTGTGTGATAAAGACAAAACTTCAACAGTGGCACCCACCATAC<br>ACACCACTGTGCCATCTCCTACTACAACACCTACTCCAAAGGA<br>AAAACCAGAAGCTGGAACCTATTCAGTTAATAATGGCAATGAT<br>ACTTGTCTGCTGGCTACCATGGGGCTGCAGCTGAACATCACTCA<br>GGATAAGGTTGCTTCAGTTATTAACATCAACCCCAATACAACTC<br>ACTCCACAGGCAGCTGCCGTTCTCACACTGCTCTACTTAGACTC<br>AATAGCAGCACCATTAAGTATCTAGACTTTGTCTTTGCTGTGAA<br>AAATGAAAACCGATTTTATCTGAAGGAAGTGAACATCAGCATG<br>TATTTGGTTAATGGCTCCGTTTTCAGCATTGCAAATAACAATCT<br>CAGCTACTGGGATGCCCCCCTGGGAAGTTCTTATATGTGCAAC<br>AAAGAGCAGACTGTTTCAGTGTCTGGAGCATTTCAGATAAATA<br>CCTTTGATCTAAGGGTTCAGCCTTTCAATGTGACACAAGGAAA<br>GTATTCTACAGCCCAAGAGTGTTCGCTGGATGATGACACCATTC<br>TAATCCCAATTATAGTTGGTGCTGGTCTTTCAGGCTTGATTATC<br>GTTATAGTGATTGCTaagaagccacgt | Coding sequence for LAMP2 surface-and-transmembrane domain and KKPR cytosolic domain from vecto 145; Artificial Sequence |
| 84 | LELNLTDSENATCLYAKWQMNFTVRYETTNKTYKTVTISDHGTV<br>TYNGISCGDDQNGPKIAVQFGPGFSWIANFTKAASTYSIDSVSFSY<br>NTGDNTTFPDAEDKGILTVDELLAIRIPLNDLFRCNSLSTLEKNDV<br>VQHYWDVLVQAFVQNGTVSTNEFLCDKDKTSTVAPTIHTTVPSPT<br>TTPTPKEKPEAGTYSVNNGNDTCLLATMGLQLNITQDKVASVINI<br>NPNTTHSTGSCRSHTALLRLNSSTIKYLDFVFAVKNENRFYLKEVN<br>ISMYLVNGSVFSIANNNLSYWDAPLGSSYMCNKEQTVSVSGAFQI<br>NTFDLRVQPFNVTQGKYSTAQECSLDDDT,<br>ILIPIIVGAGLSGLIIVIVIA, KKPR | LAMP2 surface-and-transmembrane domain and KKPR cytosolic domain amino acid sequence from vecto 145; Artificial Sequence |

*Amino acid sequences correspond to those provided in FIGS. 9-12; see figures and associated brief description of figures for location of surface, transmembrane and cytosolic domains.

The inventions disclosed herein will be better understood from the experimental details which follow. However, one skilled in the art will readily appreciate that the specific methods and results discussed are merely illustrative of the inventions as described more fully in the claims which follow thereafter. Unless otherwise indicated, the disclosure is not limited to specific procedures, materials, or the like, as such may vary. It is also to be understood that the termi-

EXAMPLES

Example 1: Extracellular Vesicle (EV) Production and Isolation

HEK293F cells were maintained in scrum-free media suspension cultures in shake flasks. Upon reaching a culture density of 2×10⁶ cells/mL, each shake flask culture was transfected with individual plasmids corresponding to vector constructs provided in FIGS. 1-2 to produce the fusion proteins with the amino acid sequence provided in FIGS. 3-8 or Table 3, using PE1 (MW: 25,000–1 mg/mL). Transfection reagent mixture was prepared in labeled tubes in 10% of the final desired culture volume of Opti-MEM® Reduced Scrum Medium with 1 μg of DNA for every 1 mL of final culture volume and a 2:1 ratio of PE1 to DNA, so 2 μg of PE1 for every 1 mL of final culture volume. For example, for a 30 mL final culture volume, 3.0 mL of Opti-MEM medium is added to 15-mL tube with 30 μg DNA and vortexed gently, 60 μL PE1 (at 1 mg/mL) is added to each 15-mL tube with DNA+medium Mixture is immediately vortexed 3×, 3 s each after PE1 addition. The mixture is incubated for 15 min at room temperature and then immediately added to the respective flasks. The incubator is set at 37° C. with 8% $CO_2$ on shaking platform at 12 RPM.

24 hours after transfection, the transfection media was exchanged for fresh media, and the cells were grown for an additional 96 hours. 96 hours following media exchange, the cultures were transferred into 50-mL, conical tubes and centrifuged at 3,220×g for 30 min. The supernatant from these cultures were transferred to Amiconr® Centrifugal Filter Units (100 kDa cut-off), concentrated and buffer exchanged into PBS. EVs are then filtered using Capto™ Core700 (Cytiva) Size Exclusion Chromatography (SEC) resin to remove non-EV-associated protein. Finally, the EVs are sterile filtered, using a 0.22 μM centrifugal filter column unit.

Other suitable cell lines that may be used to produce EVs or modified EVs include HEK293 or its variants, HEK293-F (Cellosaurus), FreeStyle™ 293-F (ThermoFisher) PER.C6, CHO-K1 or Hs 235.Sk (ATCC® CRL-7201™). In addition, transient transfection method describe above, stable cell lines may be created by co-transfecting an expression vector for a chimeric vesicle localization moiety or a fusion protein comprising a chimeric vesicle localization moiety, such as a targeting moiety-chimeric vesicle localization moiety fusion protein, and a selectable marker, such as a drug selectable marker, and selecting for the selectable marker to obtain a double transfectant which expresses both the selectable marker as well as the chimeric vesicle localization moiety or fusion protein of interest. EVs may be harvested from the culture media of such stable transfectants, wherein EVs may be modified with the chimeric vesicle localization moiety or fusion protein of interest.

Example 2: Preparation of Vesicles with Targeting Moieties

A cassette is made for cloning nucleic acids encoding one or more targeting moieties of interest. The cassette includes a polynucleotide encoding the LAMP2 or CLSTN1 vesicle localization moiety or it chimeric vesicle localization moiety (e.g., LAMP2 surface-and-transmembrane domains linked in frame to CLSTN1 cytosolic domain in the order as is naturally found for parental vesicle localization moieties, namely surface-transmembrane-cytosolic domains) for display on exomes, a polynucleotide encoding a N-terminal signal sequence for membrane insertion (e.g., insertion into the endoplasmic reticulum), and optionally, a polynucleotide encoding in epitope lag, a glycosylation sequence and linker sequences, the latter to separate functional sequences when desired, such as, for example, a linker sequence between a vesicle localization moiety or a chimeric vesicle localization moiety and a glycosylation sequence and/or a linker between a glycosylation sequence and epitope or signal sequence, A polynucleotide encoding a targeting moiety of interest is cloned into the cassette such that the open reading frame of the targeting moiety is linked in frame to the open reading frame of the signal sequence and the vesicle localization domain or chimeric vesicle localization domain, and optionally, an epitope tag, a glycosylation sequence and linker sequences, so as to produce a single open reading frame for a fusion protein comprising the signal sequence, targeting moiety of interest, vesicle localization domain or chimeric vesicle localization domain, and optionally, an epitope tag, a glycosylation sequence and linker sequences.

A targeting moiety of interest may be an affinity peptide or an scFv antibody and may be directed to a particular cell type or tissue through the affinity peptide or scFv antibody. The nucleic acid for the fusion protein is inserted in an expression vector to permit expression of the fusion protein either constitutively or inducibly. The expression vector preferably comprises a selectable or detectable marker, such as drug resistance gene (e.g., puromycine or 0418) or a gene for a fluorescent protein (e.g., GFP and its variants). Exemplary fusion proteins comprising a targeting moiety of interest and a vesicle localization domain or chimeric vesicle localization domain may be seen in lie figures.

A cell line, such as HEK293 or its variants, HEK293-F (Cellosaurus), Freestyle™ 293-F (ThermoFisher) PER.C6, CHO-K1 or Hs 235.Sk (ATCC® CRL-7201™, is transfected with vectors including the cassette with a desired marker. Positive transfectants are obtained by low cytometry or other cell sorting methods. In other cases, positive transfectants are enriched through antibiotic selection. Transfected cells are grown in exosome depleted or chemically defined media, suitable for exosome isolation. Following a period of culture, EVs are isolated from the conditioned media.

Any cells in the conditioned media are cleared by centrifugation and filtration, and the EVs in the clarified media are concentrated using ultrafiltration. After concentration the exosomes are isolated using liquid chromatography using an appropriate column (e.g., Sephacryl S-300, Capto-Core 700, etc.)

Example 3: Protocol for Labeling EVs Chemically with Fluorescent Dye for In Vivo Uptake Study and Characterizing/Marking EVs for Quantitative Analysis Extracellular vesicles labeled with a fluorescent dye or fluorescent protein permit tracking EVs in solution and cellular uptake of EVs, the latter resulting in transfer of the fluorescent dye or fluorescent protein to a cell indicating EV uptake by the cell. Such labeled EVs are useful in assessing effectiveness of a targeting moiety on surface of an EV to preferentially target one cell type over another.

Bodipy Labeling of EVs:
1. Bodipy-TR Ceramide preparation. Resuspend lyophilized BODIPY-TR Ceramide (250 ug, 705.7085 Daltons) in 354.2539 uL DMSO to a final stock concentration of 1 mM.
2. Bodipy labeling:
   a. Add PBS to EV isolated to bring final volume of each sample up to 1 mL.
   b. Add 20 µL of the stock Bodipy solution (1 mM) to 1 mL EV sample and mix. The final dye concentration in the EV sample is 20 µM.
   c. incubate at 37° C. for 1 hr (protected from light).
3. Free Bodipy clean up from the EV sample:
   a. At the end of incubation, filter the BodipyEV through a 0.22 um 33 mm PES PBS pre-cleaned Milex filter.
   b. Pipet BODIPY-FV solution into pre-cleaned (IX sterile PBS wash) Amicon 4 100 kDa.
   c. Perform 3× buffer exchange (3000 g for 7 minutes). Caution: Do not overspin because this will dry the membrane and products, causing additional loss.
   d. Add sterile PBS to the collection chamber to bring up volume to 0.5 mL.
   e. Use P200 to gently wash product off membrane pipet out the solution,
   f. Filter the BodiyEV sample through a 0.22 um 33 mm PES Millex filter.
4, BodipyEV characterization:
   a. Analyze the efficiency of EV labeling via absorption spectra measurement
   b. Analyze the particle concentration via NTA measurement
   c. Store the EVs in the dark at 4° C.

As an alternative to the labeling of EVs by chemical dyes. EVs may be labeled through the use of a fluorescent protein fusion, such as green fluorescent protein (GFP) and its variants, or protein reporters. This alternative method often involves creation of fusion proteins to generate a vesicle localization moiety-protein reporter gene constructs and cellular expression of these fusion proteins to obtain exosomes.

Example 4: Protocol for Fluorescent-Based Analysis of EV Uptake by Skeletal Muscle Cell To determine EV target specificity, targeting EVs (TEV) are prepared in which the targeting EVs comprise a targeting moiety displayed on the external surface of fluorescently labeled EVs and exposed to a cell co-culture comprising two different cell types one of which is labeled with a $2^{nd}$ fluorescent dye and expresses a cell marker targeted by the targeting moiety. Cell-based in vitro uptake assay is used to assess EV comprising a targeting moiety of interest (a targeting EV or TEV) to target a cell type or tissue. A skeletal muscle cell line labeled with a fluorescent dye and containing a skeletal muscle target protein (i.e., a skeletal muscle marker protein) and a negative cell line not containing the skeletal muscle cell target are co-cultured. Cell viability is confirmed to be >95% after 24 hours, and confluency between 40-90%, to confirm that both cell types in co-culture are representative of their functional capabilities in standalone monoculture. The co-culture is then "dosed" with EVs for an indicated period. The EVs have been engineered with a targeting motif that targets the nicotinic acetylcholine receptor round in skeletal muscle, such as an scFv for the nicotinic acetylcholine receptor or 3/5 α-conotoxin and derivatives targeting nicotinic acetylcholine receptor (see for example Tsetlin. V. and Kashev-erov, 1. (2014) Peptide and Protein Neurotoxin Toolbox in Research on Nicotinic Acetylcholine Receptors. In T. Heinbockel (Ed.), *Neurochemistry*, IntechOpen, DOI: 10.5772/58240; and Lebbe, E. K. M. et al. (2014) Conotoxins Targeting Nicotinic Acetylcholine Receptors: An Overview. Mar. Drugs 12:2970-3004; and McItosh, J. et al. (1999) Conus Peptides Targeted to Specific Nicotinic Acetylcholine Receptor Subtypes. Ann. Rev. Biochem. 68:59-88); this receptor is only present on the skeletal muscle cell line, but not the negative cell line. Cell uptake is assessed by labeling the EVs before dosing with a fluorescent dye, and then measuring fluorescence via flow cytometry, which also simultaneously permits distinguishing the labeled skeletal muscle cell from the negative cell line.

1. Preparation of Cell Co-Coculture (24 Hrs Before the Assay):
   a. CellTracker™ Violet BMQC Preparation:
      i. Thaw CellTracker™ Violet BMQC dye at room temperature 10 mins before use,
      ii. Add 59 µL DMSO to achieve 5 mM stock concentration, vortex and spin.
      iii. Add 40 µL CellTracker™ 5 mM Violet BMQC to 40 mL complete media (DMEM high glucose 10% FBS) to make 5 µM working concentration.
   b. Cell Labeling for Co-Culture System (Label Only One Cell Line in a 2-Cell Line Co-Culture System):
      i. Remove existing cell media for the Hs 235.Sk (ATCC® CRL-7201™) or HskMC (ATCC® PCS-950-010™) cells and add 20 mL CellTracker™ Violet BMQC containing media to each T-175. Incubate at 37° C. for 45 mins.
   c. Set Up Co-Culture System:
      i. Harvest both CellTracker™ Violet BMQC labeled cells (Hs23.Sk (ATCC® CRL-7201™, or HskMC (ATCC® PCS-950-010™)) and unlabeled cells (HEK293) with Trypsin-EDTA. Caution: Add excess co-culture media (DMEM low glucose+10% FBS) and pipet aggressively to achieve single cell suspension.
      ii. Count and measure viability of cells using trypan blue stain under the cell counter.
      iii. Plate cells at the desired concentration (3.4E5 cells in nonculture. 1.7E5 cells of each cell line in co-culture) in each well of a 6-well plate. Each sample will have 2 replicates in co-culture and 1 replicate for monoculture.
      iv. Allow the co-culture to grow overnight before the experiment.
2. incubation of BODIPY-labeled EV with Cell Co-culture:
   a. Prepare 1 mL of BODIPY-EV formulations in appropriate media (DMEM low glucose+10% FBS) to have a working concentration (1.02E9 particles/ml) per well.
   b. Remove culture media and add 1 mL BODIPY-EV/media to each well of the 6-well plate.
   c. Incubate for the desired amount of time (i.e., 1 hr and 2 hrs in this experiment)
   d. Harvest the cells with Trypsin EDTA.
   e. Transfer the cells to microcentrifuge tubes. Spin cells at 3000 rpm for 7 mins to aspirate media.
   f. Wash the cells with 1 ml ice cold PBS. Spin cells at 3000 rpm for 5 mins to remove PBS.
   g. Re-suspend the cells in 200 µL. PBS. The cells are now ready for flow cytometry analysis.

Example 5: Vesicle Delivery in Vitro to Skeletal Muscle Cells

EVs are obtained from the conditioned media supernatant of cultured HEK293 cells. The EVs are isolated using ultracentrifugation (size selection to enrich for a general EV population. The EVs are loaded with a reporter (e.g., CPSD) or mRNA encoding a reporter (e.g., GFP), as described in Example 8.

Skeletal muscle cell line such as Hs 235.Sk (ATCC® CRL-7201™) is grown to confluence and then the EVs with reporter are added to the skeletal muscle cell line. After incubating the skeletal muscle Hs235.Sk cells with the EVs, the excess EVs are washed away. The cells are then subjected to fluorescence microscopy to identify those cells that have obtained a reporter from the EVs. EV delivery to the cells is identified by reporter activity in cells.

Example 6: Vesicle Delivery In Vivo to Skeletal Muscle Cells

EVs are obtained from the media of Hs 235.Sk (ATCC® CRL-7201™). The EVs are isolated using ultracentrifugation (size selection to enrich for a general EV population). The EVs are loaded with a reporter (e.g., CPSD) or mRNA encoding a reporter (e.g., GFP), as described in Example 8. The animal model B6.129X1-Nfe212$^{tm1Ywk}$ mice are used for this study.

B6.129X1-Nfe212$^{tm1Ywk}$ mice are injected with EVs containing the reporter CPSD. After 24 hours, the nice are sacrificed and the animal's skeletal myocytes are examined with fluorescence microscopy. EV delivery to skeletal muscle tissue is identified by reporter activity in the skeletal muscle cells.

Example 7: Assessing EV Yield from Cell Culture Production

Exosomes presenting targeting moieties of interest are engineered as described in herein. The number of isolated exosomes are quantified using nanoparticle tracking analysis.

NTA measurements are obtained with a NanoSight NS300 instrument equipped with the Nunoparticle Tracking Analysis (NTA) 3.3 analytical software (Malvern Panalytical). Samples are diluted to achieve a particle count in the linear range of the instrument: between 20 and 150 particles on the screen at one time. Samples are loaded using the NanoSight Sample Assistant to automate the measurement of up to 96 samples in one run. Multiple 30 second videos of each sample flowing at a slow constant flow are obtained. These measurements are then analyzed using the batch process function.

Example 8: Introducing Payloads into Engineered Exosomes Carrying Markers of Interest An exosome is engineered to incorporate a targeting moiety(ies) of a skeletal muscle marker, such as a scFv or affinity peptide as a targeting moiety directed to a skeletal muscle marker, for example a subunit or multiple subunits of the nicotinic acetylcholine receptor found in skeletal muscle (e.g., α1β1δε (adult) and α1β1γδ (fetal) nAChRs; see Tsetlin, V. and Kasheverov. 1, (2014) Peptide and Protein Neurotoxin Toolbox in Research on Nicotinic Acetylcholine Receptors. In T Heinbockel (Ed.), Neurochemistry, IntechOpen, DOI: 10.5772153240: Lebbe, E. K. M. et al. (2014) Conotoxins Targeting Nicotinic Acetylcholine Receptors: An Overview, Mar. Drugs 12:2970-3004): and McIntosh. J. et al. (1999) Conus Peptides Targeted to Specific Nicotinic Acetylcholine Receptor Subtypes. Ann. Rev. Biochem. 68:59-88). Alternatively, an exosome is engineered to comprise any one of the following targeting moieties ENO2, JSRP1, VA PA, TMOD1 or a functional fragment thereof. The engineered or isolated exosome or EV is loaded with a CRISPR gene editing system, a transgene or a miRNA. miRNA may be selected from the group consisting of miR-133a, miR-1, miR-133, miR-133b, miR-181a-Sp, miR-206, and miR-499. Alternatively, the engineered or isolated exosome is loaded with fenretinide. The loaded exosome is then used to ameliorate insulin resistance of obese subject and/or reduce obesity in a subject.

Exosome protein input of ~300 µg (from about 1×10^7 exosomes) is suspended in 50 µl of sterile PBS. A reaction mixture consisting of exosomes, 10 µl of Exo-Fect Reagent and nucleic acid of interest (20 pmol si/miRNA, 1 µg mRNA or 5 µg plasmid DNA) is put together and mixed by inversion. The transfection solution is incubated in a shaker for 10 minutes at 37° C. and then placed on ice. To stop the reaction, 30 µl of ExoQuick-TC reagent provided in the kit is added to the exosome sample suspension and mixed by inverting. The transfected exosome sample is placed on ice for 30 minutes. The sample is centrifuged at 13000-14000 rpm to pellet the exosomes. The transfected exosomes are then resuspended in PBS and can be added to target cells or used in vivo fir further applications.

Alternatively, exosomes may be isolated from HEK293 or engineered cells expressing fusion protein comprising a targeting moiety and vesicle localization moiety or a chimeric vesicle localization moiety. Sample isolated EVs are prepared in PBS buffer at a concentration of 2.10E+11 particles/mL Fenretinide (Selleck Chemicals: Cat No: S5233) was dissolved in 100% DMSO. The fenretinide/DMSO stock solution can be 5 mM or 10 mM. Protocol for introducing fenretinide into RV to obtain EV comprising fenretinide (fenretinide-EV, also called fen-EV, EV-fen or EV-fenretinide) and purifying the fenretinide-EV from extra-vesicular (not associated with an EV) fenretinide not incorporated into EVs:

A. Exosome/drug substance incubation;
1. The EV samples were diluted with PBS to a final EV concentration around 2.10E11 particles per mL.
2. For every 2,000 µl, of exosome solution, 128.67 µL of 10 mM fenretinide in 100% DMSO were added to achieve a drug substance (fenretinide) mass (in µg) to 1E9 EV count ratio of 1.2 in the appropriate tube format. (Final DMSO concentration amount for this sample was ~6% of the total volume.)
3. The EVs with the drug solution were mixed by pipetting up and down a couple of times at room temperature, with no extended incubation, then processed immediately according to the clean-up steps below.

B. Corning® Costar® SpinX® (0.22 µm cellulose acetate membrane tilter) centrifuge tube filter for large drug substance aggregates removal
1. 2,000 µl, of fenretinide-EV samples were split into four 0.5 mL SpinX® filters (Corning® Costar®, VWR, 29442-752; 0.22 Jim cellulose acetate membrane filter) and filtered by centrifugation at 1.000×g.
2. Samples were pooled to obtain ~2 mL volume and aliquots were collected pre- and post-filtration for in-process analysis.

C. Amicon® Ultra-15 centrifugal filter for removing free/non-packaged drug substance:
1. 5 mL of 1×PBS buffer was added to rinse the 100 kDa Amicon® Ultra-15 concentrator tube (Sigma/Millipore, UFC910024) and centrifuged at 3.220χg for 5 mins. The flow through was removed.

2. (Wash 1) 13 mL of 1×PBS was added to each concentrator tube. 2 mL of filtered fenretinide-EV sample was added to the concentrator tube and centrifuged at 3.220×g until the sample was concenrated to 0.5 mL. The flow through was discarded.
3. (Wash 2) 14 mL of PBS was added to each concentrator tube and mixed well by pipetting. The tube was centrifuged at 3,220×g until sample and was concentrated to ~0.5 mL. The low through was discarded.
4. (Wash 3) 14 ml, of PBS was added to each concentrator tube and mixed well by pipetting. The tube was centrifuged at 3,220×g until sample and was concentrated to ~0.5 ml. The flow through was discarded.
5. P200 Pipetman® was used to rinse the concentrator membrane of each tube with the concentrated sample. Fenretinide 4V samples were transferred to a 0.22 μm Spin-X tiller. Filtered by centrifuging at 1.000×g for 5 minutes to obtain a final sterilized sample.

D. Post-Packaging QC Metrics:
1. Drug quantitation: Final drug substance amount, concentration and packaging were quantified from the final drug packaged EV sample. Final drug quantitation was performed using absorption spectra from the plate reader (using Synergy H1M, BioTek) using the following steps:
   a. The final fenretinide-EV sample was diluted 1 OX in PBS, and 200 μL were loaded into the UV-transparent plate (Corning, cat no 3635).
   b. The standard curve was generated by performing 2× serial dilutions (from about 125 μM to 0.5 μM) of the fenretinide/100% DMSO stock in DMSO/PBS (50:50) solution to generate a standard curve. The fenretinide/DMSO/PBS standard curve samples also had 200 μL in the wells.
   c. The absorption spectra were measured (250 to 800 run range) by a BioTek Synergy H1 plate reader.
   d. The linear fit from the standard curve generated from the fenretinide/DMSO/PBS samples was used to interpolate the concentration of fenretinide in the fenretinide-V samples.
2. Size measurements: Samples were run on Nanoparticle Tracking Analysis (NTA) NanoSight NS300 (Malvern) to determine EV particle size distribution and count using a sample volume ranging from about 1 μL to 1,000 μL.

Packaging of 118.2 μg fenretinide inside EV (2.0E11 particles) with 24.9% encapsulation efficiency and a final concentration of 604 μM fenretinide-EV in PBS may be achieved.

In addition to the above two methods for loading a payload of interest into an extracellular vesicle, the art is replete with other methods for loading payloads of interest including electroporation, sonication, permeabilization with saponin, free-thaw cycles, $Ca^{2+}$ method. pH gradient method, lipid vesicle fusion, mechanical vibration, extrusion through porous membranes, electric current and combinations thereof

Example 9: Construction of Chimeric Vesicle Localization Moiety

To improve performance of vesicle localization moiety in localizing at art extracellular vesicle, chimeric vesicle localization moieties were constructed as schematically presented in FIGS. 1 and 2. Vector #91 construct when introduced into HEK293F cells produces a fusion protein comprising from amino-to-carboxyl terminus in the order: a signal sequence (for improved expression and endoplasmic reticulum association)-glycosylation site (for stabilization of fusion protein)-mature LAMP2 (Lysosome-associated membrane protein 2) protein with surface, transmembrane and cytosolic domains for localization to exosomes). Note that the mature LAMP2 protein used lacks its natural signal sequence—the first 28 amino acids normally found at N-terminal of a nascent LAMP2 protein but is removed following association with a cell membrane, such as endoplasmic reticulum, such that the resulting processed, mature LAMP2 form is found associated with an exosome. The fusion protein may additionally comprise peptide linkers. Such peptide linkers rich in glycine and serine amino acids may be found between the signal sequence, glycosylation site and LAMP2 protein. In addition, optionally, epitope sequence (such as that corresponding to 3× FLAG epitope tag) and affinity peptide sequence may be found in between the signal sequence and the glycosylation site. Examples of suitable affinity peptides include, but are not limited to, THRPPMWSPVWP (SEQ ID NO.: 64), a targeting moiety or peptide for transferrin receptor (TfR), and THVSPNQGGLPS (SEQ ID NO.: 66), a targeting moiety or peptide for glypican-3 (GPC3), This LAMP2 fusion protein serves as one parental vesicle localization moiety (see FIG. 1, vector #91 flor a schematic of a fusion protein comprising the mature LAMP2 protein (lacking its native LAMP2 signal peptide sequence): see FIG. 3, vector #91 for the sequence of the LAMP2 fusion protein produced and FIG. 9, vector #91 tor the sequence of the mature LAMP2 protein with the surface, transmembrane and cytosolic domains but lacking the first 28 amino acids corresponding to its natural signal sequence). In FIGS. 9-12 or Table 5, amino acid sequences corresponding to the surface, transmembrane and cytosolic domains are extracted from the sequences of the fusion proteins provided in FIGS. 3-8 or Table 3 so that only the vesicle localization moiety or chimeric vesicle localization moiety amino acid sequences are shown. The surface domain (italic text) precedes the transmembrane domain (italic and bold) which is found between the surface and cytosolic domain (italic and underline) and connects these two domains.

A second parental vesicle localization moiety was constructed with mature CLSTN1 protein coding sequence, as schematically shown for vector #112 in FIG. 1. The mature (CLSTN1 protein coding sequence lacks the first 28 codons of the nascent full length CLSTN1 protein coding sequence: the first 28 amino acids of the nascent CLSTN1 protein corresponds to its natural CLSTN1 signal sequence, which is normally removed upon association of the nascent protein with the endoplasmic reticulum and eventual incorporation of this processed mature CLSTN1 protein into an intraluminal vesicle before secretion from a multivesicular body (MVB) (Hanson. P. I. and Cashikar, A. (2012) Multivesicular body morphogenesis. Ann, Rev, Cell Dev. Rini. 28: 17-1621 and Hessvik, N. P. and Llorente, A. (2018) Current knowledge on exosome biogenesis and release. Cell. Mol. Life Sci. 75:103-208). The primary amino acid sequence of the mature CSTN1 protein, like mature LAMP2 protein, differs from the full length nascent CLSN1 protein (similarly to full length nascent LAMP2 protein) in lacking the native signal sequence, the first 28 amino acids at the N-terminus of the full-length nascent protein. Like the LAMP2 fusion protein produced from the expression of vector #91 in mammalian cells (HEK293F), the CLSTN1 Fusion Protein has a Similar arrangement of a non-native signal sequence at the amino terminus of the fusion protein along with epitope sequence and glycosylation site. Linkers are similarly present and in addition an affinity peptide is present in the CLSTN1 fusion protein (see FIG. 1, vector #112 for a map of functional sequences encoding the fusion protein; FIG. 4 for the sequence of the parental CLSTN1 fusion protein produced from vector #112 and FIG. 9 for the sequence of the mature CLSTN1 protein).

Chimeric vesicle localization moieties were prepared primarily based on the surface domain and transmembrane domain of LAMP2 (surface-and-transmembrane domain of LAMP2) and cytosolic domain from other transmembrane proteins, Type I transmembrane proteins were used, having the following characteristic after incorporation into an extracellular vesicle (e.g., an exosome): an amino-terminal surface domain, a single pass transmembrane domain and a carboxyl-terminal lumenal domain (also referred to its topological equivalence, as a cytosolic domain prior to the formation of an exosome but following insertion into the endoplasmic reticulum). In particular, the cytosolic domain (lumenal domain) of LAMP2 is replaced with the cytosolic domain of PTGFRN (vector #135), ITGA3 (vector #140), IL3RA (vector #141), SELPLG (vector #142), ITGB3 (vector #143) and CLSTN1 (vector #144), as schematically represented in FIGS. 1 and 2. Amino acid sequences for fusion proteins prepared from these chimeric vesicle localization moieties are shown in FIG. 3-8 or Table 3. Sequences are shown in capital letter and bold for signal sequence, capital letter and underline for epitope sequence, shaded capital letter for affinity peptide, open boxed capital letter for peptide linker sequence, small letter for glycosylation site, capital letter and italic for surface domain, capital letter and bold italic for transmembrane domain and capital letter and underlined italic for cytosolic domain in FIGS. 3-8.

To assess the effect of LAMP2 cytosolic domain for LAMP2 protein localization at extracellular vesicles, the cytosolic domain of mature LAMP2 protein was removed and replaced with a highly charged tetrapeptide, KKPR, to stabilize truncated LAMP2 on surface of EVs (see FIG. 2, vector #145 for a map of the fusion protein with the truncated LAMP2 lacking its natural cytosolic domain replaced by a tetrapeptide. KKPR, and FIG. 8. #145 for the amino acid sequence of the fusion protein with the truncated LAMP2 lacking its native cytosolic domain).

Example 10: Recombinant Protein Detection on the EV Surface

To ensure that EVs displayed the fusion protein construct encoded by the transfected plasmid and the fusion protein is oriented with correct transmembrane topology, isolated EVs are stained with fluorophore-conjugated anti-FLAG tag antibody and a membrane stain. The stained vesicles are evaluated using vesicle flow cytometry (vFC) (Cytoflex—Beckman Coulter). EVs are identified as membrane stain-positive particles. The amount of recombinant protein on each EV is detected using a fluorophore-conjugated antibody that binds specifically to the epitope sequence included in the primary sequence of the protein, and would only be available on the EV surface it the fusion protein is oriented in the intended topology (C-terminal domain in the lumen; N-terminal domain on the EV surface). The amount of recombinant protein on each evaluated EV is determined by the antibody signal/membrane-stained particle.

In FIG. 13, EV populations were isolated from cells transfected with the indicated vector numbers. Isolated EVs were stained with a mouse monoclonal antibody specific to an epitope sequence encoded in the EV surface domain of each recombinant protein. The Y-axis represents the relative amount (on average) of antibody bound to each EV ignoring EVs not labeled by the anti-FLAG epitope tog antibody, serving as an indirect measure of the amount of recombinant protein incorporated into each EV. The background signal associated with EVs from mock transfected cells (Mock) has been subtracted from these values. The fraction of the total EV population displaying a detectable amount of the recombinant protein is shown in FIG. 14.

Example 11: Chimeric Vesicle Localization Moiety with a Surface-and-Transmembrane Domain of First Vesicle Localization Moiety and a Cytosolic Domain can Increase EV Localization Transient transfection of the deterrent expression vector constructs for the production of the fusion proteins shown in FIGS. 1 and 2 and having the amino acid sequences provided in FIG. 3-8 or Table 3 and analysis of the fusion protein localization at EVs isolated front culture media showed surprising alteration in the efficiency of accumulation of the fusion protein at an extracellular vesicle. Producing a fusion protein comprising it chimeric vesicle localization moiety having a LAMP1 surface-and-transmembrane domain and a non-native cytosolic domain from a number of different vesicle localization moieties PTGFRN (vector #135) ITGA3 (vector #140). IL3RA (vector #141), SELPLG (vector #142). ITGB1 (vector #143) and CLSTN1 (vector #144) showed dramatic improvement in the ability of the fusion protein to localize at an extracellular vesicle, increasing both the abundance of the fusion protein at an EV (FIG. 13) as well as the fraction or percent of EVs positive for the fusion protein (FIG. 14). In every case, replacement of the cytoplasmic domain of one vesicle localization moiety, LAMP2 protein, with that of as second vesicle localization moiety, PTGFRN (vector #135). ITGA3 (vector #140), IL3RA (vector #141). SELPLG (vector #9142), ITGB1 (vector #t 1431) and CLSTN1 (vector #144), resulted in both an increase in the abundance of fusion protein present on EV surface for EVs positively labeled by the anti-FLAG epitope tag antibody directed to the FLAG epitope tags in the fusion proteins (FIG. 13) and an increase in the fraction or percent of total EV population positive for the fusion protein (FIG. 14).

FIGS. 13 and 14 show that not only do chimeric vesicle localization moieties localize to EVs but localization of the fusion proteins is improved when a chimeric vesicle localization moiety is used in place of its non-chimeric counterpart (compare #135, 140, 141, 142, 143 and 144 with #91 or 112). Furthermore, deleting the cytosolic domain of LAMP2 and replacing with a positively charged tetrapeptide, KKPR, modestly improves localization of LAMP2 surface-and-transmembrane domain to EV (compare #145 with #91): however, the improvement in EV localization by transplanted cytosolic domains from a variety of vesicle localization moieties is much more robust-indicating that while a minimal cytosolic domain (i.e., KKPR) may be required for stable EV localization of a surface-transimembrane domain of a vesicle localization moiety (such as LAMP2), the cytosolic domain can modulate FV localization, affecting the efficiency of EV localization.

Normalization of the data in FIG. 13 to illustrate fold increase in fusion protein abundance or concentration on EV surface relative to the fusion protein comprising a mature LAMP2 (nascent LAMP2 protein lacking its native signal sequence, the first 28 amino acids at the amino terminus of the nascent protein; vector t 91 construct) is shown in FIG. 15. Similarly, normalization of the data in FIG. 14 to illustrate fold increase in percent or fraction of EVs positive for a fusion protein relative to the fusion protein comprising a mature LAMP2 protein produced by vector #99 construct is shown in FIG. 16. Replacing the cytosolic domain of the mature LAMP2 protein with the cytosolic domain of a variety of other vesicle localization moiety results in about a 4-fold increase in fusion protein abundance at an EV for a number of cytosolic domain examined obtained from PTGFRN (vector #135), ITGA3 (vector #140), IL3RA (vector #141), SELPLG (vector #142), and ITGB1 (vector #143), as seen in FIG. 15. Similar to this increase in the concentration of the fusion protein at an EV, fraction of total EVs positive for the various fusion proteins with a chimeric vesicle localization moiety (vector #135, 140, 141, 142, 143, and 144) increases 3-4 fold over the fusion protein comprising a non-chimeric vesicle localization moiety, namely the parental LAMP2 vesicle localization moiety (vector #91) which provided its LAMP2 surface-and-transmembrane domain to the various chimeric vesicle localization moieties (vector #135, 140, 141, 142, 143, and 144).

Example 12: Chimeric Vesicle Localization Moiety can Dramatically Improve EV Localization Over Parental Vesicle Localization Moieties FIG. 15 shows fold increase in fusion protein abundance (or concentration) on EV surface relative to fusion protein produced by vector #91 construct (fusion protein with a mature LAMP2 protein having a contiguous surface-transmembrane-and-cytosolic domain but no native LAMP2 signal sequence), as detected by vesicle flow cytometry using a fluorophore-conjugated anti-FLAG epitope tag antibody. Compared to the fusion protein produced by vector #91, the fusion protein produced by vector #112 (fusion protein with a mature CLSTN1 protein having its surface-transmembrane-and-cytosolic domain but no native CLSTN1 signal sequence) concentrates at a much lower level, about 25% the abundance of the mature LAMP2-containing fusion protein (compare value of #91 and #112 in FIG. 15). Surprisingly, when the cytosolic domain of the mature LAMP2 is replaced with the cytosolic domain of the mature CLSTN1, the new chimeric vesicle localization moiety increases by about 2-fold the abundance of the fusion protein over its parental LAMP2 (compare value of #91 and #144) or over 8-fold the abundance of the fusion protein over its parental CLSTN1 (compare value of #112 and #144), indicative of synergistic interaction between the surface-and-transmembrane domain of LAMP2 and the cytosolic domain of CLSTN1.

Synergistic interaction leading to increased concentration of the fusion protein at an EV is also observed when analyzing fraction of total EV population positive for a fusion protein (FIG. 16). In particular, fusion protein comprising the parental LAMP2 vesicle localization moiety is better at associating with total EV population having a normalized value of 1.00 (#91) than the fusion protein comprising the parental CLSTN1 vesicle localization moiety with a normalized value 0.15 (#112). In contrast, a fusion protein comprising a chimeric vesicle domain produced from the two parental vesicle localization moieties (#144) has a normalized value of 3.79, reflecting over 3.5-fold increase over the parental LAMP2 vesicle localization moiety and over 25-old over the parental CLSTN1 vesicle localization moiety. Such a dramatic increase in association with total EV population which reaches about 55% (see FIG. 14. #144) by a fusion protein comprising a chimeric vesicle localization moiety is unexpected. The observed increase in EV localization is not unique to the use of CLSTN1 cytosolic domain to replace the LAMP2 cytosolic domain. A number of other cytosolic domains also increase EV localization beyond that of the parental LAMP2 vesicle localization moiety, indicating that the cytosolic domain of PTGFRN, ITGA3, IL3RA, SELPLG, and ITGB1 may function in a similar manner as the cytosolic domain of CLSTN1 to synergistically increase EV localization, both concentrating at a single EV as well as associating with the total EV population.

Thus, analyses of fusion protein abundance on an EV surface and fraction (or percent) of total EV population positive for fusion protein showed that a chimeric vesicle localization moiety comprising a surface-and-transmembrane domain of a first vesicle localization moiety and a cytosolic domain of a second vesicle localization moiety can interact synergistically to increase accumulation at an extracellular vesicle. Such a finding provides an approach not only to improve EV localization but potentially to change the composition of EVs as the chimeric vesicle localization moiety may interact with a different set of proteins or has altered affinity to the set of proteins recruited to an extracellular vesicle by the two native vesicle localization moieties.

FIGS. 13-16 are bar graphs showing abundance of a vesicle localization moiety or chimeric vesicle localization moiety at an EV having the localization moiety (FIGS. 13 and 15) and fraction of total EVs positive for the vesicle localization moiety or chimeric vesicle localization moiety (FIGS. 14 and 16), EVs are isolated from culture media of cells transiently transfected with the expression construct (vector) indicated below each bar graph. The isolated EV population is labeled with a membrane-staining fluorescent dye with a spectral characteristic distinct a second fluorescent dye used to conjugate to an anti-FLAG antibody. The fluorescent dye-labeled EV population is probed with the fluorophore-conjugated anti-FLAG antibody to detect presence of fusion protein comprising it vesicle localization moiety or a chimeric vesicle localization moiety, as all fusion proteins produced have 3×FLAG epitope preceding the surface domain. The resulting EVs are analyzed by vesicle flow cytometry (VFC) in a CytoFLEX benchtop flow cytometer (Beckman Coulter) to detect the EVs based on the membrane-staining fluorescent dye. In addition, based on the second fluorescent dye, the subset of EVs additionally labeled by the anti-FLAG antibody are identified and fluorescence associated with the $2^{nd}$ fluorescent dye quantified. Fluorescence (of the $2^{nd}$ fluorescent dye) associated with EVs obtained front mock transfected cells and similarly treated is subtracted, as this fluorescence is not associated with presence of a FLAG epitope tag. FIG. 13 is a plot of mean antibody fluorescence of an EV positively labeled with the anti-FLAG antibody for the fusion protein expressed by the indicated expression vector, FIG. 14 is a plot of percent of total FN positively labeled by the anti-FLAG antibody. FIGS. 15 and 16 show the fold changes in levels reported in FIGS. 13 and 14, respectively, in relation to expression vector #191, which expresses a fusion protein comprising a nature LAMP2 protein.

All publications, gene transcript identifiers, patents and patent applications discussed and cited herein are incorporated herein by reference in their entireties. It is understood that the disclosed invention is not limited to the particular methodology, protocols and materials described as these can vary. It is also understood that the terminology used herein is for the purposes of describing particular embodiments only and is not intended to limit the scope of the present invention which will be limited only by the appended claims.

Those skilled in the art will recognize, or be able to ascertain using no more than routine experimentation, many equivalents to the specific embodiments of the invention described herein. Such equivalents are intended to be encompassed by the following claims.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A non-naturally occurring exosome comprising a chimeric vesicle localization moiety comprising
   a. surface-and-transmembrane domain of a first vesicle localization moiety, wherein the first vesicle localization moiety, is lysosome-associated membrane protein 2, isoform B (LAMP2B) and
   b. a cytosolic domain of a second vesicle localization moiety, wherein the second vesicle localization moiety is selected from the group consisting of calsyntenin 1 (CLSTN1), interleukin 3 receptor subunit alpha (IL3RA), integrin subunit alpha 3 (ITGA3), integrin subunit beta 1 (ITGB1), prostaglandin F2 receptor negative regulator (PTGFRN), and selectin P ligand (SELPLG), wherein the first and second vesicle localization moieties are single pass transmembrane proteins.

2. The exosome of claim 1, wherein the single pass transmembrane proteins are type I transmembrane proteins.

3. The exosome of claim 1, wherein the chimeric vesicle localization moiety is a mature chimeric vesicle localization moiety.

4. The exosome of claim 1, wherein the chimeric vesicle localization moiety is obtained from a nascent or full-length chimeric vesicle localization moiety which comprises a signal peptide that precedes the surface-and-transmembrane domain of the first vesicle localization moiety.

5. The exosome of claim 1, wherein the chimeric vesicle localization moiety is incorporated into the exosome, wherein the exosome comprises a lipid bilayer and a lumen, and wherein the chimeric vesicle localization moiety has a topology with an amino surface domain external to the exosome, a transmembrane domain in the lipid bilayer of the exosome, and a carboxy terminal cytosolic domain in the lumen of the exosome.

6. A method of manufacturing of an exosome of claim 1, wherein the method comprises the following steps:
   a. expressing a nucleic acid encoding the chimeric vesicle localization moiety comprising a surface-and-transmembrane domain of a first vesicle localization moiety of claim 1 and the cytosolic domain of a second vesicle localization moiety of claim 1 in a producer cell; and
   b. isolating the exosome comprising the chimeric vesicle localization moiety, wherein the exosome is secreted into a culture medium by the producer cell.

7. A pharmaceutical composition comprising the exosome of claim 1, and one or more pharmaceutically acceptable excipients.

8. A kit comprising the exosome of claim 1 and instructions.

9. The exosome of claim 1, wherein the first vesicle localization moiety is LAMP2B and wherein the second vesicle localization moiety is PTGFRN.

* * * * *